United States Patent
Lee et al.

(10) Patent No.: US 10,202,450 B2
(45) Date of Patent: Feb. 12, 2019

(54) $NA_V$ 1.7 ANTIBODIES AND METHODS OF USING THE SAME

(71) Applicant: Duke University, Durham, NC (US)

(72) Inventors: Seok-Yong Lee, Durham, NC (US); Ru-Rong Ji, Durham, NC (US)

(73) Assignee: Duke University, Durham, NC (US)

( * ) Notice: Subject to any disclaimer, the term of this patent is extended or adjusted under 35 U.S.C. 154(b) by 0 days.

(21) Appl. No.: 14/916,602

(22) PCT Filed: Sep. 5, 2014

(86) PCT No.: PCT/US2014/054305
§ 371 (c)(1),
(2) Date: Mar. 4, 2016

(87) PCT Pub. No.: WO2015/035173
PCT Pub. Date: Mar. 12, 2015

(65) Prior Publication Data
US 2016/0237153 A1 Aug. 18, 2016

Related U.S. Application Data

(60) Provisional application No. 61/944,388, filed on Feb. 25, 2014, provisional application No. 61/915,304, filed on Dec. 12, 2013, provisional application No. 61/874,234, filed on Sep. 5, 2013.

(51) Int. Cl.
*A61K 39/00* (2006.01)
*C07K 16/28* (2006.01)
*C07K 14/705* (2006.01)

(52) U.S. Cl.
CPC ............ *C07K 16/28* (2013.01); *C07K 14/705* (2013.01); *A61K 2039/505* (2013.01); *C07K 2299/00* (2013.01); *C07K 2317/33* (2013.01); *C07K 2317/34* (2013.01); *C07K 2317/55* (2013.01); *C07K 2317/56* (2013.01); *C07K 2317/76* (2013.01); *C07K 2317/92* (2013.01)

(58) Field of Classification Search
CPC combination set(s) only.
See application file for complete search history.

(56) References Cited

U.S. PATENT DOCUMENTS

| | | |
|---|---|---|
| 2008/0213252 A1 | 9/2008 | Lerner et al. |
| 2009/0130114 A1 | 5/2009 | Qian et al. |
| 2009/0246852 A1 | 10/2009 | Williams et al. |
| 2011/0135662 A1 | 6/2011 | Finney et al. |
| 2012/0039916 A1 | 2/2012 | Zurawski et al. |
| 2012/0052076 A1 | 3/2012 | Alberti et al. |
| 2012/0263728 A1 | 10/2012 | Baker et al. |

FOREIGN PATENT DOCUMENTS

WO WO/2011/051350 * 5/2011

OTHER PUBLICATIONS

Catterall, Voltage-gated Sodium Channels at 60; Structure, Function and Pathophysiology, The Journal of Physiology, 590, Apr. 2, 2012, pp. 2577-2589.
International Search Report, PCT/US2014/054305, dated Jan. 14, 2015.
Written Opinion, PCT/US2014/054305, dated Jan. 14, 2015.

\* cited by examiner

*Primary Examiner* — Kimberly Ballard
*Assistant Examiner* — Stacey N MacFarlane
(74) *Attorney, Agent, or Firm* — Michael Best & Friedrich LLP

(57) ABSTRACT

Disclosed herein is an antibody that binds to a voltage sensor paddle (VSP) of Nav1.7. Also disclosed herein are methods of treating pain, itch, neurogenic inflammation, or cough in a subject in need thereof. The methods include administrating the antibody to the subject.

22 Claims, 42 Drawing Sheets
Specification includes a Sequence Listing.

(A) MAMLPPPGPQSFVHFTKQSLALIEQRIAERKSKEPKEEKDDDEEAPKPSSDLEAGKQLPFIYGDIPPGM
VSEPLEDLDPYYADKKTFIVLNKGKTIFRFNATPALYMLSPFSPLRRISIKILVHSLFSMLIMCTILTNC
IFMTMNNPPDWTKNVEYTFTGIYTFESLVKILARGFCVGEFTFLRDPWNWLDFVVIVFAYLTEFVNLGNV
SALRTFRVLRALKTISVIPGLKTIVGALIQSVKKLSDVMILTVFCLSVFALIGLQLFMGNLKHKCFRNSL
ENNETLESIMNTLESEEDFRKYFYYLEGSKDALLCGFSTDSGQCPEGYTCVKIGRNPDYGYTSFDTFSWA
FLALFRLMTQDYWENLYQQTLRAAGKTYMIFFVVIFLGSFYLINLILAVVAMAYEEQNQANIEEAKQKE
LEFQQMLDRLKKEQEAEAIAAAAAEYTSIRRSRIMGLSESSSETSKLSSKSAKERRNRRKKNQKKLSS
GEEKGDAEKLSKSESEDSIRRKSFHLGVEGHRRAHEKRLSTPNQSPLSIRGSLFSARRSSRTLFSFKGR
GRDIGSETEFADDEHSIFGDNESRRGSLFVPHRPQERRSSNISQASRSPPMLPVNGKMHSAVDCNGVVSI
VDGRSALMLPNGQLLPEGTTNQIHKKRRCSSYLLSEDMLNDPNLRQRAMSRASILTNTVEELEESRQKCP
PWWYRFAHKFLIWNCSPYWIKFKKCIYFIVMDPFVDLAITICIVLNTLFMAMEHHPMTEEFKNVLAIGNL
VPTGIFAAEMVLKLIAMDPYEYFQVGWNIFDSLIVTLSLVELFLADVEGLSVLRSFRLLRVFKLAKSWPT
LNMLIKIIGNSVGALGNLTLVLAIIVFIFAVVGMQLFGKSYKECVCKINDDCTLPRWHMNDFFHSFLIVF
RVLCGEWIETMWDCMEVAGQAMCLIVYMMVMVIGNLVVLNLFLALLLSSFSSDNLTAIEEDPDANNLQIA
VTRIKKGINYVKQTLREFILKAFSKKPKISREIRQAEDLNTKKENYISNHTLAEMSKGHNFLKEKDKISG
FGSSVDKHLMEDSDGQSFIHNPSLTVTVPIAPGESDLENMNAEELSSDSDEYSKVRLNRSSSSECSTVD
NPLPGEGEEAEAEPMNSDEPEACFTDGCVRRFSCCQVNIESGKGKIWWNIRKTCYKIVEHSWFESFIVLM
ILLSSGALAFEDIYIERKKTIKIILEYADKIFTYIFILEMLLKWIAYGYKTYFTNAWCWLDFLIVDVSLV
TLVANTLGYSDLGPIKSLRTLRALRPLRALSRFEGMRVVVNALIGAIPSIMNVLLVCLIFWLIFSIMGVN
LFAGKFYECINTTDGSRFPASQVPNRSECFALMNVSQNVRWKNLKVNFDNVGLGYLSLLQVATFKGWTII
MYAAVDSVNVDKQPKYEYSLYMYIYFVVFIIFGSFFTLNLFIGVIIDNFNQQKKKLGGQDIFMTEEQKKY
YNAMKKLGSKKPQKPIPRPGNKIQGCIFDLVTNQAFDISIMVLICLNMVTMMVEKEGQSQHMTEVLYWIN
VVFIILFTGECVLKLISLRHYFFTVGWNIFDFVVIISIVGMFLADLIETYFVSPTLFRVIRLARIGRIL
RLVKGAKGIRTLLFALMMSLPALFNIGLLLFLVMFIYAIFGMSNFAYVKKEDGINDMFNFETFGNSMICL
FQITTSAGWDGLLAPILNSKPPDCDPKKVHPGSSVEGDCGNPSVGIFYFVSYIIISFLVVVNMYIAVILE
NFSVATEESTEPLSEDDFEMFYEVWEKFDPDATQFIEFSKLSDFAAALDPPLLIAKPNKVQLIAMDLPMV
SGDRIHCLDILFAFTKRVLGESGEMDSLRSQMEERFMSANPSKVSYEPITTTLKRKQEDVSATVIQRAYR
RYRLRQNVKNISSIYIKDGDRDDDLLNKKDMAFDNVNENSSPEKTDATSSTTSPPSYDSVTKPDKEKYEQ
DRTEKEDKGKDSKESKK (SEQ ID NO: 22)

(B) TLSLVELFLADVEGLSVLRSFRLL (SEQ ID NO: 23)

FIG. 1

(A) DNA encoding 1E16 variable heavy (VH) chain

ATGGAATGGAACTGGGTCGTTCTCTTCCTCCTGTCATTAACTGCAGGTGTCTATGCCAGGGT

CAGATGCAGCAGTCTGGAGCTGAGCTGGTGAAGCCTGGGGCTTCAGTGAAGCTGTCCTGCAAG

ACTTCTGGCTTCACCTTCAGCAGTAGCTATATAAGTTGGTTGAAGCAAAGCCTGGACAGAGT
<u>                              CDR1</u>

CTTGAGTGGATTGCATGGATTTATGCTGGAACTGGTGGTACTAGCTATAATCAGAAGTTCACA
                                  CDR2

GGCAAGGCCAACTGACTGTAGACACATCCTCCAGCACAGCTACATGCAATTCAGCAGCCTG

ACAACTGAGGACTCTGCCATCTATTACTGTGCAAGACAAGATGGTAACTACAGGTACTGGTAC
                                                     CDR3

TTCGATGTCTGGGGCGCAGGGACCACGGTCACCGTCTCCTCA   (SEQ ID NO: 12)

(B) DNA encoding 1E16 variable light (VL) chain

ATGACCATGTTCTCACTAGCTCTTCTCCTCAGTCTTCTTCTCCTCTGTGTCTCTGATTCTAGG

GCAGAAACAACTGTGACCCAGTCTCCAGCATCCCTGTCCATGGCTATAGGAGAAAAAGTCACC

ATCAGATGCATAACCAGCACTGATATTGATGATGATATGAACTGGTACCAGCAGAAGCCAGGG
                                  CDR1

GAACCTCCTAAGCTCCTTATTTCAGAAGGCAATACTCTTCGTCCTGGAGTCCCATCCCGATTC
                                      CDR2

TCCAGCAGTGGCTATGGTACAGATTTTGTTTTTACAATTGAAAACATGCTCTCAGAAGATGTT

GCAGATTACTACTGTTTGCAAAGTGATAACTTGCCTCTCACGTTCGGAGGGGGGACCAAGCTG
                              CDR3

GAAATAAAA   (SEQ ID NO: 16)

FIG. 2

(A) Amino acid sequence of 1E16 variable heavy (VH) chain

MEWNWVVLFLLSLTAGVYAQGQMQQSGAELVKPGASVKLSCKTSGFTFSSSYISWLKQKPGQS
                                                              CDR1
LEWIAWIYAGTGGTSYNQKFTGKAQLTVDTSSSTAYMQFSSLTEDSAIYYCARQDGNYRYWY
    CDR2                                                                CDR3
FDVWGAGTTVTVSS (SEQ ID NO: 4)

(B) Amino acid sequence of 1E16 variable light (VL) chain

MTMFSLALLLSLLLLCVSDSRAETTVTQSPASLSMAIGEKVTIRCITSTDIDDDMNWYQQKPGE
                                                                  CDR1
PPKLLISEGNTLRPGVPSRFSSSGYGTDFVFTIENMLSEDVADYYCLQSDNLPLTFGGGTKLEI
       CDR2                                                     CDR3
K (SEQ ID NO: 8)

Loop 3-4

```
Nav1.7  LSLVELF--LADVEGLSVLR   (SEQ ID NO: 24)
Nav1.1  LSLMELG--LANVEGLSVLR   (SEQ ID NO: 25)
Nav1.2  LSLMELG--LANVEGLSVLR   (SEQ ID NO: 26)
Nav1.3  LSLMELG--LSNVEGLSVLR   (SEQ ID NO: 27)
Nav1.4  LSLVELG--LANVQGLSVLR   (SEQ ID NO: 28)
Nav1.5  LSLMELG--LSRMSNLSVLR   (SEQ ID NO: 29)
Nav1.6  LSLMELS--LADVEGLSVLR   (SEQ ID NO: 30)
Nav1.8  VSLLELG--VAKKGSLSVLR   (SEQ ID NO: 31)
Nav1.9  LSFADVMNCVLQKRSWPFLR   (SEQ ID NO: 32)
```

(C)

Loop 1-2

```
Nav1.7  AMEHHPMTEEFKNVLAIGN   (SEQ ID NO: 33)
Nav1.1  AMEHYPMTEQFSSVLSVGN   (SEQ ID NO: 34)
Nav1.2  AMEHYPMTEQFSSVLSVGN   (SEQ ID NO: 35)
Nav1.3  AMEHYPMTEQFSSVLTVGN   (SEQ ID NO: 36)
Nav1.4  AMEHYPMTEHFDNVLTVGN   (SEQ ID NO: 37)
Nav1.5  ALEHYNMTSEFEEMLQVGN   (SEQ ID NO: 38)
Nav1.6  AMEHHPMTPQFEHVLAVGN   (SEQ ID NO: 39)
Nav1.8  AMEHHGMSPTFEAMLQIGN   (SEQ ID NO: 40)
Nav1.9  AMEHHKMEASFEKMLNIGN   (SEQ ID NO: 41)
```

FIG. 4 (con't)

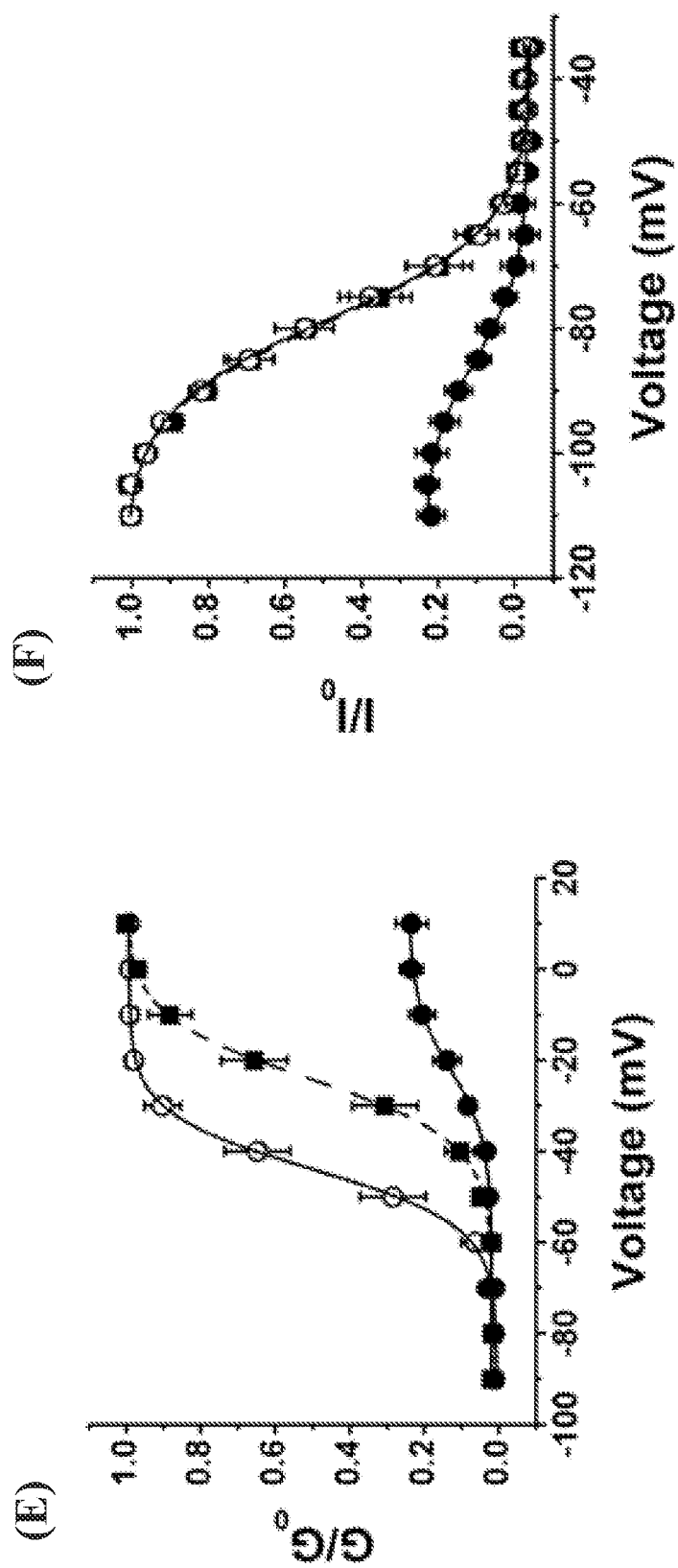
FIG. 6 (con't)

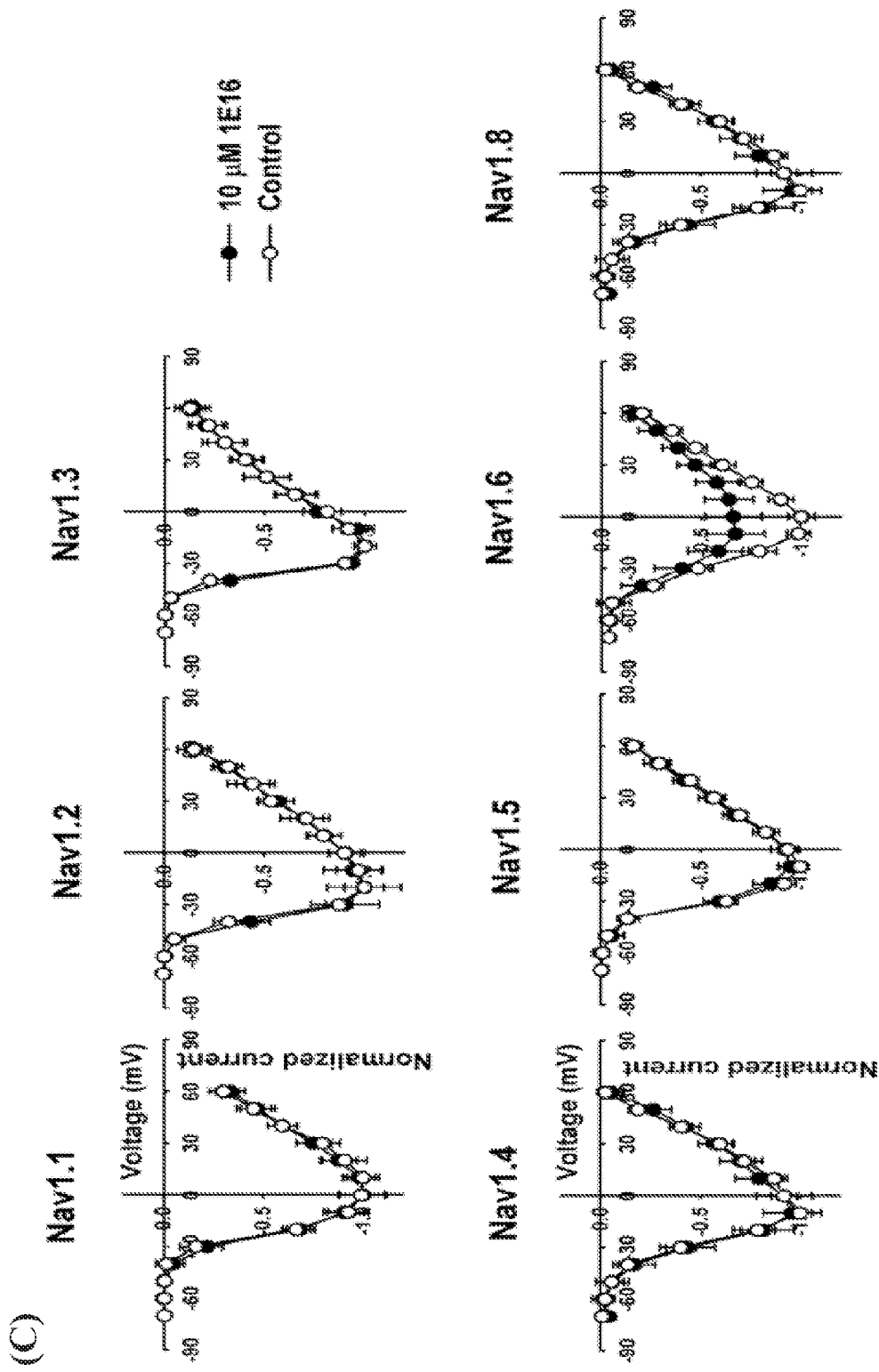
FIG. 7 (con't)

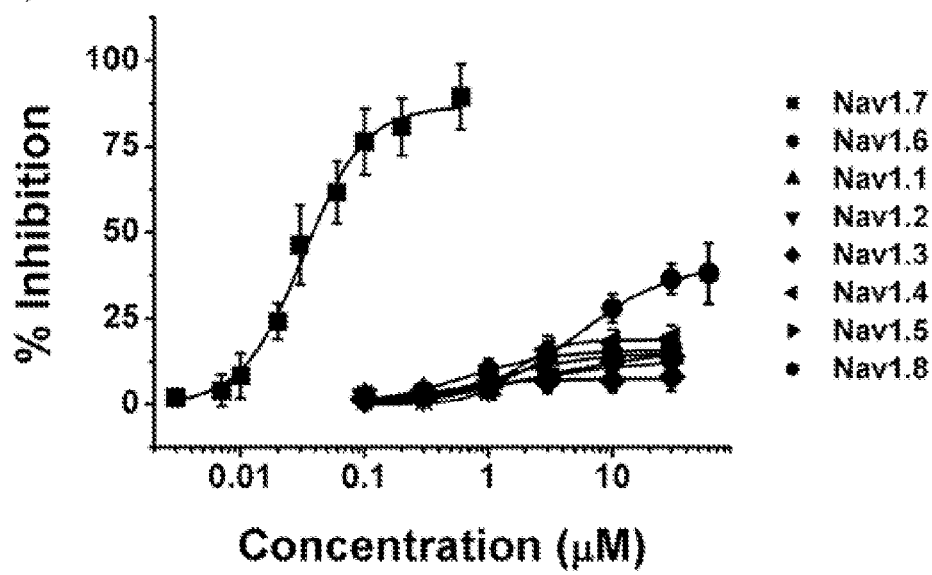
FIG. 7 (con't)

(A)

hNav1.7 LSLVELF--LADVEGLSVLR (SEQ ID NO: 24)
hNav1.1 LSLMELG--LANVEGLSVLR (SEQ ID NO: 25)
hNav1.2 LSLMELG--LANVEGLSVLR (SEQ ID NO: 26)
hNav1.3 LSLMELG--LSNVEGLSVLR (SEQ ID NO: 27)
hNav1.4 LSLVELG--LANVQGLSVLR (SEQ ID NO: 28)
hNav1.5 LSLMELG--LSRMSNLSVLR (SEQ ID NO: 29)
hNav1.6 LSLMELS--LADVEGLSVLR (SEQ ID NO: 30)
hNav1.8 VSLLELG--VAKKGSLSVLR (SEQ ID NO: 31)
hNav1.9 LSFADVMNCVLQKRSWPFLR (SEQ ID NO: 32)

(B)

hNav1.7 LSLVELF--LADVEGLSVLR (SEQ ID NO: 42)
hNav1.1 LSLMELG--LANVEGLSVLR (SEQ ID NO: 43)
rNav1.2 LSLMELG--LANVEGLSVLR (SEQ ID NO: 44)
hNav1.3 LSLMELG--LSNVEGLSVLR (SEQ ID NO: 45)
rNav1.4 LSLVELG--LANVQGLSVLR (SEQ ID NO: 46)
mNav1.5 LSLMELG--LSRMGNLSVLR (SEQ ID NO: 47)
mNav1.6 LSLMELG--LADVEGLSVLR (SEQ ID NO: 48)
rNav1.8 VSLLELS--ASKKGSLSVLR (SEQ ID NO: 49)

FIG. 8

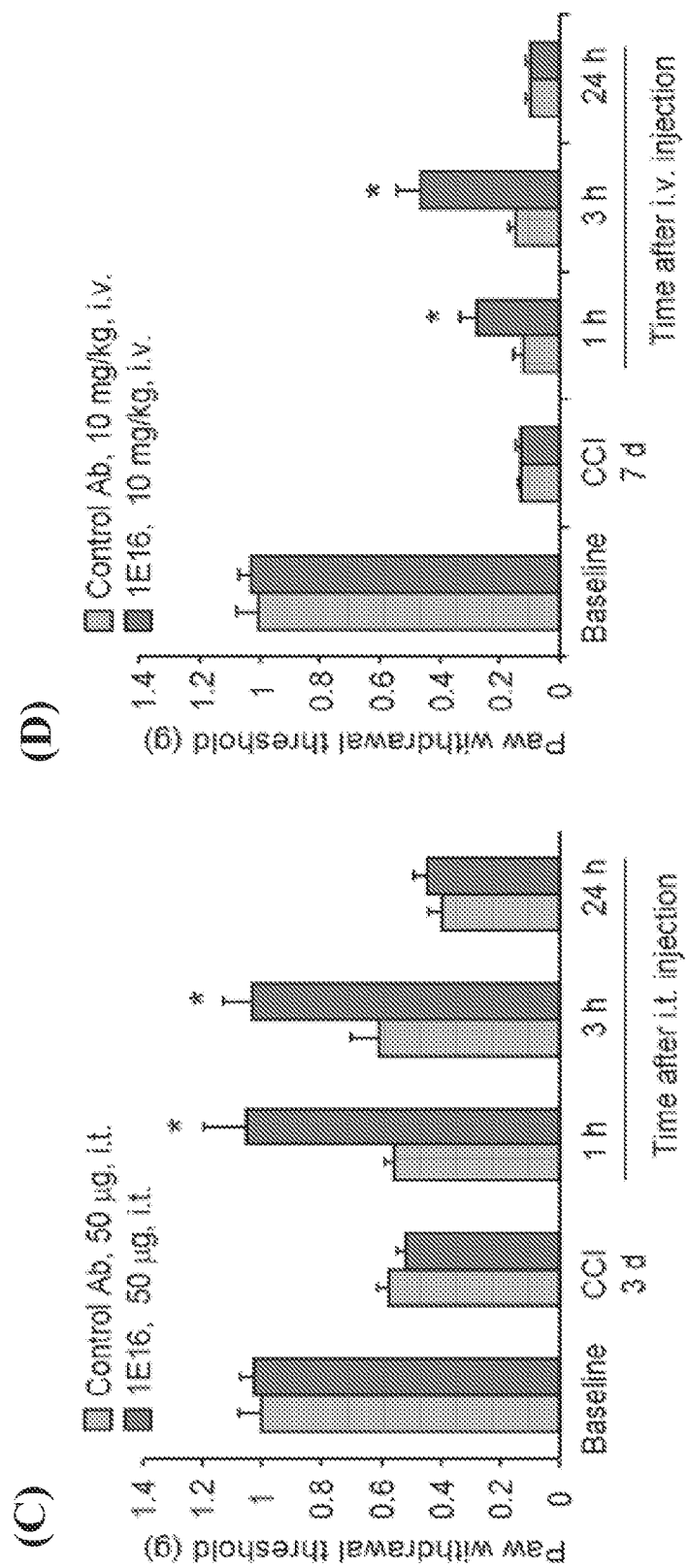
FIG. 10 (con't)

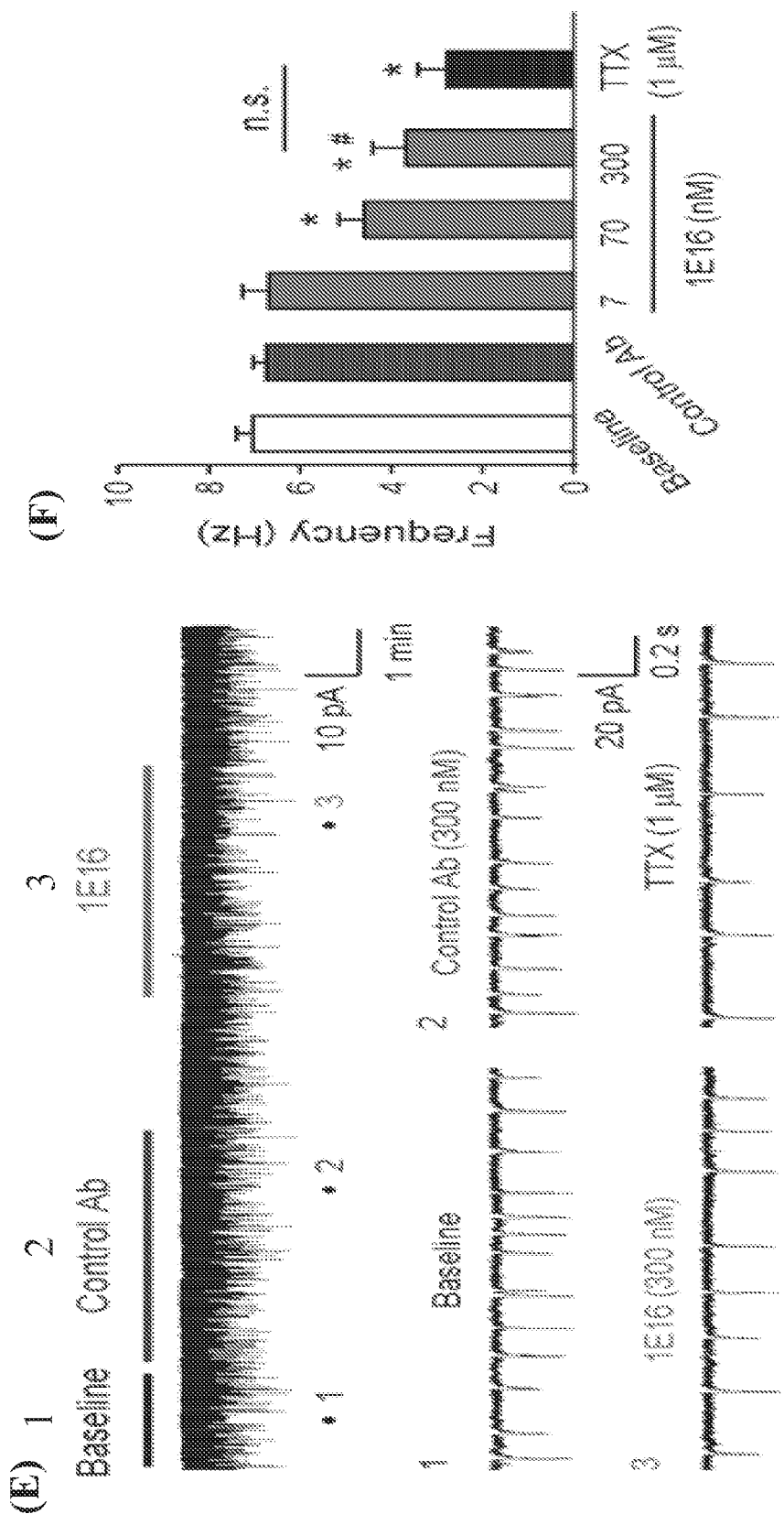
FIG. 10 (con't)

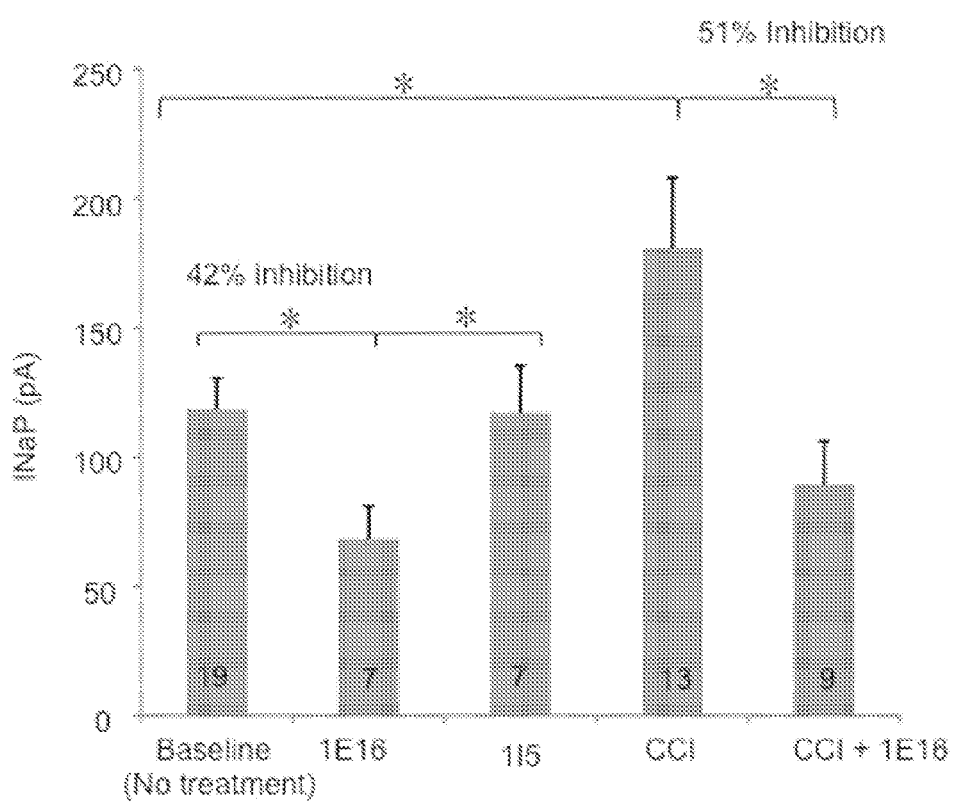
FIG. 11 (con't)

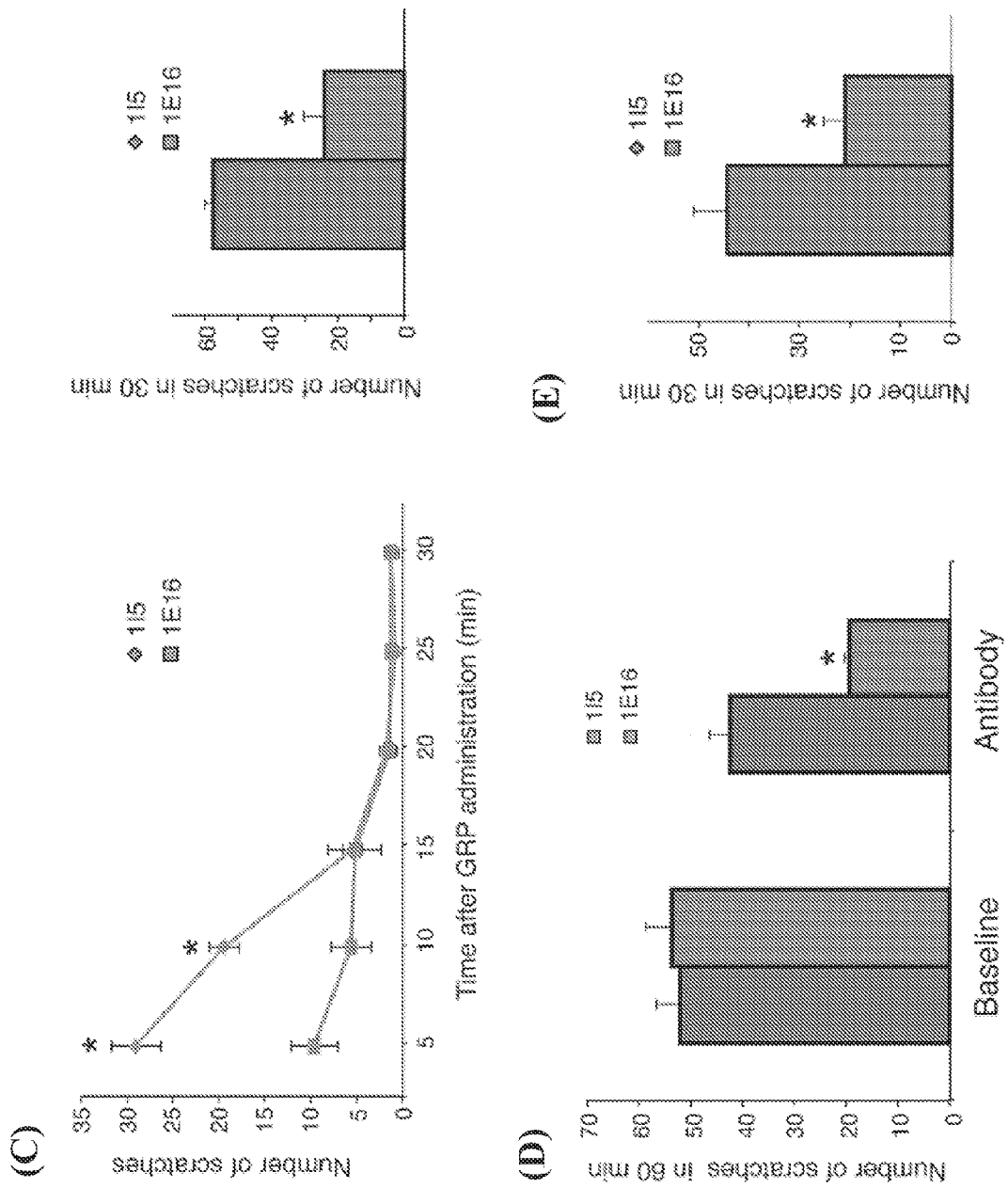
FIG. 15 (con't)

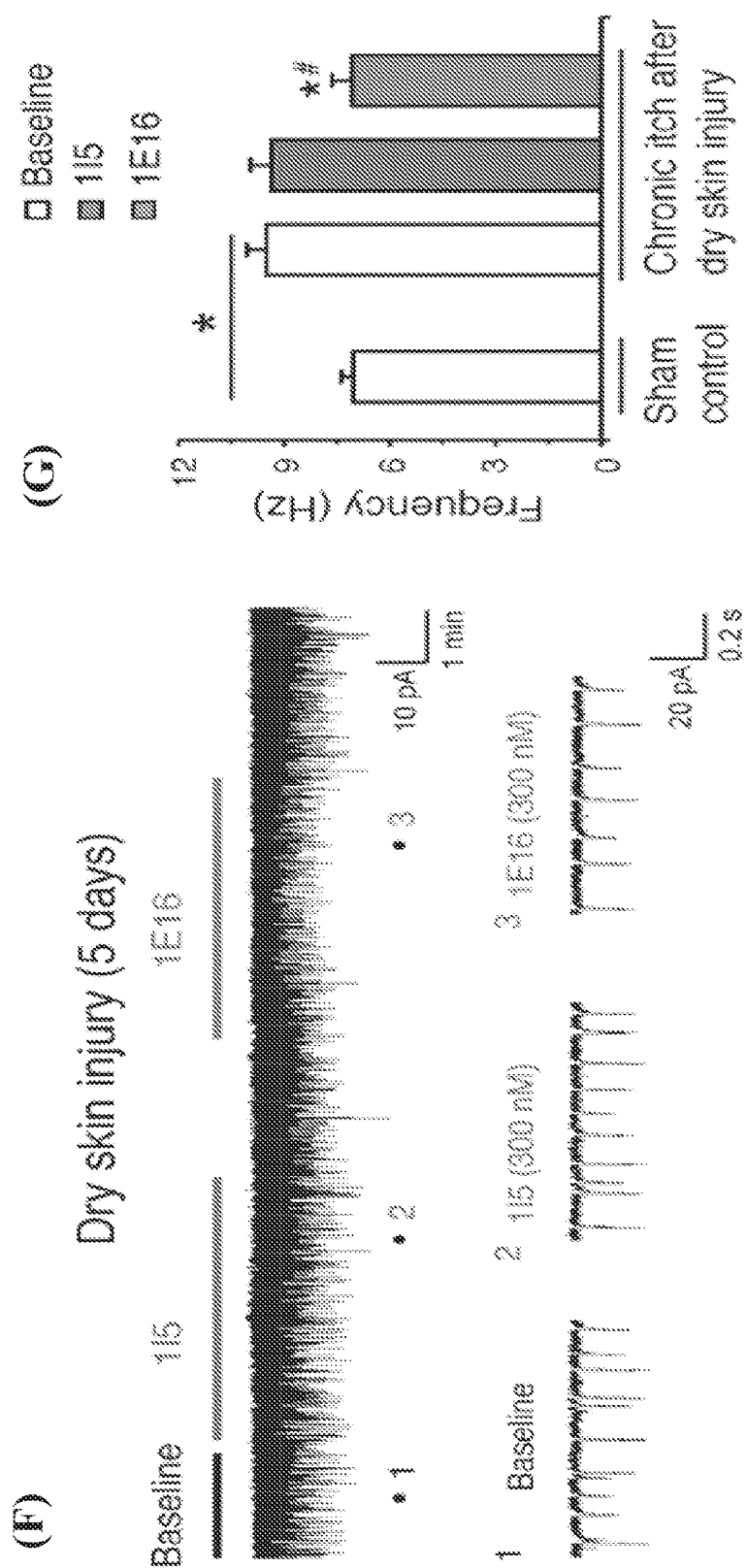
FIG. 15 (con't)

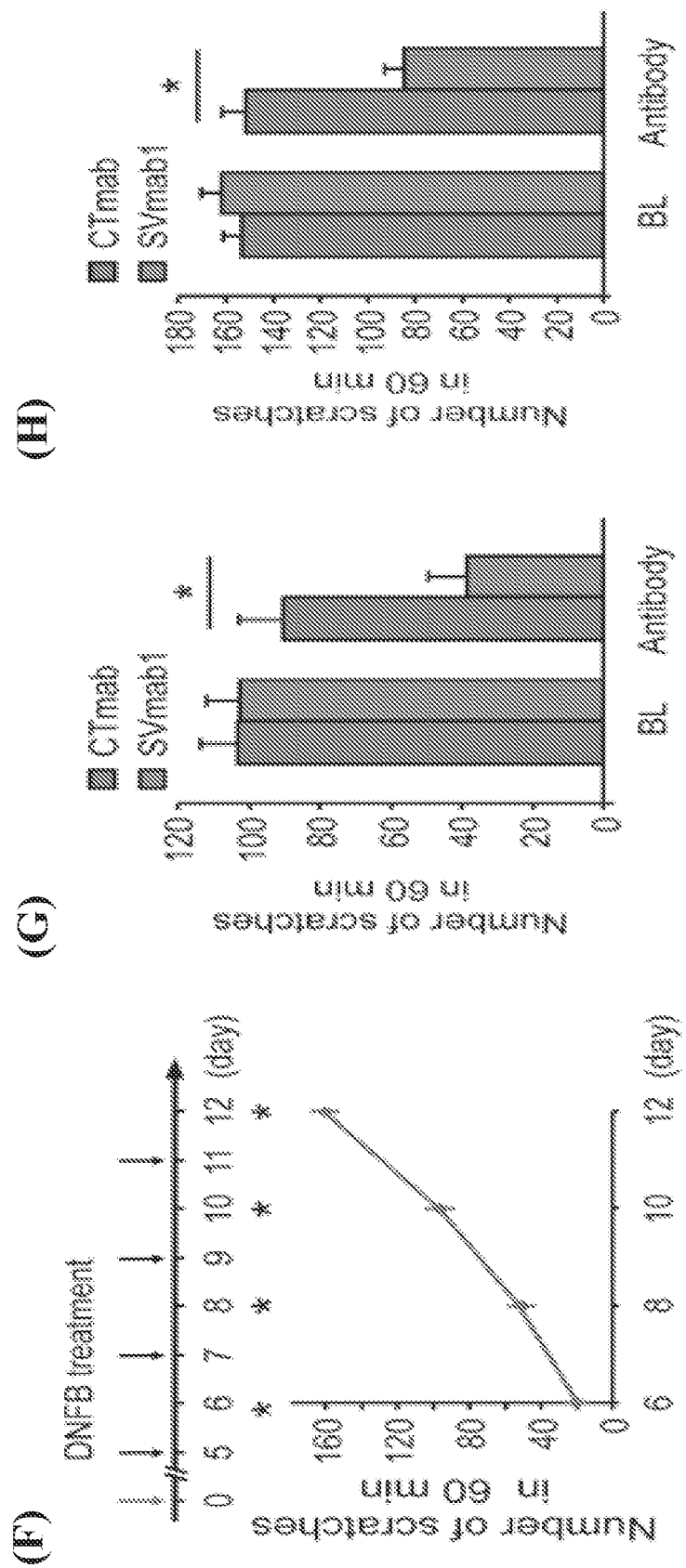
FIG. 18 (con't)

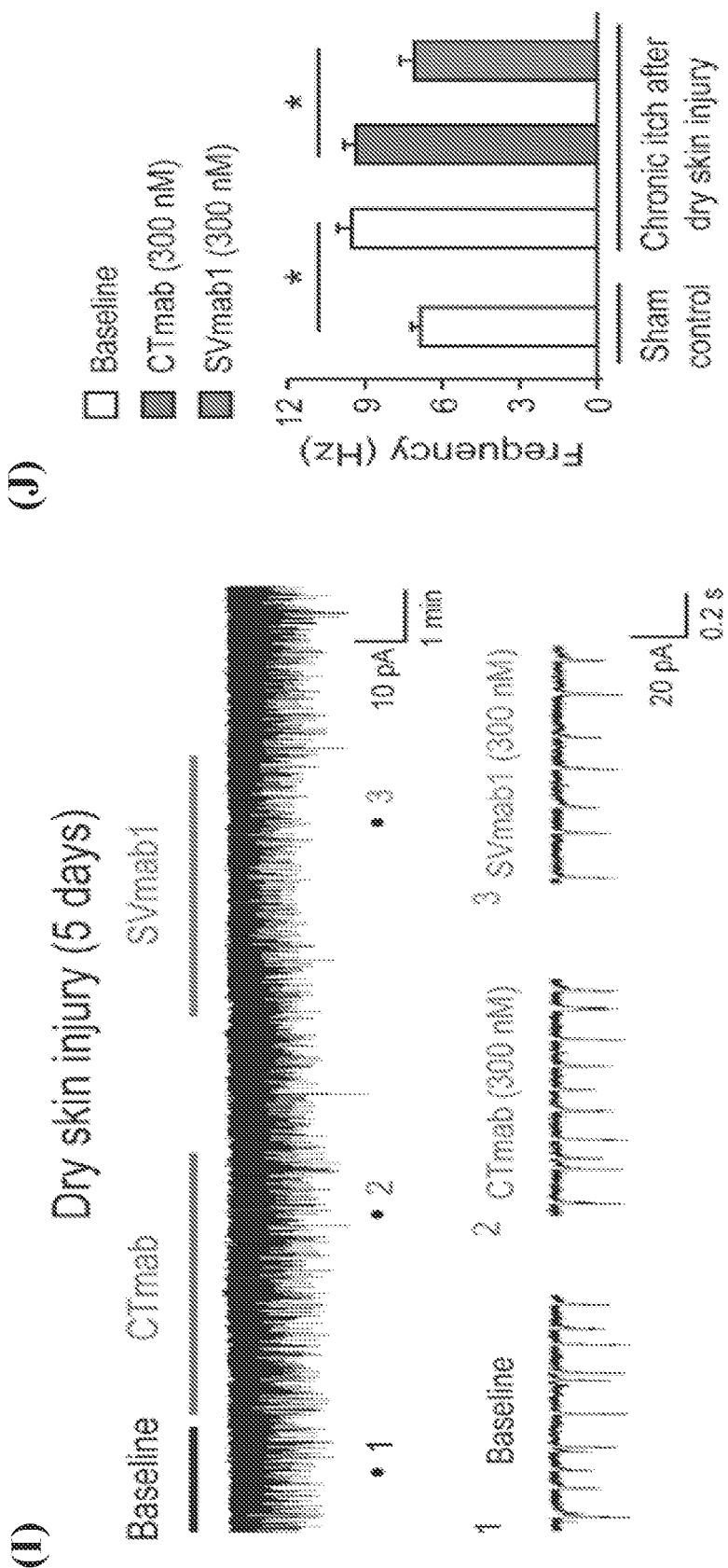
FIG. 18 (con't)

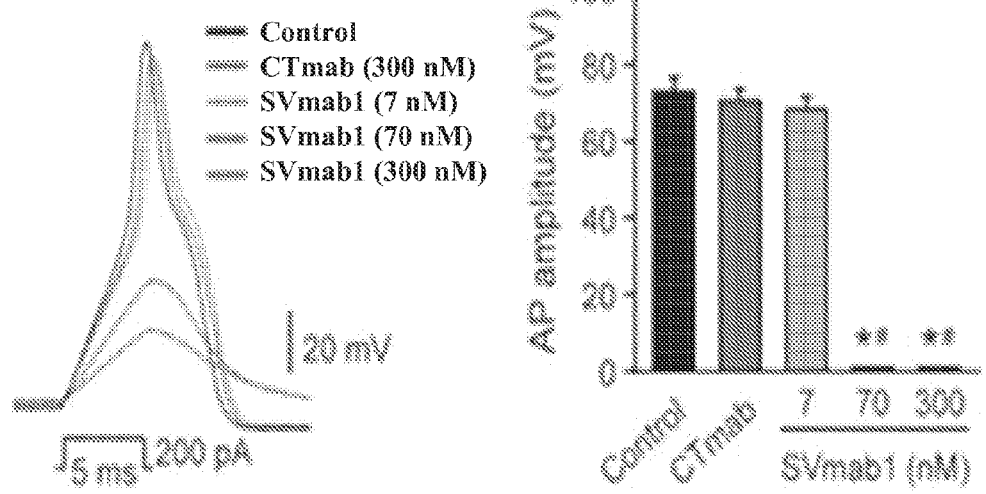
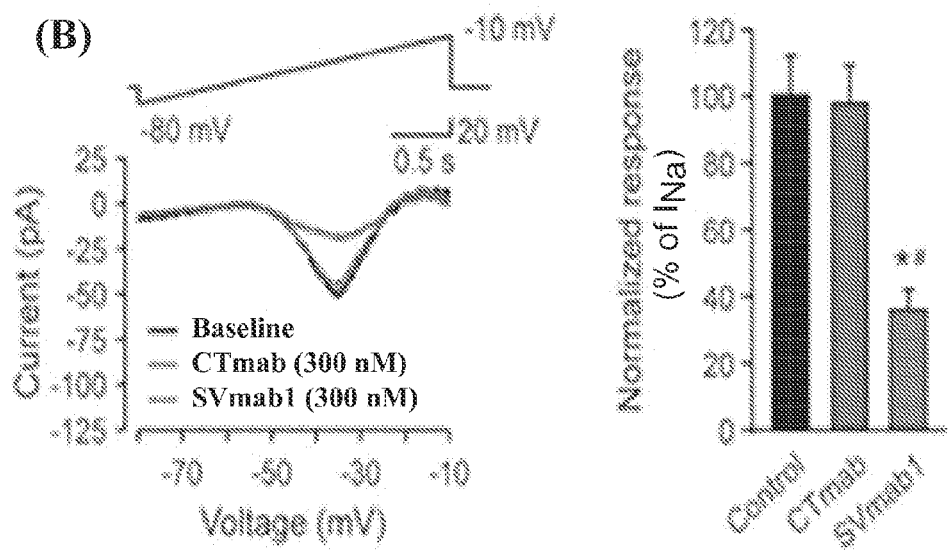
FIG. 19

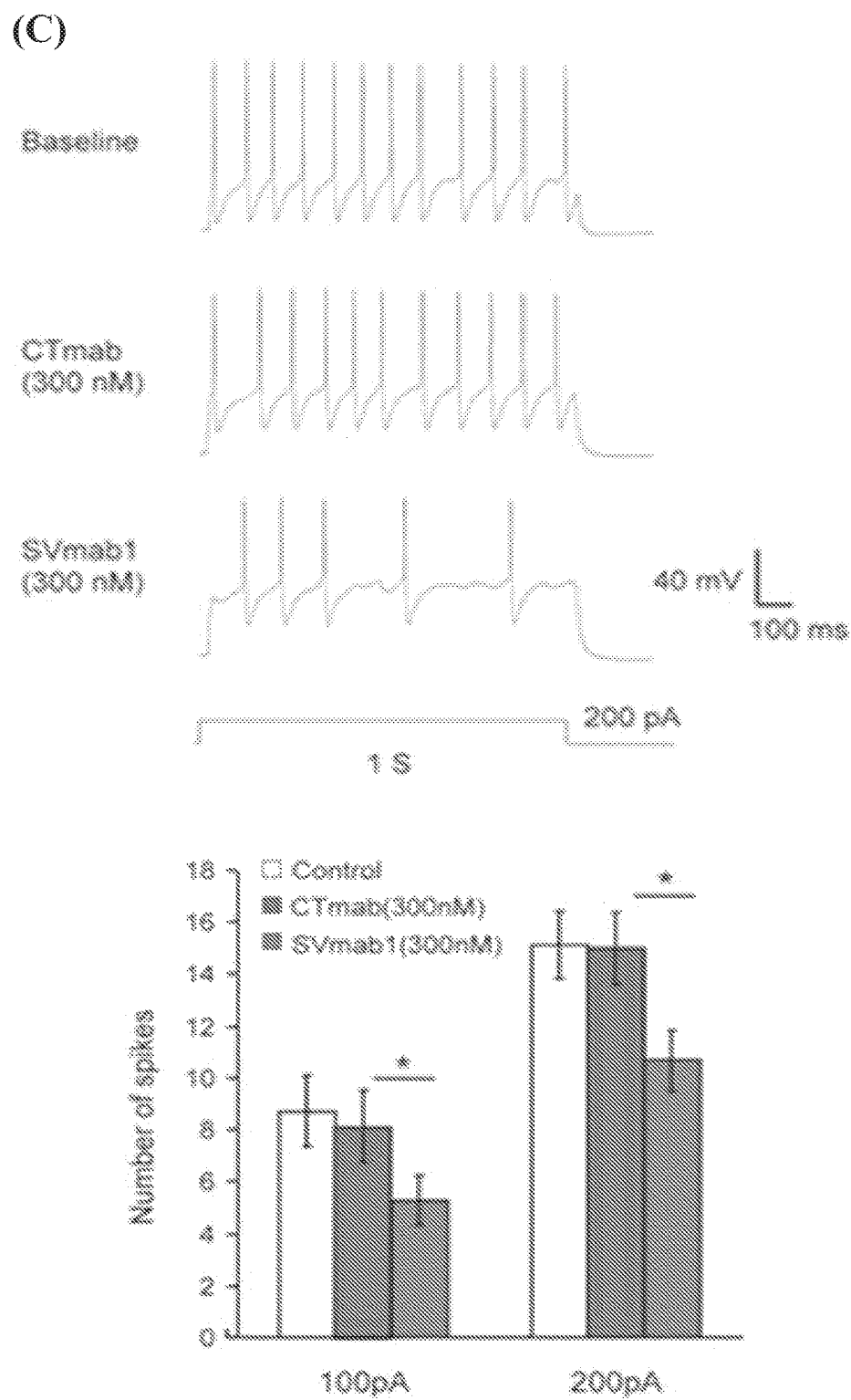
FIG. 19 (con't)

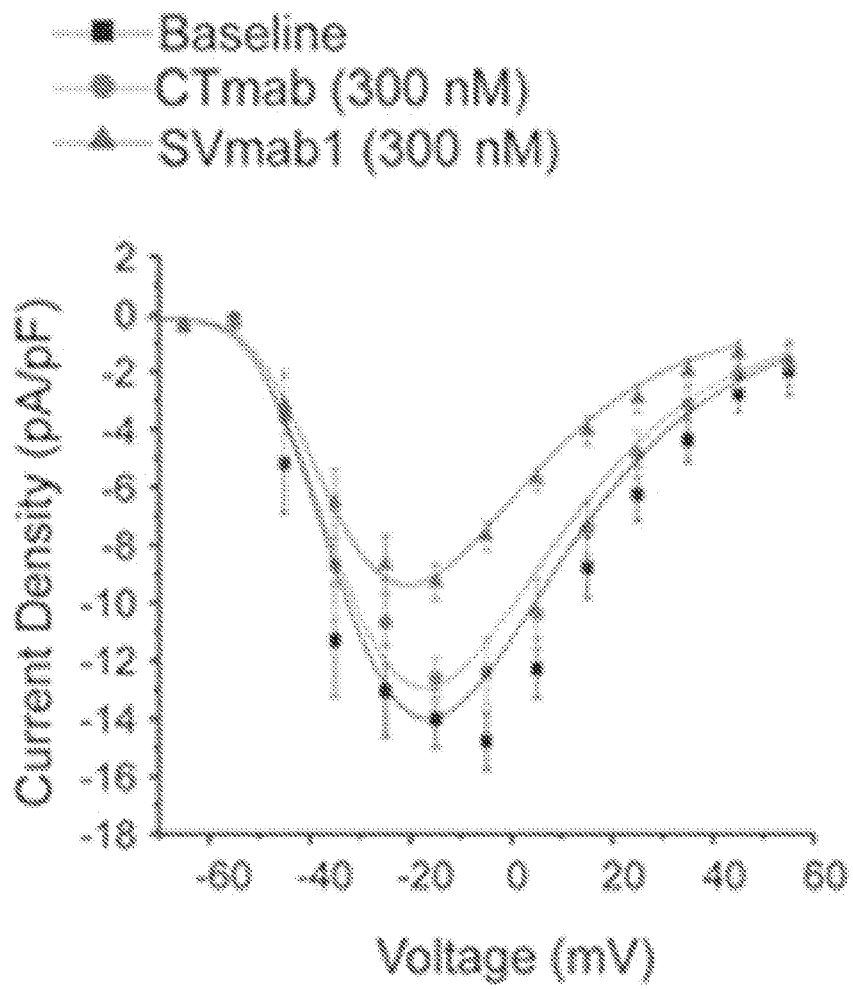
FIG. 19 (con't)

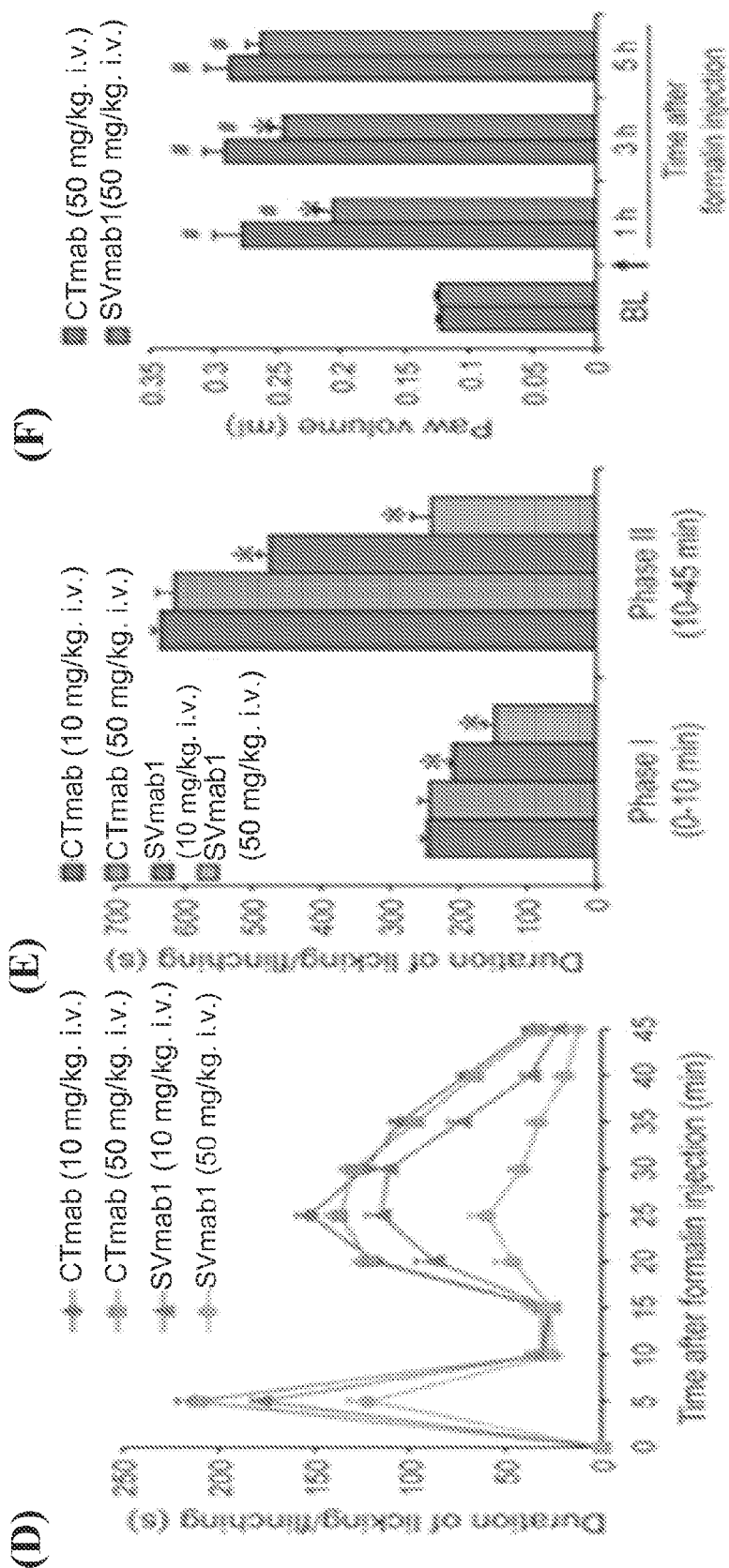
FIG. 22 (con't)

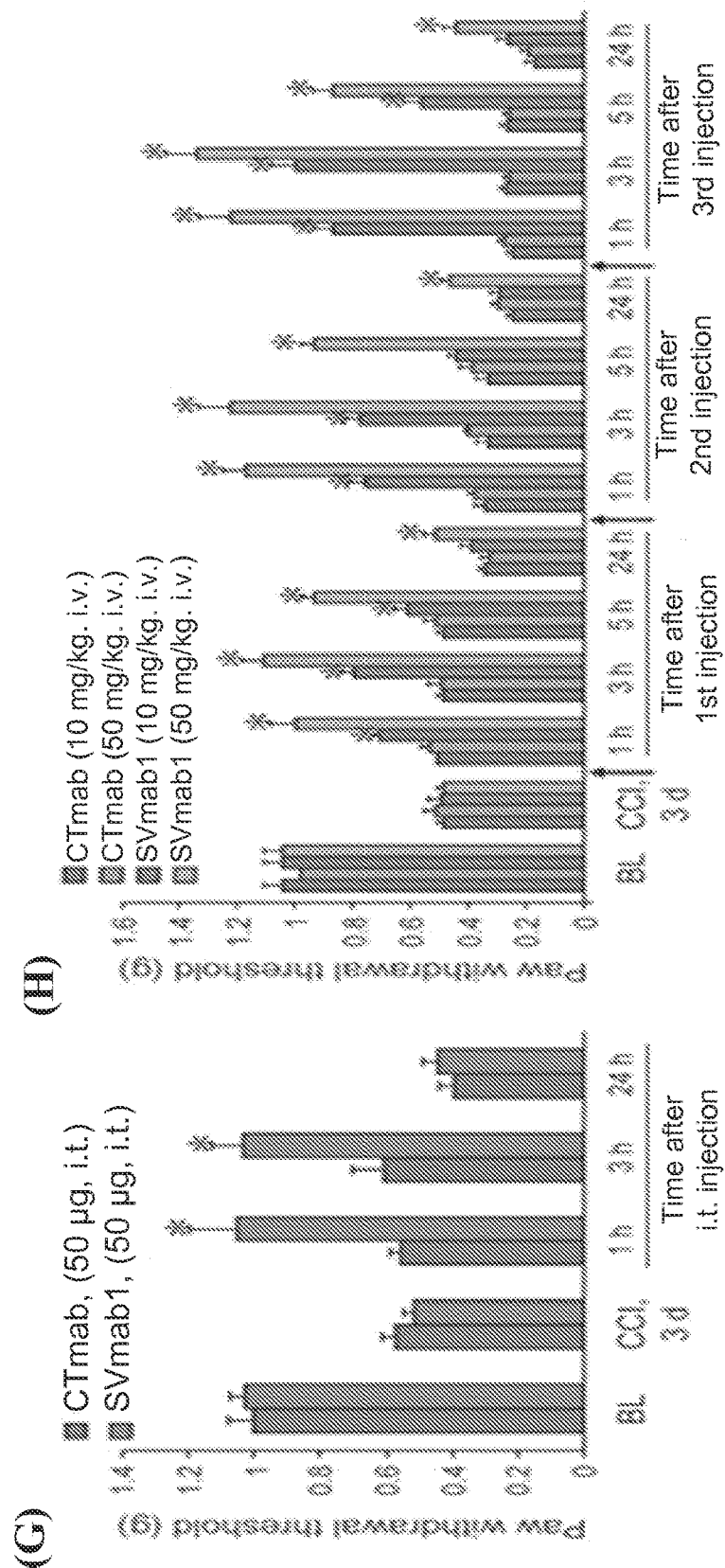
FIG. 22 (con't)

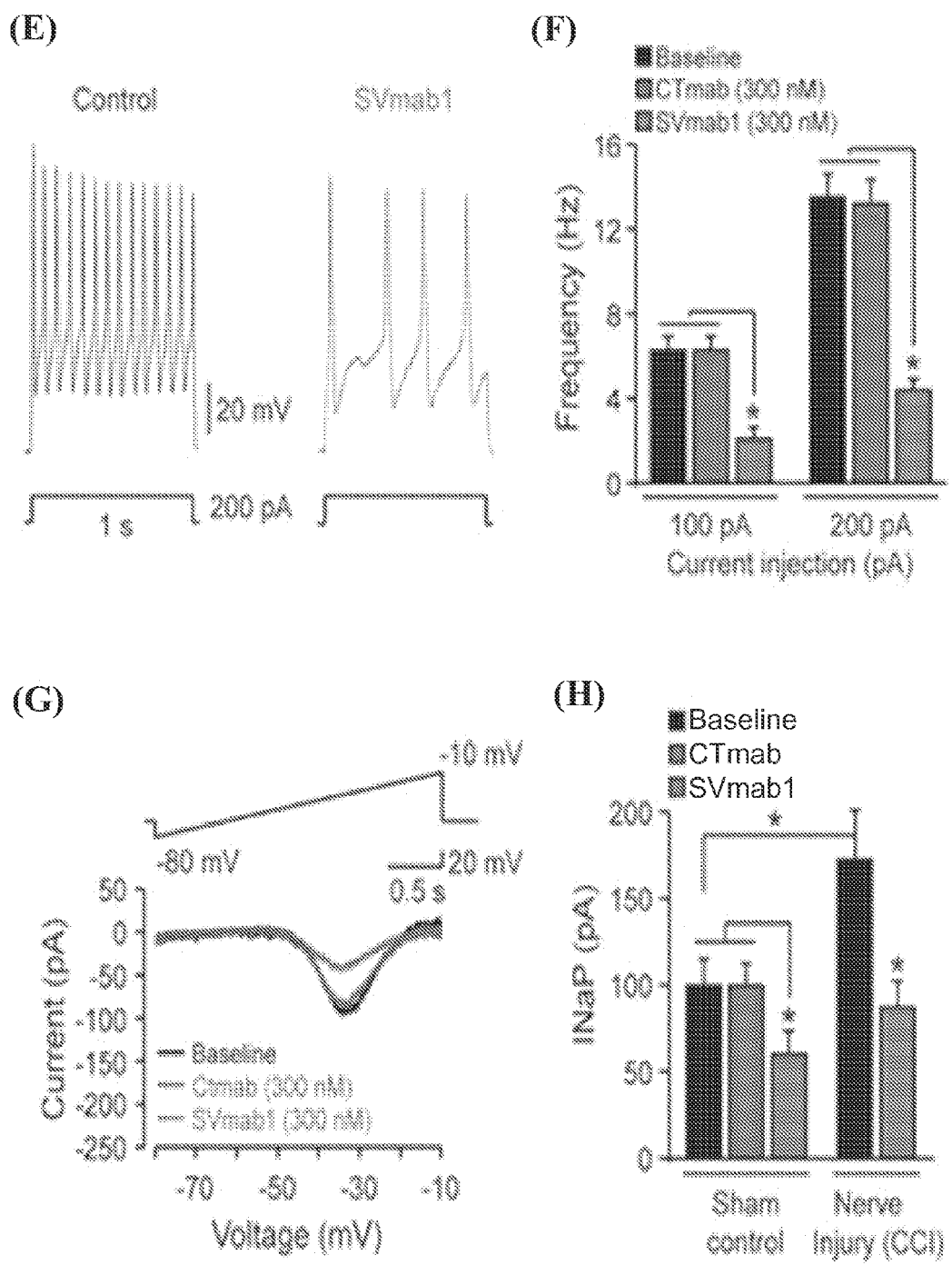
FIG. 23 (con't)

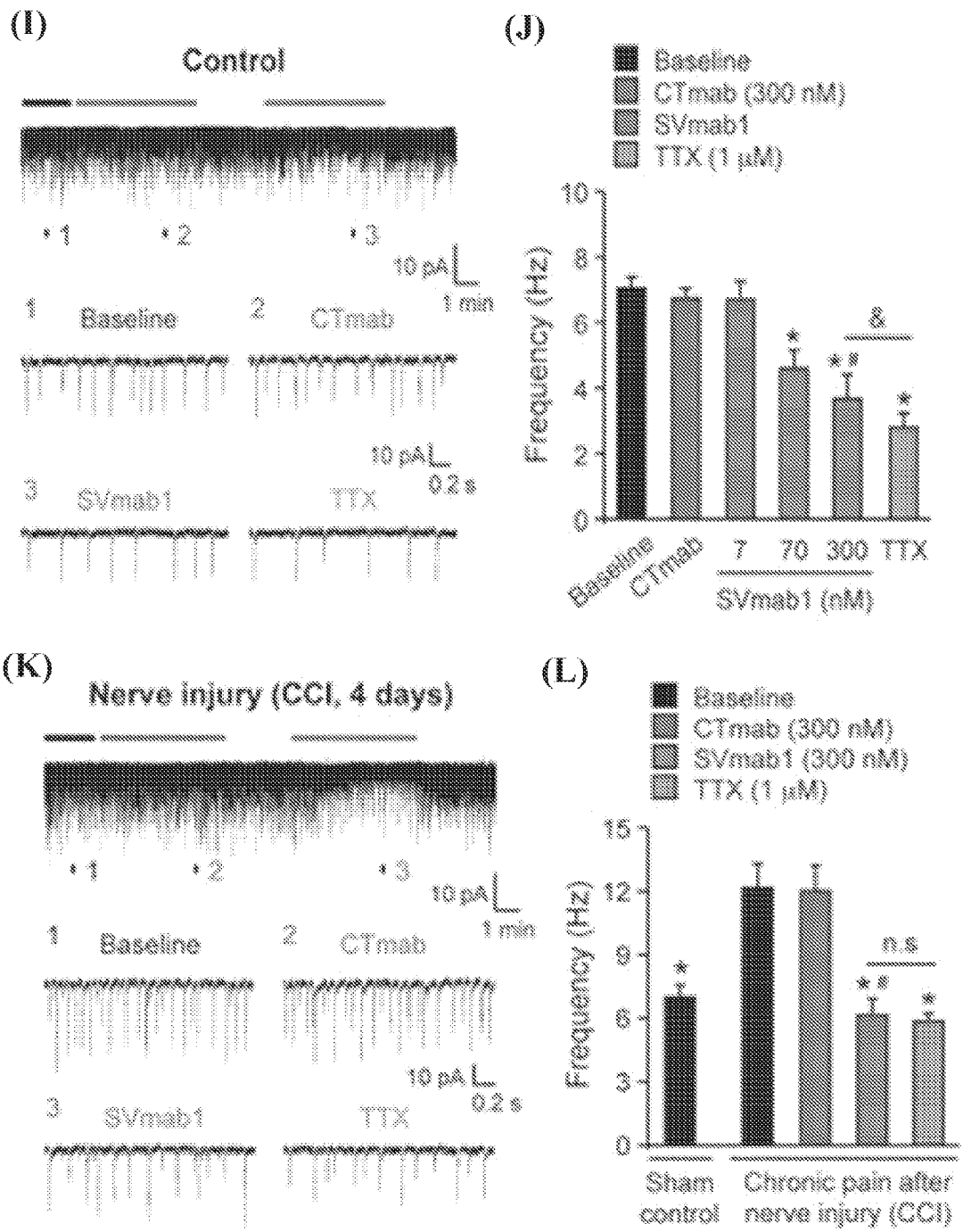
FIG. 23 (con't)

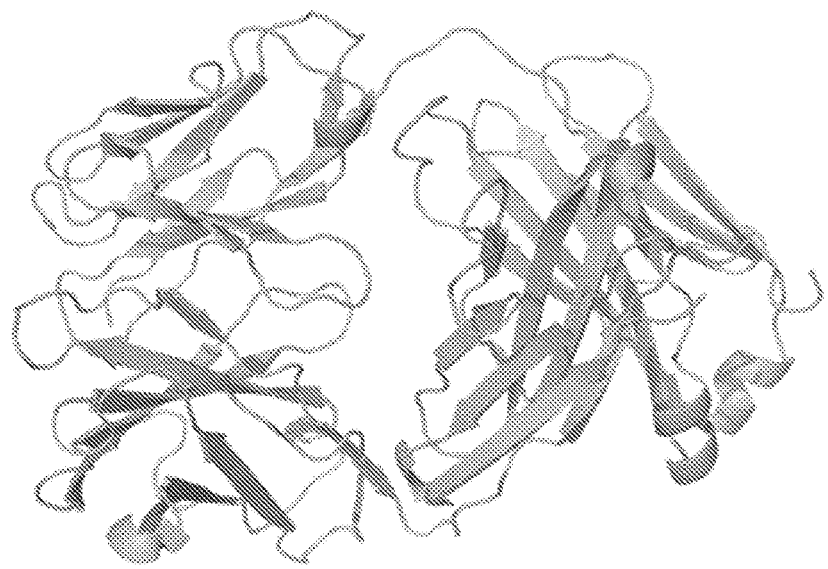
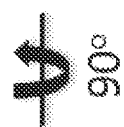
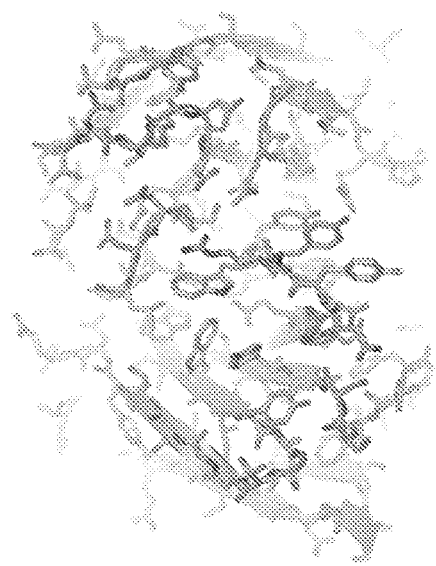
FIG. 26

SEQUENCE LISTING

```
<160> NUMBER OF SEQ ID NOS: 51

<210> SEQ ID NO 1
<211> LENGTH: 6
<212> TYPE: PRT
<213> ORGANISM: Artificial Sequence
<220> FEATURE:
<223> OTHER INFORMATION: Synthetic polypeptide

<400> SEQUENCE: 1

His His His His His His
1               5

<210> SEQ ID NO 2
<211> LENGTH: 5
<212> TYPE: PRT
<213> ORGANISM: Artificial Sequence
<220> FEATURE:
<223> OTHER INFORMATION: Synthetic polypeptide

<400> SEQUENCE: 2

Asp Asp Asp Asp Lys
1               5

<210> SEQ ID NO 3
<211> LENGTH: 6
<212> TYPE: PRT
<213> ORGANISM: Artificial Sequence
<220> FEATURE:
<223> OTHER INFORMATION: Synthetic polypeptide

<400> SEQUENCE: 3

Ala Asp Asp Asp Asp Lys
1               5

<210> SEQ ID NO 4
<211> LENGTH: 140
<212> TYPE: PRT
<213> ORGANISM: Artificial Sequence
<220> FEATURE:
<223> OTHER INFORMATION: Synthetic polypeptide

<400> SEQUENCE: 4

Met Glu Trp Asn Trp Val Val Leu Phe Leu Leu Ser Leu Thr Ala Gly
1               5                   10                  15

Val Tyr Ala Gln Gly Gln Met Gln Gln Ser Gly Ala Glu Leu Val Lys
            20                  25                  30
```

```
Pro Gly Ala Ser Val Lys Leu Ser Cys Lys Thr Ser Gly Phe Thr Phe
             35                  40                  45

Ser Ser Ser Tyr Ile Ser Trp Leu Lys Gln Lys Pro Gly Gln Ser Leu
 50                  55                  60

Glu Trp Ile Ala Trp Ile Tyr Ala Gly Thr Gly Gly Thr Ser Tyr Asn
 65                  70                  75                  80

Gln Lys Phe Thr Gly Lys Ala Gln Leu Thr Val Asp Thr Ser Ser Ser
                 85                  90                  95

Thr Ala Tyr Met Gln Phe Ser Ser Leu Thr Thr Glu Asp Ser Ala Ile
                100                 105                 110

Tyr Tyr Cys Ala Arg Gln Asp Gly Asn Tyr Arg Tyr Trp Tyr Phe Asp
            115                 120                 125

Val Trp Gly Ala Gly Thr Thr Val Thr Val Ser Ser
    130                 135                 140

<210> SEQ ID NO 5
<211> LENGTH: 10
<212> TYPE: PRT
<213> ORGANISM: Artificial Sequence
<220> FEATURE:
<223> OTHER INFORMATION: Synthetic polypeptide

<400> SEQUENCE: 5

Gly Phe Thr Phe Ser Ser Ser Tyr Ile Ser
 1               5                  10

<210> SEQ ID NO 6
<211> LENGTH: 17
<212> TYPE: PRT
<213> ORGANISM: Artificial Sequence
<220> FEATURE:
<223> OTHER INFORMATION: Synthetic polypeptide

<400> SEQUENCE: 6

Trp Ile Tyr Ala Gly Thr Gly Gly Thr Ser Tyr Asn Gln Lys Phe Thr
 1               5                  10                  15

Gly

<210> SEQ ID NO 7
<211> LENGTH: 12
<212> TYPE: PRT
<213> ORGANISM: Artificial Sequence
<220> FEATURE:
<223> OTHER INFORMATION: Synthetic polypeptide

<400> SEQUENCE: 7

Gln Asp Gly Asn Tyr Arg Tyr Trp Tyr Phe Asp Val
 1               5                  10

<210> SEQ ID NO 8
<211> LENGTH: 129
<212> TYPE: PRT
<213> ORGANISM: Artificial Sequence
<220> FEATURE:
<223> OTHER INFORMATION: Synthetic polypeptide

<400> SEQUENCE: 8

Met Thr Met Phe Ser Leu Ala Leu Leu Leu Ser Leu Leu Leu Leu Cys
 1               5                  10                  15

Val Ser Asp Ser Arg Ala Glu Thr Val Thr Gln Ser Pro Ala Ser
             20                  25                  30
```

```
Leu Ser Met Ala Ile Gly Glu Lys Val Thr Ile Arg Cys Ile Thr Ser
         35                  40                  45
Thr Asp Ile Asp Asp Asp Met Asn Trp Tyr Gln Gln Lys Pro Gly Glu
     50                  55                  60
Pro Pro Lys Leu Leu Ile Ser Glu Gly Asn Thr Leu Arg Pro Gly Val
 65                  70                  75                  80
Pro Ser Arg Phe Ser Ser Gly Tyr Gly Thr Asp Phe Val Phe Thr
                 85                  90                  95
Ile Glu Asn Met Leu Ser Glu Asp Val Ala Asp Tyr Tyr Cys Leu Gln
                100                 105                 110
Ser Asp Asn Leu Pro Leu Thr Phe Gly Gly Gly Thr Lys Leu Glu Ile
                115                 120                 125
Lys
```

<210> SEQ ID NO 9
<211> LENGTH: 11
<212> TYPE: PRT
<213> ORGANISM: Artificial Sequence
<220> FEATURE:
<223> OTHER INFORMATION: Synthetic polypeptide

<400> SEQUENCE: 9

```
Ile Thr Ser Thr Asp Ile Asp Asp Asp Met Asn
 1               5                  10
```

<210> SEQ ID NO 10
<211> LENGTH: 7
<212> TYPE: PRT
<213> ORGANISM: Artificial Sequence
<220> FEATURE:
<223> OTHER INFORMATION: Synthetic polypeptide

<400> SEQUENCE: 10

```
Glu Gly Asn Thr Leu Arg Pro
 1               5
```

<210> SEQ ID NO 11
<211> LENGTH: 9
<212> TYPE: PRT
<213> ORGANISM: Artificial Sequence
<220> FEATURE:
<223> OTHER INFORMATION: Synthetic polypeptide

<400> SEQUENCE: 11

```
Leu Gln Ser Asp Asn Leu Pro Leu Thr
 1               5
```

<210> SEQ ID NO 12
<211> LENGTH: 420
<212> TYPE: DNA
<213> ORGANISM: Artificial Sequence
<220> FEATURE:
<223> OTHER INFORMATION: Synthetic polynucleotide

<400> SEQUENCE: 12

```
atggaatgga actgggtcgt tctcttcctc ctgtcattaa ctgcaggtgt ctatgcccag      60
ggtcagatgc agcagtctgg agctgagctg gtgaagcctg ggcttcagt gaagctgtcc      120 tgcaagactt ctggcttcac cttcagcagt agctatataa gttggttgaa gcaaaagcct     180
```

```
ggacagagtc ttgagtggat tgcatggatt tatgctggaa ctggtggtac tagctataat    240
cagaagttca caggcaaggc ccaactgact gtagacacat cctccagcac agcctacatg    300
caattcagca gcctgacaac tgaggactct gccatctatt actgtgcaag acaagatggt    360
aactacaggt actggtactt cgatgtctgg ggcgcaggga ccacggtcac cgtctcctca    420
```

<210> SEQ ID NO 13
<211> LENGTH: 30
<212> TYPE: DNA
<213> ORGANISM: Artificial Sequence
<220> FEATURE:
<223> OTHER INFORMATION: Synthetic polynucleotide

<400> SEQUENCE: 13

```
ggcttcacct tcagcagtag ctatataagt                                      30
```

<210> SEQ ID NO 14
<211> LENGTH: 51
<212> TYPE: DNA
<213> ORGANISM: Artificial Sequence
<220> FEATURE:
<223> OTHER INFORMATION: Synthetic polynucleotide

<400> SEQUENCE: 14

```
tggatttatg ctggaactgg tggtactagc tataatcaga agttcacagg c              51
```

<210> SEQ ID NO 15
<211> LENGTH: 36
<212> TYPE: DNA
<213> ORGANISM: Artificial Sequence
<220> FEATURE:
<223> OTHER INFORMATION: Synthetic polynucleotide

<400> SEQUENCE: 15

```
caagatggta actacaggta ctggtacttc gatgtc                               36
```

<210> SEQ ID NO 16
<211> LENGTH: 387
<212> TYPE: DNA
<213> ORGANISM: Artificial Sequence
<220> FEATURE:
<223> OTHER INFORMATION: Synthetic polynucleotide

<400> SEQUENCE: 16

```
atgaccatgt tctcactagc tcttctcctc agtcttcttc tcctctgtgt ctctgattct    60
agggcagaaa caactgtgac ccagtctcca gcatccctgt ccatggctat aggagaaaaa    120
gtcaccatca gatgcataac cagcactgat attgatgatg atatgaactg gtaccagcag    180
aagccagggg aacctcctaa gctccttatt tcagaaggca atactcttcg tcctggagtc    240
ccatcccgat tctccagcag tggctatggt acagattttg tttttacaat tgaaaacatg    300
ctctcagaag atgttgcaga ttactactgt ttgcaaagtg ataacttgcc tctcacgttc    360
ggagggggga ccaagctgga aataaaa                                         387
```

<210> SEQ ID NO 17
<211> LENGTH: 33
<212> TYPE: DNA
<213> ORGANISM: Artificial Sequence
<220> FEATURE:
<223> OTHER INFORMATION: Synthetic polynucleotide

<400> SEQUENCE: 17

```
ataaccagca ctgatattga tgatgatatg aac                                  33
```

```
<210> SEQ ID NO 18
<211> LENGTH: 21
<212> TYPE: DNA
<213> ORGANISM: Artificial Sequence
<220> FEATURE:
<223> OTHER INFORMATION: Synthetic polynucleotide

<400> SEQUENCE: 18
gaaggcaata ctcttcgtcc t                                              21

<210> SEQ ID NO 19
<211> LENGTH: 27
<212> TYPE: DNA
<213> ORGANISM: Artificial Sequence
<220> FEATURE:
<223> OTHER INFORMATION: Synthetic polynucleotide

<400> SEQUENCE: 19
ttgcaaagtg ataacttgcc tctcacg                                        27

<210> SEQ ID NO 20
<211> LENGTH: 10
<212> TYPE: PRT
<213> ORGANISM: Artificial Sequence
<220> FEATURE:
<223> OTHER INFORMATION: Synthetic polypeptide

<400> SEQUENCE: 20

His His Pro Met Thr Glu Glu Phe Lys Asn
1               5                   10

<210> SEQ ID NO 21
<211> LENGTH: 10
<212> TYPE: PRT
<213> ORGANISM: Artificial Sequence
<220> FEATURE:
<223> OTHER INFORMATION: Synthetic polypeptide

<400> SEQUENCE: 21

Val Glu Leu Phe Leu Ala Asp Val Glu Gly
1               5                   10

<210> SEQ ID NO 22
<211> LENGTH: 1977
<212> TYPE: PRT
<213> ORGANISM: Homo sapiens

<400> SEQUENCE: 22

Met Ala Met Leu Pro Pro Pro Gly Pro Gln Ser Phe Val His Phe Thr
1               5                   10                  15

Lys Gln Ser Leu Ala Leu Ile Glu Gln Arg Ile Ala Glu Arg Lys Ser
            20                  25                  30

Lys Glu Pro Lys Glu Glu Lys Lys Asp Asp Asp Glu Glu Ala Pro Lys
        35                  40                  45

Pro Ser Ser Asp Leu Glu Ala Gly Lys Gln Leu Pro Phe Ile Tyr Gly
    50                  55                  60

Asp Ile Pro Pro Gly Met Val Ser Glu Pro Leu Glu Asp Leu Asp Pro
65                  70                  75                  80

Tyr Tyr Ala Asp Lys Lys Thr Phe Ile Val Leu Asn Lys Gly Lys Thr
                85                  90                  95

Ile Phe Arg Phe Asn Ala Thr Pro Ala Leu Tyr Met Leu Ser Pro Phe
            100                 105                 110
```

-continued

```
Ser Pro Leu Arg Arg Ile Ser Ile Lys Ile Leu Val His Ser Leu Phe
            115                 120                 125
Ser Met Leu Ile Met Cys Thr Ile Leu Thr Asn Cys Ile Phe Met Thr
130                 135                 140
Met Asn Asn Pro Pro Asp Trp Thr Lys Asn Val Glu Tyr Thr Phe Thr
145                 150                 155                 160
Gly Ile Tyr Thr Phe Glu Ser Leu Val Lys Ile Leu Ala Arg Gly Phe
                165                 170                 175
Cys Val Gly Glu Phe Thr Phe Leu Arg Asp Pro Trp Asn Trp Leu Asp
                180                 185                 190
Phe Val Val Ile Val Phe Ala Tyr Leu Thr Glu Phe Val Asn Leu Gly
                195                 200                 205
Asn Val Ser Ala Leu Arg Thr Phe Arg Val Leu Arg Ala Leu Lys Thr
            210                 215                 220
Ile Ser Val Ile Pro Gly Leu Lys Thr Ile Val Gly Ala Leu Ile Gln
225                 230                 235                 240
Ser Val Lys Lys Leu Ser Asp Val Met Ile Leu Thr Val Phe Cys Leu
                245                 250                 255
Ser Val Phe Ala Leu Ile Gly Leu Gln Leu Phe Met Gly Asn Leu Lys
                260                 265                 270
His Lys Cys Phe Arg Asn Ser Leu Glu Asn Asn Glu Thr Leu Glu Ser
            275                 280                 285
Ile Met Asn Thr Leu Glu Ser Glu Glu Asp Phe Arg Lys Tyr Phe Tyr
            290                 295                 300
Tyr Leu Glu Gly Ser Lys Asp Ala Leu Leu Cys Gly Phe Ser Thr Asp
305                 310                 315                 320
Ser Gly Gln Cys Pro Glu Gly Tyr Thr Cys Val Lys Ile Gly Arg Asn
                325                 330                 335
Pro Asp Tyr Gly Tyr Thr Ser Phe Asp Thr Phe Ser Trp Ala Phe Leu
                340                 345                 350
Ala Leu Phe Arg Leu Met Thr Gln Asp Tyr Trp Glu Asn Leu Tyr Gln
            355                 360                 365
Gln Thr Leu Arg Ala Ala Gly Lys Thr Tyr Met Ile Phe Phe Val Val
            370                 375                 380
Val Ile Phe Leu Gly Ser Phe Tyr Leu Ile Asn Leu Ile Leu Ala Val
385                 390                 395                 400
Val Ala Met Ala Tyr Glu Glu Gln Asn Gln Ala Asn Ile Glu Glu Ala
                405                 410                 415
Lys Gln Lys Glu Leu Glu Phe Gln Gln Met Leu Asp Arg Leu Lys Lys
            420                 425                 430
Glu Gln Glu Glu Ala Glu Ala Ile Ala Ala Ala Ala Ala Glu Tyr Thr
            435                 440                 445
Ser Ile Arg Arg Ser Arg Ile Met Gly Leu Ser Glu Ser Ser Ser Glu
            450                 455                 460
Thr Ser Lys Leu Ser Ser Lys Ser Ala Lys Glu Arg Arg Asn Arg Arg
465                 470                 475                 480
Lys Lys Lys Asn Gln Lys Lys Leu Ser Ser Gly Glu Glu Lys Gly Asp
                485                 490                 495
Ala Glu Lys Leu Ser Lys Ser Glu Ser Glu Asp Ser Ile Arg Arg Lys
            500                 505                 510
Ser Phe His Leu Gly Val Glu Gly His Arg Arg Ala His Glu Lys Arg
            515                 520                 525
```

```
Leu Ser Thr Pro Asn Gln Ser Pro Leu Ser Ile Arg Gly Ser Leu Phe
    530                 535                 540

Ser Ala Arg Arg Ser Ser Arg Thr Ser Leu Phe Ser Phe Lys Gly Arg
545                 550                 555                 560

Gly Arg Asp Ile Gly Ser Glu Thr Glu Phe Ala Asp Asp Glu His Ser
                565                 570                 575

Ile Phe Gly Asp Asn Glu Ser Arg Arg Gly Ser Leu Phe Val Pro His
            580                 585                 590

Arg Pro Gln Glu Arg Arg Ser Ser Asn Ile Ser Gln Ala Ser Arg Ser
        595                 600                 605

Pro Pro Met Leu Pro Val Asn Gly Lys Met His Ser Ala Val Asp Cys
    610                 615                 620

Asn Gly Val Val Ser Leu Val Asp Gly Arg Ser Ala Leu Met Leu Pro
625                 630                 635                 640

Asn Gly Gln Leu Leu Pro Glu Gly Thr Thr Asn Gln Ile His Lys Lys
                645                 650                 655

Arg Arg Cys Ser Ser Tyr Leu Leu Ser Glu Asp Met Leu Asn Asp Pro
            660                 665                 670

Asn Leu Arg Gln Arg Ala Met Ser Arg Ala Ser Ile Leu Thr Asn Thr
        675                 680                 685

Val Glu Glu Leu Glu Glu Ser Arg Gln Lys Cys Pro Pro Trp Trp Tyr
    690                 695                 700

Arg Phe Ala His Lys Phe Leu Ile Trp Asn Cys Ser Pro Tyr Trp Ile
705                 710                 715                 720

Lys Phe Lys Lys Cys Ile Tyr Phe Ile Val Met Asp Pro Phe Val Asp
                725                 730                 735

Leu Ala Ile Thr Ile Cys Ile Val Leu Asn Thr Leu Phe Met Ala Met
            740                 745                 750

Glu His His Pro Met Thr Glu Glu Phe Lys Asn Val Leu Ala Ile Gly
        755                 760                 765

Asn Leu Val Phe Thr Gly Ile Phe Ala Ala Glu Met Val Leu Lys Leu
    770                 775                 780

Ile Ala Met Asp Pro Tyr Glu Tyr Phe Gln Val Gly Trp Asn Ile Phe
785                 790                 795                 800

Asp Ser Leu Ile Val Thr Leu Ser Leu Val Glu Leu Phe Leu Ala Asp
                805                 810                 815

Val Glu Gly Leu Ser Val Leu Arg Ser Phe Arg Leu Leu Arg Val Phe
            820                 825                 830

Lys Leu Ala Lys Ser Trp Pro Thr Leu Asn Met Leu Ile Lys Ile Ile
        835                 840                 845

Gly Asn Ser Val Gly Ala Leu Gly Asn Leu Thr Leu Val Leu Ala Ile
    850                 855                 860

Ile Val Phe Ile Phe Ala Val Val Gly Met Gln Leu Phe Gly Lys Ser
865                 870                 875                 880

Tyr Lys Glu Cys Val Cys Lys Ile Asn Asp Asp Cys Thr Leu Pro Arg
                885                 890                 895

Trp His Met Asn Asp Phe Phe His Ser Phe Leu Ile Val Phe Arg Val
            900                 905                 910

Leu Cys Gly Glu Trp Ile Glu Thr Met Trp Asp Cys Met Glu Val Ala
        915                 920                 925

Gly Gln Ala Met Cys Leu Ile Val Tyr Met Met Val Met Val Ile Gly
    930                 935                 940
```

```
Asn Leu Val Val Leu Asn Leu Phe Leu Ala Leu Leu Ser Ser Phe
945                 950                 955                 960

Ser Ser Asp Asn Leu Thr Ala Ile Glu Glu Asp Pro Asp Ala Asn Asn
                965                 970                 975

Leu Gln Ile Ala Val Thr Arg Ile Lys Lys Gly Ile Asn Tyr Val Lys
            980                 985                 990

Gln Thr Leu Arg Glu Phe Ile Leu Lys Ala Phe Ser Lys Lys Pro Lys
        995                 1000                1005

Ile Ser Arg Glu Ile Arg Gln Ala Glu Asp Leu Asn Thr Lys Lys
    1010                1015                1020

Glu Asn Tyr Ile Ser Asn His Thr Leu Ala Glu Met Ser Lys Gly
    1025                1030                1035

His Asn Phe Leu Lys Glu Lys Asp Lys Ile Ser Gly Phe Gly Ser
    1040                1045                1050

Ser Val Asp Lys His Leu Met Glu Asp Ser Asp Gly Gln Ser Phe
    1055                1060                1065

Ile His Asn Pro Ser Leu Thr Val Thr Val Pro Ile Ala Pro Gly
    1070                1075                1080

Glu Ser Asp Leu Glu Asn Met Asn Ala Glu Glu Leu Ser Ser Asp
    1085                1090                1095

Ser Asp Ser Glu Tyr Ser Lys Val Arg Leu Asn Arg Ser Ser Ser
    1100                1105                1110

Ser Glu Cys Ser Thr Val Asp Asn Pro Leu Pro Gly Glu Gly Glu
    1115                1120                1125

Glu Ala Glu Ala Glu Pro Met Asn Ser Asp Glu Pro Glu Ala Cys
    1130                1135                1140

Phe Thr Asp Gly Cys Val Arg Arg Phe Ser Cys Cys Gln Val Asn
    1145                1150                1155

Ile Glu Ser Gly Lys Gly Lys Ile Trp Trp Asn Ile Arg Lys Thr
    1160                1165                1170

Cys Tyr Lys Ile Val Glu His Ser Trp Phe Glu Ser Phe Ile Val
    1175                1180                1185

Leu Met Ile Leu Leu Ser Ser Gly Ala Leu Ala Phe Glu Asp Ile
    1190                1195                1200

Tyr Ile Glu Arg Lys Lys Thr Ile Lys Ile Ile Leu Glu Tyr Ala
    1205                1210                1215

Asp Lys Ile Phe Thr Tyr Ile Phe Ile Leu Glu Met Leu Leu Lys
    1220                1225                1230

Trp Ile Ala Tyr Gly Tyr Lys Thr Tyr Phe Thr Asn Ala Trp Cys
    1235                1240                1245

Trp Leu Asp Phe Leu Ile Val Asp Val Ser Leu Val Thr Leu Val
    1250                1255                1260

Ala Asn Thr Leu Gly Tyr Ser Asp Leu Gly Pro Ile Lys Ser Leu
    1265                1270                1275

Arg Thr Leu Arg Ala Leu Arg Pro Leu Arg Ala Leu Ser Arg Phe
    1280                1285                1290

Glu Gly Met Arg Val Val Asn Ala Leu Ile Gly Ala Ile Pro
    1295                1300                1305

Ser Ile Met Asn Val Leu Val Cys Leu Ile Phe Trp Leu Ile
    1310                1315                1320

Phe Ser Ile Met Gly Val Asn Leu Phe Ala Gly Lys Phe Tyr Glu
    1325                1330                1335
```

-continued

Cys Ile Asn Thr Thr Asp Gly Ser Arg Phe Pro Ala Ser Gln Val
1340                1345                1350

Pro Asn Arg Ser Glu Cys Phe Ala Leu Met Asn Val Ser Gln Asn
1355                1360                1365

Val Arg Trp Lys Asn Leu Lys Val Asn Phe Asp Asn Val Gly Leu
1370                1375                1380

Gly Tyr Leu Ser Leu Leu Gln Val Ala Thr Phe Lys Gly Trp Thr
1385                1390                1395

Ile Ile Met Tyr Ala Ala Val Asp Ser Val Asn Val Asp Lys Gln
1400                1405                1410

Pro Lys Tyr Glu Tyr Ser Leu Tyr Met Tyr Ile Tyr Phe Val Val
1415                1420                1425

Phe Ile Ile Phe Gly Ser Phe Phe Thr Leu Asn Leu Phe Ile Gly
1430                1435                1440

Val Ile Ile Asp Asn Phe Asn Gln Gln Lys Lys Lys Leu Gly Gly
1445                1450                1455

Gln Asp Ile Phe Met Thr Glu Glu Gln Lys Lys Tyr Tyr Asn Ala
1460                1465                1470

Met Lys Lys Leu Gly Ser Lys Lys Pro Gln Lys Pro Ile Pro Arg
1475                1480                1485

Pro Gly Asn Lys Ile Gln Gly Cys Ile Phe Asp Leu Val Thr Asn
1490                1495                1500

Gln Ala Phe Asp Ile Ser Ile Met Val Leu Ile Cys Leu Asn Met
1505                1510                1515

Val Thr Met Met Val Glu Lys Glu Gly Gln Ser Gln His Met Thr
1520                1525                1530

Glu Val Leu Tyr Trp Ile Asn Val Val Phe Ile Ile Leu Phe Thr
1535                1540                1545

Gly Glu Cys Val Leu Lys Leu Ile Ser Leu Arg His Tyr Tyr Phe
1550                1555                1560

Thr Val Gly Trp Asn Ile Phe Asp Phe Val Val Val Ile Ile Ser
1565                1570                1575

Ile Val Gly Met Phe Leu Ala Asp Leu Ile Glu Thr Tyr Phe Val
1580                1585                1590

Ser Pro Thr Leu Phe Arg Val Ile Arg Leu Ala Arg Ile Gly Arg
1595                1600                1605

Ile Leu Arg Leu Val Lys Gly Ala Lys Gly Ile Arg Thr Leu Leu
1610                1615                1620

Phe Ala Leu Met Met Ser Leu Pro Ala Leu Phe Asn Ile Gly Leu
1625                1630                1635

Leu Leu Phe Leu Val Met Phe Ile Tyr Ala Ile Phe Gly Met Ser
1640                1645                1650

Asn Phe Ala Tyr Val Lys Lys Glu Asp Gly Ile Asn Asp Met Phe
1655                1660                1665

Asn Phe Glu Thr Phe Gly Asn Ser Met Ile Cys Leu Phe Gln Ile
1670                1675                1680

Thr Thr Ser Ala Gly Trp Asp Gly Leu Leu Ala Pro Ile Leu Asn
1685                1690                1695

Ser Lys Pro Pro Asp Cys Asp Pro Lys Lys Val His Pro Gly Ser
1700                1705                1710

Ser Val Glu Gly Asp Cys Gly Asn Pro Ser Val Gly Ile Phe Tyr
1715                1720                1725

```
Phe Val Ser Tyr Ile Ile Ile Ser Phe Leu Val Val Val Asn Met
    1730            1735                1740
Tyr Ile Ala Val Ile Leu Glu Asn Phe Ser Val Ala Thr Glu Glu
    1745            1750                1755
Ser Thr Glu Pro Leu Ser Glu Asp Asp Phe Glu Met Phe Tyr Glu
    1760            1765                1770
Val Trp Glu Lys Phe Asp Pro Asp Ala Thr Gln Phe Ile Glu Phe
    1775            1780                1785
Ser Lys Leu Ser Asp Phe Ala Ala Ala Leu Asp Pro Pro Leu Leu
    1790            1795                1800
Ile Ala Lys Pro Asn Lys Val Gln Leu Ile Ala Met Asp Leu Pro
    1805            1810                1815
Met Val Ser Gly Asp Arg Ile His Cys Leu Asp Ile Leu Phe Ala
    1820            1825                1830
Phe Thr Lys Arg Val Leu Gly Glu Ser Gly Glu Met Asp Ser Leu
    1835            1840                1845
Arg Ser Gln Met Glu Glu Arg Phe Met Ser Ala Asn Pro Ser Lys
    1850            1855                1860
Val Ser Tyr Glu Pro Ile Thr Thr Thr Leu Lys Arg Lys Gln Glu
    1865            1870                1875
Asp Val Ser Ala Thr Val Ile Gln Arg Ala Tyr Arg Arg Tyr Arg
    1880            1885                1890
Leu Arg Gln Asn Val Lys Asn Ile Ser Ser Ile Tyr Ile Lys Asp
    1895            1900                1905
Gly Asp Arg Asp Asp Asp Leu Leu Asn Lys Lys Asp Met Ala Phe
    1910            1915                1920
Asp Asn Val Asn Glu Asn Ser Ser Pro Glu Lys Thr Asp Ala Thr
    1925            1930                1935
Ser Ser Thr Thr Ser Pro Pro Ser Tyr Asp Ser Val Thr Lys Pro
    1940            1945                1950
Asp Lys Glu Lys Tyr Glu Gln Asp Arg Thr Glu Lys Glu Asp Lys
    1955            1960                1965
Gly Lys Asp Ser Lys Glu Ser Lys Lys
    1970            1975

<210> SEQ ID NO 23
<211> LENGTH: 24
<212> TYPE: PRT
<213> ORGANISM: Artificial Sequence
<220> FEATURE:
<223> OTHER INFORMATION: Synthetic polypeptide

<400> SEQUENCE: 23

Thr Leu Ser Leu Val Glu Leu Phe Leu Ala Asp Val Glu Gly Leu Ser
1               5                   10                  15

Val Leu Arg Ser Phe Arg Leu Leu
            20

<210> SEQ ID NO 24
<211> LENGTH: 18
<212> TYPE: PRT
<213> ORGANISM: Artificial Sequence
<220> FEATURE:
<223> OTHER INFORMATION: Synthetic polypeptide
```

```
<400> SEQUENCE: 24

Leu Ser Leu Val Glu Leu Phe Leu Ala Asp Val Glu Gly Leu Ser Val
1               5                   10                  15

Leu Arg

<210> SEQ ID NO 25
<211> LENGTH: 18
<212> TYPE: PRT
<213> ORGANISM: Artificial Sequence
<220> FEATURE:
<223> OTHER INFORMATION: Synthetic polypeptide

<400> SEQUENCE: 25

Leu Ser Leu Met Glu Leu Gly Leu Ala Asn Val Glu Gly Leu Ser Val
1               5                   10                  15

Leu Arg

<210> SEQ ID NO 26
<211> LENGTH: 18
<212> TYPE: PRT
<213> ORGANISM: Artificial Sequence
<220> FEATURE:
<223> OTHER INFORMATION: Synthetic polypeptide

<400> SEQUENCE: 26

Leu Ser Leu Met Glu Leu Gly Leu Ala Asn Val Glu Gly Leu Ser Val
1               5                   10                  15

Leu Arg

<210> SEQ ID NO 27
<211> LENGTH: 18
<212> TYPE: PRT
<213> ORGANISM: Artificial Sequence
<220> FEATURE:
<223> OTHER INFORMATION: Synthetic polypeptide

<400> SEQUENCE: 27

Leu Ser Leu Met Glu Leu Gly Leu Ser Asn Val Glu Gly Leu Ser Val
1               5                   10                  15

Leu Arg

<210> SEQ ID NO 28
<211> LENGTH: 18
<212> TYPE: PRT
<213> ORGANISM: Artificial Sequence
<220> FEATURE:
<223> OTHER INFORMATION: Synthetic polypeptide

<400> SEQUENCE: 28

Leu Ser Leu Val Glu Leu Gly Leu Ala Asn Val Gln Gly Leu Ser Val
1               5                   10                  15

Leu Arg

<210> SEQ ID NO 29
<211> LENGTH: 18
<212> TYPE: PRT
<213> ORGANISM: Artificial Sequence
<220> FEATURE:
<223> OTHER INFORMATION: Synthetic polypeptide
```

```
<400> SEQUENCE: 29

Leu Ser Leu Met Glu Leu Gly Leu Ser Arg Met Ser Asn Leu Ser Val
1               5                   10                  15

Leu Arg

<210> SEQ ID NO 30
<211> LENGTH: 18
<212> TYPE: PRT
<213> ORGANISM: Artificial Sequence
<220> FEATURE:
<223> OTHER INFORMATION: Synthetic polypeptide

<400> SEQUENCE: 30

Leu Ser Leu Met Glu Leu Ser Leu Ala Asp Val Glu Gly Leu Ser Val
1               5                   10                  15

Leu Arg

<210> SEQ ID NO 31
<211> LENGTH: 18
<212> TYPE: PRT
<213> ORGANISM: Artificial Sequence
<220> FEATURE:
<223> OTHER INFORMATION: Synthetic polypeptide

<400> SEQUENCE: 31

Val Ser Leu Leu Glu Leu Gly Val Ala Lys Lys Gly Ser Leu Ser Val
1               5                   10                  15

Leu Arg

<210> SEQ ID NO 32
<211> LENGTH: 20
<212> TYPE: PRT
<213> ORGANISM: Artificial Sequence
<220> FEATURE:
<223> OTHER INFORMATION: Synthetic polypeptide

<400> SEQUENCE: 32

Leu Ser Phe Ala Asp Val Met Asn Cys Val Leu Gln Lys Arg Ser Trp
1               5                   10                  15

Pro Phe Leu Arg
            20

<210> SEQ ID NO 33
<211> LENGTH: 19
<212> TYPE: PRT
<213> ORGANISM: Artificial Sequence
<220> FEATURE:
<223> OTHER INFORMATION: Synthetic polypeptide

<400> SEQUENCE: 33

Ala Met Glu His His Pro Met Thr Glu Glu Phe Lys Asn Val Leu Ala
1               5                   10                  15

Ile Gly Asn

<210> SEQ ID NO 34
<211> LENGTH: 19
<212> TYPE: PRT
<213> ORGANISM: Artificial Sequence
<220> FEATURE:
<223> OTHER INFORMATION: Synthetic polypeptide
```

```
<400> SEQUENCE: 34

Ala Met Glu His Tyr Pro Met Thr Glu Gln Phe Ser Ser Val Leu Ser
1               5                   10                  15

Val Gly Asn

<210> SEQ ID NO 35
<211> LENGTH: 19
<212> TYPE: PRT
<213> ORGANISM: Artificial Sequence
<220> FEATURE:
<223> OTHER INFORMATION: Synthetic polypeptide

<400> SEQUENCE: 35

Ala Met Glu His Tyr Pro Met Thr Glu Gln Phe Ser Ser Val Leu Ser
1               5                   10                  15

Val Gly Asn

<210> SEQ ID NO 36
<211> LENGTH: 19
<212> TYPE: PRT
<213> ORGANISM: Artificial Sequence
<220> FEATURE:
<223> OTHER INFORMATION: Synthetic polypeptide

<400> SEQUENCE: 36

Ala Met Glu His Tyr Pro Met Thr Glu Gln Phe Ser Ser Val Leu Thr
1               5                   10                  15

Val Gly Asn

<210> SEQ ID NO 37
<211> LENGTH: 19
<212> TYPE: PRT
<213> ORGANISM: Artificial Sequence
<220> FEATURE:
<223> OTHER INFORMATION: Synthetic polypeptide

<400> SEQUENCE: 37

Ala Met Glu His Tyr Pro Met Thr Glu His Phe Asp Asn Val Leu Thr
1               5                   10                  15

Val Gly Asn

<210> SEQ ID NO 38
<211> LENGTH: 19
<212> TYPE: PRT
<213> ORGANISM: Artificial Sequence
<220> FEATURE:
<223> OTHER INFORMATION: Synthetic polypeptide

<400> SEQUENCE: 38

Ala Leu Glu His Tyr Asn Met Thr Ser Glu Phe Glu Glu Met Leu Gln
1               5                   10                  15

Val Gly Asn

<210> SEQ ID NO 39
<211> LENGTH: 19
<212> TYPE: PRT
<213> ORGANISM: Artificial Sequence
<220> FEATURE:
<223> OTHER INFORMATION: Synthetic polypeptide
```

<400> SEQUENCE: 39

Ala Met Glu His His Pro Met Thr Pro Gln Phe Glu His Val Leu Ala
1               5                   10                  15

Val Gly Asn

<210> SEQ ID NO 40
<211> LENGTH: 19
<212> TYPE: PRT
<213> ORGANISM: Artificial Sequence
<220> FEATURE:
<223> OTHER INFORMATION: Synthetic polypeptide

<400> SEQUENCE: 40

Ala Met Glu His His Gly Met Ser Pro Thr Phe Glu Ala Met Leu Gln
1               5                   10                  15

Ile Gly Asn

<210> SEQ ID NO 41
<211> LENGTH: 19
<212> TYPE: PRT
<213> ORGANISM: Artificial Sequence
<220> FEATURE:
<223> OTHER INFORMATION: Synthetic polypeptide

<400> SEQUENCE: 41

Ala Met Glu His His Lys Met Glu Ala Ser Phe Glu Lys Met Leu Asn
1               5                   10                  15

Ile Gly Asn

<210> SEQ ID NO 42
<211> LENGTH: 18
<212> TYPE: PRT
<213> ORGANISM: Artificial Sequence
<220> FEATURE:
<223> OTHER INFORMATION: Synthetic polypeptide

<400> SEQUENCE: 42

Leu Ser Leu Val Glu Leu Phe Leu Ala Asp Val Glu Gly Leu Ser Val
1               5                   10                  15

Leu Arg

<210> SEQ ID NO 43
<211> LENGTH: 18
<212> TYPE: PRT
<213> ORGANISM: Artificial Sequence
<220> FEATURE:
<223> OTHER INFORMATION: Synthetic polypeptide

<400> SEQUENCE: 43

Leu Ser Leu Met Glu Leu Gly Leu Ala Asn Val Glu Gly Leu Ser Val
1               5                   10                  15

Leu Arg

<210> SEQ ID NO 44
<211> LENGTH: 18
<212> TYPE: PRT
<213> ORGANISM: Artificial Sequence
<220> FEATURE:
<223> OTHER INFORMATION: Synthetic polypeptide

```
-continued

<400> SEQUENCE: 44

Leu Ser Leu Met Glu Leu Gly Leu Ala Asn Val Glu Gly Leu Ser Val
1               5                   10                  15

Leu Arg

<210> SEQ ID NO 45
<211> LENGTH: 18
<212> TYPE: PRT
<213> ORGANISM: Artificial Sequence
<220> FEATURE:
<223> OTHER INFORMATION: Synthetic polypeptide

<400> SEQUENCE: 45

Leu Ser Leu Met Glu Leu Gly Leu Ser Asn Val Glu Gly Leu Ser Val
1               5                   10                  15

Leu Arg

<210> SEQ ID NO 46
<211> LENGTH: 18
<212> TYPE: PRT
<213> ORGANISM: Artificial Sequence
<220> FEATURE:
<223> OTHER INFORMATION: Synthetic polypeptide

<400> SEQUENCE: 46

Leu Ser Leu Val Glu Leu Gly Leu Ala Asn Val Gln Gly Leu Ser Val
1               5                   10                  15

Leu Arg

<210> SEQ ID NO 47
<211> LENGTH: 18
<212> TYPE: PRT
<213> ORGANISM: Artificial Sequence
<220> FEATURE:
<223> OTHER INFORMATION: Synthetic polypeptide

<400> SEQUENCE: 47

Leu Ser Leu Met Glu Leu Gly Leu Ser Arg Met Gly Asn Leu Ser Val
1               5                   10                  15

Leu Arg

<210> SEQ ID NO 48
<211> LENGTH: 18
<212> TYPE: PRT
<213> ORGANISM: Artificial Sequence
<220> FEATURE:
<223> OTHER INFORMATION: Synthetic polypeptide

<400> SEQUENCE: 48

Leu Ser Leu Met Glu Leu Gly Leu Ala Asp Val Glu Gly Leu Ser Val
1               5                   10                  15

Leu Arg

<210> SEQ ID NO 49
<211> LENGTH: 18
<212> TYPE: PRT
<213> ORGANISM: Artificial Sequence
<220> FEATURE:
<223> OTHER INFORMATION: Synthetic polypeptide
```

```
<400> SEQUENCE: 49

Val Ser Leu Leu Glu Leu Ser Ala Ser Lys Lys Gly Ser Leu Ser Val
1               5                   10                  15

Leu Arg

<210> SEQ ID NO 50
<211> LENGTH: 30
<212> TYPE: PRT
<213> ORGANISM: Artificial Sequence
<220> FEATURE:
<223> OTHER INFORMATION: Synthetic polypeptide

<400> SEQUENCE: 50

Ser Ile Val Gly Met Phe Leu Ala Asp Leu Ile Glu Thr Tyr Phe Val
1               5                   10                  15

Ser Pro Thr Leu Phe Arg Val Ile Arg Leu Ala Arg Ile Gly
            20                  25                  30

<210> SEQ ID NO 51
<211> LENGTH: 11
<212> TYPE: PRT
<213> ORGANISM: Artificial Sequence
<220> FEATURE:
<223> OTHER INFORMATION: Synthetic polypeptide

<400> SEQUENCE: 51

Met Phe Leu Ala Asp Leu Ile Glu Thr Tyr Phe
1               5                   10
```

$Na_V$ 1.7 ANTIBODIES AND METHODS OF USING THE SAME

CROSS-REFERENCE TO RELATED APPLICATIONS

This application is a national stage filing under 35 U.S.C. § 371 of International Patent Application No. PCT/US2014/054305, filed Sep. 5, 2014, which claims the benefit of priority to U.S. Provisional Patent Application No. 61/874,234, filed Sep. 5, 2013, U.S. Provisional Patent Application No. 61/915,304, filed Dec. 12, 2013, and U.S. Provisional Patent Application No. 61/944,388, filed Feb. 25, 2014, all of which are hereby incorporated by reference.

STATEMENT OF GOVERNMENT INTEREST

This invention was made with government support under contract numbers NIH 1 DP2 OD008380-01, R01DE17794, R01DE22743, and R01NS67686 awarded by the National Institutes of Health. The government has certain rights in the invention.

SEQUENCE LISTING

The sequence listing is filed with the application in electronic format only and is incorporated by reference herein. The sequence listing text file "028193-9166-WO00 Seq Listing ST25.txt" was created on Sep. 5, 2014, and is 33,070 bytes in size.

TECHNICAL FIELD

The present invention relates to anti-$Na_V$1.7 antibodies and methods of using said antibodies for detecting and/or inhibiting $Na_V$1.7. The antibodies may be used to treat a subject suffering from disease, cough, pain, and/or itch.

BACKGROUND

Voltage-gated sodium ($Na_V$) channels are responsible for the upstroke of the action potential in excitable cells. $Na_V$ channels contain tetrameric repeats (i.e., DI to DIV) and each repeat is composed of six transmembrane helices or segments (i.e., segments S1 to S6). The first four segments (S1-S4) comprise a voltage-sensor domain (VSD), in which segment S4 moves in response to a change in membrane potential. Particularly, segment S4 contains an arginine residue that senses the change in membrane potential, and together with the carboxy (C)-terminal half of the segment S3, forms a helix-turn (loop)-helix known as the voltage sensor paddle. The segments S5 and S6 from each tetrameric repeat D1-DIV form a pore domain when the tetrameric repeats D1-DIV are assembled together. Accordingly, the pore domain is opened, closed, and inactivated (i.e., gated) by the movement of the voltage sensor paddle in response to the change in membrane potential.

Humans possess nine highly homologous $Na_V$ channel subtypes (i.e., $Na_V$1.1 to $Na_V$1.9), each of which play a distinct role in various tissues, for example, neurons and myocytes to affect nerve and cardiac excitability, respectively. Dysregulation of $Na_V$ channel subtypes leads to numerous diseases including cardiac arrhythmia, epilepsy, ataxia, periodic paralysis, and pain disorder. $Na_V$ channels are the targets of various drugs, for example, anti-convulsants, local anesthetics, anti-arrhythmics, and analgesics. These drugs often bind an open-inactivated state of the $Na_V$ channel. These drugs, however, exhibit poor selectivity among the nine $Na_V$ channel subtypes, and thus, non-selective targeting of multiple $Na_V$ channel subtypes can lead to off-target effects, which in turn, lead to severe side effects (e.g., cardiac toxicity).

Accordingly, a need exists for the identification and development of new molecules that are selective for one $Na_V$ channel subtype over the other eight $Na_V$ channel subtypes. Such selectively would allow for the treatment of disease associated with a $Na_V$ channel subtype and the prevention of off-target effects that lead to unwanted and serious side effects.

SUMMARY

The present invention is directed to an isolated antibody or antibody fragment thereof that binds to a voltage sensor paddle (VSP) of $Na_V$1.7.

The VSP may be located in domain II (DII) of $Na_V$1.7. The VSP may comprise an amino acid sequence as set forth in SEQ ID NO:23. The isolated antibody or antibody fragment may bind to a loop of the VSP. The loop may comprise an amino acid sequence as set forth in SEQ ID NO:21.

The VSP may be located in domain IV (DIV) of $Na_V$1.7. The VSP may comprise an amino acid sequence as set forth in SEQ ID NO:50. The isolated antibody or antibody fragment may bind to a loop of the VSP. The loop may comprise an amino acid sequence as set forth in SEQ ID NO:51.

The VSP may comprise an amino acid sequence selected from the group consisting of: SEQ ID NO:23 and SEQ ID NO:50. The VSP may comprise the amino acid sequence as set forth in SEQ ID NO:23. The VSP may comprise the amino acid sequence as set forth in SEQ ID NO:50.

The isolated antibody or antibody fragment thereof may bind to a loop of the VSP. The loop may comprise an amino acid sequence selected from the group consisting of: SEQ ID NO:21 and SEQ ID NO:51. The loop may comprise the amino acid sequence as set forth in SEQ ID NO:21. The loop may comprise the amino acid sequence as set forth in SEQ ID NO:51.

The antibody or antibody fragment may inhibit $Na_V$1.7. The antibody or antibody fragment may inhibit $Na_V$1.7 with an $IC_{50}$ of about 0.03 µM. The antibody or antibody fragment may dissociates from $Na_V$1.7 with a $K_D$ of about 23 nM.

The antibody may be selected from the group consisting of: a human antibody, an immunoglobulin molecule, a disulfide linked Fv, a monoclonal antibody, an affinity matured, a scFv, a chimeric antibody, a single domain antibody, a CDR-grafted antibody, a diabody, a humanized antibody, a bovinized antibody, a caninized antibody, an equinized antibody, a felinized antibody, a porcinized antibody, a multispecific antibody, a Fab, a dual specific antibody, a DVD, a Fab', a bispecific antibody, a F(ab')$_2$, and a Fv.

The antibody or antibody fragment may be human, bovine, canine, equine, feline, or porcine.

The antibody or antibody fragment may comprise a heavy chain immunoglobulin constant domain selected from the group consisting of: a human IgM constant domain, a human IgG4 constant domain, a human IgG1 constant domain, a human IgE constant domain, a human IgG2 constant domain, a human igG3 constant domain, and a human IgA constant domain.

The antibody or antibody fragment may comprise a heavy chain bovine immunoglobulin constant domain, a heavy chain canine immunoglobulin constant domain, a heavy chain equine immunoglobulin constant domain, a heavy chain feline immunoglobulin constant domain, or a heavy chain porcine immunoglobulin constant domain.

The antibody or antibody fragment may comprise a light chain bovine immunoglobulin constant domain, a light chain canine immunoglobulin constant domain, a light chain equine immunoglobulin constant domain, a light chain feline immunoglobulin constant domain, or a light chain porcine immunoglobulin constant domain.

The antibody may be a monoclonal antibody.

The antibody or antibody fragment may comprises: (a) a variable heavy domain comprising an amino acid sequence having at least 80% identity with an amino acid sequence as set forth in SEQ ID NO:4; (b) a variable light domain comprising an amino acid sequence having at least 80% identity with an amino acid sequence as set forth in SEQ ID NO:8; (c) a variable heavy chain comprising a complementarity determining region (CDR) 1 comprising an amino acid sequence having at least 80% identity with an amino acid sequence as set forth in SEQ ID NO:5, a CDR2 comprising an amino acid sequence having at least 80% identity with an amino acid sequence as set forth in SEQ ID NO:6, and a CDR3 comprising an amino acid sequence having at least 80% identity with an amino acid sequence as set forth in SEQ ID NO:7; or (d) a variable light chain comprising a CDR1 comprising an amino acid sequence having at least 80% identity with an amino acid sequence as set forth in SEQ ID NO:9, a CDR2 comprising an amino acid sequence having at least 80% identity with an amino acid sequence as set forth in SEQ ID NO:10, and a CDR3 comprising an amino acid sequence having at least 80% identity with an amino acid sequence as set forth in SEQ ID NO:11.

The antibody or antibody fragment may comprise: (a) a variable heavy domain comprising an amino acid sequence having at least 90% identity with an amino acid sequence as set forth in SEQ ID NO:4; (b) a variable light domain comprising an amino acid sequence having at least 90% identity with an amino acid sequence as set forth in SEQ ID NO:8; (c) a variable heavy chain comprising a CDR1 comprising an amino acid sequence having at least 90% identity with an amino acid sequence as set forth in SEQ ID NO:5, a CDR2 comprising an amino acid sequence having at least 90% identity with an amino acid sequence as set forth in SEQ ID NO:6, and a CDR3 comprising an amino acid sequence having at least 90% identity with an amino acid sequence as set forth in SEQ ID NO:7; or (d) a variable light chain comprising a CDR1 comprising an amino acid sequence having at least 90% identity with an amino acid sequence as set forth in SEQ ID NO:9, a CDR2 comprising an amino acid sequence having at least 90% identity with an amino acid sequence as set forth in SEQ ID NO:10, and a CDR3 comprising an amino acid sequence having at least 90% identity with an amino acid sequence as set forth in SEQ ID NO:11.

The antibody or antibody fragment may comprise: (a) a variable heavy domain comprising the amino acid sequence of SEQ ID NO:4; (b) a variable light domain comprising the amino acid sequence of SEQ ID NO:8; (c) a variable heavy chain comprising a CDR1 comprising the amino acid sequence of SEQ ID NO:5, a CDR2 comprising the amino acid sequence of SEQ ID NO:6, and a CDR3 comprising the amino acid sequence of SEQ ID NO:7; or (d) a variable light chain comprising a CDR1 comprising the amino acid sequence of SEQ ID NO:9, a CDR2 comprising the amino acid sequence of SEQ ID NO:10, and a CDR3 comprising the amino acid sequence of SEQ ID NO:11.

The antibody or antibody fragment may comprise a variable heavy domain that comprises SEQ ID NO:5, SEQ ID NO:6, and SEQ ID NO:7.

The antibody or antibody fragment may comprise a variable light domain that comprises SEQ ID NO:9, SEQ ID NO:10, and SEQ ID NO:11.

The antibody or antibody fragment may comprise a variable heavy domain that comprises SEQ ID NO:5, SEQ ID NO:6, and SEQ ID NO:7, and a variable light domain that comprises SEQ ID NO:9, SEQ ID NO:10, and SEQ ID NO:11.

The antibody or antibody fragment may comprise the variable heavy domain comprising the amino acid sequence of SEQ ID NO:4 and the variable light domain comprising the amino acid sequence of SEQ ID NO:8.

The antibody or antibody fragment may comprise the variable heavy chain comprising the CDR1 comprising the amino acid sequence of SEQ ID NO:5, the CDR2 comprising the amino acid sequence of SEQ ID NO:6, and the CDR3 comprising the amino acid sequence of SEQ ID NO:7, and the variable light chain comprising the CDR1 comprising the amino acid sequence of SEQ ID NO:9, the CDR2 comprising the amino acid sequence of SEQ ID NO:10, and the CDR3 comprising the amino acid sequence of SEQ ID NO:11.

The present invention is also directed to an isolated antibody or antibody fragment thereof that binds to a voltage sensor paddle (VSP) of $Na_v1.7$, wherein the antibody or antibody fragment may comprises: (a) a variable heavy domain comprising an amino acid sequence having at least 80% identity with an amino acid sequence as set forth in SEQ ID NO:4; (b) a variable light domain comprising an amino acid sequence having at least 80% identity with an amino acid sequence as set forth in SEQ ID NO:8; (c) a variable heavy chain comprising a complementarity determining region (CDR) 1 comprising an amino acid sequence having at least 80% identity with an amino acid sequence as set forth in SEQ ID NO:5, a CDR2 comprising an amino acid sequence having at least 80% identity with an amino acid sequence as set forth in SEQ ID NO:6, and a CDR3 comprising an amino acid sequence having at least 80% identity with an amino acid sequence as set forth in SEQ ID NO:7; or (d) a variable light chain comprising a CDR1 comprising an amino acid sequence having at least 80% identity with an amino acid sequence as set forth in SEQ ID NO:9, a CDR2 comprising an amino acid sequence having at least 80% identity with an amino acid sequence as set forth in SEQ ID NO:10, and a CDR3 comprising an amino acid sequence having at least 80% identity with an amino acid sequence as set forth in SEQ ID NO:11. The antibody or antibody fragment binds to a loop between transmembrane helices S3 and S4 from domain II of $Na_v1.7$. the loop between transmembrane helices S3 and S4 from domain II of $Na_v1.7$ may comprise an amino acid sequence as set forth in SEQ ID NO:21.

The present invention is further directed to an isolated antibody or antibody fragment thereof that binds to a voltage sensor paddle (VSP) of $Na_v1.7$, wherein the antibody or antibody fragment may comprise: (a) a variable heavy domain comprising an amino acid sequence having at least 90% identity with an amino acid sequence as set forth in SEQ ID NO:4; (b) a variable light domain comprising an amino acid sequence having at least 90% identity with an amino acid sequence as set forth in SEQ ID NO:8; (c) a variable heavy chain comprising a CDR1 comprising an amino acid sequence having at least 90% identity with an amino acid sequence as set forth in SEQ ID NO:5, a CDR2 comprising an amino acid sequence having at least 90% identity with an amino acid sequence as set forth in SEQ ID NO:6, and a CDR3 comprising an amino acid sequence having at least 90% identity with an amino acid sequence as set forth in SEQ ID NO:7; or (d) a variable light chain comprising a CDR1 comprising an amino acid sequence having at least 90% identity with an amino acid sequence as set forth in SEQ ID NO:9, a CDR2 comprising an amino acid sequence having at least 90% identity with an amino acid sequence as set forth in SEQ ID NO:10, and a CDR3 comprising an amino acid sequence having at least 90% identity with an amino acid sequence as set forth in SEQ ID NO:11. The antibody or antibody fragment binds to a loop between transmembrane helices S3 and S4 from domain II of $Na_v1.7$. The loop between transmembrane helices S3 and S4 from domain II of $Na_v1.7$ may comprise an amino acid sequence as set forth in SEQ ID NO:21.

The present invention is further directed to an isolated antibody or antibody fragment thereof that binds to a voltage sensor paddle (VSP) of $Na_v1.7$, wherein the antibody or antibody fragment may comprise: (a) a variable heavy domain comprising the amino acid sequence of SEQ ID NO:4; (b) a variable light domain comprising the amino acid sequence of SEQ ID NO:8; (c) a variable heavy chain comprising a CDR1 comprising the amino acid sequence of SEQ ID NO:5, a CDR2 comprising the amino acid sequence of SEQ ID NO:6, and a CDR3 comprising the amino acid sequence of SEQ ID NO:7; or (d) a variable light chain comprising a CDR1 comprising the amino acid sequence of SEQ ID NO:9, a CDR2 comprising the amino acid sequence of SEQ ID NO:10, and a CDR3 comprising the amino acid sequence of SEQ ID NO:11. The antibody or antibody fragment binds to a loop between transmembrane helices S3 and S4 from domain II of $Na_v1.7$. the loop between transmembrane helices S3 and S4 from domain II of $Na_v1.7$ may comprise an amino acid sequence as set forth in SEQ ID NO:21.

The present invention is further directed to an isolated antibody or antibody fragment thereof that binds to a voltage sensor paddle (VSP) of $Na_v1.7$, wherein the antibody or antibody fragment may comprises: (a) a variable heavy domain comprising an amino acid sequence having at least 80% identity with an amino acid sequence as set forth in SEQ ID NO:4; (b) a variable light domain comprising an amino acid sequence having at least 80% identity with an amino acid sequence as set forth in SEQ ID NO:8; (c) a variable heavy chain comprising a complementarity determining region (CDR) 1 comprising an amino acid sequence having at least 80% identity with an amino acid sequence as set forth in SEQ ID NO:5, a CDR2 comprising an amino acid sequence having at least 80% identity with an amino acid sequence as set forth in SEQ ID NO:6, and a CDR3 comprising an amino acid sequence having at least 80% identity with an amino acid sequence as set forth in SEQ ID NO:7; or (d) a variable light chain comprising a CDR1 comprising an amino acid sequence having at least 80% identity with an amino acid sequence as set forth in SEQ ID NO:9, a CDR2 comprising an amino acid sequence having at least 80% identity with an amino acid sequence as set forth in SEQ ID NO:10, and a CDR3 comprising an amino acid sequence having at least 80% identity with an amino acid sequence as set forth in SEQ ID NO:11. The antibody or antibody fragment may inhibit $Na_v1.7$. The antibody or antibody fragment may inhibit $Na_v1.7$ by stabilizing a closed state of $Na_v1.7$.

The present invention is further directed to an isolated antibody or antibody fragment thereof that binds to a voltage sensor paddle (VSP) of $Na_v1.7$, wherein the antibody or antibody fragment may comprise: (a) a variable heavy domain comprising an amino acid sequence having at least 90% identity with an amino acid sequence as set forth in SEQ ID NO:4; (b) a variable light domain comprising an amino acid sequence having at least 90% identity with an amino acid sequence as set forth in SEQ ID NO:8; (c) a variable heavy chain comprising a CDR1 comprising an amino acid sequence having at least 90% identity with an amino acid sequence as set forth in SEQ ID NO:5, a CDR2 comprising an amino acid sequence having at least 90% identity with an amino acid sequence as set forth in SEQ ID NO:6, and a CDR3 comprising an amino acid sequence having at least 90% identity with an amino acid sequence as set forth in SEQ ID NO:7; or (d) a variable light chain comprising a CDR1 comprising an amino acid sequence having at least 90% identity with an amino acid sequence as set forth in SEQ ID NO:9, a CDR2 comprising an amino acid sequence having at least 90% identity with an amino acid sequence as set forth in SEQ ID NO:10, and a CDR3 comprising an amino acid sequence having at least 90% identity with an amino acid sequence as set forth in SEQ ID NO:11. The antibody or antibody fragment may inhibit $Na_v1.7$. The antibody or antibody fragment may inhibit $Na_v1.7$ by stabilizing a closed state of $Na_v1.7$.

The present invention is further directed to an isolated antibody or antibody fragment thereof that binds to a voltage sensor paddle (VSP) of $Na_v1.7$, wherein the antibody or antibody fragment may comprise: (a) a variable heavy domain comprising the amino acid sequence of SEQ ID NO:4; (b) a variable light domain comprising the amino acid sequence of SEQ ID NO:8; (c) a variable heavy chain comprising a CDR1 comprising the amino acid sequence of SEQ ID NO:5, a CDR2 comprising the amino acid sequence of SEQ ID NO:6, and a CDR3 comprising the amino acid sequence of SEQ ID NO:7; or (d) a variable light chain comprising a CDR1 comprising the amino acid sequence of SEQ ID NO:9, a CDR2 comprising the amino acid sequence of SEQ ID NO:10, and a CDR3 comprising the amino acid sequence of SEQ ID NO:11. The antibody or antibody fragment may inhibit $Na_v1.7$. The antibody or antibody fragment may inhibit $Na_v1.7$ by stabilizing a closed state of $Na_v1.7$.

The present invention is further directed to an isolated antibody or antibody fragment thereof that binds to a voltage sensor paddle (VSP) of $Na_v1.7$, wherein the antibody or antibody fragment may comprises: (a) a variable heavy domain comprising an amino acid sequence having at least 80% identity with an amino acid sequence as set forth in SEQ ID NO:4; (b) a variable light domain comprising an amino acid sequence having at least 80% identity with an amino acid sequence as set forth in SEQ ID NO:8; (c) a variable heavy chain comprising a complementarity determining region (CDR) 1 comprising an amino acid sequence having at least 80% identity with an amino acid sequence as set forth in SEQ ID NO:5, a CDR2 comprising an amino acid sequence having at least 80% identity with an amino acid sequence as set forth in SEQ ID NO:6, and a CDR3 comprising an amino acid sequence having at least 80% identity with an amino acid sequence as set forth in SEQ ID NO:7; or (d) a variable light chain comprising a CDR1 comprising an amino acid sequence having at least 80% identity with an amino acid sequence as set forth in SEQ ID NO:9, a CDR2 comprising an amino acid sequence having at least 80% identity with an amino acid sequence as set forth in SEQ ID NO:10, and a CDR3 comprising an amino acid sequence having at least 80% identity with an amino acid sequence as set forth in SEQ ID NO:11. The antibody may be selected from the group consisting of a human antibody, an immunoglobulin molecule, a disulfide linked Fv, a monoclonal antibody, an affinity matured, a scFv, a chimeric antibody, a single domain antibody, a CDR-grafted antibody, a diabody, a humanized antibody, a bovinized antibody, a caninized antibody, an equinized antibody, a felinized antibody, a porcinized antibody, a multispecific antibody, a Fab, a dual specific antibody, a DVD, a Fab', a bispecific antibody, a F(ab')$_2$, and a Fv.

The present invention is further directed to an isolated antibody or antibody fragment thereof that binds to a voltage sensor paddle (VSP) of Na$_v$1.7, wherein the antibody or antibody fragment may comprise: (a) a variable heavy domain comprising an amino acid sequence having at least 90% identity with an amino acid sequence as set forth in SEQ ID NO:4; (b) a variable light domain comprising an amino acid sequence having at least 90% identity with an amino acid sequence as set forth in SEQ ID NO:8; (c) a variable heavy chain comprising a CDR1 comprising an amino acid sequence having at least 90% identity with an amino acid sequence as set forth in SEQ ID NO:5, a CDR2 comprising an amino acid sequence having at least 90% identity with an amino acid sequence as set forth in SEQ ID NO:6, and a CDR3 comprising an amino acid sequence having at least 90% identity with an amino acid sequence as set forth in SEQ ID NO:7; or (d) a variable light chain comprising a CDR1 comprising an amino acid sequence having at least 90% identity with an amino acid sequence as set forth in SEQ ID NO:9, a CDR2 comprising an amino acid sequence having at least 90% identity with an amino acid sequence as set forth in SEQ ID NO:10, and a CDR3 comprising an amino acid sequence having at least 90% identity with an amino acid sequence as set forth in SEQ ID NO:11. The antibody may be selected from the group consisting of a human antibody, an immunoglobulin molecule, a disulfide linked Fv, a monoclonal antibody, an affinity matured, a scFv, a chimeric antibody, a single domain antibody, a CDR-grafted antibody, a diabody, a humanized antibody, a bovinized antibody, a caninized antibody, an equinized antibody, a felinized antibody, a porcinized antibody, a multispecific antibody, a Fab, a dual specific antibody, a DVD, a Fab', a bispecific antibody, a F(ab')$_2$, and a Fv.

The present invention is further directed to an isolated antibody or antibody fragment thereof that binds to a voltage sensor paddle (VSP) of Na$_v$1.7, wherein the antibody or antibody fragment may comprise: (a) a variable heavy domain comprising the amino acid sequence of SEQ ID NO:4; (b) a variable light domain comprising the amino acid sequence of SEQ ID NO:8; (c) a variable heavy chain comprising a CDR1 comprising the amino acid sequence of SEQ ID NO:5, a CDR2 comprising the amino acid sequence of SEQ ID NO:6, and a CDR3 comprising the amino acid sequence of SEQ ID NO:7; or (d) a variable light chain comprising a CDR1 comprising the amino acid sequence of SEQ ID NO:9, a CDR2 comprising the amino acid sequence of SEQ ID NO:10, and a CDR3 comprising the amino acid sequence of SEQ ID NO:11. The antibody may be selected from the group consisting of a human antibody, an immunoglobulin molecule, a disulfide linked Fv, a monoclonal antibody, an affinity matured, a scFv, a chimeric antibody, a single domain antibody, a CDR-grafted antibody, a diabody, a humanized antibody, a bovinized antibody, a caninized antibody, an equinized antibody, a felinized antibody, a porcinized antibody, a multispecific antibody, a Fab, a dual specific antibody, a DVD, a Fab', a bispecific antibody, a F(ab')$_2$, and a Fv.

The present invention is further directed to an isolated antibody or antibody fragment thereof that binds to a voltage sensor paddle (VSP) of Na$_v$1.7, wherein the antibody or antibody fragment may comprises: (a) a variable heavy domain comprising an amino acid sequence having at least 80% identity with an amino acid sequence as set forth in SEQ ID NO:4; (b) a variable light domain comprising an amino acid sequence having at least 80% identity with an amino acid sequence as set forth in SEQ ID NO:8; (c) a variable heavy chain comprising a complementarity determining region (CDR) 1 comprising an amino acid sequence having at least 80% identity with an amino acid sequence as set forth in SEQ ID NO:5, a CDR2 comprising an amino acid sequence having at least 80% identity with an amino acid sequence as set forth in SEQ ID NO:6, and a CDR3 comprising an amino acid sequence having at least 80% identity with an amino acid sequence as set forth in SEQ ID NO:7; or (d) a variable light chain comprising a CDR1 comprising an amino acid sequence having at least 80% identity with an amino acid sequence as set forth in SEQ ID NO:9, a CDR2 comprising an amino acid sequence having at least 80% identity with an amino acid sequence as set forth in SEQ ID NO:10, and a CDR3 comprising an amino acid sequence having at least 80% identity with an amino acid sequence as set forth in SEQ ID NO:11. The antibody or antibody fragment may be human, bovine, canine, equine, feline, or porcine.

The present invention is further directed to an isolated antibody or antibody fragment thereof that binds to a voltage sensor paddle (VSP) of Na$_v$1.7, wherein the antibody or antibody fragment may comprise: (a) a variable heavy domain comprising an amino acid sequence having at least 90% identity with an amino acid sequence as set forth in SEQ ID NO:4; (b) a variable light domain comprising an amino acid sequence having at least 90% identity with an amino acid sequence as set forth in SEQ ID NO:8; (c) a variable heavy chain comprising a CDR1 comprising an amino acid sequence having at least 90% identity with an amino acid sequence as set forth in SEQ ID NO:5, a CDR2 comprising an amino acid sequence having at least 90% identity with an amino acid sequence as set forth in SEQ ID NO:6, and a CDR3 comprising an amino acid sequence having at least 90% identity with an amino acid sequence as set forth in SEQ ID NO:7; or (d) a variable light chain comprising a CDR1 comprising an amino acid sequence having at least 90% identity with an amino acid sequence as set forth in SEQ ID NO:9, a CDR2 comprising an amino acid sequence having at least 90% identity with an amino acid sequence as set forth in SEQ ID NO:10, and a CDR3 comprising an amino acid sequence having at least 90% identity with an amino acid sequence as set forth in SEQ ID NO:11. The antibody or antibody fragment may be human, bovine, canine, equine, feline, or porcine.

The present invention is further directed to an isolated antibody or antibody fragment thereof that binds to a voltage sensor paddle (VSP) of Na$_v$1.7, wherein the antibody or antibody fragment may comprise: (a) a variable heavy domain comprising the amino acid sequence of SEQ ID NO:4; (b) a variable light domain comprising the amino acid sequence of SEQ ID NO:8; (c) a variable heavy chain comprising a CDR1 comprising the amino acid sequence of SEQ ID NO:5, a CDR2 comprising the amino acid sequence of SEQ ID NO:6, and a CDR3 comprising the amino acid sequence of SEQ ID NO:7; or (d) a variable light chain comprising a CDR1 comprising the amino acid sequence of SEQ ID NO:9, a CDR2 comprising the amino acid sequence of SEQ ID NO:10, and a CDR3 comprising the amino acid sequence of SEQ ID NO:11. The antibody or antibody fragment may be human, bovine, canine, equine, feline, or porcine.

The present invention is further directed to an isolated antibody or antibody fragment thereof that binds to a voltage sensor paddle (VSP) of $Na_v1.7$, wherein the antibody or antibody fragment may comprises: (a) a variable heavy domain comprising an amino acid sequence having at least 80% identity with an amino acid sequence as set forth in SEQ ID NO:4; (b) a variable light domain comprising an amino acid sequence having at least 80% identity with an amino acid sequence as set forth in SEQ ID NO:8; (c) a variable heavy chain comprising a complementarity determining region (CDR) 1 comprising an amino acid sequence having at least 80% identity with an amino acid sequence as set forth in SEQ ID NO:5, a CDR2 comprising an amino acid sequence having at least 80% identity with an amino acid sequence as set forth in SEQ ID NO:6, and a CDR3 comprising an amino acid sequence having at least 80% identity with an amino acid sequence as set forth in SEQ ID NO:7; or (d) a variable light chain comprising a CDR1 comprising an amino acid sequence having at least 80% identity with an amino acid sequence as set forth in SEQ ID NO:9, a CDR2 comprising an amino acid sequence having at least 80% identity with an amino acid sequence as set forth in SEQ ID NO:10, and a CDR3 comprising an amino acid sequence having at least 80% identity with an amino acid sequence as set forth in SEQ ID NO:11. The antibody may be a monoclonal antibody.

The present invention is further directed to an isolated antibody or antibody fragment thereof that binds to a voltage sensor paddle (VSP) of $Na_v1.7$, wherein the antibody or antibody fragment may comprise: (a) a variable heavy domain comprising an amino acid sequence having at least 90% identity with an amino acid sequence as set forth in SEQ ID NO:4; (b) a variable light domain comprising an amino acid sequence having at least 90% identity with an amino acid sequence as set forth in SEQ ID NO:8; (c) a variable heavy chain comprising a CDR1 comprising an amino acid sequence having at least 90% identity with an amino acid sequence as set forth in SEQ ID NO:5, a CDR2 comprising an amino acid sequence having at least 90% identity with an amino acid sequence as set forth in SEQ ID NO:6, and a CDR3 comprising an amino acid sequence having at least 90% identity with an amino acid sequence as set forth in SEQ ID NO:7; or (d) a variable light chain comprising a CDR1 comprising an amino acid sequence having at least 90% identity with an amino acid sequence as set forth in SEQ ID NO:9, a CDR2 comprising an amino acid sequence having at least 90% identity with an amino acid sequence as set forth in SEQ ID NO:10, and a CDR3 comprising an amino acid sequence having at least 90% identity with an amino acid sequence as set forth in SEQ ID NO:11. The antibody may be a monoclonal antibody.

The present invention is further directed to an isolated antibody or antibody fragment thereof that binds to a voltage sensor paddle (VSP) of $Na_v1.7$, wherein the antibody or antibody fragment may comprise: (a) a variable heavy domain comprising the amino acid sequence of SEQ ID NO:4; (b) a variable light domain comprising the amino acid sequence of SEQ ID NO:8; (c) a variable heavy chain comprising a CDR1 comprising the amino acid sequence of SEQ ID NO:5, a CDR2 comprising the amino acid sequence of SEQ ID NO:6, and a CDR3 comprising the amino acid sequence of SEQ ID NO:7; or (d) a variable light chain comprising a CDR1 comprising the amino acid sequence of SEQ ID NO:9, a CDR2 comprising the amino acid sequence of SEQ ID NO:10, and a CDR3 comprising the amino acid sequence of SEQ ID NO:11. The antibody may be a monoclonal antibody.

The present invention is further directed to an isolated antibody or antibody fragment thereof that binds to a voltage sensor paddle (VSP) of $Na_v1.7$, wherein the antibody or antibody fragment may comprises: (a) a variable heavy domain comprising an amino acid sequence having at least 80% identity with an amino acid sequence as set forth in SEQ ID NO:4; (b) a variable light domain comprising an amino acid sequence having at least 80% identity with an amino acid sequence as set forth in SEQ ID NO:8; (c) a variable heavy chain comprising a complementarity determining region (CDR) 1 comprising an amino acid sequence having at least 80% identity with an amino acid sequence as set forth in SEQ ID NO:5, a CDR2 comprising an amino acid sequence having at least 80% identity with an amino acid sequence as set forth in SEQ ID NO:6, and a CDR3 comprising an amino acid sequence having at least 80% identity with an amino acid sequence as set forth in SEQ ID NO:7; or (d) a variable light chain comprising a CDR1 comprising an amino acid sequence having at least 80% identity with an amino acid sequence as set forth in SEQ ID NO:9, a CDR2 comprising an amino acid sequence having at least 80% identity with an amino acid sequence as set forth in SEQ ID NO:10, and a CDR3 comprising an amino acid sequence having at least 80% identity with an amino acid sequence as set forth in SEQ ID NO:11. The antibody or antibody fragment may comprise a heavy chain immunoglobulin constant domain selected from the group consisting of a human IgM constant domain, a human IgG4 constant domain, a human IgG1 constant domain, a human IgE constant domain, a human IgG2 constant domain, a human IgG3 constant domain, and a human IgA constant domain.

The present invention is further directed to an isolated antibody or antibody fragment thereof that binds to a voltage sensor paddle (VSP) of $Na_v1.7$, wherein the antibody or antibody fragment may comprise: (a) a variable heavy domain comprising an amino acid sequence having at least 90% identity with an amino acid sequence as set forth in SEQ ID NO:4; (b) a variable light domain comprising an amino acid sequence having at least 90% identity with an amino acid sequence as set forth in SEQ ID NO:8; (c) a variable heavy chain comprising a CDR1 comprising an amino acid sequence having at least 90% identity with an amino acid sequence as set forth in SEQ ID NO:5, a CDR2 comprising an amino acid sequence having at least 90% identity with an amino acid sequence as set forth in SEQ ID NO:6, and a CDR3 comprising an amino acid sequence having at least 90% identity with an amino acid sequence as set forth in SEQ ID NO:7; or (d) a variable light chain comprising a CDR1 comprising an amino acid sequence having at least 90% identity with an amino acid sequence as set forth in SEQ ID NO:9, a CDR2 comprising an amino acid sequence having at least 90% identity with an amino acid sequence as set forth in SEQ ID NO:10, and a CDR3 comprising an amino acid sequence having at least 90% identity with an amino acid sequence as set forth in SEQ ID NO:11. The antibody or antibody fragment may comprise a heavy chain immunoglobulin constant domain selected from the group consisting of a human IgM constant domain, a human IgG4 constant domain, a human IgG1 constant domain, a human IgE constant domain, a human IgG2 constant domain, a human IgG3 constant domain, and a human IgA constant domain.

The present invention is further directed to an isolated antibody or antibody fragment thereof that binds to a voltage sensor paddle (VSP) of $Na_v1.7$, wherein the antibody or antibody fragment may comprise: (a) a variable heavy domain comprising the amino acid sequence of SEQ ID NO:4; (b) a variable light domain comprising the amino acid sequence of SEQ ID NO:8; (c) a variable heavy chain comprising a CDR1 comprising the amino acid sequence of SEQ ID NO:5, a CDR2 comprising the amino acid sequence of SEQ ID NO:6, and a CDR3 comprising the amino acid sequence of SEQ ID NO:7; or (d) a variable light chain comprising a CDR1 comprising the amino acid sequence of SEQ ID NO:9, a CDR2 comprising the amino acid sequence of SEQ ID NO:10, and a CDR3 comprising the amino acid sequence of SEQ ID NO:11. The antibody or antibody fragment may comprise a heavy chain immunoglobulin constant domain selected from the group consisting of a human IgM constant domain, a human IgG4 constant domain, a human IgG1 constant domain, a human IgE constant domain, a human IgG2 constant domain, a human IgG3 constant domain, and a human IgA constant domain.

The present invention is also directed to an isolated antibody or antibody fragment thereof that binds to a voltage sensor paddle (VSP) of $Na_v1.7$, wherein the antibody or antibody fragment may comprises: (a) a variable heavy domain comprising an amino acid sequence having at least 80% identity with an amino acid sequence as set forth in SEQ ID NO:4; (b) a variable light domain comprising an amino acid sequence having at least 80% identity with an amino acid sequence as set forth in SEQ ID NO:8; (c) a variable heavy chain comprising a complementarity determining region (CDR) 1 comprising an amino acid sequence having at least 80% identity with an amino acid sequence as set forth in SEQ ID NO:5, a CDR2 comprising an amino acid sequence having at least 80% identity with an amino acid sequence as set forth in SEQ ID NO:6, and a CDR3 comprising an amino acid sequence having at least 80% identity with an amino acid sequence as set forth in SEQ ID NO:7; or (d) a variable light chain comprising a CDR1 comprising an amino acid sequence having at least 80% identity with an amino acid sequence as set forth in SEQ ID NO:9, a CDR2 comprising an amino acid sequence having at least 80% identity with an amino acid sequence as set forth in SEQ ID NO:10, and a CDR3 comprising an amino acid sequence having at least 80% identity with an amino acid sequence as set forth in SEQ ID NO:11. The antibody or antibody fragment may comprise a heavy chain bovine immunoglobulin constant domain, a heavy chain canine immunoglobulin constant domain, a heavy chain equine immunoglobulin constant domain, a heavy chain feline immunoglobulin constant domain, or a heavy chain porcine immunoglobulin constant domain.

The present invention is further directed to an isolated antibody or antibody fragment thereof that binds to a voltage sensor paddle (VSP) of $Na_v1.7$, wherein the antibody or antibody fragment may comprise: (a) a variable heavy domain comprising an amino acid sequence having at least 90% identity with an amino acid sequence as set forth in SEQ ID NO:4; (b) a variable light domain comprising an amino acid sequence having at least 90% identity with an amino acid sequence as set forth in SEQ ID NO:8; (c) a variable heavy chain comprising a CDR1 comprising an amino acid sequence having at least 90% identity with an amino acid sequence as set forth in SEQ ID NO:5, a CDR2 comprising an amino acid sequence having at least 90% identity with an amino acid sequence as set forth in SEQ ID NO:6, and a CDR3 comprising an amino acid sequence having at least 90% identity with an amino acid sequence as set forth in SEQ ID NO:7; or (d) a variable light chain comprising a CDR1 comprising an amino acid sequence having at least 90% identity with an amino acid sequence as set forth in SEQ ID NO:9, a CDR2 comprising an amino acid sequence having at least 90% identity with an amino acid sequence as set forth in SEQ ID NO:10, and a CDR3 comprising an amino acid sequence having at least 90% identity with an amino acid sequence as set forth in SEQ ID NO:11. The antibody or antibody fragment may comprise a heavy chain bovine immunoglobulin constant domain, a heavy chain canine immunoglobulin constant domain, a heavy chain equine immunoglobulin constant domain, a heavy chain feline immunoglobulin constant domain, or a heavy chain porcine immunoglobulin constant domain.

The present invention is further directed to an isolated antibody or antibody fragment thereof that binds to a voltage sensor paddle (VSP) of $Na_v1.7$, wherein the antibody or antibody fragment may comprise: (a) a variable heavy domain comprising the amino acid sequence of SEQ ID NO:4; (b) a variable light domain comprising the amino acid sequence of SEQ ID NO:8; (c) a variable heavy chain comprising a CDR1 comprising the amino acid sequence of SEQ ID NO:5, a CDR2 comprising the amino acid sequence of SEQ ID NO:6, and a CDR3 comprising the amino acid sequence of SEQ ID NO:7; or (d) a variable light chain comprising a CDR1 comprising the amino acid sequence of SEQ ID NO:9, a CDR2 comprising the amino acid sequence of SEQ ID NO:10, and a CDR3 comprising the amino acid sequence of SEQ ID NO:11. The antibody or antibody fragment may comprise a heavy chain bovine immunoglobulin constant domain, a heavy chain canine immunoglobulin constant domain, a heavy chain equine immunoglobulin constant domain, a heavy chain feline immunoglobulin constant domain, or a heavy chain porcine immunoglobulin constant domain.

The present invention is also directed to an isolated antibody or antibody fragment thereof that binds to a voltage sensor paddle (VSP) of $Na_v1.7$, wherein the antibody or antibody fragment may comprises: (a) a variable heavy domain comprising an amino acid sequence having at least 80% identity with an amino acid sequence as set forth in SEQ ID NO:4; (b) a variable light domain comprising an amino acid sequence having at least 80% identity with an amino acid sequence as set forth in SEQ ID NO:8; (c) a variable heavy chain comprising a complementarity determining region (CDR) 1 comprising an amino acid sequence having at least 80% identity with an amino acid sequence as set forth in SEQ ID NO:5, a CDR2 comprising an amino acid sequence having at least 80% identity with an amino acid sequence as set forth in SEQ ID NO:6, and a CDR3 comprising an amino acid sequence having at least 80% identity with an amino acid sequence as set forth in SEQ ID NO:7; or (d) a variable light chain comprising a CDR1 comprising an amino acid sequence having at least 80% identity with an amino acid sequence as set forth in SEQ ID NO:9, a CDR2 comprising an amino acid sequence having at least 80% identity with an amino acid sequence as set forth in SEQ ID NO:10, and a CDR3 comprising an amino acid sequence having at least 80% identity with an amino acid sequence as set forth in SEQ ID NO:11. The antibody or antibody fragment may comprise a light chain bovine immunoglobulin constant domain, a light chain canine immunoglobulin constant domain, a light chain equine immunoglobulin constant domain, a light chain feline immunoglobulin constant domain, or a light chain porcine immunoglobulin constant domain.

The present invention is further directed to an isolated antibody or antibody fragment thereof that binds to a voltage sensor paddle (VSP) of $Na_v1.7$, wherein the antibody or antibody fragment may comprise: (a) a variable heavy domain comprising an amino acid sequence having at least 90% identity with an amino acid sequence as set forth in SEQ ID NO:4; (b) a variable light domain comprising an amino acid sequence having at least 90% identity with an amino acid sequence as set forth in SEQ ID NO:8; (c) a variable heavy chain comprising a CDR1 comprising an amino acid sequence having at least 90% identity with an amino acid sequence as set forth in SEQ ID NO:5, a CDR2 comprising an amino acid sequence having at least 90% identity with an amino acid sequence as set forth in SEQ ID NO:6, and a CDR3 comprising an amino acid sequence having at least 90% identity with an amino acid sequence as set forth in SEQ ID NO:7; or (d) a variable light chain comprising a CDR1 comprising an amino acid sequence having at least 90% identity with an amino acid sequence as set forth in SEQ ID NO:9, a CDR2 comprising an amino acid sequence having at least 90% identity with an amino acid sequence as set forth in SEQ ID NO:10, and a CDR3 comprising an amino acid sequence having at least 90% identity with an amino acid sequence as set forth in SEQ ID NO:11. The antibody or antibody fragment may comprise a light chain bovine immunoglobulin constant domain, a light chain canine immunoglobulin constant domain, a light chain equine immunoglobulin constant domain, a light chain feline immunoglobulin constant domain, or a light chain porcine immunoglobulin constant domain.

The present invention is further directed to an isolated antibody or antibody fragment thereof that binds to a voltage sensor paddle (VSP) of $Na_v1.7$, wherein the antibody or antibody fragment may comprise: (a) a variable heavy domain comprising the amino acid sequence of SEQ ID NO:4; (b) a variable light domain comprising the amino acid sequence of SEQ ID NO:8; (c) a variable heavy chain comprising a CDR1 comprising the amino acid sequence of SEQ ID NO:5, a CDR2 comprising the amino acid sequence of SEQ ID NO:6, and a CDR3 comprising the amino acid sequence of SEQ ID NO:7; or (d) a variable light chain comprising a CDR1 comprising the amino acid sequence of SEQ ID NO:9, a CDR2 comprising the amino acid sequence of SEQ ID NO:10, and a CDR3 comprising the amino acid sequence of SEQ ID NO:11. The antibody or antibody fragment may comprise a light chain bovine immunoglobulin constant domain, a light chain canine immunoglobulin constant domain, a light chain equine immunoglobulin constant domain, a light chain feline immunoglobulin constant domain, or a light chain porcine immunoglobulin constant domain.

The present invention is further directed to an isolated nucleic acid encoding an isolated antibody or antibody fragment thereof that binds to a voltage sensor paddle (VSP) of $Na_v1.7$. The nucleic acid may encode at least one amino acid sequence of SEQ ID NO:4-11. The nucleic acid may comprise at least one nucleotide sequence of SEQ ID NO:12-19.

The present invention is further directed to an isolated nucleic acid encoding an isolated antibody or antibody fragment thereof that binds to a voltage sensor paddle (VSP) of $Na_v1.7$, wherein the antibody or antibody fragment may comprises: (a) a variable heavy domain comprising an amino acid sequence having at least 80% identity with an amino acid sequence as set forth in SEQ ID NO:4; (b) a variable light domain comprising an amino acid sequence having at least 80% identity with an amino acid sequence as set forth in SEQ ID NO:8; (c) a variable heavy chain comprising a complementarity determining region (CDR) 1 comprising an amino acid sequence having at least 80% identity with an amino acid sequence as set forth in SEQ ID NO:5, a CDR2 comprising an amino acid sequence having at least 80% identity with an amino acid sequence as set forth in SEQ ID NO:6, and a CDR3 comprising an amino acid sequence having at least 80% identity with an amino acid sequence as set forth in SEQ ID NO:7; or (d) a variable light chain comprising a CDR1 comprising an amino acid sequence having at least 80% identity with an amino acid sequence as set forth in SEQ ID NO:9, a CDR2 comprising an amino acid sequence having at least 80% identity with an amino acid sequence as set forth in SEQ ID NO:10, and a CDR3 comprising an amino acid sequence having at least 80% identity with an amino acid sequence as set forth in SEQ ID NO:11. The nucleic acid may encode at least one amino acid sequence of SEQ ID NO:4-11. The nucleic acid may comprise at least one nucleotide sequence of SEQ ID NO:12-19.

The present invention is further directed to an isolated nucleic acid encoding an isolated antibody or antibody fragment thereof that binds to a voltage sensor paddle (VSP) of $Na_v1.7$, wherein the antibody or antibody fragment may comprise: (a) a variable heavy domain comprising an amino acid sequence having at least 90% identity with an amino acid sequence as set forth in SEQ ID NO:4; (b) a variable light domain comprising an amino acid sequence having at least 90% identity with an amino acid sequence as set forth in SEQ ID NO:8; (c) a variable heavy chain comprising a CDR1 comprising an amino acid sequence having at least 90% identity with an amino acid sequence as set forth in SEQ ID NO:5, a CDR2 comprising an amino acid sequence having at least 90% identity with an amino acid sequence as set forth in SEQ ID NO:6, and a CDR3 comprising an amino acid sequence having at least 90% identity with an amino acid sequence as set forth in SEQ ID NO:7; or (d) a variable light chain comprising a CDR1 comprising an amino acid sequence having at least 90% identity with an amino acid sequence as set forth in SEQ ID NO:9, a CDR2 comprising an amino acid sequence having at least 90% identity with an amino acid sequence as set forth in SEQ ID NO:10, and a CDR3 comprising an amino acid sequence having at least 90% identity with an amino acid sequence as set forth in SEQ ID NO:11. The nucleic acid may encode at least one amino acid sequence of SEQ ID NO:4-11. The nucleic acid may comprise at least one nucleotide sequence of SEQ ID NO:12-19.

The present invention is further directed to an isolated nucleic acid encoding an isolated antibody or antibody fragment thereof that binds to a voltage sensor paddle (VSP) of $Na_v1.7$, wherein the antibody or antibody fragment may comprise: (a) a variable heavy domain comprising the amino acid sequence of SEQ ID NO:4; (b) a variable light domain comprising the amino acid sequence of SEQ ID NO:8; (c) a variable heavy chain comprising a CDR1 comprising the amino acid sequence of SEQ ID NO:5, a CDR2 comprising the amino acid sequence of SEQ ID NO:6, and a CDR3 comprising the amino acid sequence of SEQ ID NO:7; or (d) a variable light chain comprising a CDR1 comprising the amino acid sequence of SEQ ID NO:9, a CDR2 comprising the amino acid sequence of SEQ ID NO:10, and a CDR3 comprising the amino acid sequence of SEQ ID NO:11. The nucleic acid may encode at least one amino acid sequence of SEQ ID NO:4-11. The nucleic acid may comprise at least one nucleotide sequence of SEQ ID NO:12-19.

The present invention is further directed to a vector comprising an isolated nucleic acid encoding an isolated antibody or antibody fragment thereof that binds to a voltage sensor paddle (VSP) of Na$_v$1.7.

The present invention is further directed to a vector comprising an isolated nucleic acid encoding an isolated antibody or antibody fragment thereof that binds to a voltage sensor paddle (VSP) of Na$_v$1.7, wherein the antibody or antibody fragment may comprises: (a) a variable heavy domain comprising an amino acid sequence having at least 80% identity with an amino acid sequence as set forth in SEQ ID NO:4; (b) a variable light domain comprising an amino acid sequence having at least 80% identity with an amino acid sequence as set forth in SEQ ID NO:8; (c) a variable heavy chain comprising a complementarity determining region (CDR) 1 comprising an amino acid sequence having at least 80% identity with an amino acid sequence as set forth in SEQ ID NO:5, a CDR2 comprising an amino acid sequence having at least 80% identity with an amino acid sequence as set forth in SEQ ID NO:6, and a CDR3 comprising an amino acid sequence having at least 80% identity with an amino acid sequence as set forth in SEQ ID NO:7; or (d) a variable light chain comprising a CDR1 comprising an amino acid sequence having at least 80% identity with an amino acid sequence as set forth in SEQ ID NO:9, a CDR2 comprising an amino acid sequence having at least 80% identity with an amino acid sequence as set forth in SEQ ID NO:10, and a CDR3 comprising an amino acid sequence having at least 80% identity with an amino acid sequence as set forth in SEQ ID NO:11.

The present invention is further directed to a vector comprising an isolated nucleic acid encoding an isolated nucleic acid encoding an isolated antibody or antibody fragment thereof that binds to a voltage sensor paddle (VSP) of Na$_v$1.7, wherein the antibody or antibody fragment may comprise: (a) a variable heavy domain comprising an amino acid sequence having at least 90% identity with an amino acid sequence as set forth in SEQ ID NO:4; (b) a variable light domain comprising an amino acid sequence having at least 90% identity with an amino acid sequence as set forth in SEQ ID NO:8; (c) a variable heavy chain comprising a CDR1 comprising an amino acid sequence having at least 90% identity with an amino acid sequence as set forth in SEQ ID NO:5, a CDR2 comprising an amino acid sequence having at least 90% identity with an amino acid sequence as set forth in SEQ ID NO:6, and a CDR3 comprising an amino acid sequence having at least 90% identity with an amino acid sequence as set forth in SEQ ID NO:7; or (d) a variable light chain comprising a CDR1 comprising an amino acid sequence having at least 90% identity with an amino acid sequence as set forth in SEQ ID NO:9, a CDR2 comprising an amino acid sequence having at least 90% identity with an amino acid sequence as set forth in SEQ ID NO:10, and a CDR3 comprising an amino acid sequence having at least 90% identity with an amino acid sequence as set forth in SEQ ID NO:11.

The present invention is further directed to a vector comprising an isolated nucleic acid encoding an isolated nucleic acid encoding an isolated antibody or antibody fragment thereof that binds to a voltage sensor paddle (VSP) of Na$_v$1.7, wherein the antibody or antibody fragment may comprise: (a) a variable heavy domain comprising the amino acid sequence of SEQ ID NO:4; (b) a variable light domain comprising the amino acid sequence of SEQ ID NO:8; (c) a variable heavy chain comprising a CDR1 comprising the amino acid sequence of SEQ ID NO:5, a CDR2 comprising the amino acid sequence of SEQ ID NO:6, and a CDR3 comprising the amino acid sequence of SEQ ID NO:7; or (d) a variable light chain comprising a CDR1 comprising the amino acid sequence of SEQ ID NO:9, a CDR2 comprising the amino acid sequence of SEQ ID NO:10, and a CDR3 comprising the amino acid sequence of SEQ ID NO:11.

The present invention is further directed to a host cell comprising a vector comprising an isolated nucleic acid encoding an isolated antibody or antibody fragment thereof that binds to a voltage sensor paddle (VSP) of Na$_v$1.7.

The present invention is further directed to a host cell comprising a vector comprising an isolated nucleic acid encoding an isolated antibody or antibody fragment thereof that binds to a voltage sensor paddle (VSP) of Na$_v$1.7, wherein the antibody or antibody fragment may comprises: (a) a variable heavy domain comprising an amino acid sequence having at least 80% identity with an amino acid sequence as set forth in SEQ ID NO:4; (b) a variable light domain comprising an amino acid sequence having at least 80% identity with an amino acid sequence as set forth in SEQ ID NO:8; (c) a variable heavy chain comprising a complementarity determining region (CDR) 1 comprising an amino acid sequence having at least 80% identity with an amino acid sequence as set forth in SEQ ID NO:5, a CDR2 comprising an amino acid sequence having at least 80% identity with an amino acid sequence as set forth in SEQ ID NO:6, and a CDR3 comprising an amino acid sequence having at least 80% identity with an amino acid sequence as set forth in SEQ ID NO:7; or (d) a variable light chain comprising a CDR1 comprising an amino acid sequence having at least 80% identity with an amino acid sequence as set forth in SEQ ID NO:9, a CDR2 comprising an amino acid sequence having at least 80% identity with an amino acid sequence as set forth in SEQ ID NO:10, and a CDR3 comprising an amino acid sequence having at least 80% identity with an amino acid sequence as set forth in SEQ ID NO:11.

The present invention is further directed to a host cell comprising a vector comprising an isolated nucleic acid encoding an isolated nucleic acid encoding an isolated antibody or antibody fragment thereof that binds to a voltage sensor paddle (VSP) of Na$_v$1.7, wherein the antibody or antibody fragment may comprise: (a) a variable heavy domain comprising an amino acid sequence having at least 90% identity with an amino acid sequence as set forth in SEQ ID NO:4; (b) a variable light domain comprising an amino acid sequence having at least 90% identity with an amino acid sequence as set forth in SEQ ID NO:8; (c) a variable heavy chain comprising a CDR1 comprising an amino acid sequence having at least 90% identity with an amino acid sequence as set forth in SEQ ID NO:5, a CDR2 comprising an amino acid sequence having at least 90% identity with an amino acid sequence as set forth in SEQ ID NO:6, and a CDR3 comprising an amino acid sequence having at least 90% identity with an amino acid sequence as set forth in SEQ ID NO:7; or (d) a variable light chain comprising a CDR1 comprising an amino acid sequence having at least 90% identity with an amino acid sequence as set forth in SEQ ID NO:9, a CDR2 comprising an amino acid sequence having at least 90% identity with an amino acid sequence as set forth in SEQ ID NO:10, and a CDR3 comprising an amino acid sequence having at least 90% identity with an amino acid sequence as set forth in SEQ ID NO:11.

The present invention is further directed to a host cell comprising a vector comprising an isolated nucleic acid encoding an isolated nucleic acid encoding an isolated antibody or antibody fragment thereof that binds to a voltage sensor paddle (VSP) of $Na_v1.7$, wherein the antibody or antibody fragment may comprise: (a) a variable heavy domain comprising the amino acid sequence of SEQ ID NO:4; (b) a variable light domain comprising the amino acid sequence of SEQ ID NO:8; (c) a variable heavy chain comprising a CDR1 comprising the amino acid sequence of SEQ ID NO:5, a CDR2 comprising the amino acid sequence of SEQ ID NO:6, and a CDR3 comprising the amino acid sequence of SEQ ID NO:7; or (d) a variable light chain comprising a CDR1 comprising the amino acid sequence of SEQ ID NO:9, a CDR2 comprising the amino acid sequence of SEQ ID NO:10, and a CDR3 comprising the amino acid sequence of SEQ ID NO:11.

The present invention is further directed to a pharmaceutical composition comprising an isolated antibody or antibody fragment thereof that binds to a voltage sensor paddle (VSP) of $Na_v1.7$. The pharmaceutical composition may further comprise a pharmaceutically acceptable carrier, excipient, or diluent. The pharmaceutical composition may comprise a therapeutically effective amount of the above-described antibody or antibody fragment.

The present invention is further directed to a pharmaceutical composition comprising an isolated antibody or antibody fragment thereof that binds to a voltage sensor paddle (VSP) of $Na_v1.7$, wherein the antibody or antibody fragment may comprises: (a) a variable heavy domain comprising an amino acid sequence having at least 80% identity with an amino acid sequence as set forth in SEQ ID NO:4; (b) a variable light domain comprising an amino acid sequence having at least 80% identity with an amino acid sequence as set forth in SEQ ID NO:8; (c) a variable heavy chain comprising a complementarity determining region (CDR) 1 comprising an amino acid sequence having at least 80% identity with an amino acid sequence as set forth in SEQ ID NO:5, a CDR2 comprising an amino acid sequence having at least 80% identity with an amino acid sequence as set forth in SEQ ID NO:6, and a CDR3 comprising an amino acid sequence having at least 80% identity with an amino acid sequence as set forth in SEQ ID NO:7; or (d) a variable light chain comprising a CDR1 comprising an amino acid sequence having at least 80% identity with an amino acid sequence as set forth in SEQ ID NO:9, a CDR2 comprising an amino acid sequence having at least 80% identity with an amino acid sequence as set forth in SEQ ID NO:10, and a CDR3 comprising an amino acid sequence having at least 80% identity with an amino acid sequence as set forth in SEQ ID NO:11. The pharmaceutical composition may further comprise a pharmaceutically acceptable carrier, excipient, or diluent. The pharmaceutical composition may comprise a therapeutically effective amount of the above-described antibody or antibody fragment.

The present invention is further directed to a pharmaceutical composition comprising an isolated antibody or antibody fragment thereof that binds to a voltage sensor paddle (VSP) of $Na_v1.7$, wherein the antibody or antibody fragment may comprise: (a) a variable heavy domain comprising an amino acid sequence having at least 90% identity with an amino acid sequence as set forth in SEQ ID NO:4; (b) a variable light domain comprising an amino acid sequence having at least 90% identity with an amino acid sequence as set forth in SEQ ID NO:8; (c) a variable heavy chain comprising a CDR1 comprising an amino acid sequence having at least 90% identity with an amino acid sequence as set forth in SEQ ID NO:5, a CDR2 comprising an amino acid sequence having at least 90% identity with an amino acid sequence as set forth in SEQ ID NO:6, and a CDR3 comprising an amino acid sequence having at least 90% identity with an amino acid sequence as set forth in SEQ ID NO:7; or (d) a variable light chain comprising a CDR1 comprising an amino acid sequence having at least 90% identity with an amino acid sequence as set forth in SEQ ID NO:9, a CDR2 comprising an amino acid sequence having at least 90% identity with an amino acid sequence as set forth in SEQ ID NO:10, and a CDR3 comprising an amino acid sequence having at least 90% identity with an amino acid sequence as set forth in SEQ ID NO:11. The pharmaceutical composition may further comprise a pharmaceutically acceptable carrier, excipient, or diluent. The pharmaceutical composition may comprise a therapeutically effective amount of the above-described antibody or antibody fragment.

The present invention is further directed to a pharmaceutical composition comprising an isolated antibody or antibody fragment thereof that binds to a voltage sensor paddle (VSP) of $Na_v1.7$, wherein the antibody or antibody fragment may comprise: (a) a variable heavy domain comprising the amino acid sequence of SEQ ID NO:4; (b) a variable light domain comprising the amino acid sequence of SEQ ID NO:8; (c) a variable heavy chain comprising a CDR1 comprising the amino acid sequence of SEQ ID NO:5, a CDR2 comprising the amino acid sequence of SEQ ID NO:6, and a CDR3 comprising the amino acid sequence of SEQ ID NO:7; or (d) a variable light chain comprising a CDR1 comprising the amino acid sequence of SEQ ID NO:9, a CDR2 comprising the amino acid sequence of SEQ ID NO:10, and a CDR3 comprising the amino acid sequence of SEQ ID NO:11. The pharmaceutical composition may further comprise a pharmaceutically acceptable carrier, excipient, or diluent. The pharmaceutical composition may comprise a therapeutically effective amount of the above-described antibody or antibody fragment.

The present invention is further directed to a method of treating pain in a subject in need thereof. The method may comprise administering an isolated antibody or antibody fragment thereof that binds to a voltage sensor paddle (VSP) of $Na_v1.7$.

The pain may be inflammatory pain, neuropathic pain, hyperalgesia, allodynia, paroxysmal extreme pain disorder, inherited erythromelalgia, cancer-associated pain, atypical pain, neurogenic inflammation-associated pain, chronic pain, or pathological pain or a combination thereof. The inflammatory pain may be arthritis pain, dental pain, low back pain, pain associated with inflammatory bowel disease, or pain associated with temporomandibular joint (TMJ), or a combination thereof. The neuropathic pain may be associated with diabetic neuropathy, chemotherapy, human immunodeficiency virus (HIV) infection, postherpetic neuralgia (PHN), surgery, spinal cord injury, or stroke, or a combination thereof. The surgery may be an amputation, thoracotomy, hernia surgery, or mastectomy. The neurogenic inflammation-associated pain condition may be complex regional pain syndrome (CRPS), headache, or migraine, or a combination thereof.

The pain may be associated with itch. The itch may be acute itch, chronic itch, histamine-dependent itch, or histamine-independent itch, or a combination thereof. The acute itch may be mediated by gastrin-releasing peptide (GRP). The acute itch may be mediated by GRP in superficial dorsal horn neurons. The chronic itch may be associated with atopic dermatitis, allergic contact dermatitis, psoriasis, renal disease, liver disease, zoster virus, or eczema, or a combination thereof.

The above method may further comprise suppressing pain in the subject.

The above method may further comprise increasing a threshold of pain in the subject.

The subject may be human, bovine, canine, equine, feline, or porcine.

The present invention is further directed to a method of treating pain in a subject in need thereof. The method may comprise administering an isolated antibody or antibody fragment thereof that binds to a voltage sensor paddle (VSP) of $Na_v1.7$, wherein the antibody or antibody fragment may comprises: (a) a variable heavy domain comprising an amino acid sequence having at least 80% identity with an amino acid sequence as set forth in SEQ ID NO:4; (b) a variable light domain comprising an amino acid sequence having at least 80% identity with an amino acid sequence as set forth in SEQ ID NO:8; (c) a variable heavy chain comprising a complementarity determining region (CDR) 1 comprising an amino acid sequence having at least 80% identity with an amino acid sequence as set forth in SEQ ID NO:5, a CDR2 comprising an amino acid sequence having at least 80% identity with an amino acid sequence as set forth in SEQ ID NO:6, and a CDR3 comprising an amino acid sequence having at least 80% identity with an amino acid sequence as set forth in SEQ ID NO:7; or (d) a variable light chain comprising a CDR1 comprising an amino acid sequence having at least 80% identity with an amino acid sequence as set forth in SEQ ID NO:9, a CDR2 comprising an amino acid sequence having at least 80% identity with an amino acid sequence as set forth in SEQ ID NO:10, and a CDR3 comprising an amino acid sequence having at least 80% identity with an amino acid sequence as set forth in SEQ ID NO:11.

The pain may be inflammatory pain, neuropathic pain, hyperalgesia, allodynia, paroxysmal extreme pain disorder, inherited erythromelalgia, cancer-associated pain, atypical pain, neurogenic inflammation-associated pain, chronic pain, or pathological pain or a combination thereof. The inflammatory pain may be arthritis pain, dental pain, low back pain, pain associated with inflammatory bowel disease, or pain associated with temporomandibular joint (TMJ), or a combination thereof. The neuropathic pain may be associated with diabetic neuropathy, chemotherapy, human immunodeficiency virus (HIV) infection, postherpetic neuralgia (PHN), surgery, spinal cord injury, or stroke, or a combination thereof. The surgery may be an amputation, thoracotomy, hernia surgery, or mastectomy. The neurogenic inflammation-associated pain condition may be complex regional pain syndrome (CRPS), headache, or migraine, or a combination thereof.

The pain may be associated with itch. The itch may be acute itch, chronic itch, histamine-dependent itch, or histamine-independent itch, or a combination thereof. The acute itch may be mediated by gastrin-releasing peptide (GRP). The acute itch may be mediated by GRP in superficial dorsal horn neurons. The chronic itch may be associated with atopic dermatitis, allergic contact dermatitis, psoriasis, renal disease, liver disease, zoster virus, or eczema, or a combination thereof.

The above method may further comprise suppressing pain in the subject.

The above method may further comprise increasing a threshold of pain in the subject.

The subject may be human, bovine, canine, equine, feline, or porcine.

The present invention is further directed to a method of treating pain in a subject in need thereof. The method may comprise administering an isolated antibody or antibody fragment thereof that binds to a voltage sensor paddle (VSP) of $Na_v1.7$, wherein the antibody or antibody fragment may comprise: (a) a variable heavy domain comprising an amino acid sequence having at least 90% identity with an amino acid sequence as set forth in SEQ ID NO:4; (b) a variable light domain comprising an amino acid sequence having at least 90% identity with an amino acid sequence as set forth in SEQ ID NO:8; (c) a variable heavy chain comprising a CDR1 comprising an amino acid sequence having at least 90% identity with an amino acid sequence as set forth in SEQ ID NO:5, a CDR2 comprising an amino acid sequence having at least 90% identity with an amino acid sequence as set forth in SEQ ID NO:6, and a CDR3 comprising an amino acid sequence having at least 90% identity with an amino acid sequence as set forth in SEQ ID NO:7; or (d) a variable light chain comprising a CDR1 comprising an amino acid sequence having at least 90% identity with an amino acid sequence as set forth in SEQ ID NO:9, a CDR2 comprising an amino acid sequence having at least 90% identity with an amino acid sequence as set forth in SEQ ID NO:10, and a CDR3 comprising an amino acid sequence having at least 90% identity with an amino acid sequence as set forth in SEQ ID NO:11.

The pain may be inflammatory pain, neuropathic pain, hyperalgesia, allodynia, paroxysmal extreme pain disorder, inherited erythromelalgia, cancer-associated pain, atypical pain, neurogenic inflammation-associated pain, chronic pain, or pathological pain or a combination thereof. The inflammatory pain may be arthritis pain, dental pain, low back pain, pain associated with inflammatory bowel disease, or pain associated with temporomandibular joint (TMJ), or a combination thereof. The neuropathic pain may be associated with diabetic neuropathy, chemotherapy, human immunodeficiency virus (HIV) infection, postherpetic neuralgia (PHN), surgery, spinal cord injury, or stroke, or a combination thereof. The surgery may be an amputation, thoracotomy, hernia surgery, or mastectomy. The neurogenic inflammation-associated pain condition may be complex regional pain syndrome (CRPS), headache, or migraine, or a combination thereof.

The pain may be associated with itch. The itch may be acute itch, chronic itch, histamine-dependent itch, or histamine-independent itch, or a combination thereof. The acute itch may be mediated by gastrin-releasing peptide (GRP). The acute itch may be mediated by GRP in superficial dorsal horn neurons. The chronic itch may be associated with atopic dermatitis, allergic contact dermatitis, psoriasis, renal disease, liver disease, zoster virus, or eczema, or a combination thereof.

The above method may further comprise suppressing pain in the subject.

The above method may further comprise increasing a threshold of pain in the subject.

The subject may be human, bovine, canine, equine, feline, or porcine.

The present invention is further directed to a method of treating pain in a subject in need thereof. The method may comprise administering an isolated antibody or antibody fragment thereof that binds to a voltage sensor paddle (VSP) of $Na_v1.7$, wherein the antibody or antibody fragment may comprise: (a) a variable heavy domain comprising the amino acid sequence of SEQ ID NO:4; (b) a variable light domain comprising the amino acid sequence of SEQ ID NO:8; (c) a variable heavy chain comprising a CDR1 comprising the amino acid sequence of SEQ ID NO:5, a CDR2 comprising the amino acid sequence of SEQ ID NO:6, and a CDR3 comprising the amino acid sequence of SEQ ID NO:7; or (d) a variable light chain comprising a CDR1 comprising the amino acid sequence of SEQ ID NO:9, a CDR2 comprising the amino acid sequence of SEQ ID NO:10, and a CDR3 comprising the amino acid sequence of SEQ ID NO:11.

The pain may be inflammatory pain, neuropathic pain, hyperalgesia, allodynia, paroxysmal extreme pain disorder, inherited erythromelalgia, cancer-associated pain, atypical pain, neurogenic inflammation-associated pain, chronic pain, or pathological pain or a combination thereof. The inflammatory pain may be arthritis pain, dental pain, low back pain, pain associated with inflammatory bowel disease, or pain associated with temporomandibular joint (TMJ), or a combination thereof. The neuropathic pain may be associated with diabetic neuropathy, chemotherapy, human immunodeficiency virus (HIV) infection, postherpetic neuralgia (PHN), surgery, spinal cord injury, or stroke, or a combination thereof. The surgery may be an amputation, thoracotomy, hernia surgery, or mastectomy. The neurogenic inflammation-associated pain condition may be complex regional pain syndrome (CRPS), headache, or migraine, or a combination thereof.

The pain may be associated with itch. The itch may be acute itch, chronic itch, histamine-dependent itch, or histamine-independent itch, or a combination thereof. The acute itch may be mediated by gastrin-releasing peptide (GRP). The acute itch may be mediated by GRP in superficial dorsal horn neurons. The chronic itch may be associated with atopic dermatitis, allergic contact dermatitis, psoriasis, renal disease, liver disease, zoster virus, or eczema, or a combination thereof.

The above method may further comprise suppressing pain in the subject.

The above method may further comprise increasing a threshold of pain in the subject.

The subject may be human, bovine, canine, equine, feline, or porcine.

The present invention is further directed to a method of treating itch in a subject in need thereof. The method may comprise administering an isolated antibody or antibody fragment thereof that binds to a voltage sensor paddle (VSP) of $Na_v1.7$.

The itch may be acute itch, chronic itch, histamine-dependent itch, or histamine-independent itch, or a combination thereof. The acute itch may be mediated by gastrin-releasing peptide (GRP). The acute itch may be mediated by GRP in superficial dorsal horn neurons. The chronic itch may be associated with atopic dermatitis, allergic contact dermatitis, psoriasis, renal disease, liver disease, zoster virus, or eczema, or a combination thereof.

The itch may be associated with allergic contact dermatitis.

The subject may be human, bovine, canine, equine, feline, or porcine.

The present invention is further directed to a method of treating itch in a subject in need thereof. The method may comprise administering an isolated antibody or antibody fragment thereof that binds to a voltage sensor paddle (VSP) of $Na_v1.7$, wherein the antibody or antibody fragment may comprises: (a) a variable heavy domain comprising an amino acid sequence having at least 80% identity with an amino acid sequence as set forth in SEQ ID NO:4; (b) a variable light domain comprising an amino acid sequence having at least 80% identity with an amino acid sequence as set forth in SEQ ID NO:8; (c) a variable heavy chain comprising a complementarity determining region (CDR) 1 comprising an amino acid sequence having at least 80% identity with an amino acid sequence as set forth in SEQ ID NO:5, a CDR2 comprising an amino acid sequence having at least 80% identity with an amino acid sequence as set forth in SEQ ID NO:6, and a CDR3 comprising an amino acid sequence having at least 80% identity with an amino acid sequence as set forth in SEQ ID NO:7; or (d) a variable light chain comprising a CDR1 comprising an amino acid sequence having at least 80% identity with an amino acid sequence as set forth in SEQ ID NO:9, a CDR2 comprising an amino acid sequence having at least 80% identity with an amino acid sequence as set forth in SEQ ID NO:10, and a CDR3 comprising an amino acid sequence having at least 80% identity with an amino acid sequence as set forth in SEQ ID NO:11.

The itch may be acute itch, chronic itch, histamine-dependent itch, or histamine-independent itch, or a combination thereof. The acute itch may be mediated by gastrin-releasing peptide (GRP). The acute itch may be mediated by GRP in superficial dorsal horn neurons. The chronic itch may be associated with atopic dermatitis, allergic contact dermatitis, psoriasis, renal disease, liver disease, zoster virus, or eczema, or a combination thereof.

The itch may be associated with allergic contact dermatitis.

The subject may be human, bovine, canine, equine, feline, or porcine.

The present invention is further directed to a method of treating itch in a subject in need thereof. The method may comprise administering an isolated antibody or antibody fragment thereof that binds to a voltage sensor paddle (VSP) of $Na_v1.7$, wherein the antibody or antibody fragment may comprise: (a) a variable heavy domain comprising an amino acid sequence having at least 90% identity with an amino acid sequence as set forth in SEQ ID NO:4; (b) a variable light domain comprising an amino acid sequence having at least 90% identity with an amino acid sequence as set forth in SEQ ID NO:8; (c) a variable heavy chain comprising a CDR1 comprising an amino acid sequence having at least 90% identity with an amino acid sequence as set forth in SEQ ID NO:5, a CDR2 comprising an amino acid sequence having at least 90% identity with an amino acid sequence as set forth in SEQ ID NO:6, and a CDR3 comprising an amino acid sequence having at least 90% identity with an amino acid sequence as set forth in SEQ ID NO:7; or (d) a variable light chain comprising a CDR1 comprising an amino acid sequence having at least 90% identity with an amino acid sequence as set forth in SEQ ID NO:9, a CDR2 comprising an amino acid sequence having at least 90% identity with an amino acid sequence as set forth in SEQ ID NO:10, and a CDR3 comprising an amino acid sequence having at least 90% identity with an amino acid sequence as set forth in SEQ ID NO:11.

The itch may be acute itch, chronic itch, histamine-dependent itch, or histamine-independent itch, or a combination thereof. The acute itch may be mediated by gastrin-releasing peptide (GRP). The acute itch may be mediated by GRP in superficial dorsal horn neurons. The chronic itch may be associated with atopic dermatitis, allergic contact dermatitis, psoriasis, renal disease, liver disease, zoster virus, or eczema, or a combination thereof.

The itch may be associated with allergic contact dermatitis.

The subject may be human, bovine, canine, equine, feline, or porcine.

The present invention is further directed to a method of treating itch in a subject in need thereof. The method may comprise administering an isolated antibody or antibody fragment thereof that binds to a voltage sensor paddle (VSP) of Na$_v$1.7, wherein the antibody or antibody fragment may comprise: (a) a variable heavy domain comprising the amino acid sequence of SEQ ID NO:4; (b) a variable light domain comprising the amino acid sequence of SEQ ID NO:8; (c) a variable heavy chain comprising a CDR1 comprising the amino acid sequence of SEQ ID NO:5, a CDR2 comprising the amino acid sequence of SEQ ID NO:6, and a CDR3 comprising the amino acid sequence of SEQ ID NO:7; or (d) a variable light chain comprising a CDR1 comprising the amino acid sequence of SEQ ID NO:9, a CDR2 comprising the amino acid sequence of SEQ ID NO:10, and a CDR3 comprising the amino acid sequence of SEQ ID NO:11.

The itch may be acute itch, chronic itch, histamine-dependent itch, or histamine-independent itch, or a combination thereof. The acute itch may be mediated by gastrin-releasing peptide (GRP). The acute itch may be mediated by GRP in superficial dorsal horn neurons. The chronic itch may be associated with atopic dermatitis, allergic contact dermatitis, psoriasis, renal disease, liver disease, zoster virus, or eczema, or a combination thereof.

The itch may be associated with allergic contact dermatitis.

The subject may be human, bovine, canine, equine, feline, or porcine.

The present invention is further directed to a method of treating neurogenic inflammation in a subject in need thereof. The method may comprise administering an isolated antibody or antibody fragment thereof that binds to a voltage sensor paddle (VSP) of Na$_v$1.7.

The neurogenic inflammation may be associated with asthma, arthritis, eczema, headache, migraine, or psoriasis, or a combination thereof.

The subject may be human, bovine, canine, equine, feline, or porcine.

The present invention is further directed to a method of treating neurogenic inflammation in a subject in need thereof. The method may comprise administering an isolated antibody or antibody fragment thereof that binds to a voltage sensor paddle (VSP) of Na$_v$1.7, wherein the antibody or antibody fragment may comprises: (a) a variable heavy domain comprising an amino acid sequence having at least 80% identity with an amino acid sequence as set forth in SEQ ID NO:4; (b) a variable light domain comprising an amino acid sequence having at least 80% identity with an amino acid sequence as set forth in SEQ ID NO:8; (c) a variable heavy chain comprising a complementarity determining region (CDR) 1 comprising an amino acid sequence having at least 80% identity with an amino acid sequence as set forth in SEQ ID NO:5, a CDR2 comprising an amino acid sequence having at least 80% identity with an amino acid sequence as set forth in SEQ ID NO:6, and a CDR3 comprising an amino acid sequence having at least 80% identity with an amino acid sequence as set forth in SEQ ID NO:7; or (d) a variable light chain comprising a CDR1 comprising an amino acid sequence having at least 80% identity with an amino acid sequence as set forth in SEQ ID NO:9, a CDR2 comprising an amino acid sequence having at least 80% identity with an amino acid sequence as set forth in SEQ ID NO:10, and a CDR3 comprising an amino acid sequence having at least 80% identity with an amino acid sequence as set forth in SEQ ID NO:11.

The neurogenic inflammation may be associated with asthma, arthritis, eczema, headache, migraine, or psoriasis, or a combination thereof.

The subject may be human, bovine, canine, equine, feline, or porcine.

The present invention is further directed to a method of treating neurogenic inflammation in a subject in need thereof. The method may comprise administering an isolated antibody or antibody fragment thereof that binds to a voltage sensor paddle (VSP) of Na$_v$1.7, wherein the antibody or antibody fragment may comprise: (a) a variable heavy domain comprising an amino acid sequence having at least 90% identity with an amino acid sequence as set forth in SEQ ID NO:4; (b) a variable light domain comprising an amino acid sequence having at least 90% identity with an amino acid sequence as set forth in SEQ ID NO:8; (c) a variable heavy chain comprising a CDR1 comprising an amino acid sequence having at least 90% identity with an amino acid sequence as set forth in SEQ ID NO:5, a CDR2 comprising an amino acid sequence having at least 90% identity with an amino acid sequence as set forth in SEQ ID NO:6, and a CDR3 comprising an amino acid sequence having at least 90% identity with an amino acid sequence as set forth in SEQ ID NO:7; or (d) a variable light chain comprising a CDR1 comprising an amino acid sequence having at least 90% identity with an amino acid sequence as set forth in SEQ ID NO:9, a CDR2 comprising an amino acid sequence having at least 90% identity with an amino acid sequence as set forth in SEQ ID NO:10, and a CDR3 comprising an amino acid sequence having at least 90% identity with an amino acid sequence as set forth in SEQ ID NO:11.

The neurogenic inflammation may be associated with asthma, arthritis, eczema, headache, migraine, or psoriasis, or a combination thereof.

The subject may be human, bovine, canine, equine, feline, or porcine.

The present invention is further directed to a method of treating neurogenic inflammation in a subject in need thereof. The method may comprise administering an isolated antibody or antibody fragment thereof that binds to a voltage sensor paddle (VSP) of Na$_v$1.7, wherein the antibody or antibody fragment may comprise: (a) a variable heavy domain comprising the amino acid sequence of SEQ ID NO:4; (b) a variable light domain comprising the amino acid sequence of SEQ ID NO:8; (c) a variable heavy chain comprising a CDR1 comprising the amino acid sequence of SEQ ID NO:5, a CDR2 comprising the amino acid sequence of SEQ ID NO:6, and a CDR3 comprising the amino acid sequence of SEQ ID NO:7; or (d) a variable light chain comprising a CDR1 comprising the amino acid sequence of SEQ ID NO:9, a CDR2 comprising the amino acid sequence of SEQ ID NO:10, and a CDR3 comprising the amino acid sequence of SEQ ID NO:11.

The neurogenic inflammation may be associated with asthma, arthritis, eczema, headache, migraine, or psoriasis, or a combination thereof.

The subject may be human, bovine, canine, equine, feline, or porcine.

The present invention is further directed to a method of treating cough in a subject in need thereof. The method may comprise administering an isolated antibody or antibody fragment thereof that binds to a voltage sensor paddle (VSP) of Na$_v$1.7.

The cough may be pathological or chronic cough.

The subject may be human, bovine, canine, equine, feline, or porcine.

The present invention is further directed to a method of treating cough in a subject in need thereof. The method may comprise administering an isolated antibody or antibody fragment thereof that binds to a voltage sensor paddle (VSP) of Na$_v$1.7, wherein the antibody or antibody fragment may comprises: (a) a variable heavy domain comprising an amino acid sequence having at least 80% identity with an amino acid sequence as set forth in SEQ ID NO:4; (b) a variable light domain comprising an amino acid sequence having at least 80% identity with an amino acid sequence as set forth in SEQ ID NO:8; (c) a variable heavy chain comprising a complementarity determining region (CDR) 1 comprising an amino acid sequence having at least 80% identity with an amino acid sequence as set forth in SEQ ID NO:5, a CDR2 comprising an amino acid sequence having at least 80% identity with an amino acid sequence as set forth in SEQ ID NO:6, and a CDR3 comprising an amino acid sequence having at least 80% identity with an amino acid sequence as set forth in SEQ ID NO:7; or (d) a variable light chain comprising a CDR1 comprising an amino acid sequence having at least 80% identity with an amino acid sequence as set forth in SEQ ID NO:9, a CDR2 comprising an amino acid sequence having at least 80% identity with an amino acid sequence as set forth in SEQ ID NO:10, and a CDR3 comprising an amino acid sequence having at least 80% identity with an amino acid sequence as set forth in SEQ ID NO:11.

The cough may be pathological or chronic cough.

The subject may be human, bovine, canine, equine, feline, or porcine.

The present invention is further directed to a method of treating cough in a subject in need thereof. The method may comprise administering an isolated antibody or antibody fragment thereof that binds to a voltage sensor paddle (VSP) of $Na_v1.7$, wherein the antibody or antibody fragment may comprise: (a) a variable heavy domain comprising an amino acid sequence having at least 90% identity with an amino acid sequence as set forth in SEQ ID NO:4; (b) a variable light domain comprising an amino acid sequence having at least 90% identity with an amino acid sequence as set forth in SEQ ID NO:8; (c) a variable heavy chain comprising a CDR1 comprising an amino acid sequence having at least 90% identity with an amino acid sequence as set forth in SEQ ID NO:5, a CDR2 comprising an amino acid sequence having at least 90% identity with an amino acid sequence as set forth in SEQ ID NO:6, and a CDR3 comprising an amino acid sequence having at least 90% identity with an amino acid sequence as set forth in SEQ ID NO:7; or (d) a variable light chain comprising a CDR1 comprising an amino acid sequence having at least 90% identity with an amino acid sequence as set forth in SEQ ID NO:9, a CDR2 comprising an amino acid sequence having at least 90% identity with an amino acid sequence as set forth in SEQ ID NO:10, and a CDR3 comprising an amino acid sequence having at least 90% identity with an amino acid sequence as set forth in SEQ ID NO:11.

The cough may be pathological or chronic cough.

The subject may be human, bovine, canine, equine, feline, or porcine.

The present invention is further directed to a method of treating cough in a subject in need thereof. The method may comprise administering an isolated antibody or antibody fragment thereof that binds to a voltage sensor paddle (VSP) of $Na_v1.7$, wherein the antibody or antibody fragment may comprise: (a) a variable heavy domain comprising the amino acid sequence of SEQ ID NO:4; (b) a variable light domain comprising the amino acid sequence of SEQ ID NO:8; (c) a variable heavy chain comprising a CDR1 comprising the amino acid sequence of SEQ ID NO:5, a CDR2 comprising the amino acid sequence of SEQ ID NO:6, and a CDR3 comprising the amino acid sequence of SEQ ID NO:7; or (d) a variable light chain comprising a CDR1 comprising the amino acid sequence of SEQ ID NO:9, a CDR2 comprising the amino acid sequence of SEQ ID NO:10, and a CDR3 comprising the amino acid sequence of SEQ ID NO:11.

The cough may be pathological or chronic cough.

The subject may be human, bovine, canine, equine, feline, or porcine.

The present invention is further directed to a kit for detecting $Na_v1.7$, wherein the kit comprises an isolated antibody or antibody fragment thereof that binds to a voltage sensor paddle (VSP) of $Na_v1.7$.

The present invention is further directed to a kit for detecting $Na_v1.7$, wherein the kit comprises an isolated antibody or antibody fragment thereof that binds to a voltage sensor paddle (VSP) of $Na_v1.7$, wherein the antibody or antibody fragment may comprises: (a) a variable heavy domain comprising an amino acid sequence having at least 80% identity with an amino acid sequence as set forth in SEQ ID NO:4; (b) a variable light domain comprising an amino acid sequence having at least 80% identity with an amino acid sequence as set forth in SEQ ID NO:8; (c) a variable heavy chain comprising a complementarity determining region (CDR) 1 comprising an amino acid sequence having at least 80% identity with an amino acid sequence as set forth in SEQ ID NO:5, a CDR2 comprising an amino acid sequence having at least 80% identity with an amino acid sequence as set forth in SEQ ID NO:6, and a CDR3 comprising an amino acid sequence having at least 80% identity with an amino acid sequence as set forth in SEQ ID NO:7; or (d) a variable light chain comprising a CDR1 comprising an amino acid sequence having at least 80% identity with an amino acid sequence as set forth in SEQ ID NO:9, a CDR2 comprising an amino acid sequence having at least 80% identity with an amino acid sequence as set forth in SEQ ID NO:10, and a CDR3 comprising an amino acid sequence having at least 80% identity with an amino acid sequence as set forth in SEQ ID NO:11.

The present invention is further directed to a kit for detecting $Na_v1.7$, wherein the kit comprises an isolated antibody or antibody fragment thereof that binds to a voltage sensor paddle (VSP) of $Na_v1.7$, wherein the antibody or antibody fragment may comprise: (a) a variable heavy domain comprising an amino acid sequence having at least 90% identity with an amino acid sequence as set forth in SEQ ID NO:4; (b) a variable light domain comprising an amino acid sequence having at least 90% identity with an amino acid sequence as set forth in SEQ ID NO:8; (c) a variable heavy chain comprising a CDR1 comprising an amino acid sequence having at least 90% identity with an amino acid sequence as set forth in SEQ ID NO:5, a CDR2 comprising an amino acid sequence having at least 90% identity with an amino acid sequence as set forth in SEQ ID NO:6, and a CDR3 comprising an amino acid sequence having at least 90% identity with an amino acid sequence as set forth in SEQ ID NO:7; or (d) a variable light chain comprising a CDR1 comprising an amino acid sequence having at least 90% identity with an amino acid sequence as set forth in SEQ ID NO:9, a CDR2 comprising an amino acid sequence having at least 90% identity with an amino acid sequence as set forth in SEQ ID NO:10, and a CDR3 comprising an amino acid sequence having at least 90% identity with an amino acid sequence as set forth in SEQ ID NO:11.

The present invention is further directed to a kit for detecting $Na_v1.7$, wherein the kit comprises an isolated antibody or antibody fragment thereof that binds to a voltage sensor paddle (VSP) of $Na_v1.7$, wherein the antibody or antibody fragment may comprise: (a) a variable heavy domain comprising the amino acid sequence of SEQ ID NO:4; (b) a variable light domain comprising the amino acid sequence of SEQ ID NO:8; (c) a variable heavy chain comprising a CDR1 comprising the amino acid sequence of SEQ ID NO:5, a CDR2 comprising the amino acid sequence of SEQ ID NO:6, and a CDR3 comprising the amino acid sequence of SEQ ID NO:7; or (d) a variable light chain comprising a CDR1 comprising the amino acid sequence of SEQ ID NO:9, a CDR2 comprising the amino acid sequence of SEQ ID NO:10, and a CDR3 comprising the amino acid sequence of SEQ ID NO:11.

The present invention is further directed to an isolated antibody or antibody fragment thereof which binds to $Na_v1.7$, wherein the antibody or antibody fragment binds to an amino acid sequence as set forth in SEQ ID NO:20. The antibody or antibody fragment may not inhibit $Na_v1.7$.

The present invention is further directed to a peptide comprising (a) an amino acid sequence having at least 80% identity with an amino sequence as set forth in SEQ ID NO:21; (b) an amino acid sequence having at least 80% identity with an amino acid sequence as set forth in SEQ ID NO:23; (c) an amino acid sequence having at least 80% identity with an amino acid sequence as set forth in SEQ ID NO:50; or (d) an amino acid sequence having at least 80% identity with an amino acid sequence as set forth in SEQ ID NO:51.

The peptide may comprise (a) an amino acid sequence having at least 95% identity with the amino sequence as set forth in SEQ ID NO:21; (b) an amino acid sequence having at least 95% identity with the amino acid sequence as set forth in SEQ ID NO:23; (c) an amino acid sequence having at least 95% identity with the amino acid sequence as set forth in SEQ ID NO:50; or (d) an amino acid sequence having at least 95% identity with the amino acid sequence as set forth in SEQ ID NO:51.

The peptide may comprise (a) the amino acid sequence as set forth in SEQ ID NO:21; (b) the amino acid sequence as set forth in SEQ ID NO:23; (c) the amino acid sequence as set forth in SEQ ID NO:50; or (d) the amino acid sequence as set forth in SEQ ID NO:51.

The peptide may comprise the amino acid sequence as set forth in SEQ ID NO:21.

The peptide may comprise the amino acid sequence as set forth in SEQ ID NO:23.

The peptide may comprise the amino acid sequence as set forth in SEQ ID NO:50.

The peptide may comprise the amino acid sequence as set forth in SEQ ID NO:51.

The present invention is further directed to an isolated nucleic acid encoding a peptide comprising (a) an amino acid sequence having at least 80% identity with an amino sequence as set forth in SEQ ID NO:21; (b) an amino acid sequence having at least 80% identity with an amino acid sequence as set forth in SEQ ID NO:23; (c) an amino acid sequence having at least 80% identity with an amino acid sequence as set forth in SEQ ID NO:50; or (d) an amino acid sequence having at least 80% identity with an amino acid sequence as set forth in SEQ ID NO:51.

The present invention is further directed to an isolated nucleic acid encoding the peptide may comprise (a) an amino acid sequence having at least 95% identity with the amino sequence as set forth in SEQ ID NO:21; (b) an amino acid sequence having at least 95% identity with the amino acid sequence as set forth in SEQ ID NO:23; (c) an amino acid sequence having at least 95% identity with the amino acid sequence as set forth in SEQ ID NO:50; or (d) an amino acid sequence having at least 95% identity with the amino acid sequence as set forth in SEQ ID NO:51.

The present invention is further directed to an isolated nucleic acid encoding the peptide may comprise (a) the amino acid sequence as set forth in SEQ ID NO:21; (b) the amino acid sequence as set forth in SEQ ID NO:23; (c) the amino acid sequence as set forth in SEQ ID NO:50; or (d) the amino acid sequence as set forth in SEQ ID NO:51.

The present invention is further directed to an isolated nucleic acid encoding the peptide may comprise the amino acid sequence as set forth in SEQ ID NO:21.

The present invention is further directed to an isolated nucleic acid encoding the peptide may comprise the amino acid sequence as set forth in SEQ ID NO:23.

The present invention is further directed to an isolated nucleic acid encoding the peptide may comprise the amino acid sequence as set forth in SEQ ID NO:50.

The present invention is further directed to an isolated nucleic acid encoding the peptide may comprise the amino acid sequence as set forth in SEQ ID NO:51.

BRIEF DESCRIPTION OF THE DRAWINGS

FIG. 1 shows (A) the amino acid sequence of human $Na_v1.7$ (GenBank Accession No. NP_002968), in which the underlining denotes an epitope recognized by the 1E16 monoclonal antibody; and (B) shows the amino acid sequence of an human $Na_v1.7$ epitope recognized by the 1E16 monoclonal antibody.

FIG. 2 shows (A) the nucleotide sequence encoding the variable heavy chain of the 1E16 monoclonal antibody; and (B) the nucleotide sequence encoding the variable light chain of the 1E16 monoclonal antibody. The respective complementarity determining regions (CDRs) of the variable heavy and light chains are denoted by underlining.

FIG. 3 shows (A) the amino acid sequence of the variable heavy chain of the 1E16 monoclonal antibody; and (B) the amino acid sequence of the variable light chain of the 1E16 monoclonal antibody. The respective CDRs of the variable heavy and light chains are denoted by underlining.

FIG. 8 shows (A) an alignment of the respective amino acid sequences of the loop region between transmembrane helices S3 and S4 from DII of human $Na_v$ subtypes; and (B) an alignment of the respective amino acid sequences of the loop region between transmembrane helices S3 and S4 from different species of $Na_v$ subtypes that were used for the electrophysiological recordings in HEK293 cells (The sequence differences among the $Na_v$ subtypes used for electrophysiological recording was as significant as that of human $Na_v$ subtypes). The brackets in (A) and (B) denote the region of human $Na_v1.7$ that was used to raise the 1E16 mAb. The underlined residues in (B) denote species-specific differences, and also in (B) h=human, r=rat, and m=mouse.

*P<0.05, compared with corresponding control antibody. n=5 mice/group. (C) Intrathecal (i.t.) injection of 1E16 (50 μg) reduces the CCI-induced neuropathic pain (mechanical allodynia). *P<0.05, compared with control antibody, n=6 mice/group. (D) Systemic injection of 1E16 (10 mg/kg, i.v.) reduces the CCI-induced neuropathic pain (mechanical allodynia). *P<0.05, compared with control antibody, n=6 mice/group. (E, F) 1E16 inhibits excitatory synaptic transmission in spinal cord slices. (e) Traces of spontaneous EPSCs (sEPSCs) in lamina IIo neurons. Low panel, enlargements of traces (1, 2, 3) before and during the control Ab (1I5) and 1E16 treatment (300 nM). (f) Frequency of sEPSCs in lamina IIo neurons. *P<0.05, compared with no treatment baseline; #P<0.05, compared with control Ab (300 nM), n=5 neurons/group.

Figure 11:
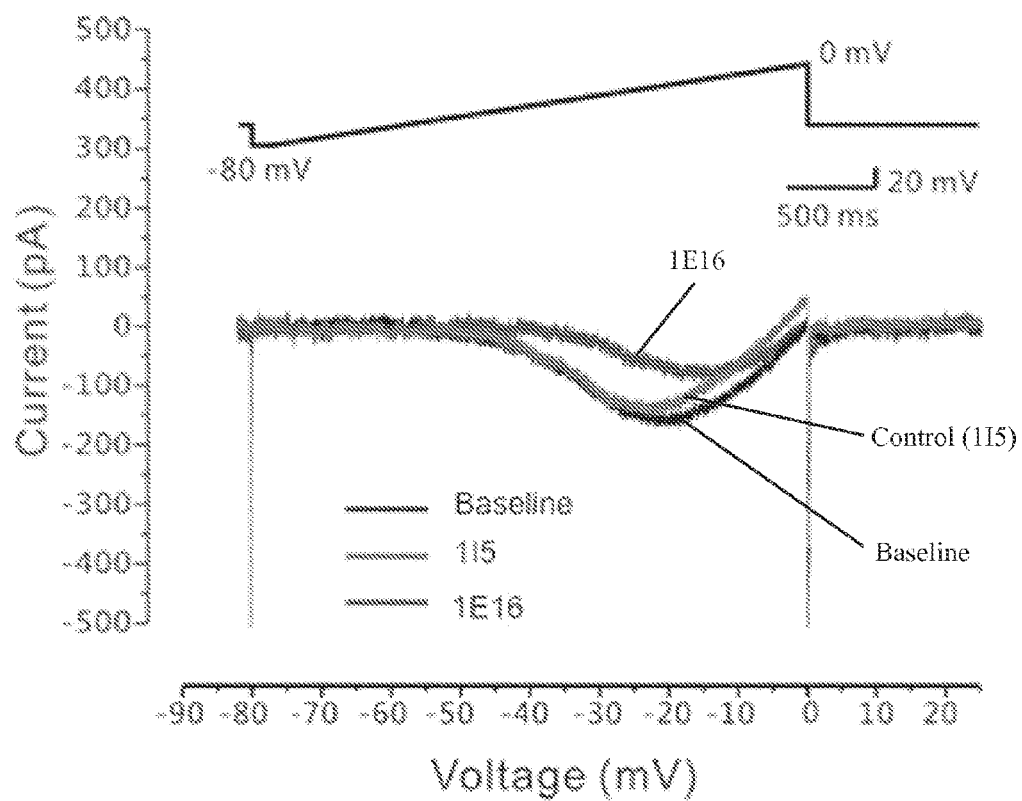

FIG. 11 shows the effect of the 1E16 mAb on persistent sodium currents (INaPs) in small-sized neurons of whole mount dorsal root ganglions (DRGs) from naïve mice and mice with nerve injury (CCI.). (A) shows traces of persistent sodium currents (INaPs) in normal conditions (without treatment) and after treatment with the control 1I5 antibody (300 nM) and 1E16 antibody (300 nM). (B) shows the amplitudes of INaP currents in the DRG neurons. In (b), CCI (1 w) increased the INaP currents and 1E16 mAb (300 nM) produced greater inhibition of INaP in the neuropathic pain condition. In contrast, the control mAb 1I5 had no effect. *P<0.05, n=5-17 neurons/group. The number of recorded neurons is indicated in each column. Data are shown as means±S.E.M.

Figure 12:
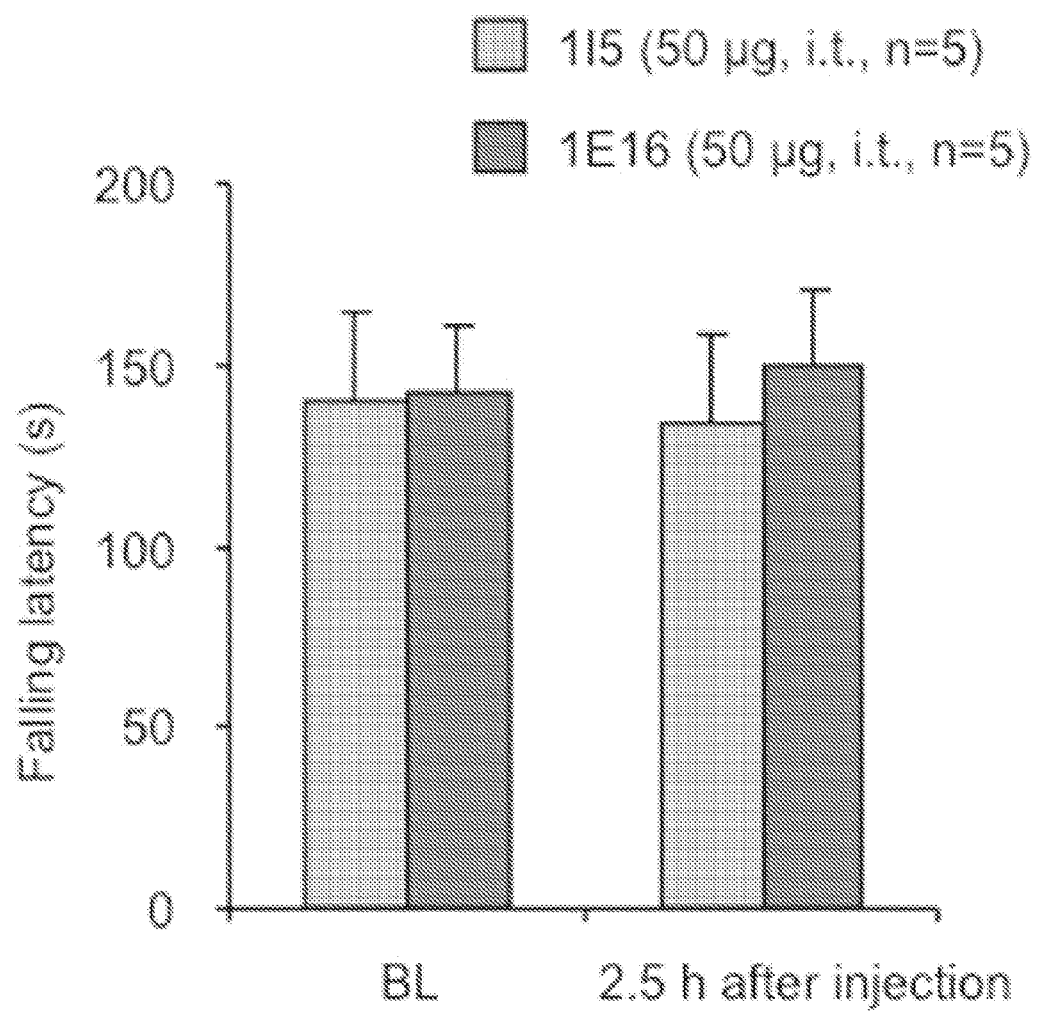

FIG. 12 shows the falling latency (i.e., time on the rota-rod) of mice in a rota-rod test before and after intrathecal injection of 1E16 Ab and the control Ab 1I5 (50 μg). The 1E16 Ab had no effect on motor function following intrathecal injection. Data are shown as means±S.E.M. P>0.05, compared to the control Ab 1I5 and baseline, n=5 mice.

Figure 13:
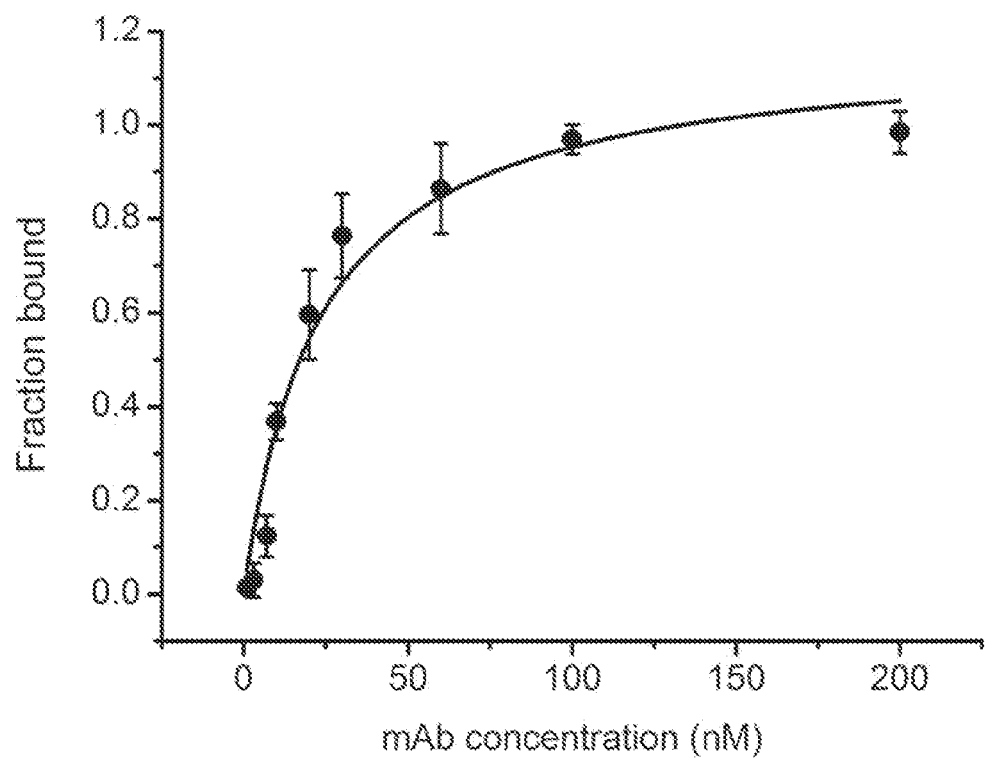

FIG. 13 shows the binding of the 1E16 antibody to human $Na_v1.7$. The data are shown as means±S.E.M. (n=10).

Figure 14:
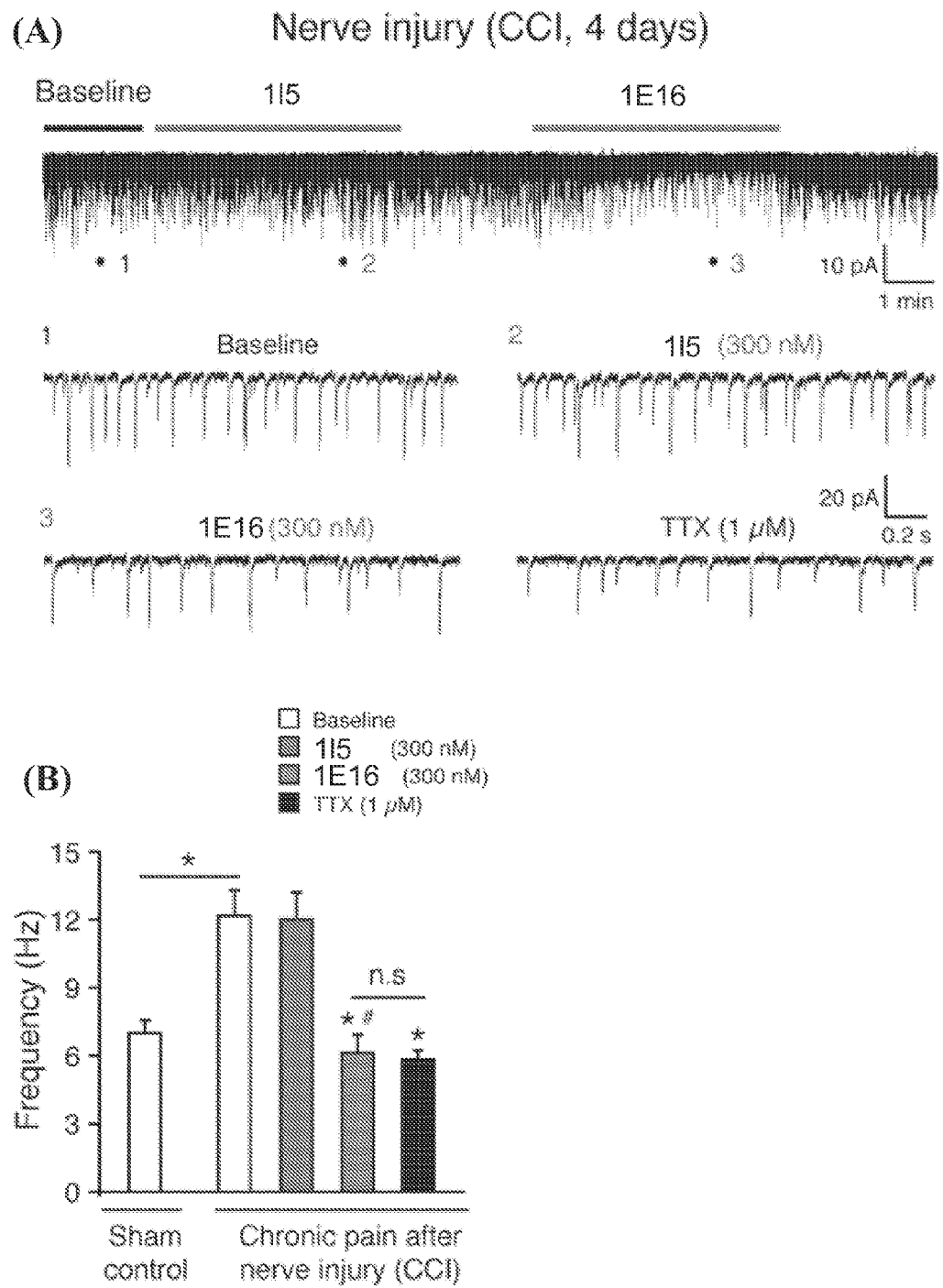

FIG. 14 shows (A, B) 1E16 inhibited chronic pain enhanced excitatory nociceptive synaptic transmission in spinal cord slices 4 days after CCI. (A) Traces of spontaneous EPSCs (sEPSCs) in lamina IIo neurons. Low panel, enlargements of traces (1, 2, and 3) before and during the 1I5 and 1E16 treatment (300 nM). (B) Frequency of sEPSCs in lamina IIo neurons. *P<0.05, compared with no treatment baseline; #P<0.05, compared with 1I5 (300 nM), n=5 neurons/group. Note that 1E16 was more effective in suppressing synaptic transmission in chronic pain, and there was no difference between TTX and 1E16 treated groups.

Figure 15:
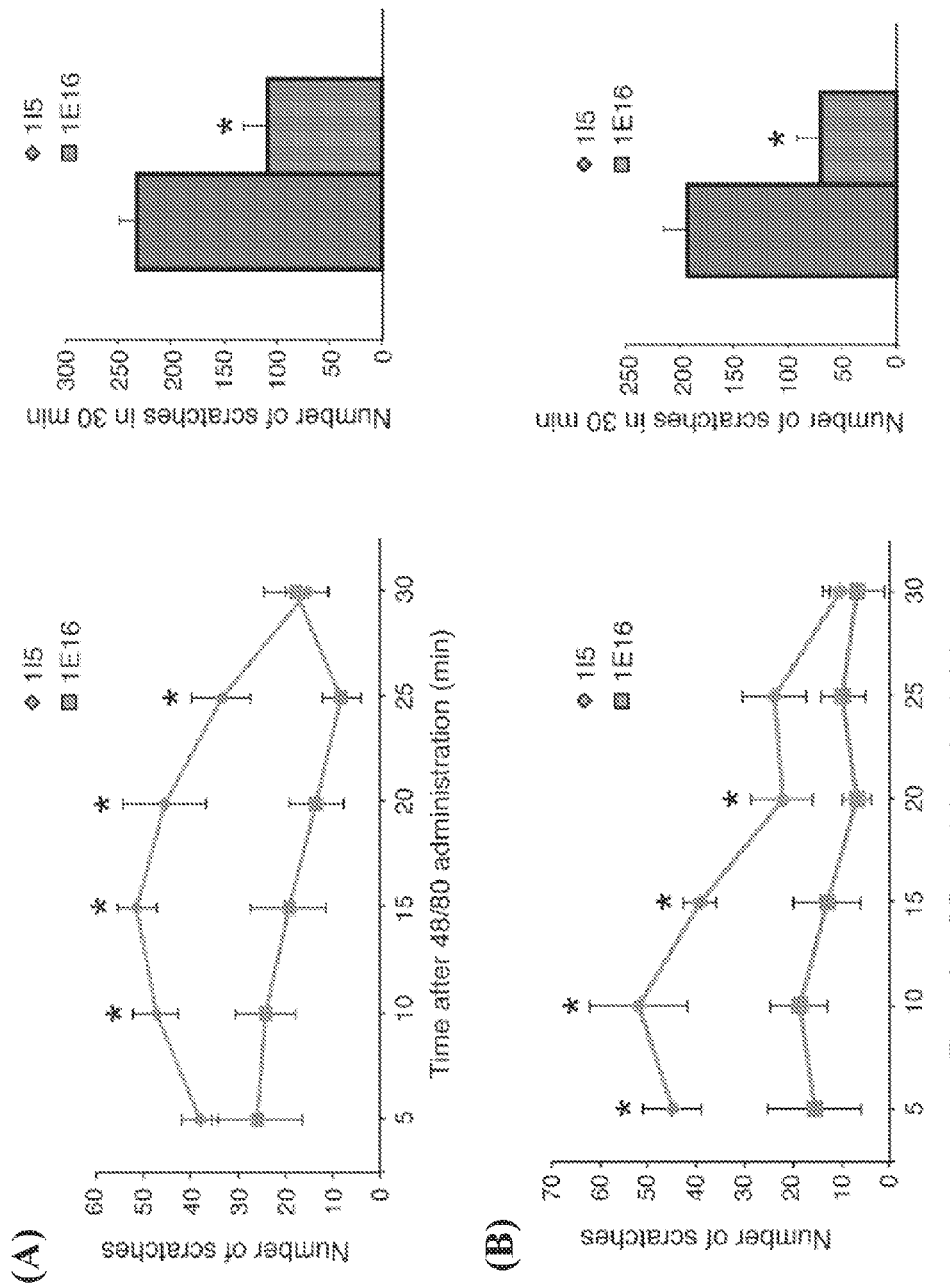

FIG. 15 shows that 1E16 suppressed acute and chronic itch and chronic itch enhanced synaptic transmission in spinal cord slices in mice. (A-C) Intrathecal injection of 1E16 reduced acute itch induced by compound 48/80 (A, intradermal), chloroquine (CQ) (B, intradermal), and GRP (C, intrathecal). *P<0.05, compared with the corresponding control (1I5). n=5-8 mice/group. (D, E) Intrathecal (50 μg, D) or i.v. (10 mg/kg, E) injection of 1E16 reduced chronic itch 5 days following AEW treatment on the back skin. *P<0.05, n=6 mice/group. (F, G) 1E16 inhibited chronic itch-enhanced excitatory synaptic transmission in spinal cord slices 5 days after AEW treatment. (F) Traces of spontaneous EPSCs (sEPSCs) in lamina IIo neurons. Low panel, enlargements of traces (1, 2, and 3) before and during the 1I5 and 1E16 treatment (300 nM). (G) Frequency of sEPSCs in lamina IIo neurons. Note sEPSCs were potentiated in chronic itch and this potentiation was inhibited by 1E16 (300 nM). *P<0.05, compared with no treatment baseline; #P<0.05, compared with 1I5 (300 nM), n=5 neurons/group.

Figure 16:
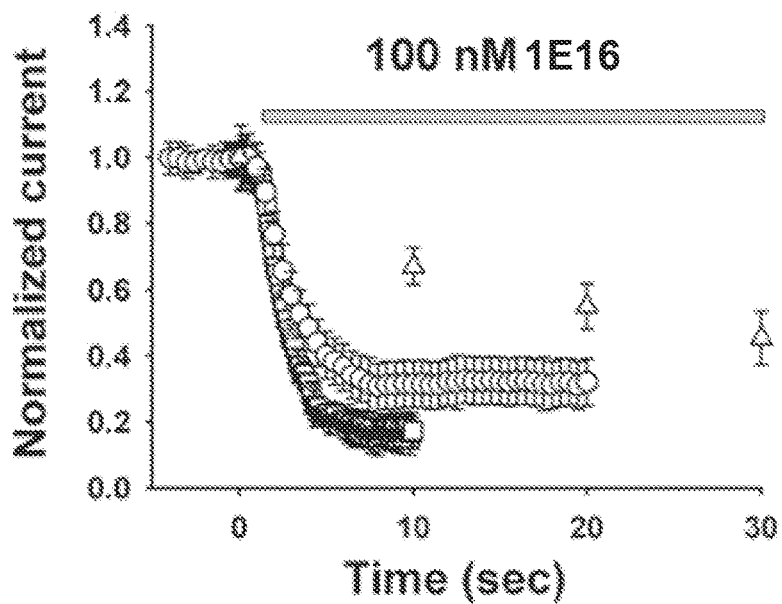

FIG. 16 shows state (use)-dependent inhibition of human $Na_v1.7$ by 1E16. Plot of normalized current amplitudes during 30-ms depolarizing pulses to −10 mV applied from a holding potential of −120 mV at 0.1 (Δ), 2 (○), and 10 (□) Hz in the presence of 100 nM 1E16.

Figure 17:
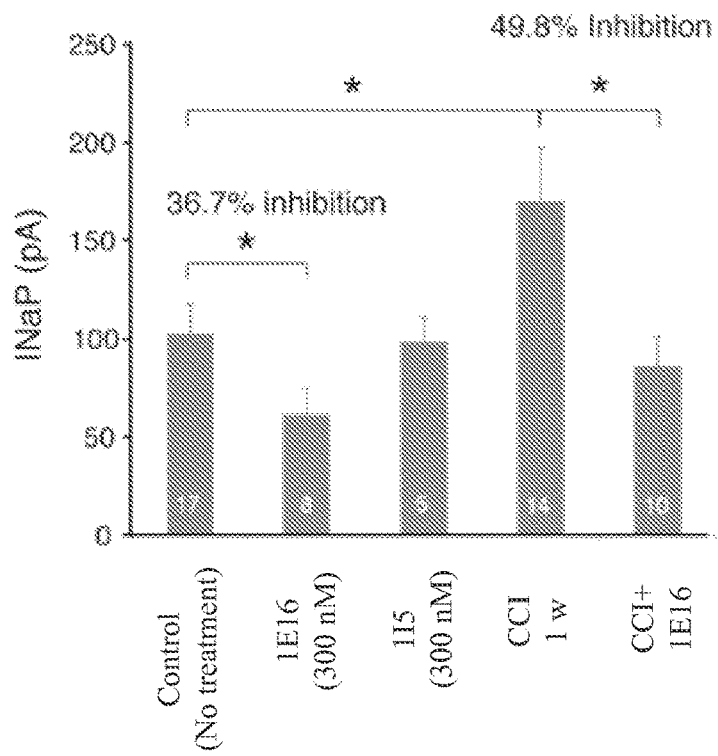

FIG. 17 shows amplitudes of INaP currents in DRG neurons. Note that CCI increased the INaP currents. 1E16 (300 nM) produced a greater inhibition of INaP in the neuropathic pain condition. In contrast, 1I5 had no effects. *P<0.05, n=5-17 neurons/group. Data are shown as means±S.E.M.

Figure 18:
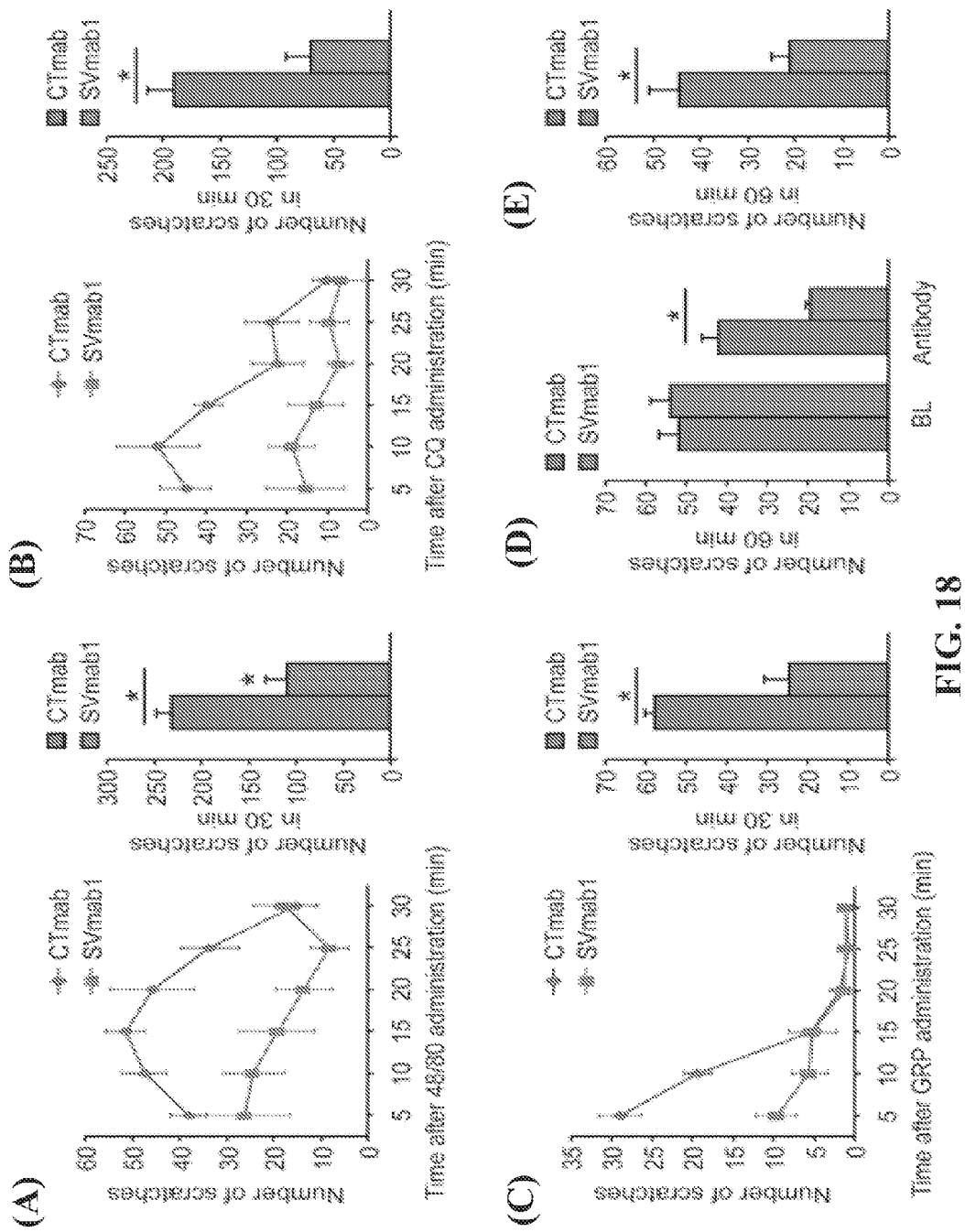

FIG. 18 shows that SVmab1 (1E16 mAb) suppressed acute and chronic itch and chronic itch enhanced synaptic transmission in spinal cord slices in mice. (A-C) Intrathecal injection of SVmab1 reduced acute itch induced by compound 48/80 (A, intradermal), CQ (B, intradermal), and GRP (C, intrathecal). *P<0.05, n=5-8 mice/group. (D, E) Intrathecal (50 μg, D) or i.v. (10 mg/kg, E) injection of SVmab1 reduced dry skin-induced chronic itch following AEW treatment (5 days). *P<0.05, n=6 mice/group. (F-H) Intrathecal or systemic injection of SVmab1 reduced DNFB-induced chronic itch. (F) Paradigm and time course of DNFB-induced chronic itch. (G) Intrathecal (50 μg) injection of SVmab1 on day 10 reduced chronic itch. (H) Systemic injection of SVmab1 (50 mg/kg, i.v.) on day 12 reduced chronic itch. *P<0.05, n=6 mice/group. (I, J) SVmab1 inhibited chronic itch-enhanced excitatory synaptic transmission in spinal cord slices 5 days after AEW treatment. (I) Traces of spontaneous EPSCs (sEPSCs) in lamina IIo neurons. Low panel, enlargements of traces (1, 2, 3) before and during the CTmab (1I5 mAb) and SVmab1 treatment (300 nM). (J) Frequency of sEPSCs in lamina IIo neurons. Note sEPSCs are potentiated in chronic itch and this potentiation was inhibited by SVmab1. *P<0.05, n=5 neurons/group. All the data are shown as means±S.E.M.

FIG. 19 shows that SVmab1 suppressed action potentials and transient and persistent sodium currents in small-sized DRG neurons. (A) SVmab1 (1E16 mAb) dose-dependently suppressed action potential in dissociated DRG neurons. Left, traces of single action potentials. Right, action potential amplitude. *P<0.05, n=25-30 neurons/group. n.s., no significance. (B) SVmab1 inhibited persistent sodium currents ($I_{Na}Ps$) in dissociated DRG neurons. Left, traces of persistent sodium currents ($I_{Na}Ps$) before treatment (control) and after treatment with CTmab (1I5 mAb, 300 nM) and SVmab1 (300 nM). Right, amplitudes of $I_{Na}Ps$ in dissociated neurons. *P<0.05, compared to control; #P<0.05, compared with CTmab (300 nM); n=10-15 neurons/group. (C) SVmab1 (300 nM) inhibited action potentials in small-sized neurons of whole mount DRGs from naïve mice. Top, traces of action potentials. Bottom, number of spikes, *P<0.05, n=5-10 neurons/group. (D) SVmab1 (300 nM) suppressed transient sodium currents ($I_{Na}s$, density) in small-sized neurons of whole mount DRGs. n=5-10 neurons/group. All the data are shown as means±S.E.M.

Figure 20:
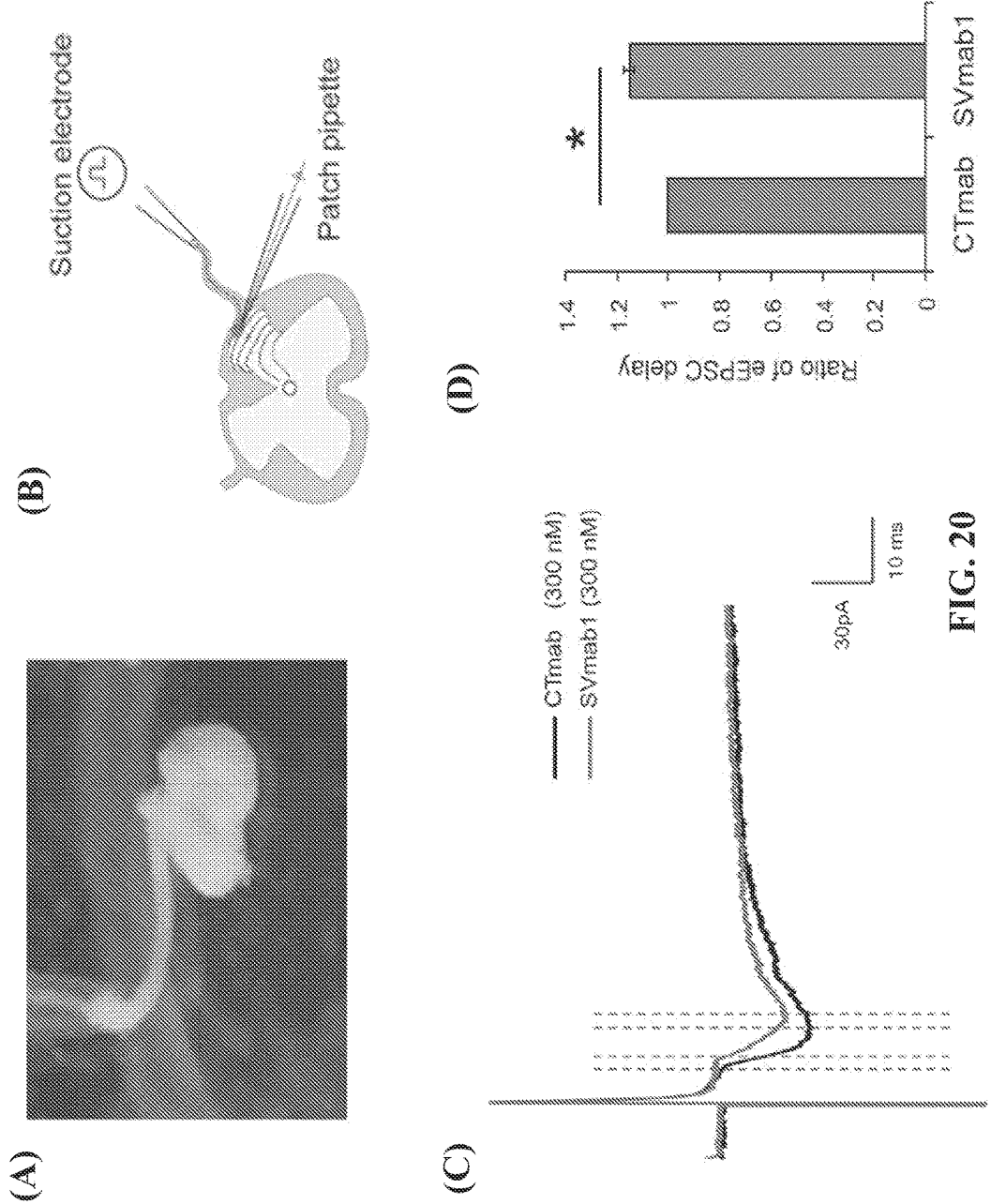

FIG. 20 shows that SVmab1 delayed the conduction of C-fiber stimulation-induced synaptic responses in lamina II neurons in spinal cord slices. (A) Photo of a mouse spinal cord slice with the dorsal root attached. Note the distal end of the dorsal root was inserted into a suction electrode. (B) Schematic showing the patch clamp recording in the superficial dorsal horn of a spinal cord slice. (C) Traces of evoked EPSCs (eEPSCs) following treatment of SVmab1 (1E16 mAb, 300 nM) and CTmab (1I5 mAb, 300 nM). Note that the sEPSC was delayed by SVmab1. (D) Ratio of sEPSC delay. *P<0.05, n=5 neurons/group. The data are shown as means±S.E.M.

Figure 21:
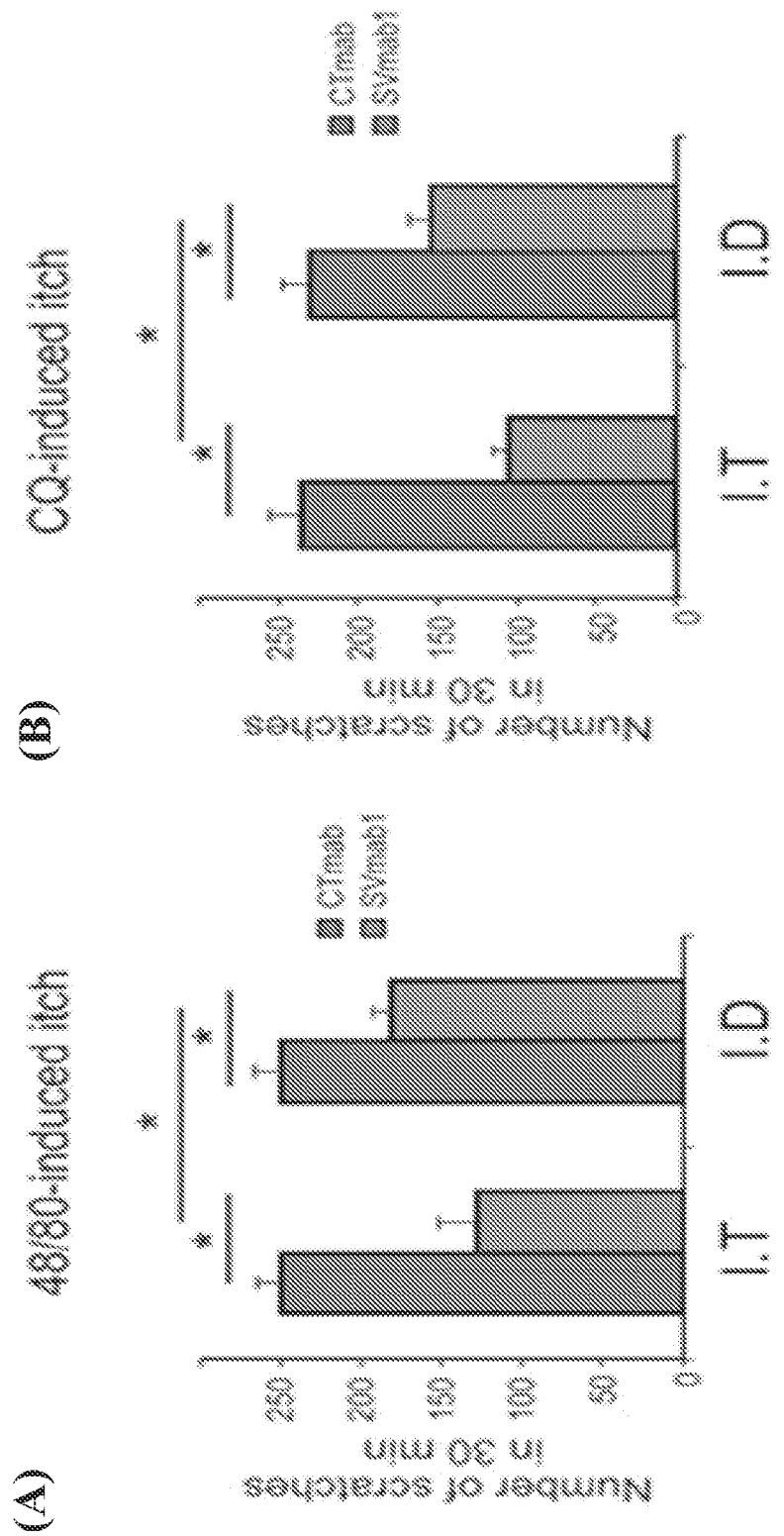

FIG. 21 shows a comparison of the effects of intrathecal (I.T. 50 μg) and intradermal (I.D. 50 μg) injection of SVmab1 (1E16 mAb) on compound 48/80 and CQ-induced acute itch. *P<0.05, n=5 mice/group.

Figure 22:
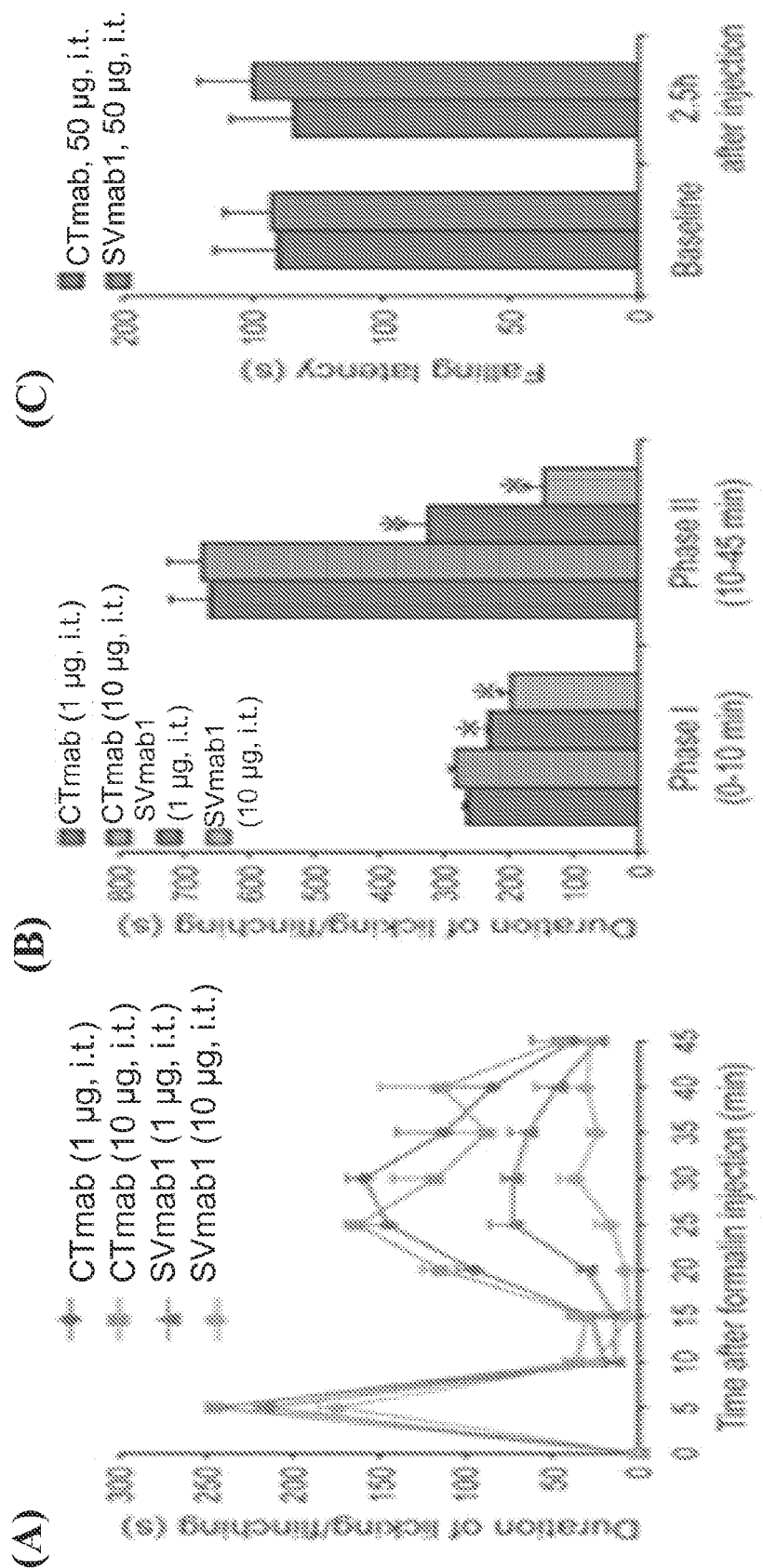

FIG. 22 shows that SVmab1 (1E16 mAb) reduced inflammatory and neuropathic pain without affecting motor coordination and balance. (A, B) Intrathecal injection of SVmab1 reduced the formalin-induced inflammatory pain. (A) Time course of licking and flinching behavior following intraplantar injection of 5% formalin. (B) Formalin-induced Phase-I (1-10 min) and Phase-II (10-45 min) responses. *P<0.05, compared with the corresponding control (CTmab). (C) Falling latency (time on rota-rod) in the rota-rod test and the effects of SVmab1 and CTmab (50 μg, i.t.). (D-F) Systemic injection of SVmab1 (10 and 50 mg/kg, i.v.) also reduced the formalin-induced inflammatory pain and edema. (D) Time course of formalin-induced pain. (E) Formalin-induced 1st and 2nd phase responses. (F) Formalin-induced paw edema (volume of an affected hindpaw). (G) Intrathecal (i.t.) injection of SVmab1 (50 μg) reduced the CCI-induced neuropathic pain (mechanical allodynia). (H) Systemic injections of SVmab1 (10 and 50 mg/kg, i.v.) dose-dependently reduced the CCI induced neuropathic pain (mechanical allodynia). Arrows indicate the time at which antibodies were injected. All the data are shown as means±S.E.M. BL, baseline. *P<0.05, vs. corresponding CTmab at the same dose (B, E, F, G, H); #P<0.05, vs. baseline (F). n=5-6 mice/group.

Figure 23:
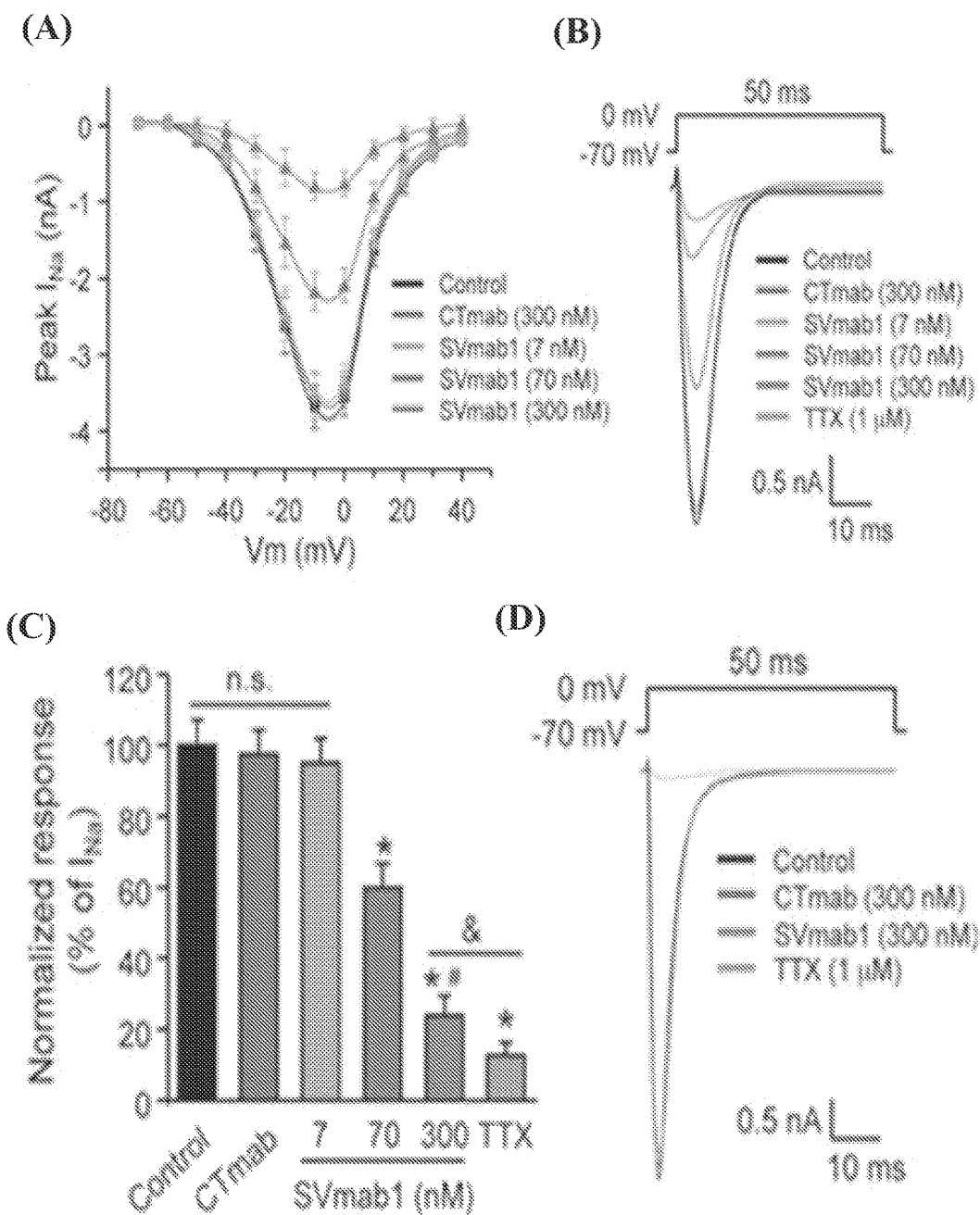

FIG. 23 shows that SVmab1 (1E16 mAb) suppressed transient and persistent sodium currents and action potentials in small-sized DRG neurons and nociceptive synaptic transmission in spinal cord slices. (A-D) SVmab1 suppressed transient sodium currents ($I_{Na}s$) in dissociated DRG neurons. (A) Current/Voltage (I/V) relationship of INas and the effects of SVmab1 (7, 70, and 300 nM) and CTmab (1I5 mAb, 300 nM), n=15-20 neurons/group. (B) Traces of $I_{Na}s$ and the effects of SVmab1, CTmab (300 nM), and TTX (1 μM). (C) Percentage inhibition of $I_{Na}s$ by SVmab1 and TTX (1 μM). *P<0.05, vs. control (no treatment); #P<0.05, vs. CTmab (300 nM), &P<0.05, n=15-20. Note that TTX (1 μM) further inhibited $I_{Na}s$ compared with SVmab1 (300 nM). (D) TTX (1 μM) but not SVmab1 (300 nM) inhibited $I_{Na}s$ in large-sized DRG neurons. n=10. (E, F) SVmab1 inhibited the action potential frequency in dissociated small-sized DRG neurons. (E) Traces of action potentials. (F) Action potential frequencies following current injection (100 and 200 pA). *P<0.05, n=15-20 neurons/group. (G, H) SVmab1 inhibited persistent sodium currents ($I_{Na}Ps$) in small-sized neurons of whole mount DRGs from naïve mice and mice with nerve injury (CCI). (G) Traces of $I_{Na}Ps$ before treatment (control) and after treatment with CTmab (300 nM) and SVmab1 (300 nM). (H) Amplitudes of $I_{Na}Ps$ in DRG neurons, which were increased after CCI. Note that SVmab1 (300 nM) produced a greater inhibition of $I_{Na}Ps$ after CCI. *P<0.05, n=6-7 neurons/group. (I, J) SVmab1 inhibited excitatory synaptic transmission in IIo neurons of spinal cord slices of normal mice. (I) Traces of spontaneous EPSCs (sEPSCs). Low panel, enlargements of traces (1, 2, 3) before and during the CTmab and SVmab1 treatment (300 nM). (J) Frequency of sEPSCs. *P<0.05, vs. baseline; #P<0.05, vs. CTmab (300 nM); &P<0.05, n=5-6 neurons/group. (K, L) SVmab1 inhibited chronic pain enhanced excitatory nociceptive synaptic transmission in lamina IIo neurons of spinal cord slices 4 days after CCI. (K) Traces of sEPSCs. Low panel, enlargements of traces (1, 2, 3) before and during the CTmab and SVmab1 treatment (300 nM). (L) Frequency of sEPSCs. *P<0.05, vs. no treatment baseline after CCI; #P<0.05, vs. CTmab (300 nM), n=5 neurons/group. Note that SVmab1 was as effectively as TTX in suppressing synaptic transmission in chronic pain. n.s., no significance. All the data are shown as means±S.E.M.

Figure 24:
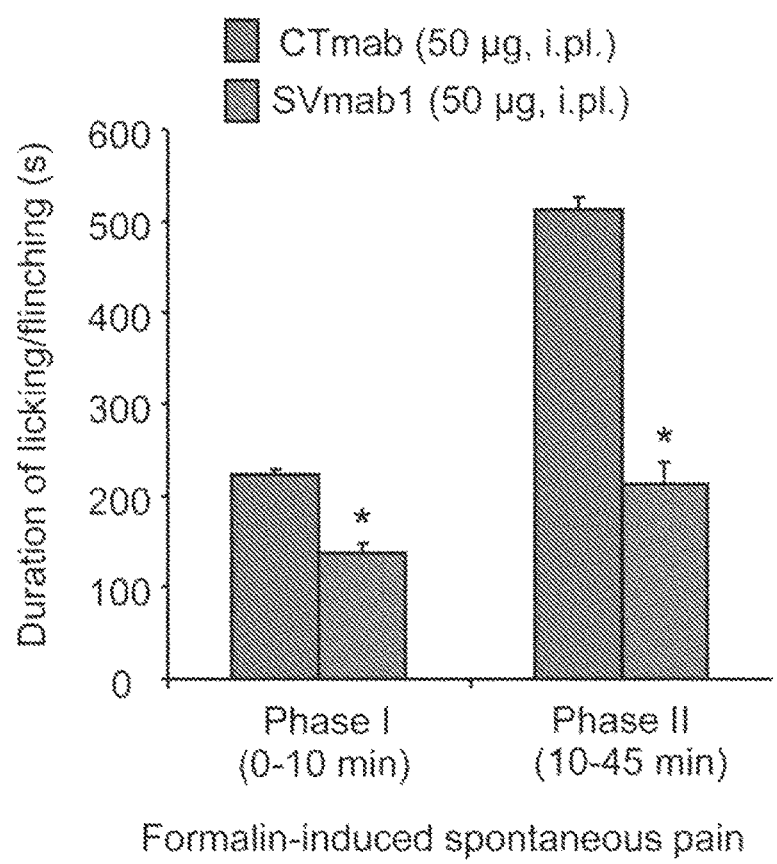

FIG. 24 shows that intraplantar (i.pl.) injection of SVmab1 (1E16 mAb) reduced formalin-induced inflammatory pain in the $1^{st}$ and $2^{nd}$ phase. *P<0.05, vs. control antibody (CTmab, also known herein as 1I5 mAb or 1I5), n=6 mice/group. Antibody was injected 30 min prior to the formalin injection.

Figure 25:
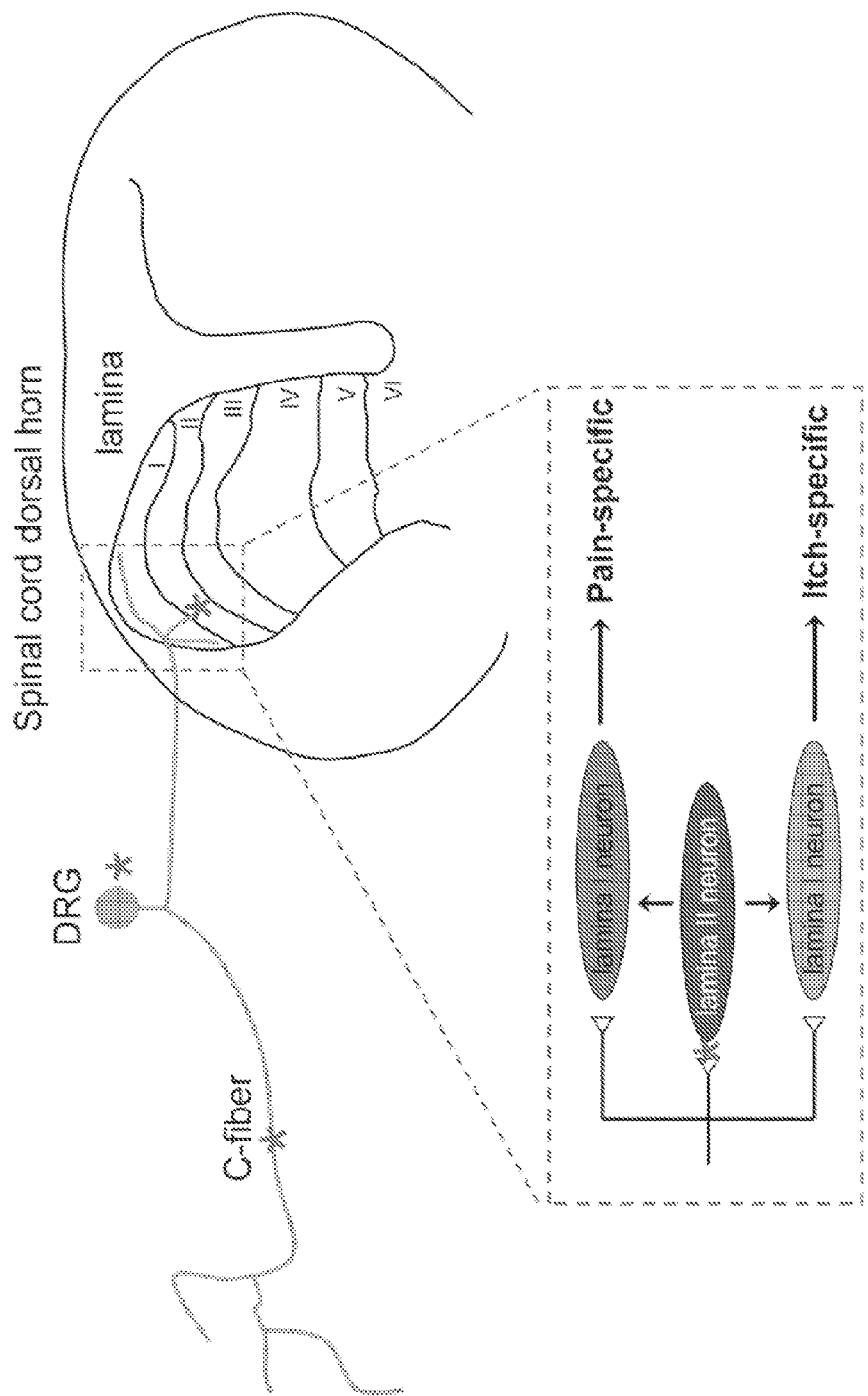

FIG. 25 shows a schematic of peripheral and central actions of the $Na_v1.7$ monoclonal antibody SVmab1 (also known herein as 1E16 mAb or 1E16) on pain and itch. $Na_v1.7$ was expressed by pain and itch conducting unmyelinated C-fiber primary sensory neurons in DRGs. The peripheral terminals of these nociceptive/pruriceptive neurons innervated skin, muscle, and joint, and the central terminals of these neurons project to the spinal cord superficial dorsal horn (lamina I and lamina II). $Na_v1.7$, synthesized in cell bodies of C-fiber DRG neurons, was transported to spinal cord central terminals which formed synapses to itch- and pain-selective projection neurons in the lamina I (ovals in the dotted box). These $Na_v1.7$-expressing C type afferent terminals also formed synapses with excitatory interneurons (oval) in the lamina IIo, where patch-clamp recordings were performed. Furthermore, these lamina II interneurons synapse to pain- and itch-selective projection neurons and were essential for both pain and itch transmission. Systemic injection of SVmab1 produced peripheral actions by suppressing $Na_v1.7$-mediated neuronal excitability in DRG neuronal somata and conduction of action potentials in peripheral and central axons. Intrathecal injection of SVmab1 had central actions by suppressing $Na_v1.7$-mediated glutamatergic synaptic transmission in lamina IIo interneurons. As a result of peripheral and central modulation of SVmab1, pain and itch in both acute and chronic conditions were suppressed. * indicates the action site of the $Na_v1.7$ antibody (i.e., 1E16 mAb, also known herein as SVmab1).

FIG. 26 shows (A) a stick representation of the epitope-binding region of 1E16 mAb (i.e., also known herein as SVmab1) and (B) a ribbon diagram of the Fab fragment of 1E16 mAb.

DETAILED DESCRIPTION

The present invention relates to an antibody that binds $Na_v1.7$. Such an antibody has a high selectivity for $Na_v1.7$ over other $Na_v$ channel subtypes and inhibits $Na_v1.7$ by stabilizing a closed state of $Na_v1.7$. In humans, loss-of-function mutations in $Na_v1.7$ result in an inability to sense pain while gain-of-function mutations in $Na_v1.7$ result in a hypersensitivity to pain. Accordingly, the anti-$Na_v1.7$ antibody by inhibiting $Na_v1.7$ may suppress or alleviate pain in a subject in need thereof. The pain may be associated with itch, for example, acute itch, chronic itch, histamine-dependent itch, histamine-independent itch or a combination thereof. The $Na_v1.7$ antibody may also increase a threshold for pain in the subject. As such, the present invention also relates to a method of treating pain in a subject in need thereof, in which the $Na_v1.7$ antibody is administered to the subject.

Furthermore, the anti-$Na_v1.7$ antibody by inhibiting $Na_v1.7$ may suppress or alleviate itch in a subject in need thereof. The itch may be acute itch, chronic itch, histamine-dependent itch, histamine independent itch, allergic contact dermatitis, or a combination thereof. The acute itch may be gastrin-releasing peptide (GRP)-induced or mediated acute itch. Accordingly, the present invention also relates to a method of treating itch in a subject in need thereof, in which the $Na_v1.7$ antibody is administered to the subject.

Additionally, the anti-$Na_v1.7$ antibody by inhibiting $Na_v1.7$ may suppress neurogenic inflammation in a subject in need thereof. Accordingly, the present invention further relates to a method of treating neurogenic inflammation in a subject in need thereof, in which the $Na_v1.7$ antibody is administered to the subject.

Section headings as used in this section and the entire disclosure herein are merely for organization purposes and are not intended to be limiting.

1. Definitions

Unless otherwise defined, all technical and scientific terms used herein have the same meaning as commonly understood by one of ordinary skill in the art. In case of conflict, the present document, including definitions, will control. Preferred methods and materials are described below, although methods and materials similar or equivalent to those described herein can be used in practice or testing of the present invention. All publications, patent applications, patents and other references mentioned herein are incorporated by reference in their entirety. The materials, methods, and examples disclosed herein are illustrative only and not intended to be limiting.

The terms "comprise(s)," "include(s)," "having," "has," "can," "contain(s)," and variants thereof, as used herein, are intended to be open-ended transitional phrases, terms, or words that do not preclude the possibility of additional acts or structures. The singular forms "a," "and" and "the" include plural references unless the context clearly dictates otherwise. The present disclosure also contemplates other embodiments "comprising," "consisting of" and "consisting essentially of," the embodiments or elements presented herein, whether explicitly set forth or not.

For the recitation of numeric ranges herein, each intervening number there between with the same degree of precision is explicitly contemplated. For example, for the range of 6-9, the numbers 7 and 8 are contemplated in addition to 6 and 9, and for the range 6.0-7.0, the number 6.0, 6.1, 6.2, 6.3, 6.4, 6.5, 6.6, 6.7, 6.8, 6.9, and 7.0 are explicitly contemplated.

"Acceptor" and "acceptor antibody" are used herein to refer to the antibody or nucleic acid sequence providing or encoding at least 80%, at least 85%, at least 90%, at least 91%, at least 92%, at least 93%, at least 94%, at least 95%, at least 96%, at least 97%, at least 98%, at least 99% or 100% of the amino acid sequences of one or more framework regions. The term "acceptor" encompasses an antibody amino acid or nucleic acid sequence providing or encoding the constant region(s). The term also encompasses the antibody amino acid or nucleic acid sequence providing or encoding one or more of the framework regions and the constant region(s). For example, the term "acceptor" may refer to a human antibody amino acid or nucleic acid sequence that provides or encodes at least 80%, at least 85%, at least 90%, at least 91%, at least 92%, at least 93%, at least 94%, at least 95%, at least 96%, at least 97%, at least 98%, at least 99% or 100% of the amino acid sequences of one or more of the framework regions. Such an acceptor may contain at least 1, at least 2, at least 3, at least 4, at least 5, or at least 10 amino acid residues that does (do) not occur at one or more specific positions of a human antibody. An acceptor framework region and/or acceptor constant region(s) may be, e.g., derived or obtained from a germline antibody gene, a mature antibody gene, or a functional antibody (e.g., antibodies well-known in the art, antibodies in development, or antibodies commercially available).

"Affinity Matured Antibody" is used herein to refer to an antibody with one or more alterations in one or more CDRs, which result in an improvement in the affinity (i.e. $K_D$, $k_d$ or $k_a$) of the antibody for a target antigen compared to a parent antibody, which does not possess the alteration(s). Exemplary affinity matured antibodies will have nanomolar or even picomolar affinities for the target antigen. A variety of procedures for producing affinity matured antibodies is known in the art, including the screening of a combinatory antibody library that has been prepared using bio-display. For example, Marks et al., BioTechnology, 10: 779-783 (1992) describes affinity maturation by VH and VL domain shuffling. Random mutagenesis of CDR and/or framework residues is described by Barbas et al., Proc. Nat. Acad. Sci. USA, 91: 3809-3813 (1994); Schier et al., Gene, 169: 147-155 (1995); Yelton et al., J. Immunol., 155: 1994-2004 (1995); Jackson et al., J. Immunol., 154(7): 3310-3319 (1995); and Hawkins et al, J. Mol. Biol., 226: 889-896 (1992). Selective mutation at selective mutagenesis positions and at contact or hypermutation positions with an activity-enhancing amino acid residue is described in U.S. Pat. No. 6,914,128 B1.

"Antibody" and "antibodies" as used herein refers to monoclonal antibodies, multispecific antibodies, human antibodies, humanized antibodies (fully or partially humanized), animal antibodies such as, but not limited to, a bird (for example, a duck or a goose), a shark, a whale, and a mammal, including a non-primate (for example, a cow, a pig, a camel, a llama, a horse, a goat, a rabbit, a sheep, a hamster, a guinea pig, a cat, a dog, a rat, a mouse, etc.) or a non-human primate (for example, a monkey, a chimpanzee, etc.), recombinant antibodies, chimeric antibodies, single-chain Fvs ("scFv"), single chain antibodies, single domain antibodies, Fab fragments, F(ab') fragments, F(ab')2 fragments, disulfide-linked Fvs ("sdFv"), and anti-idiotypic ("anti-Id") antibodies, dual-domain antibodies, dual variable domain (DVD) or triple variable domain (TVD) antibodies (dual-variable domain immunoglobulins and methods for making them are described in Wu, C., et al., Nature Biotechnology, 25(11):1290-1297 (2007) and PCT International Application WO 2001/058956, the contents of each of which are herein incorporated by reference), and functionally active epitope-binding fragments of any of the above. In particular, antibodies include immunoglobulin molecules and immunologically active fragments of immunoglobulin molecules, namely, molecules that contain an analyte-binding site. Immunoglobulin molecules can be of any type (for example, IgG, IgE, IgM, IgD, IgA, and IgY), class (for example, IgG1, IgG2, IgG3, IgG4, IgA1, and IgA2), or subclass. For simplicity sake, an antibody against an analyte is frequently referred to herein as being either an "anti-analyte antibody" or merely an "analyte antibody" (e.g., an anti-$Na_v1.7$ antibody or a $Na_v1.7$ antibody).

"Antibody fragment" as used herein refers to a portion of an intact antibody comprising the antigen-binding site or variable region. The portion does not include the constant heavy chain domains (i.e. CH2, CH3, or CH4, depending on the antibody isotype) of the Fc region of the intact antibody. Examples of antibody fragments include, but are not limited to, Fab fragments, Fab' fragments, Fab'-SH fragments, F(ab')2 fragments, Fd fragments, Fv fragments, diabodies, single-chain Fv (scFv) molecules, single-chain polypeptides containing only one light chain variable domain, single-chain polypeptides containing the three CDRs of the light-chain variable domain, single-chain polypeptides containing only one heavy chain variable region, and single-chain polypeptides containing the three CDRs of the heavy chain variable region.

"Binding Constants" are described herein. The term "association rate constant," "kon" or "ka" as used herein, refers to the value indicating the binding rate of an antibody to its target antigen or the rate of complex formation between an antibody and antigen as shown by the equation below:

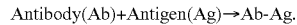
Antibody(Ab)+Antigen(Ag)→Ab-Ag.

The term "dissociation rate constant," "koff" or "kd" as used interchangeably herein, refers to the value indicating the dissociation rate of an antibody form its target antigen or separation of Ab-Ag complex over time into free antibody and antigen as shown by the equation below:

Antibody(Ab)+Antigen(Ag)←Ab-Ag.

Methods for determining association and dissociation rate constants are well known in the art. Using fluorescence-based techniques offers high sensitivity and the ability to examine samples in physiological buffers at equilibrium. Other experimental approaches and instruments such as a BIACORE (biomolecular interaction analysis) assay can be used (e.g., instrument available from BIAcore International AB, a GE Healthcare company, Uppsala, Sweden). Additionally, a KINEXA (Kinetic Exclusion Assay) assay, available from Sapidyne Instruments (Boise, Id.) can also be used.

The term "equilibrium dissociation constant", "Kd", "$K_d$" or "KD" as used interchangeably, herein, refers to the value obtained by dividing the dissociation rate (koff) by the association rate (kon). The association rate, the dissociation rate and the equilibrium dissociation constant are used to represent the binding affinity of an antibody to an antigen.

"Binding Protein" is used herein to refer to a monomeric or multimeric protein that binds to and forms a complex with a binding partner, such as, for example, a polypeptide, an antigen, a chemical compound or other molecule, or a substrate of any kind. A binding protein specifically binds a binding partner. Binding proteins include antibodies, as well as antigen-binding fragments thereof and other various forms and derivatives thereof as are known in the art and described herein below, and other molecules comprising one or more antigen-binding domains that bind to an antigen molecule or a particular site (epitope) on the antigen molecule. Accordingly, a binding protein includes, but is not limited to, an antibody a tetrameric immunoglobulin, an IgG molecule, an $IgG_1$ molecule, a monoclonal antibody, a chimeric antibody, a CDR-grafted antibody, a humanized antibody, an affinity matured antibody, and fragments of any such antibodies that retain the ability to bind to an antigen.

"Bispecific antibody" is used herein to refer to a full-length antibody that is generated by quadroma technology (see Milstein et al., Nature, 305(5934): 537-540 (1983)), by chemical conjugation of two different monoclonal antibodies (see, Staerz et al., Nature, 314(6012): 628-631 (1985)), or by knob-into-hole or similar approaches, which introduce mutations in the Fc region (see Holliger et al., Proc. Natl. Acad. Sci. USA, 90(14): 6444-6448 (1993)), resulting in multiple different immunoglobulin species of which only one is the functional bispecific antibody. A bispecific antibody binds one antigen (or epitope) on one of its two binding arms (one pair of HC/LC), and binds a different antigen (or epitope) on its second arm (a different pair of HC/LC). By this definition, a bispecific antibody has two distinct antigen-binding arms (in both specificity and CDR sequences), and is monovalent for each antigen to which it binds to.

"Bovine antibody" is used herein to refer to a naturally-occurring or recombinantly produced immunoglobulin composed of amino acid sequences representative of natural antibodies isolated from bovines of various breeds. Bovine antibodies are antibodies having variable and constant regions derived from bovine germline immunoglobulin sequences. The bovine antibodies of the disclosure may include amino acid residues not encoded by bovine germline immunoglobulin sequences (e.g., mutations introduced by random or site-specific mutagenesis in vitro or by somatic mutation in vivo), for example, in the CDRs. However, the term "bovine antibody" is not intended to include antibodies in which CDR sequences derived from the germline of another mammalian species, such as mouse, have been grafted onto bovine framework sequences.

"Bovinization" is used herein to refer to a method for transferring non-bovine antigen-binding amino acids from a donor antibody to a bovine antibody acceptor framework to generate protein therapeutic treatments useful in cows.

"Bovinized antibody" is used herein to refer to antibodies which comprise heavy and light chain variable region sequences from a non-bovine species (e.g., a mouse) but in which at least a portion of the VH and/or VL sequence has been altered to be more "bovine-like," i.e., more similar to bovine germline variable sequences. One type of bovinized antibody is a CDR-grafted antibody, in which non-bovine CDR sequences are introduced into bovine VH and VL sequences to replace the corresponding bovine CDR sequences.

Bovinized forms of non-bovine antibodies provided herein are bovine antibodies that contain sequence from a non-bovine antibody. For the most part, bovinized antibodies are bovine antibody sequences ("acceptor" or "recipient" antibody) in which hypervariable region residues of the recipient are replaced by hypervariable region residues from a non-bovine species ("donor" antibody) such as mouse, rat, rabbit, cat, dog, goat, chicken, horse, llama, camel, dromedaries, sharks, non-human primates, human, humanized, recombinant sequence, or an engineered sequence having the desired properties. In some instances, framework region (FR) residues of the bovine antibody are replaced by corresponding non-bovine FR residues. Furthermore, bovinized antibodies may include residues that are not found in the recipient antibody or in the donor antibody. These modifications are made to further refine antibody performance. The bovinized antibody may also comprise at least a portion of an immunoglobulin constant region (Fc) of a bovine antibody.

The bovinized antibody is an antibody or a variant, derivative, analog, or fragment thereof which immunospecifically binds to an antigen of interest and which comprises a framework region (FR) having substantially the amino acid sequence of a bovine antibody and a complementary determining region (CDR) having substantially the amino acid sequence of a non-bovine antibody. A bovinized antibody comprises substantially all of at least one, and typically two, variable domains (Fab, Fab', F(ab')$_2$, FabC, Fv) in which all or substantially all of the CDR regions correspond to those of a non-bovine immunoglobulin (i.e., donor antibody) and all or substantially all of the framework regions are those of a bovine immunoglobulin consensus sequence. A bovinized antibody also comprises at least a portion of an immunoglobulin constant region (Fc), typically that of a bovine immunoglobulin. A bovine or bovinized antibody may contain both the light chain as well as at least the variable domain of a heavy chain. The antibody also may include the CH1, hinge, CH2, CH3, and CH4 regions of the heavy chain. A bovinized antibody may only contain a bovinized light chain or a bovinized heavy chain. An exemplary bovinized antibody only contains a bovinized variable domain of a light chain and a bovinized variable domain of a heavy chain.

"Canine antibody" is used herein to refer to a naturally-occurring or recombinantly produced immunoglobulin composed of amino acid sequences representative of natural antibodies isolated from canines of different breeds. Canine antibodies are antibodies having variable and constant regions derived from canine germline immunoglobulin sequences. The canine antibodies of the disclosure may include amino acid residues not encoded by canine germline immunoglobulin sequences (e.g., mutations introduced by random or site-specific mutagenesis in vitro or by somatic mutation in vivo), for example, in the CDRs. However, the term "canine antibody" is not intended to include antibodies in which CDR sequences derived from the germline of another mammalian species, such as a mouse, have been grafted onto canine framework sequences.

"Caninization" is used herein to refer to a method for transferring non-canine antigen-binding amino acids from a donor antibody to a canine antibody acceptor framework to generate protein therapeutic treatments useful in dogs.

"Caninized antibody" is used herein to refer to antibodies which comprise heavy and light chain variable region sequences from a non-canine species (e.g., a mouse) but in which at least a portion of the variable heavy (VH) and/or variable light (VL) sequence has been altered to more "canine-like," i.e., more similar to canine germline variable sequences. One type of caninized antibody is a CDR-grafted antibody, in which non-canine CDR sequences are introduced into canine VH and VL sequences to replace the corresponding canine CDR sequences.

Caninized forms of non-canine antibodies provided herein are canine antibodies that contain sequence derived from a non-canine antibody. For the most part, caninized antibodies are canine antibody sequences ("acceptor" or "recipient" antibody) in which hypervariable region residues of the recipient are replaced by hypervariable region residues from a non-canine species ("donor" antibody) such as mouse, rat, rabbit, cat, goat, chicken, bovine, horse, llama, camel, dromedaries, sharks, non-human primates, human, humanized, recombinant sequence, or an engineered sequence having the desired properties. In some instances, framework region (FR) residues of the canine antibody are replaced by corresponding non-canine FR residues. Furthermore, caninized antibodies may include residues that are not found in the recipient antibody or in the donor antibody. These modifications are made to further refine antibody performance. The caninized antibody may also comprise at least a portion of an immunoglobulin constant region (Fc) of a canine antibody. Strategies for canonization of antibodies include, but are not limited to, the strategies disclosed in WO 2003/060080.

The caninized antibody is an antibody or a variant, derivative, analog, or fragment thereof which immunospecifically binds to an antigen of interest and which comprises a framework (FR) region having substantially the amino acid sequence of a non-canine antibody and a complementary determining region (CDR) having substantially the amino acid sequence of a non-canine antibody. A caninized antibody comprises substantially all of at least one, and typically two, variable domains (Fab, Fab', F(ab')$_2$, FabC, Fv) in which all or substantially all of the CDR regions correspond to those of a non-canine immunoglobulin (i.e., donor antibody) and all or substantially all of the framework regions are those of a canine immunoglobulin consensus sequence. A caninized antibody also comprises at least a portion of an immunoglobulin constant region (Fc), typically that of a canine immunoglobulin. A canine or caninized antibody may contain both the light chain as well as at least the variable domain of a heavy chain. The antibody also may include the CH1, hinge, CH2, CH3, and CH4 regions of the heavy chain. A caninized antibody may only contain a caninized light chain, or may only contain a caninized heavy chain. An exemplary caninized antibody contains a caninized variable domain of a light chain and a caninized variable domain of a heavy chain.

"CDR" is used herein to refer to the "complementarity determining region" within an antibody variable sequence. There are three CDRs in each of the variable regions of the heavy chain and the light chain, which are designated "CDR1", "CDR2", and "CDR3", for each of the variable regions. The term "CDR set" as used herein refers to a group of three CDRs that occur in a single variable region that binds the antigen. The exact boundaries of these CDRs have been defined differently according to different systems. The system described by Kabat (Kabat et al., Sequences of Proteins of Immunological Interest (National Institutes of Health, Bethesda, Md. (1987) and (1991)) not only provides an unambiguous residue numbering system applicable to any variable region of an antibody, but also provides precise residue boundaries defining the three CDRs. These CDRs may be referred to as "Kabat CDRs". Chothia and coworkers (Chothia and Lesk, J. Mol. Biol., 196: 901-917 (1987); and Chothia et al., Nature, 342: 877-883 (1989)) found that certain sub-portions within Kabat CDRs adopt nearly identical peptide backbone conformations, despite having great diversity at the level of amino acid sequence. These sub-portions were designated as "L1", "L2", and "L3", or "H1", "H2", and "H3", where the "L" and the "H" designate the light chain and the heavy chain regions, respectively. These regions may be referred to as "Chothia CDRs", which have boundaries that overlap with Kabat CDRs. Other boundaries defining CDRs overlapping with the Kabat CDRs have been described by Padlan, FASEB J., 9: 133-139 (1995), and MacCallum, J. Mol. Biol., 262(5): 732-745 (1996). Still other CDR boundary definitions may not strictly follow one of the herein systems, but will nonetheless overlap with the Kabat CDRs, although they may be shortened or lengthened in light of prediction or experimental findings that particular residues or groups of residues or even entire CDRs do not significantly impact antigen binding. The methods used herein may utilize CDRs defined according to any of these systems, although certain embodiments use Kabat- or Chothia-defined CDRs.

"CDR-grafted antibody" is used herein to refer to antibodies which comprise heavy and light chain variable region sequences from one species but in which the sequences of one or more of the CDR regions of VH and/or VL are replaced with CDR sequences of another species, such as antibodies having murine heavy and light chain variable regions in which one or more of the murine CDRs (e.g., CDR3) has been replaced with human CDR sequences.

"Chimeric antibody" is used herein to refer to antibodies which comprise heavy and light chain variable region sequences from one species and constant region sequences from another species, such as antibodies having murine heavy and light chain variable regions linked to human, canine, equine, or feline constant regions. Chimeric antibodies comprise a portion of the heavy and/or light chain that is identical to or homologous with corresponding sequences from antibodies derived from a particular species or belonging to a particular antibody class or subclass, while the remainder of the chain(s) is identical to or homologous with corresponding sequences in antibodies from another species or belonging to another antibody class or subclass, as well as fragments of such antibodies, exhibiting the desired biological activity (see e.g., U.S. Pat. No. 4,816,567 and Morrison et al., Proc. Natl. Acad. Sci. USA 81:6851-6855 (1984)).

"Component," "components," or "at least one component," refer generally to a capture antibody, a detection or conjugate a calibrator, a control, a sensitivity panel, a container, a buffer, a diluent, a salt, an enzyme, a co-factor for an enzyme, a detection reagent, a pretreatment reagent/solution, a substrate (e.g., as a solution), a stop solution, and the like that can be included in a kit for assay of a test sample, such as a patient urine, serum or plasma sample, in accordance with the methods described herein and other methods known in the art. Some components can be in solution or lyophilized for reconstitution for use in an assay.

"Derivative" of an antibody as used herein may refer to an antibody having one or more modifications to its amino acid sequence when compared to a genuine or parent antibody and exhibit a modified domain structure. The derivative may still be able to adopt the typical domain configuration found in native antibodies, as well as an amino acid sequence, which is able to bind to targets (antigens) with specificity. Typical examples of antibody derivatives are antibodies coupled to other polypeptides, rearranged antibody domains, or fragments of antibodies. The derivative may also comprise at least one further compound, e.g. a protein domain, said protein domain being linked by covalent or non-covalent bonds. The linkage can be based on genetic fusion according to the methods known in the art. The additional domain present in the fusion protein comprising the antibody employed in accordance with the invention may preferably be linked by a flexible linker, advantageously a peptide linker, wherein said peptide linker comprises plural, hydrophilic, peptide-bonded amino acids of a length sufficient to span the distance between the C-terminal end of the further protein domain and the N-terminal end of the antibody or vice versa. The antibody may be linked to an effector molecule having a conformation suitable for biological activity or selective binding to a solid support, a biologically active substance (e.g. a cytokine or growth hormone), a chemical agent, a peptide, a protein, or a drug, for example.

"Diabodies" is used herein to refer to small antibody fragments with two antigen-binding sites, which fragments comprise a heavy chain variable domain (VH) connected to a light chain variable domain (VL) in the same polypeptide chain (VH-VL). By using a linker that is short to allow pairing between the two domains on the same chain, the domains are forced to pair with the complementary domains of another chain and create two antigen-binding sites.

"Donor" and "donor antibody" are used herein to refer to an antibody providing one or more CDRs. A donor antibody may be an antibody from a species different from the antibody from which the framework regions are obtained or derived. In the context of a humanized antibody, the term "donor antibody" refers to a non-human antibody providing one or more CDRs. In the context of a bovinized antibody, the term "donor antibody" refers to a non-bovine antibody providing one or more CDRs. In the context of a porcinized antibody, the term "donor antibody" refers to a non-porcine antibody providing one or more CDRs. In the context of a caninized antibody, the term "donor antibody" refers to a non-canine antibody providing one or more CDRs. In the context of a felinized antibody, the term "donor antibody" refers to a non-feline antibody providing one or more CDRs. In the context of an equinized antibody, the term "donor antibody" refers to a non-equine antibody providing one or more CDRs.

"Dual-specific antibody" is used herein to refer to a full-length antibody that can bind two different antigens (or epitopes) in each of its two binding arms (a pair of HC/LC) (see PCT publication WO 02/02773). Accordingly, a dual-specific binding protein has two identical antigen binding arms, with identical specificity and identical CDR sequences, and is bivalent for each antigen to which it binds.

"Dual variable domain" is used herein to refer to two or more antigen binding sites on a binding protein, which may be divalent (two antigen binding sites), tetravalent (four antigen binding sites), or multivalent binding proteins. DVDs may be monospecific, i.e., capable of binding one antigen (or one specific epitope), or multispecific, i.e., capable of binding two or more antigens (i.e., two or more epitopes of the same target antigen molecule or two or more epitopes of different target antigens). A preferred DVD binding protein comprises two heavy chain DVD polypeptides and two light chain DVD polypeptides and is referred to as a "DVD immunoglobulin" or "DVD-Ig". Such a DVD-Ig binding protein is thus tetrameric and reminiscent of an IgG molecule, but provides more antigen binding sites than an IgG molecule. Thus, each half of a tetrameric DVD-Ig molecule is reminiscent of one half of an IgG molecule and comprises a heavy chain DVD polypeptide and a light chain DVD polypeptide, but unlike a pair of heavy and light chains of an IgG molecule that provides a single antigen binding domain, a pair of heavy and light chains of a DVD-Ig provide two or more antigen binding sites.

Each antigen binding site of a DVD-Ig binding protein may be derived from a donor ("parental") monoclonal antibody and thus comprises a heavy chain variable domain (VH) and a light chain variable domain (VL) with a total of six CDRs involved in antigen binding per antigen binding site. Accordingly, a DVD-Ig binding protein that binds two different epitopes (i.e., two different epitopes of two different antigen molecules or two different epitopes of the same antigen molecule) comprises an antigen binding site derived from a first parental monoclonal antibody and an antigen binding site of a second parental monoclonal antibody.

A description of the design, expression, and characterization of DVD-Ig binding molecules is provided in PCT Publication No. WO 2007/024715, U.S. Pat. No. 7,612,181, and Wu et al., Nature Biotech., 25: 1290-1297 (2007). A preferred example of such DVD-Ig molecules comprises a heavy chain that comprises the structural formula VD1-(X1)n-VD2-C-(X2)n, wherein VD1 is a first heavy chain variable domain, VD2 is a second heavy chain variable domain, C is a heavy chain constant domain, X1 is a linker with the proviso that it is not CH1, X2 is an Fc region, and n is 0 or 1, but preferably 1; and a light chain that comprises the structural formula VD1-(X1)n-VD2-C-(X2)n, wherein VD1 is a first light chain variable domain, VD2 is a second light chain variable domain, C is a light chain constant domain, X1 is a linker with the proviso that it is not CH1, and X2 does not comprise an Fc region; and n is 0 or 1, but preferably 1. Such a DVD-Ig may comprise two such heavy chains and two such light chains, wherein each chain comprises variable domains linked in tandem without an intervening constant region between variable regions, wherein a heavy chain and a light chain associate to form tandem functional antigen binding sites, and a pair of heavy and light chains may associate with another pair of heavy and light chains to form a tetrameric binding protein with four functional antigen binding sites. In another example, a DVD-Ig molecule may comprise heavy and light chains that each comprise three variable domains (VD1, VD2, VD3) linked in tandem without an intervening constant region between variable domains, wherein a pair of heavy and light chains may associate to form three antigen binding sites, and wherein a pair of heavy and light chains may associate with another pair of heavy and light chains to form a tetrameric binding protein with six antigen binding sites.

In a preferred embodiment, a DVD-Ig binding protein according to the invention not only binds the same target molecules bound by its parental monoclonal antibodies, but also possesses one or more desirable properties of one or more of its parental monoclonal antibodies. Preferably, such an additional property is an antibody parameter of one or more of the parental monoclonal antibodies. Antibody parameters that may be contributed to a DVD-Ig binding protein from one or more of its parental monoclonal antibodies include, but are not limited to, antigen specificity, antigen affinity, potency, biological function, epitope recognition, protein stability, protein solubility, production efficiency, immunogenicity, pharmacokinetics, bioavailability, tissue cross reactivity, and orthologous antigen binding.

A DVD-Ig binding protein binds at least one epitope of $Na_v1.7$. Non-limiting examples of a DVD-Ig binding protein include a DVD-Ig binding protein that binds one or more epitopes of $Na_v1.7$, a DVD-Ig binding protein that binds an epitope of a human $Na_v1.7$ and an epitope of a $Na_v1.7$ of another species (for example, mouse), and a DVD-Ig binding protein that binds an epitope of $Na_v1.7$ and an epitope of another target molecule.

"Epitope," or "epitopes," or "epitopes of interest" refer to a site(s) on any molecule that is recognized and can bind to a complementary site(s) on its specific binding partner. The molecule and specific binding partner are part of a specific binding pair. For example, an epitope can be on a polypeptide, a protein, a hapten, a carbohydrate antigen (such as, but not limited to, glycolipids, glycoproteins or lipopolysaccharides), or a polysaccharide. Its specific binding partner can be, but is not limited to, an antibody.

"Equine antibody" is used herein to refer to a naturally-occurring or recombinantly produced immunoglobulin composed of amino acid sequences representative of natural antibodies isolated from equines of various breeds. Equine antibodies are antibodies having variable and constant regions derived from equine germline immunoglobulin sequences. The equine antibodies of this disclosure may include amino acid residues not encoded by equine germline immunoglobulin sequences (e.g., mutations introduced by random or site-specific mutagenesis in vitro or by somatic mutation in vivo), for example, in the CDRs. However, the term "equine antibody" is not intended to include antibodies in which CDR sequences derived from the germline of another mammalian species, such as a mouse, have been grafted onto equine framework sequences.

"Equinization" is used herein to refer to a method for transferring non-equine antigen-binding amino acids from a donor antibody to an equine antibody acceptor framework to generate protein therapeutic treatments useful in horses.

"Equinized antibody" is used herein to refer to antibodies which comprise heavy and light chain variable region sequences from a non-equine species (e.g., a mouse) but in which at least a portion of the variable heavy (VH) and/or variable light (VL) sequence has been altered to be more "equine-like," i.e., more similar to equine germline variable sequences. One type of equinized antibody is a CDR-grafted antibody, in which non-equine CDR sequences are introduced into equine VH and VL sequences to replace the corresponding equine CDR sequences.

Equinized forms of non-equine antibodies provided herein are equine antibodies that contain sequence derived from a non-equine antibody. For the most part, equinized antibodies are equine antibody sequences ("acceptor" or "recipient" antibody) in which hypervariable region residues of the recipient are replaced by hypervariable region residues from a non-equine species ("donor" antibody) such as mouse, rat, rabbit, cat, dogs, goat, chicken, bovine, horse, llama, camel, dromedaries, sharks, non-human primates, human, humanized, recombinant sequence, or an engineered sequence having the desired properties. In some instances, framework region (FR) residues of the equine antibody are replaced by corresponding non-equine FR residues. Furthermore, equinized antibodies may include residues that are not found in the recipient antibody or in the donor antibody. These modifications are made to further refine antibody performance. The equinized antibody may also comprise at least a portion of an immunoglobulin constant region (Fc) of an equine antibody.

The equinized antibody is an antibody or a variant, derivative, analog, or fragment thereof which immunospecifically binds to an antigen of interest and which comprises a framework region (FR) having substantially the amino acid sequence of an equine antibody and a complementary determining region (CDR) having substantially the amino acid sequence of a non-equine antibody. An equinized antibody comprises substantially all of at least one, and typically two, variable domains (Fab, Fab', F(ab')$_2$, FabC, Fv) in which all or substantially all of the CDR regions correspond to those of a non-equine immunoglobulin (i.e., donor antibody) and all or substantially all of the framework regions are those of an equine immunoglobulin consensus sequence. An equinized antibody also comprises at least a portion of an immunoglobulin constant region (Fc), typically that of an equine immunoglobulin. An equine or equinized antibody, for example, may contain both the light chain as well as at least the variable domain of a heavy chain. The antibody may also include the CH1, hinge, CH2, CH3, and CH4 regions of the heavy chain. An equinized antibody may only contain an equinized light chain, or an equinized heavy chain. An exemplary equinized antibody contains an equinized variable domain of a light chain and an equinized variable domain of a heavy chain. Equine isotypes include, for example, IgGa, IgGb, IgGc, IgG(T), IgM, and IgA.

"Fab" is used herein to refer to antibody fragments. Papain digestion of antibodies produces two identical antigen-binding fragments called "Fab" fragments, each with a single antigen-binding site, and a residual "Fc" fragment, whose name reflects its ability to readily crystallize. Pepsin treatment yields a binding cross-linking antigen. The Fab fragment also contains the constant domain of the light chain and the first domain (CH1) of the heavy chain. Fab' fragments differ from Fab fragments by the addition of a few residues at the carboxyl terminus of the heavy chain CH1 domain including one or more cysteine(s) from the antibody hinge region. Fab'-SH is the designation herein for Fab' in which the cysteine(s) of the constant domains bear a free thiol group. F(ab')$_2$ antibody fragments originally were produced as pairs of Fab' fragments which have hinge cysteines between them. Other chemical couplings of antibody fragments are also known.

"F(ab')$_2$ fragment" as used herein refers to antibodies generated by pepsin digestion of whole IgG antibodies to remove most of the Fc region while leaving intact some of the hinge region. F(ab')$_2$ fragments have two antigen-binding F(ab) portions linked together by disulfide bonds, and therefore are divalent with a molecular weight of about 110 kDa. Divalent antibody fragments (F(ab')$_2$ fragments) are smaller than whole IgG molecules and enable a better penetration into tissue thus facilitating better antigen recognition in immunohistochemistry. The use of F(ab')$_2$ fragments also avoids unspecific binding to Fc receptor on live cells or to Protein A/G. F(ab')$_2$ fragments can both bind and precipitate antigens.

"Feline antibody" is used herein to refer to a naturally-occurring or recombinantly produced immunoglobulin composed of amino acid sequences representative of natural antibodies isolated from felines of various breeds. Feline antibodies are antibodies having variable and constant regions derived from feline germline immunoglobulin sequences. The feline antibodies of the disclosure may include amino acid residues not encoded by feline germline immunoglobulin sequences (e.g., mutations introduced by random or site-specific mutagenesis in vitro or by somatic mutation in vivo), for example, in the. However, the term "feline antibody" is not intended to include antibodies in which CDR sequences derived from the germline of another mammalian species, such as a mouse, have been grafted onto feline framework sequences.

"Felinization" is used herein to refer to a method for transferring non-feline antigen-binding amino acids from a donor antibody to a feline antibody acceptor framework to generate protein therapeutic treatments useful in cats.

"Felinized antibody" is used herein to refer to antibodies which comprise heavy and light chain variable region sequences from a non-feline species (e.g., a mouse) but in which at least a portion of the variable heavy (VH) and/or variable light (VL) sequence has been altered to be more "feline-like," i.e., more similar to feline germline variable sequences. One type of felinized antibody is a CDR-grafted antibody, in which non-feline CDR sequences are introduced into feline VH and VL sequences to replace the corresponding feline CDR sequences.

Felinized forms of non-feline antibodies provided herein are feline antibodies that contain sequence derived from a non-feline antibody. For the most part, felinized antibodies are feline antibody sequences ("acceptor" or "recipient" antibody) in which hypervariable region residues of the recipient are replaced by hypervariable region residues from a non-feline species ("donor" antibody) such as mouse, rat, rabbit, cat, dogs, goat, chicken, bovine, horse, llama, camel, dromedaries, sharks, non-human primates, human, humanized, recombinant sequence, or an engineered sequence having the desired properties. In some instances, framework region (FR) residues of the feline antibody are replaced by corresponding non-feline FR residues. Furthermore, felinized antibodies may include residues that are not found in the recipient antibody or in the donor antibody. These modifications are made to further refine antibody performance. The felinized antibody may also comprise at least a portion of an immunoglobulin constant region (Fc) of a feline antibody.

The felinized antibody is an antibody or a variant, derivative, analog, or fragment thereof which immunospecifically binds to an antigen of interest and which comprises a framework region (FR) having substantially the amino acid sequence of a feline antibody and a complementary determining region (CDR) having substantially the amino acid sequence of a non-feline antibody. A felinized antibody comprises substantially all of at least one, and typically two, variable domains (Fab, Fab', F(ab')$_2$, FabC, Fv) in which all or substantially all of the CDR regions correspond to those of a non-feline immunoglobulin (i.e., donor antibody) and all or substantially all of the framework regions are those of a feline immunoglobulin consensus sequence. A felinized antibody also comprises at least a portion of an immunoglobulin constant region (Fc), typically that of a feline immunoglobulin. A feline or felinized antibody may contain both the light chain as well as at least the variable domain of a heavy chain. The antibody also may include the CH1, hinge, CH2, CH3, and CH4 regions of the heavy chain. A felinized antibody may only contain a felinized light chain or a felinized heavy chain. An exemplary felinized antibody only contains a felinized variable domain of a light chain and a felinized variable domain of a heavy chain.

"Framework" (FR) or "Framework sequence" as used herein may mean the remaining sequences of a variable region minus the CDRs. Because the exact definition of a CDR sequence can be determined by different systems (for example, see above), the meaning of a framework sequence is subject to correspondingly different interpretations. The six CDRs (CDR-L1, -L2, and -L3 of light chain and CDR-H1, -H2, and -H3 of heavy chain) also divide the framework regions on the light chain and the heavy chain into four sub-regions (FR1, FR2, FR3, and FR4) on each chain, in which CDR1 is positioned between FR1 and FR2, CDR2 between FR2 and FR3, and CDR3 between FR3 and FR4. Without specifying the particular sub-regions as FR1, FR2, FR3, or FR4, a framework region, as referred by others, represents the combined FRs within the variable region of a single, naturally occurring immunoglobulin chain. As used herein, a FR represents one of the four sub-regions, and FRs represents two or more of the four sub-regions constituting a framework region.

Human heavy chain and light chain FR sequences are known in the art that can be used as heavy chain and light chain "acceptor" framework sequences (or simply, "acceptor" sequences) to humanize a non-human antibody using techniques known in the art. In one embodiment, human heavy chain and light chain acceptor sequences are selected from the framework sequences listed in publicly available databases such as V-base (hypertext transfer protocol://vbase.mrc-cpe.cam.ac.uk/) or in the international ImMunoGeneTics® (IMGT®) information system (hypertext transfer protocol://imgt.cines.fr/texts/IMGTrepertoire/LocusGenes/).

"Functional antigen binding site" as used herein may mean a site on a binding protein (e.g. an antibody) that is capable of binding a target antigen. The antigen binding affinity of the antigen binding site may not be as strong as the parent binding protein, e.g., parent antibody, from which the antigen binding site is derived, but the ability to bind antigen must be measurable using any one of a variety of methods known for evaluating protein, e.g., antibody, binding to an antigen. Moreover, the antigen binding affinity of each of the antigen binding sites of a multivalent protein, e.g., multivalent antibody, herein need not be quantitatively the same.

"Fv" is used herein to refer to the minimum antibody fragment that contains a complete antigen-recognition and binding site. This region consists of a dimer of one heavy chain and one light chain variable domain.

"Germline antibody gene" or "gene fragment" is used herein to refer to an immunoglobulin sequence encoded by non-lymphoid cells that have not undergone the maturation process that leads to genetic rearrangement and mutation for expression of a particular immunoglobulin (Shapiro et al., Crit. Rev. Immunol. 22(3):183-200 (2002); Marchalonis et al., Adv. Exp. Med. Biol. 484:13-30 (2001)). One of the advantages provided by the binding proteins of the present disclosure stems from the recognition that germline antibody genes are more likely than mature antibody genes to conserve essential amino acid sequence structures characteristic of individuals in the species, hence less likely to be recognized as from a foreign source when used therapeutically in that species.

"Human antibody" is used herein to refer to antibodies having variable and constant regions derived from human germline immunoglobulin sequences. The human antibodies of the disclosure may include amino acid residues not encoded by human germline immunoglobulin sequences (e.g., mutations introduced by random or site-specific mutagenesis in vitro or by somatic mutation in vivo), for example, in the CDRs. However, the term "human antibody" is not intended to include antibodies in which CDR sequences derived from the germline of another mammalian species, such as a mouse, have been grafted onto human framework sequences.

"Humanized antibody" is used herein to describe an antibody that comprises heavy and light chain variable region sequences from a non-human species (e.g. a mouse) but in which at least a portion of the VH and/or VL sequence has been altered to be more "human-like," i.e., more similar to human germline variable sequences. A "humanized antibody" is an antibody or a variant, derivative, analog, or fragment thereof, which immunospecifically binds to an antigen of interest and which comprises a framework (FR) region having substantially the amino acid sequence of a human antibody and a complementary determining region (CDR) having substantially the amino acid sequence of a non-human antibody. As used herein, the term "substantially" in the context of a CDR refers to a CDR having an amino acid sequence at least 80%, at least 85%, at least 90%, at least 95%, at least 98%, or at least 99% identical to the amino acid sequence of a non-human antibody CDR. A humanized antibody comprises substantially all of at least one, and typically two, variable domains (Fab, Fab', F(ab')$_2$, FabC, Fv) in which all or substantially all of the CDR regions correspond to those of a non-human immunoglobulin (i.e., donor antibody) and all or substantially all of the framework regions are those of a human immunoglobulin consensus sequence. In an embodiment, a humanized antibody also comprises at least a portion of an immunoglobulin constant region (Fc), typically that of a human immunoglobulin. In some embodiments, a humanized antibody contains the light chain as well as at least the variable domain of a heavy chain. The antibody also may include the CH1, hinge, CH2, CH3, and CH4 regions of the heavy chain. In some embodiments, a humanized antibody only contains a humanized light chain. In some embodiments, a humanized antibody only contains a humanized heavy chain. In specific embodiments, a humanized antibody only contains a humanized variable domain of a light chain and/or humanized heavy chain.

A humanized antibody can be selected from any class of immunoglobulins, including IgM, IgG, IgD, IgA, and IgE, and any isotype, including without limitation IgG1, IgG2, IgG3, and IgG4. A humanized antibody may comprise sequences from more than one class or isotype, and particular constant domains may be selected to optimize desired effector functions using techniques well-known in the art.

The framework regions and CDRs of a humanized antibody need not correspond precisely to the parental sequences, e.g., the donor antibody CDR or the consensus framework may be mutagenized by substitution, insertion, and/or deletion of at least one amino acid residue so that the CDR or framework residue at that site does not correspond to either the donor antibody or the consensus framework. In a preferred embodiment, such mutations, however, will not be extensive. Usually, at least 80%, preferably at least 85%, more preferably at least 90%, and most preferably at least 95% of the humanized antibody residues will correspond to those of the parental FR and CDR sequences. As used herein, the term "consensus framework" refers to the framework region in the consensus immunoglobulin sequence. As used herein, the term "consensus immunoglobulin sequence" refers to the sequence formed from the most frequently occurring amino acids (or nucleotides) in a family of related immunoglobulin sequences (see, e.g., Winnaker, From Genes to Clones (Verlagsgesellschaft, Weinheim, 1987)). A "consensus immunoglobulin sequence" may thus comprise a "consensus framework region(s)" and/or a "consensus CDR(s)". In a family of immunoglobulins, each position in the consensus sequence is occupied by the amino acid occurring most frequently at that position in the family. If two amino acids occur equally frequently, either can be included in the consensus sequence.

"Hypervariable region" is used herein to refer to the amino acid residues of an antibody which are responsible for antigen-binding. The hypervariable region comprises amino acid residues from a "complementarity determining region" or "CDR" in the light chain variable domain and in the heavy chain variable domain as defined by Kabat et al., $5^{th}$ Ed. Public Health Service, National Institutes of Health, Bethesda, Md. (1991) and/or defined by Chothia and Lesk, Mol. Biol. 196:901-917 (1987) and/or as defined as "AbM loops" by Martin et al., Proc. Natl. Acad. Sci. USA, 86:9268-9272 (1989) and/or as defined by Lefranc et al., Nucleic Acids Res., 27:209-212 (1999) in the international ImMunoGeneTics information systems database. "Framework" or "FR" residues are those variable domain residues other than the hypervariable region residues as herein defined.

"Identical" or "identity," as used herein in the context of two or more polypeptide or polynucleotide sequences, can mean that the sequences have a specified percentage of residues that are the same over a specified region. The percentage can be calculated by optimally aligning the two sequences, comparing the two sequences over the specified region, determining the number of positions at which the identical residue occurs in both sequences to yield the number of matched positions, dividing the number of matched positions by the total number of positions in the specified region, and multiplying the result by 100 to yield the percentage of sequence identity. In cases where the two sequences are of different lengths or the alignment produces one or more staggered ends and the specified region of comparison includes only a single sequence, the residues of the single sequence are included in the denominator but not the numerator of the calculation.

"Inflammation" as used herein may refer to a biological response of a vascular tissue to stimuli, for example, but not limited to, tissue injury, infection, and irritants. Signs of acute inflammation may include pain, heat, redness, swelling, and/or loss of function.

"Neurogenic inflammation" as used herein may refer to inflammation that may be triggered by the activation of primary afferent neurons and the subsequent release of inflammatory mediators, for example, but not limited to, substance P and calcitonin gene-related peptide.

"Neuroinflammation" as used herein may refer to local inflammation that may occur in the peripheral nervous system (PNS, e.g., peripheral nerves and ganglia) and/or central nervous system (CNS; e.g., spinal cord and brain). In some embodiments, neuroinflammation may include infiltration of leukocytes and increased production of inflammatory mediators in the PNS and CNS. In some embodiments, neuroinflammation may include activation of glial cells (e.g., microglia and astrocytes) in the PNS and CNS.

"Isolated antibody" as used herein refers to an antibody that is substantially free of other antibodies having different antigenic specificities (e.g., an isolated antibody that specifically binds $Na_v1.7$ is substantially free of antibodies that specifically bind antigens other than $Na_v1.7$). Moreover, an isolated antibody may be substantially free of other cellular material and/or chemicals.

"Isolated polynucleotide" as used herein may mean a polynucleotide (e.g. of genomic, cDNA, or synthetic origin, or a combination thereof) that, by virtue of its origin, the isolated polynucleotide is not associated with all or a portion of a polynucleotide with which the "isolated polynucleotide" is found in nature; is operably linked to a polynucleotide that it is not linked to in nature; or does not occur in nature as part of a larger sequence.

"$K_d$" as used herein refers to the dissociation constant of a particular antibody-antigen interaction as is known in the art.

"$K_{on}$" as used herein refers to the on rate constant for association of an antibody to the antigen to form the antibody/antigen complex as is known in the art.

"$K_{off}$" refers to the off rate constant for dissociation of an antibody from the antibody/antigen complex as is known in the art.

"Kabat numbering," "Kabat definitions," and "Kabat labeling" as used interchangeably herein. These terms, which are recognized in the art, refer to a system of numbering amino acid residues which are more variable (i.e., hypervariable) than other amino acid residues in the heavy and light chain variable regions of an antibody, or an antigen binding portion thereof (Kabat et al., Ann. NY Acad. Sci., 190:382-391 (1971) and Kabat et al., Sequences of Proteins of Immunological Interest, Fifth Edition, U.S. Department of Health and Human Services, NIH Publication No. 91-3242 (1991)). For the heavy chain variable region, the hypervariable region ranges from amino acid positions 31 to 35 for CDR1, amino acid positions 50 to 65 for CDR2, and amino acid positions 95 to 102 for CDR3. For the light chain variable region, the hypervariable region ranges from amino acid positions 24 to 34 for CDR1, amino acid positions 50 to 56 for CDR2, and amino acid positions 89 to 97 for CDR3.

"Label" and "detectable label" as used herein refer to a moiety attached to an antibody or an analyte to render the reaction between the antibody and the analyte detectable, and the antibody or analyte so labeled is referred to as "detectably labeled." A label can produce a signal that is detectable by visual or instrumental means. Various labels include signal-producing substances, such as chromogens, fluorescent compounds, chemiluminescent compounds, radioactive compounds, and the like. Representative examples of labels include moieties that produce light, e.g., acridinium compounds, and moieties that produce fluorescence, e.g., fluorescein. Other labels are described herein. In this regard, the moiety, itself, may not be detectable but may become detectable upon reaction with yet another moiety. Use of the term "detectably labeled" is intended to encompass such labeling.

Any suitable detectable label as is known in the art can be used. For example, the detectable label can be a radioactive label (such as $^{3}$H, $^{14}$C, $^{32}$P, $^{33}$P, $^{35}$S, $^{90}$Y, $^{99}$Tc, $^{111}$In, $^{125}$I, $^{131}$I, $^{177}$Lu, $^{166}$Ho, and $^{153}$Sm), an enzymatic label (such as horseradish peroxidase, alkaline peroxidase, glucose 6-phosphate dehydrogenase, and the like), a chemiluminescent label (such as acridinium esters, thioesters, or sulfonamides; luminol, isoluminol, phenanthridinium esters, and the like), a fluorescent label (such as fluorescein (e.g., 5-fluorescein, 6-carboxyfluorescein, 3'6-carboxyfluorescein, 5(6)-carboxyfluorescein, 6-hexachloro-fluorescein, 6-tetrachlorofluorescein, fluorescein isothiocyanate, and the like)), rhodamine, phycobiliproteins, R-phycoerythrin, quantum dots (e.g., zinc sulfide-capped cadmium selenide), a thermometric label, or an immuno-polymerase chain reaction label. An introduction to labels, labeling procedures and detection of labels is found in Polak and Van Noorden, *Introduction to Immunocytochemistry*, $2^{nd}$ ed., Springer Verlag, N.Y. (1997), and in Haugland, *Handbook of Fluorescent Probes and Research Chemicals* (1996), which is a combined handbook and catalogue published by Molecular Probes, Inc., Eugene, Oreg. A fluorescent label can be used in FPIA (see, e.g., U.S. Pat. Nos. 5,593,896, 5,573,904, 5,496,925, 5,359,093, and 5,352,803, which are hereby incorporated by reference in their entireties). An acridinium compound can be used as a detectable label in a homogeneous chemiluminescent assay (see, e.g., Adamczyk et al., Bioorg. Med. Chem. Lett. 16: 1324-1328 (2006); Adamczyk et al., Bioorg. Med. Chem. Lett. 4: 2313-2317 (2004); Adamczyk et al., Biorg. Med. Chem. Lett. 14: 3917-3921 (2004); and Adamczyk et al., Org. Lett. 5: 3779-3782 (2003)).

In one aspect, the acridinium compound is an acridinium-9-carboxamide. Methods for preparing acridinium 9-carboxamides are described in Mattingly, J. Biolumin. Chemilumin. 6: 107-114 (1991); Adamczyk et al., J. Org. Chem. 63: 5636-5639 (1998); Adamczyk et al., Tetrahedron 55: 10899-10914 (1999); Adamczyk et al., Org. Lett. 1: 779-781 (1999); Adamczyk et al., Bioconjugate Chem. 11: 714-724 (2000); Mattingly et al., In *Luminescence Biotechnology: Instruments and Applications*; Dyke, K. V. Ed.; CRC Press: Boca Raton, pp. 77-105 (2002); Adamczyk et al., Org. Lett. 5: 3779-3782 (2003); and U.S. Pat. Nos. 5,468,646, 5,543,524 and 5,783,699 (each of which is incorporated herein by reference in its entirety for its teachings regarding same).

Another example of an acridinium compound is an acridinium-9-carboxylate aryl ester. An example of an acridinium-9-carboxylate aryl ester of formula II is 10-methyl-9-(phenoxycarbonyl)acridinium fluorosulfonate (available from Cayman Chemical, Ann Arbor, Mich.). Methods for preparing acridinium 9-carboxylate aryl esters are described in McCapra et al., Photochem. Photobiol. 4: 1111-21 (1965); Razavi et al., Luminescence 15: 245-249 (2000); Razavi et al., Luminescence 15: 239-244 (2000); and U.S. Pat. No. 5,241,070 (each of which is incorporated herein by reference in its entirety for its teachings regarding same). Such acridinium-9-carboxylate aryl esters are efficient chemiluminescent indicators for hydrogen peroxide produced in the oxidation of an analyte by at least one oxidase in terms of the intensity of the signal and/or the rapidity of the signal. The course of the chemiluminescent emission for the acridinium-9-carboxylate aryl ester is completed rapidly, i.e., in under 1 second, while the acridinium-9-carboxamide chemiluminescent emission extends over 2 seconds. Acridinium-9-carboxylate aryl ester, however, loses its chemiluminescent properties in the presence of protein. Therefore, its use requires the absence of protein during signal generation and detection. Methods for separating or removing proteins in the sample are well-known to those skilled in the art and include, but are not limited to, ultrafiltration, extraction, precipitation, dialysis, chromatography, and/or digestion (see, e.g., Wells, *High Throughput Bioanalytical Sample Preparation. Methods and Automation Strategies*, Elsevier (2003)). The amount of protein removed or separated from the test sample can be about 40%, about 45%, about 50%, about 55%, about 60%, about 65%, about 70%, about 75%, about 80%, about 85%, about 90%, or about 95%. Further details regarding acridinium-9-carboxylate aryl ester and its use are set forth in U.S. patent application Ser. No. 11/697,835, filed Apr. 9, 2007. Acridinium-9-carboxylate aryl esters can be dissolved in any suitable solvent, such as degassed anhydrous N,N-dimethylformamide (DMF) or aqueous sodium cholate.

"Linking sequence" or "linking peptide sequence" refers to a natural or artificial polypeptide sequence that is connected to one or more polypeptide sequences of interest (e.g., full-length, fragments, etc.). The term "connected" refers to the joining of the linking sequence to the polypeptide sequence of interest. Such polypeptide sequences are preferably joined by one or more peptide bonds. Linking sequences can have a length of from about 4 to about 50 amino acids. Preferably, the length of the linking sequence is from about 6 to about 30 amino acids. Natural linking sequences can be modified by amino acid substitutions, additions, or deletions to create artificial linking sequences. Exemplary linking sequences include, but are not limited to: (i) Histidine (His) tags, such as a 6×His tag, which has an amino acid sequence of HHHHHH (SEQ ID NO:1), are useful as linking sequences to facilitate the isolation and purification of polypeptides and antibodies of interest; (ii) Enterokinase cleavage sites, like His tags, are used in the isolation and purification of proteins and antibodies of interest. Often, enterokinase cleavage sites are used together with His tags in the isolation and purification of proteins and antibodies of interest. Various enterokinase cleavage sites are known in the art. Examples of enterokinase cleavage sites include, but are not limited to, the amino acid sequence of DDDDK (SEQ ID NO:2) and derivatives thereof (e.g., ADDDDK (SEQ ID NO:3), etc.); (iii) Miscellaneous sequences can be used to link or connect the light and/or heavy chain variable regions of single chain variable region fragments. Examples of other linking sequences can be found in Bird et al., Science 242: 423-426 (1988); Huston et al., PNAS USA 85: 5879-5883 (1988); and McCafferty et al., Nature 348: 552-554 (1990). Linking sequences also can be modified for additional functions, such as attachment of drugs or attachment to solid supports. In the context of the present disclosure, the monoclonal antibody, for example, can contain a linking sequence, such as a His tag, an enterokinase cleavage site, or both.

"Mammalization" as used herein refers to a method for transferring donor antigen-binding information to a mammalian antibody acceptor to generate useful therapeutic treatments. More specifically, the invention provides methods for felinization, equinization, caninization, bovinization, and porcinization of antibodies.

"Mammalized antibody" as used herein refers to antibodies which comprise heavy and light chain variable region sequences for a mammal species (e.g., a mouse) but in which at least a portion of the VH and/or VL sequences has been altered to be more like "mammal of interest," see for example, humanized, bovinized, caninized, equinized, felinized, or porcinized antibodies defined herein. Such mammalized antibodies include, but are not limited to, bovinized, caninized, equinized, felinized, humanized, or porcinized antibodies.

"Monoclonal antibody" as used herein refers to an antibody obtained from a population of substantially homogeneous antibodies, i.e., the individual antibodies comprising the population are identical except for possible naturally occurring mutations that may be present in minor amounts. Monoclonal antibodies are highly specific, being directed against a single antigen. Furthermore, in contrast to polyclonal antibody preparations that typically include different antibodies directed against different determinants (epitopes), each monoclonal antibody is directed against a single determinant on the antigen. The monoclonal antibodies herein specifically include "chimeric" antibodies in which a portion of the heavy and/or light chain is identical with or homologous to corresponding sequences in antibodies derived from a particular species or belonging to a particular antibody class or subclass, while the remainder of the chain(s) is identical with or homologous to corresponding sequences in antibodies derived from another species or belonging to another antibody class or subclass, as well as fragments of such antibodies, so long as they exhibit the desired biological.

"Multivalent binding protein" is used herein to refer to a binding protein comprising two or more antigen binding sites (also referred to herein as "antigen binding domains"). A multivalent binding protein is preferably engineered to have three or more antigen binding sites, and is generally not a naturally occurring antibody. The term "multispecific binding protein" refers to a binding protein that can bind two or more related or unrelated targets, including a binding protein capable of binding two or more different epitopes of the same target molecule.

"Operably linked" as used herein refers to a juxtaposition wherein the components described are in a relationship permitting them to function in their intended manner. A control sequence "operably linked" to a coding sequence is ligated in such a way that expression of the coding sequence is achieved under conditions compatible with the control sequences. "Operably linked" sequences include both expression control sequences that are contiguous with the gene of interest and expression control sequences that act in trans or at a distance to control the gene of interest. The term "expression control sequence" refers to polynucleotide sequences which are necessary to effect the expression and processing of coding sequences to which they are ligated. Expression control sequences include appropriate transcription initiation, termination, promoter, and enhancer sequences; efficient RNA processing signals such as splicing and polyadenylation signals; sequences that stabilize cytoplasmic mRNA; sequences that enhance translation efficiency (i.e., Kozak consensus sequence); sequences that enhance protein stability; and when desired, sequences that enhance protein secretion. The nature of such control sequences differs depending upon the host organism; in prokaryotes, such control sequences generally include promoter, ribosomal binding site, and transcription termination sequence; in eukaryotes, generally, such control sequences include promoters and transcription termination sequence. The term "control sequences" is intended to include components whose presence is essential for expression and processing, and may also include additional components whose presence is advantageous, for example, leader sequences and fusion partner sequences.

"Pharmaceutically acceptable carrier" as used herein includes any and all solvents, dispersion media, coatings, antibacterial and antifungal agents, isotonic and absorption delaying agents, and the like that are physiologically compatible. Examples of pharmaceutically acceptable carriers include one or more of water, saline, phosphate buffered saline, dextrose, glycerol, ethanol, and the like, as well as combinations thereof. In many cases, it will be preferable to include isotonic agents, for example, sugars, polyalcohols such as mannitol, sorbitol, or sodium chloride in the composition. Pharmaceutically acceptable carriers may further comprise minor amounts of auxiliary substances such as wetting or emulsifying agents, preservatives or buffers, which enhance the shelf life or effectiveness of the antibody or antibody portion.

"Polynucleotide" as used herein refers to a polymeric form of two or more nucleotides, either ribonucleotides or deoxyribonucleotides or a modified form of either type of nucleotide. The term includes single and double stranded forms of DNA. The term "isolated polynucleotide" shall mean a polynucleotide (e.g., of genomic, cDNA, or synthetic origin, or some combination thereof) that, by virtue of its origin, the "isolated polynucleotide" is not associated with all or a portion of a polynucleotide with which the "isolated polynucleotide" is found in nature; is operably linked to a polynucleotide that it is not linked to in nature; or does not occur in nature as part of a larger sequence.

"Polypeptide" as used herein refers to any polymeric chain of amino acids. The terms "peptide" and "protein" are used interchangeably with the term polypeptide and also refer to a polymeric chain of amino acids. The term "polypeptide" encompasses native or artificial proteins, protein fragments, and polypeptide analogs of a protein sequence. A polypeptide may be monomeric or polymeric.

"Porcine antibody" is used herein to refer to a naturally-occurring or recombinantly produced immunoglobulin composed of amino acid sequences representative of natural antibodies isolated from porcines of various breeds. Porcine antibodies are antibodies having variable and constant regions derived from porcine germline immunoglobulin sequences. The porcine antibodies of the disclosure may include amino acid residues not encoded by porcine germline immunoglobulin sequences (e.g., mutations introduced by random or site-specific mutagenesis in vitro or by somatic mutation in vivo), for example, in the CDRs. However, the term "porcine antibody" is not intended to include antibodies in which CDR sequences derived from the germline of another mammalian species, such as a mouse, have been grafted onto porcine framework sequences.

"Porcinization" is used herein to refer to a method for transferring non-porcine antigen-binding amino acids from a donor antibody to a porcine antibody acceptor framework to generate protein therapeutic treatments useful in pigs.

"Porcinized antibody" is used herein to refer to antibodies which comprise heavy and light chain variable region sequences from a non-porcine species (e.g., a mouse) but in which at least a portion of the VH and/or VL sequence has been altered to be more "porcine-like," i.e., more similar to porcine germline variable sequences. One type of porcinized antibody is a CDR-grafted antibody, in which non-porcine CDR sequences are introduced into porcine VH and VL sequences to replace the corresponding porcine CDR sequences.

Porcinized forms of non-porcine antibodies provided herein are porcine antibodies that contain sequence derived from a non-porcine antibody. For the most part, porcinized antibodies are porcine antibody sequences ("acceptor" or "recipient" antibody) in which hypervariable region residues of the recipient are replaced by hypervariable region residues from a non-porcine species ("donor" antibody) such as mouse, rat, rabbit, cat, dog, goat, chicken, bovine, horse, llama, camel, dromedaries, sharks, non-human primates, human, humanized, recombinant sequence, or an engineered sequence having the desired properties. In some instances, framework region (FR) residues of the porcine antibody are replaced by corresponding non-porcine FR residues. Furthermore, porcinized antibodies may include residues that are not found in the recipient antibody or in the donor antibody. These modifications are made to further refine antibody performance. The porcinized antibody may also comprise at least a portion of an immunoglobulin constant region (Fc) of a porcine antibody.

The porcinized antibody is an antibody or a variant, derivative, analog, or fragment thereof which immunospecifically binds to an antigen of interest and which comprises a framework region (FR) having substantially the amino acid sequence of a porcine antibody and a complementary determining region (CDR) having substantially the amino acid sequence of a non-porcine antibody. A porcinized antibody comprises substantially all of at least one, and typically two, variable domains (Fab, Fab', F(ab')$_2$, FabC, Fv) in which all or substantially all of the CDR regions correspond to those of a non-porcine immunoglobulin (i.e., donor antibody) and all or substantially all of the framework regions are those of a porcine immunoglobulin consensus sequence. A porcinized antibody also comprises at least a portion of an immunoglobulin constant region (Fc), typically that of a porcine immunoglobulin. A porcine or porcinized antibody may contain both the light chain as well as at least the variable domain of a heavy chain. The antibody also may include the CH1, hinge, CH2, CH3, and CH4 regions of the heavy chain. A porcinized antibody may only contain a porcinized light chain or a porcinized heavy chain. An exemplary porcinized antibody only contains a porcinized variable domain of a light chain and a porcinized variable domain of a heavy chain.

"Pretreatment reagent," e.g., lysis, precipitation and/or solubilization reagent, as used in a diagnostic assay as described herein is one that lyses any cells and/or solubilizes any analyte that is/are present in a test sample. Pretreatment is not necessary for all samples, as described further herein. Among other things, solubilizing the analyte (e.g., Na$_v$1.7, fragments of Na$_v$1.7, variants of Na$_v$1.7 or any combinations thereof) entails release of the analyte from any endogenous binding proteins present in the sample. A pretreatment reagent may be homogeneous (not requiring a separation step) or heterogeneous (requiring a separation step). With use of a heterogeneous pretreatment reagent, there is removal of any precipitated analyte binding proteins from the test sample prior to proceeding to the next step of the assay. The pretreatment reagent optionally can comprise: (a) one or more solvents and salt, (b) one or more solvents, salt and detergent, (c) detergent, (d) detergent and salt, or (e) any reagent or combination of reagents appropriate for cell lysis and/or solubilization of analyte.

"Prophylactically effective amount" as used herein refers to an amount effective, at dosages and for periods of time necessary, to achieve the desired prophylactic result.

"Quality control reagents" in the context of immunoassays and kits described herein, include, but are not limited to, calibrators, controls, and sensitivity panels. A "calibrator" or "standard" typically is used (e.g., one or more, such as a plurality) in order to establish calibration (standard) curves for interpolation of the concentration of an analyte, such as an antibody or an analyte. Alternatively, a single calibrator, which is near a predetermined positive/negative cutoff, can be used. Multiple calibrators (i.e., more than one calibrator or a varying amount of calibrator(s)) can be used in conjunction to comprise a "sensitivity panel."

"Recombinant antibody" and "recombinant antibodies" refer to antibodies prepared by one or more steps, including cloning nucleic acid sequences encoding all or a part of one or more monoclonal antibodies into an appropriate expression vector by recombinant techniques and subsequently expressing the antibody in an appropriate host cell. The terms include, but are not limited to, recombinantly produced monoclonal antibodies, chimeric antibodies, humanized antibodies (fully or partially humanized), multi-specific or multi-valent structures formed from antibody fragments, bifunctional antibodies, heteroconjugate Abs, DVD-Ig®s, and other antibodies as described in (i) herein. (Dual-variable domain immunoglobulins and methods for making them are described in Wu, C., et al., Nature Biotechnology, 25:1290-1297 (2007)). The term "bifunctional antibody," as used herein, refers to an antibody that comprises a first arm having a specificity for one antigenic site and a second arm having a specificity for a different antigenic site, i.e., the bifunctional antibodies have a dual specificity.

"Recombinant host cell" (or simply "host cell") as used herein refers to a cell into which exogenous DNA has been introduced. It should be understood that such terms are intended to refer not only to the particular cell, but, to the progeny of such a cell. Because certain modifications may occur in succeeding generations due to either mutation or environmental influences, such progeny may not, in fact, be identical to the parent cell, but are still included within the scope of the term "host cell." In one aspect, host cells include prokaryotic and eukaryotic cells selected from any of the Kingdoms of life. Eukaryotic cells include protist, fungal, plant, and animal cells. In another aspect, host cells include, but are not limited to, the prokaryotic cell line *E. coli*; mammalian cell lines CHO, HEK 293, and COS; the insect cell line Sf9; and the fungal cell *Saccharomyces cerevisiae*.

Standard techniques may be used for recombinant DNA, oligonucleotide synthesis, and tissue culture and transformation (e.g., electroporation, lipofection). Enzymatic reactions and purification techniques may be performed according to manufacturer's specifications or as commonly accomplished in the art or as described herein. The foregoing techniques and procedures may be generally performed according to conventional methods well known in the art and as described in various general and more specific references that are cited and discussed throughout the present specification. See e.g., Sambrook et al. Molecular Cloning: A Laboratory Manual (2d ed., Cold Spring Harbor Laboratory Press, Cold Spring Harbor, N.Y. (1989)), which is incorporated herein by reference for any purpose.

"Sample," "test sample," "specimen," "sample from a subject," and "patient sample" as used herein may be used interchangeable and may be a sample of blood, tissue, urine, serum, plasma, amniotic fluid, cerebrospinal fluid, placental cells or tissue, endothelial cells, leukocytes, or monocytes. The sample can be used directly as obtained from a patient or can be pre-treated, such as by filtration, distillation, extraction, concentration, centrifugation, inactivation of interfering components, addition of reagents, and the like, to modify the character of the sample in some manner as discussed herein or otherwise as is known in the art.

Any cell type, tissue, or bodily fluid may be utilized to obtain a sample. Such cell types, tissues, and fluid may include sections of tissues such as biopsy and autopsy samples, frozen sections taken for histologic purposes, blood (such as whole blood), plasma, serum, sputum, stool, tears, mucus, saliva, bronchioalveolar lavage (BAL) fluid, hair, skin, red blood cells, platelets, interstitial fluid, ocular lens fluid, cerebral spinal fluid, sweat, nasal fluid, synovial fluid, menses, amniotic fluid, semen, etc. Cell types and tissues may also include lymph fluid, ascetic fluid, gynecological fluid, urine, peritoneal fluid, cerebrospinal fluid, a fluid collected by vaginal rinsing, or a fluid collected by vaginal flushing. A tissue or cell type may be provided by removing a sample of cells from an animal, but can also be accomplished by using previously isolated cells (e.g., isolated by another person, at another time, and/or for another purpose). Archival tissues, such as those having treatment or outcome history, may also be used. Protein or nucleotide isolation and/or purification may not be necessary.

"Series of calibrating compositions" refers to a plurality of compositions comprising a known concentration of $Na_v1.7$, wherein each of the compositions differs from the other compositions in the series by the concentration of $Na_v1.7$.

"Single-chain Fv or "scFv" as used herein refers to antibody fragments comprising the VH and VL domains of an antibody, wherein these domains are present in a single polypeptide chain. Generally, the Fv polypeptide further comprises a polypeptide linker between the VH and VL domains which enables the scFv to form the desired structure for antigen binding. For a review of scFv, see Pluckthun in the Pharmacology of Monoclonal Antibodies, vol. 113, Rosenburg and Moore eds. Springer-Verlag, N.Y., pp. 269-315 (1994).

"Solid phase" refers to any material that is insoluble, or can be made insoluble by a subsequent reaction. The solid phase can be chosen for its intrinsic ability to attract and immobilize a capture agent. Alternatively, the solid phase can have affixed thereto a linking agent that has the ability to attract and immobilize the capture agent. For example, the linking agent can include a charged substance that is oppositely charged with respect to the capture agent itself or to a charged substance conjugated to the capture agent. In general, the linking agent can be any binding partner (preferably specific) that is immobilized on (attached to) the solid phase and that has the ability to immobilize the capture agent through a binding reaction. The linking agent enables the indirect binding of the capture agent to a solid phase material before the performance of the assay or during the performance of the assay. For examples, the solid phase can be plastic, derivatized plastic, magnetic, or non-magnetic metal, glass or silicon, including, for example, a test tube, microtiter well, sheet, bead, microparticle, chip, and other configurations known to those of ordinary skill in the art.

"Specific binding" or "specifically binding" as used herein may refer to the interaction of an antibody, a protein, or a peptide with a second chemical species, wherein the interaction is dependent upon the presence of a particular structure (e.g., an antigenic determinant or epitope) on the chemical species; for example, an antibody recognizes and binds to a specific protein structure rather than to proteins generally. If an antibody is specific for epitope "A", the presence of a molecule containing epitope A (or free, unlabeled A), in a reaction containing labeled "A" and the antibody, will reduce the amount of labeled A bound to the antibody.

"Specific binding partner" is a member of a specific binding pair. A specific binding pair comprises two different molecules, which specifically bind to each other through chemical or physical means. Therefore, in addition to antigen and antibody specific binding pairs of common immunoassays, other specific binding pairs can include biotin and avidin (or streptavidin), carbohydrates and lectins, complementary nucleotide sequences, effector and receptor molecules, cofactors and enzymes, enzymes and enzyme inhibitors, and the like. Furthermore, specific binding pairs can include members that are analogs of the original specific binding members, for example, an analyte-analog. Immunoreactive specific binding members include antigens, antigen fragments, and antibodies, including monoclonal and polyclonal antibodies as well as complexes and fragments thereof, whether isolated or recombinantly produced.

"Subject" and "patient" as used herein interchangeably refers to any vertebrate, including, but not limited to, a mammal (e.g., cow, pig, camel, llama, horse, goat, rabbit, sheep, hamsters, guinea pig, cat, dog, rat, and mouse, a non-human primate (for example, a monkey, such as a cynomolgous or rhesus monkey, chimpanzee, etc) and a human). In some embodiments, the subject may be a human or a non-human. In other embodiments, the subject may be a bovine, a canine, an equine, a feline, or a porcine. The subject or patient may be undergoing other forms of treatment.

"Therapeutically effective amount" as used herein refers to an amount effective, at dosages and for periods of time necessary, to achieve the desired therapeutic result. A therapeutically effective amount may be the amount and/or duration of a therapy which is sufficient to reduce or ameliorate the severity and/or duration of a disorder or one or more symptoms thereof, prevent the advancement of a disorder, cause regression of a disorder, prevent the recurrence, development, onset, or progression of one or more symptoms associated with a disorder, detect a disorder, or enhance or improve the prophylactic or therapeutic effect(s) of another therapy (e.g., prophylactic or therapeutic agent). A therapeutically effective amount of the antibody or antibody portion may be determined by a person skilled in the art and may vary according to factors such as the disease state, age, sex, and weight of the individual, and the ability of the antibody or antibody portion to elicit a desired response in the individual. A therapeutically effective amount is also one in which any toxic or detrimental effects of the antibody, or antibody portion, are outweighed by the therapeutically beneficial effects.

"Transformation" as used herein refers to any process by which exogenous DNA enters a host cell. Transformation may occur under natural or artificial conditions using various methods well known in the art. Transformation may rely on any known method for the insertion of foreign nucleic acid sequences into a prokaryotic or eukaryotic host cell. The method is selected based on the host cell being transformed and may include, but is not limited to, viral infection, electroporation, lipofection, and particle bombardment. Such "transformed" cells include stably transformed cells in which the inserted DNA is capable of replication either as an autonomously replicating plasmid or as part of the host chromosome. They also include cells which transiently express the inserted DNA or RNA for limited periods of time.

"Transgenic organism" as used herein refers to an organism having cells that contain a transgene, wherein the transgene introduced into the organism (or an ancestor of the organism) expresses a polypeptide not naturally expressed in the organism. A "transgene" is a DNA construct, which is stably and operably integrated into the genome of a cell from which a transgenic organism develops, directing the expression of an encoded gene product in one or more cell types or tissues of the transgenic organism.

"Treat", "treating" or "treatment" are each used interchangeably herein to describe reversing, alleviating, or inhibiting the progress of a disease, or one or more symptoms of such disease, to which such term applies. Depending on the condition of the subject, the term also refers to preventing a disease, and includes preventing the onset of a disease, or preventing the symptoms associated with a disease. A treatment may be either performed in an acute or chronic way. The term also refers to reducing the severity of a disease or symptoms associated with such disease prior to affliction with the disease. Such prevention or reduction of the severity of a disease prior to affliction refers to administration of an antibody or pharmaceutical composition of the present invention to a subject that is not at the time of administration afflicted with the disease. "Preventing" also refers to preventing the recurrence of a disease or of one or more symptoms associated with such disease. "Treatment" and "therapeutically," refer to the act of treating, as "treating" is defined above.

"Variant" is used herein to describe a peptide or polypeptide that differs in amino acid sequence by the insertion, deletion, or conservative substitution of amino acids, but retain at least one biological activity. Representative examples of "biological activity" include the ability to be bound by a specific antibody or to promote an immune response. Variant is also used herein to describe a protein with an amino acid sequence that is substantially identical to a referenced protein with an amino acid sequence that retains at least one biological activity. A conservative substitution of an amino acid, i.e., replacing an amino acid with a different amino acid of similar properties (e.g., hydrophilicity, degree, and distribution of charged regions) is recognized in the art as typically involving a minor change. These minor changes can be identified, in part, by considering the hydropathic index of amino acids, as understood in the art. Kyte et al., J. Mol. Biol. 157:105-132 (1982). The hydropathic index of an amino acid is based on a consideration of its hydrophobicity and charge. It is known in the art that amino acids of similar hydropathic indexes can be substituted and still retain protein function. In one aspect, amino acids having hydropathic indexes of ±2 are substituted. The hydrophilicity of amino acids can also be used to reveal substitutions that would result in proteins retaining biological function. A consideration of the hydrophilicity of amino acids in the context of a peptide permits calculation of the greatest local average hydrophilicity of that peptide, a useful measure that has been reported to correlate well with antigenicity and immunogenicity. U.S. Pat. No. 4,554,101, incorporated fully herein by reference. Substitution of amino acids having similar hydrophilicity values can result in peptides retaining biological activity, for example immunogenicity, as is understood in the art. Substitutions may be performed with amino acids having hydrophilicity values within ±2 of each other. Both the hydrophobicity index and the hydrophilicity value of amino acids are influenced by the particular side chain of that amino acid. Consistent with that observation, amino acid substitutions that are compatible with biological function are understood to depend on the relative similarity of the amino acids, and particularly the side chains of those amino acids, as revealed by the hydrophobicity, hydrophilicity, charge, size, and other properties. "Variant" also can be used to refer to an antigenically reactive fragment of an anti-$Na_v1.7$ antibody that differs from the corresponding fragment of anti-$Na_v1.7$ antibody in amino acid sequence but is still antigenically reactive and can compete with the corresponding fragment of anti-$Na_v1.7$ antibody for binding with $Na_v1.7$. "Variant" also can be used to describe a polypeptide or a fragment thereof that has been differentially processed, such as by proteolysis, phosphorylation, or other post-translational modification, yet retains its antigen reactivity.

"Vector" is used herein to describe a nucleic acid molecule that can transport another nucleic acid to which it has been linked. One type of vector is a "plasmid", which refers to a circular double-stranded DNA loop into which additional DNA segments may be ligated. Another type of vector is a viral vector, wherein additional DNA segments may be ligated into the viral genome. Certain vectors can replicate autonomously in a host cell into which they are introduced (e.g., bacterial vectors having a bacterial origin of replication and episomal mammalian vectors). Other vectors (e.g., non-episomal mammalian vectors) can be integrated into the genome of a host cell upon introduction into the host cell, and thereby are replicated along with the host genome. Moreover, certain vectors are capable of directing the expression of genes to which they are operatively linked. Such vectors are referred to herein as "recombinant expression vectors" (or simply, "expression vectors"). In general, expression vectors of utility in recombinant DNA techniques are often in the form of plasmids. "Plasmid" and "vector" may be used interchangeably as the plasmid is the most commonly used form of vector. However, other forms of expression vectors, such as viral vectors (e.g., replication defective retroviruses, adenoviruses and adeno-associated viruses), which serve equivalent functions, can be used. In this regard, RNA versions of vectors (including RNA viral vectors) may also find use in the context of the present disclosure.

"Vernier zone" as used herein refers to a subset of framework residues that may adjust CDR structure and fine-tune the fit to antigen as described by Foote and Winter (1992, J. Mol. Biol. 224:487-499, which is incorporated herein by reference). Vernier zone residues form a layer underlying the CDRs and may impact the structure of CDRs and the affinity of the antibody.

Unless otherwise defined herein, scientific and technical terms used in connection with the present disclosure shall have the meanings that are commonly understood by those of ordinary skill in the art. For example, any nomenclatures used in connection with, and techniques of, cell and tissue culture, molecular biology, immunology, microbiology, genetics and protein and nucleic acid chemistry and hybridization described herein are those that are well known and commonly used in the art. The meaning and scope of the terms should be clear; in the event, however of any latent ambiguity, definitions provided herein take precedent over any dictionary or extrinsic definition. Further, unless otherwise required by context, singular terms shall include pluralities and plural terms shall include the singular.

2. $NA_v1.7$ Antibody

Provided herein are antibodies for use in methods of detecting and/or inhibiting $Na_v1.7$ and treating diseases, such as pain and/or itch disorders. The antibody herein described has been selected for binding to $Na_v1.7$.

a. $Na_v1.7$

Voltage-gated sodium ($Na_v$) channel subtype 1.7 ($Na_v1.7$) is expressed in dorsal root ganglion (DRG) neurons, which sense pain. Particularly, $Na_v1.7$ facilitates pain sensation and deletion of $Na_v1.7$ in mice, specifically in DRG neurons, suppresses pain. As demonstrated herein, $Na_v1.7$ also functions in spinal cord nociceptive and pruriceptive synaptic transmission. Like nociceptive neurons, afferent nerves express $Na_v1.7$. Afferent nerves are involved in initiating cough.

As further demonstrated herein, inhibition of $Na_v1.7$ suppresses itch associated with allergic contact dermatitis, acute itch, chronic itch, histamine-dependent itch, and histamine-independent itch. Also demonstrated herein, peripheral and central modulation of $Na_v1.7$ suppressed both acute and chronic conditions of itch. The acute itch may be induced or mediated by gastrin-releasing peptide (GRP). The acute itch may be induced or mediated by GRP in superficial dorsal horn neurons.

In humans, loss-of-function mutations in SCN9A (i.e., the gene that encodes human $Na_v1.7$) lead to a congenital inability to sense pain (CIP) while other sensations such as touch and temperature are unaffected by the loss-of-function mutations. Gain-of-function mutations in the gene encoding human $Na_v1.7$ lead to a hypersensitivity to pain, paroxysmal extreme pain disorder, and inherited erythromelalgia.

Human $Na_v1.7$ has the amino acid sequence shown in FIG. 1A, which is also accessible at GenBank accession no. NP_002968.

$Na_v1.7$ contains tetrameric repeats DI to DIV and each repeat is composed of six transmembrane helices. The first four segments S1-S4 comprise the voltage-sensor domain (VSD). The voltage-sensor domain includes a voltage-sensor paddle (VSP), which is a helix-turn (loop)-helix comprising portions of S3, S4, and the loop between S3 and S4.

In particular, SEQ ID NO:23 may be the amino acid sequence of the VSP of DII of $Na_v1.7$. SEQ ID NO:21 may be the amino acid sequence of the loop between S3 and S4 of the VSP of DII of $Na_v1.7$.

Accordingly, also provided herein is a peptide comprising an amino acid sequence having at least about 80%, 81%, 82%, 83%, 84%, 85%, 86%, 87%, 88%, 89%, 90%, 91%, 92%, 93%, 94%, 95%, 96%, 97%, 98%, or 99% identity to the amino acid sequence as set forth in SEQ ID NO:23. In some embodiments, the peptide comprises the amino acid sequence as set forth in SEQ ID NO:23.

Also provided herein is a peptide comprising an amino acid sequence having at least about 80%, 81%, 82%, 83%, 84%, 85%, 86%, 87%, 88%, 89%, 90%, 91%, 92%, 93%, 94%, 95%, 96%, 97%, 98%, or 99% identity to the amino acid sequence as set forth in SEQ ID NO:21. In some embodiments, the peptide comprises the amino acid sequence as set forth in SEQ ID NO:21.

SEQ ID NO:50 may be the amino acid sequence of the VSP of DIV of $Na_v1.7$. SEQ ID NO:51 may be the amino acid sequence of the loop between S3 and S4 of the VSP of DIV of $Na_v1.7$.

Accordingly, also provided herein is a peptide comprising an amino acid sequence having at least about 80%, 81%, 82%, 83%, 84%, 85%, 86%, 87%, 88%, 89%, 90%, 91%, 92%, 93%, 94%, 95%, 96%, 97%, 98%, or 99% identity to the amino acid sequence as set forth in SEQ ID NO:50. In some embodiments, the peptide comprises the amino acid sequence as set forth in SEQ ID NO:50.

Also provided herein is a peptide comprising an amino acid sequence having at least about 80%, 81%, 82%, 83%, 84%, 85%, 86%, 87%, 88%, 89%, 90%, 91%, 92%, 93%, 94%, 95%, 96%, 97%, 98%, or 99% identity to the amino acid sequence as set forth in SEQ ID NO:51. In some embodiments, the peptide comprises the amino acid sequence as set forth in SEQ ID NO:51.

b. Nav1.7-Recognizing Antibody

The antibody is an antibody that binds to $Na_v1.7$, a fragment thereof, an epitope of $Na_v1.7$ (e.g., SEQ ID NO:21, SEQ ID NO:23, SEQ ID NO:50, or SEQ ID NO:51), or a variant thereof. SEQ ID NO:21 may be the amino acid sequence of the loop between S3 and S4 of the VSP of DII of $Na_v1.7$. SEQ ID NO:23 may be the amino acid sequence of the VSP of DII of $Na_v1.7$. SEQ ID NO:51 may be the amino acid sequence of the loop between S3 and S4 of the VSP of DII of $Na_v1.7$. The antibody may be a fragment of the anti-$Na_v1.7$ antibody or a variant or a derivative thereof. SEQ ID NO:50 may be the amino acid sequence of the VSP of DIV of $Na_v1.7$. The amino acid sequences of SEQ ID NOS:21, 23, 50, and 51 are shown below in Table 1.

TABLE 1

| | DII voltage-sensor paddle (S3b-loop-S4) | DII VSP loop | DIV voltage-sensor paddle (S3b-loop-S4) | DIV VSP loop |
|---|---|---|---|---|
| hNav1.7 gi14506813 NP_002968.1 | TLSLVELFLADVEGLS VLRSFRLL (SEQ ID NO: 23) | VELFLA DVEG (SEQ ID NO: 21) | SIVGMFLADLIETYFVSPTL FRVIRLARIG (SEQ ID NO: 50) | MFLADLI ETYF (SEQ ID NO: 51) |

The antibody may be a polyclonal or monoclonal antibody. The antibody may be a chimeric antibody, a single chain antibody, an affinity matured antibody, a human antibody, a humanized antibody, a bovinized antibody, a caninized antibody, equinized antibody, a felinized antibody, a porcinized antibody, a fully human antibody or an antibody fragment, such as a Fab fragment, or a mixture thereof. Antibody fragments or derivatives may comprise $F(ab')_2$, Fv or scFv fragments. The antibody derivatives can be produced by peptidomimetics. Further, techniques described for the production of single chain antibodies can be adapted to produce single chain antibodies.

The anti-Nav1.7 antibodies may be a chimeric anti-$Na_v1.7$ or humanized anti-$Na_v1.7$ antibody. In one embodiment, both the humanized antibody and chimeric antibody are monovalent. In one embodiment, both the humanized antibody and chimeric antibody comprise a single Fab region linked to an Fc region.

Human antibodies may be derived from phage-display technology or from transgenic mice that express human immunoglobulin genes. The human antibody may be generated as a result of a human in vivo immune response and isolated. See, for example, Funaro et al., BMC Biotechnology, 2008(8):85. Therefore, the antibody may be a product of the human and not animal repertoire. Because it is of human origin, the risks of reactivity against self-antigens may be minimized. Alternatively, standard yeast display libraries and display technologies may be used to select and isolate human anti-Na$_v$1.7 antibodies. For example, libraries of naïve human single chain variable fragments (scFv) may be used to select human anti-Na$_v$1.7 antibodies. Transgenic animals may be used to express human antibodies.

Humanized antibodies may be antibody molecules from non-human species antibody that binds the desired antigen having one or more complementarity determining regions (CDRs) from the non-human species and framework regions from a human immunoglobulin molecule.

The anti-Nav1.7 antibodies may be a chimeric anti-$Na_v1.7$ or bovinized anti-$Na_v1.7$ antibody. In one embodiment, both the bovinized antibody and chimeric antibody are monovalent. In one embodiment, both the bovinized antibody and chimeric antibody comprise a single Fab region linked to an Fc region.

Bovinized antibodies may be antibody molecules from non-bovine species antibody that binds the desired antigen having one or more complementarity determining regions (CDRs) from the non-bovine species and framework regions from a bovine immunoglobulin molecule.

The anti-Nav1.7 antibodies may be a chimeric anti-$Na_v1.7$ or caninized anti-$Na_v1.7$ antibody. In one embodiment, both the caninized antibody and chimeric antibody are monovalent. In one embodiment, both the caninized antibody and chimeric antibody comprise a single Fab region linked to an Fc region.

Caninized antibodies may be antibody molecules from non-human species antibody that binds the desired antigen having one or more complementarity determining regions (CDRs) from the non-canine species and framework regions from a canine immunoglobulin molecule.

The anti-Nav1.7 antibodies may be a chimeric anti-$Na_v1.7$ or equinized anti-$Na_v1.7$ antibody. In one embodiment, both the equinized antibody and chimeric antibody are monovalent. In one embodiment, both the equinized antibody and chimeric antibody comprise a single Fab region linked to an Fc region.

Equinized antibodies may be antibody molecules from non-equine species antibody that binds the desired antigen having one or more complementarity determining regions (CDRs) from the non-equine species and framework regions from a equine immunoglobulin molecule.

The anti-Nav1.7 antibodies may be a chimeric anti-$Na_v1.7$ or felinized anti-$Na_v1.7$ antibody. In one embodiment, both the felinized antibody and chimeric antibody are monovalent. In one embodiment, both the felinized antibody and chimeric antibody comprise a single Fab region linked to an Fc region.

Felinized antibodies may be antibody molecules from non-feline species antibody that binds the desired antigen having one or more complementarity determining regions (CDRs) from the non-feline species and framework regions from a feline immunoglobulin molecule.

The anti-Nav1.7 antibodies may be a chimeric anti-$Na_v1.7$ or porcinized anti-$Na_v1.7$ antibody. In one embodiment, both the porcinized antibody and chimeric antibody are monovalent. In one embodiment, both the porcinized antibody and chimeric antibody comprise a single Fab region linked to an Fc region.

Porcinized antibodies may be antibody molecules from non-porcine species antibody that binds the desired antigen having one or more complementarity determining regions (CDRs) from the non-porcine species and framework regions from a porcine immunoglobulin molecule.

The antibody may inhibit $Na_v1.7$ in a specific and state-dependent manner. Comparison of abilities to inhibit $Na_v1.7$ can be performed according to various methods known in the art. In one embodiment, $IC_{50}$ values are determined across an antibody concentration range from about 0.01 nM to about 1000 nM, about 0.1 nM to about 1000 nM, about 1.0 nM to about 1000 nM, about 10.0 nM to about 1000 nM, about 20.0 nM to about 1000 nM, about 50.0 nM to about 1000 nM, about 100.0 nM to about 1000 nM, about 200.0 nM to about 1000 nM, about 0.01 nM to about 900 nM, about 0.1 nM to about 900 nM, about 1.0 nM to about 900 nM, about 10.0 nM to about 900 nM, about 20.0 nM to about 900 nM, about 50.0 nM to about 900 nM, about 100.0 nM to about 900 nM, about 200.0 nM to about 900 nM, about 0.01 nM to about 800 nM, about 0.1 nM to about 800 nM, about 1.0 nM to about 800 nM, about 10.0 nM to about 800 nM, about 20.0 nM to about 800 nM, about 50.0 nM to about 800 nM, about 100.0 nM to about 800 nM, about 200.0 nM to about 800 nM, about 0.01 nM to about 700 nM, about 0.1 nM to about 700 nM, about 1.0 nM to about 700 nM, about 10.0 nM to about 700 nM, about 20.0 nM to about 700 nM, about 50.0 nM to about 700 nM, about 100.0 nM to about 700 nM, about 200.0 nM to about 700 nM, about 0.01 nM to about 500 nM, about 0.1 nM to about 500 nM, about 1.0 nM to about 500 nM, about 10.0 nM to about 500 nM, about 20.0 nM to about 500 nM, about 50.0 nM to about 500 nM, about 100.0 nM to about 500 nM, or about 200.0 nM to about 500 nM. For example, not only does the antibody of the invention recognize and bind $Na_v1.7$, it is also further characterized by having an additional biological activity, for example, the ability to attenuate clinical symptoms associated with diseases such as neurogenic inflammation, pain, itch, inflammatory pain, neuropathic pain, chronic pain, pathological pain, allergic contact dermatitis, allodynia, hyperalgesia, paroxysmal extreme pain disorder, and inherited erythromelalgia. The antibody may also be characterized by the additional biological activity of suppressing or reducing pathological cough.

Diseases associated with neurogenic inflammation may include, but are not limited to, asthma, arthritis, eczema, psoriasis, and migraine or headache.

In some embodiments, the pain may be inflammatory pain, neuropathic pain, hyperalgesia, chronic pain, pathological pain, allodynia, cancer-associated pain, atypical pain, neuroinflammation-associated pain conditions, neurogenic inflammation-associated pain, paroxysmal extreme pain disorder, inherited erythromelalgia, or a combination thereof. The inflammatory pain may be arthritis pain, dental pain, low back pain, pain associated inflammatory bowel disease, temporomandibular joint (TMJ), or a combination thereof. The neuropathic pain may be pain associated with diabetic neuropathy, chemotherapy, human immunodeficiency virus (HIV) infection, postherpetic neuralgia (PHN; also known as shingles), surgery (e.g., amputation, thoracotomy, mastectomy, hernia surgery, and so forth), spinal cord injury, stroke, or a combination thereof. The shingles may occur after infection with varicella zoser virus (VZV). The atypical pain may be fibromyalgia or sickle cell disease associated pain. Neuroinflammation-associated pain conditions may be complex regional pain syndrome (CRPS), headache, migraine, or a combination thereof. Neurogenic inflammation-associated pain may be complex regional pain syndrome (CRPS), headache, migraine, or a combination thereof.

The pain may be associated with itch, for example, but not limited to, acute itch, chronic itch, histamine-dependent itch, histamine-independent itch, or a combination thereof. The chronic itch may be associated with atopic dermatitis, allergic contact dermatitis, psoriasis, renal disease, liver disease, zoster virus, eczema, or a combination thereof. The acute itch may be gastrin-releasing peptide (GRP)-induced or mediated acute itch. The acute itch may be mediated by GRP in superficial dorsal horn neurons.

(1) Antibody Characteristics

The antibody may immunospecifically bind to human $Na_v1.7$ (SEQ ID NO:22; FIG. 1A), SEQ ID NO:21 (Table 1), SEQ ID NO:23 (FIG. 1B and Table 1), SEQ ID NO:50 (Table 1), SEQ ID NO:51 (Table 1), a fragment thereof, or a variant thereof and has a $K_d$ of at least 0.10 nM, of at least 0.20 nM, of at least 0.30 nM, of at least 0.40 nM, of at least 0.50 nM, of at least 0.60 nM, of at least 0.70 nM, of at least 0.80 nM, of at least 0.90 nM, of at least 1.00 nM, of at least 1.50 nM, of at least 2.00 nM, of at least 2.50 nM, of at least 3.00 nM, of at least 3.50 nM, of at least 4.00 nM, of at least 4.50 nM, of at least 5.00 nM, of at least 5.50 nM, of at least 6.00 nM, of at least 6.50 nM, of at least 7.00 nM, of at least 7.50 nM, of at least 8.00 nM, of at least 8.50 nM, of at least 9.00 nM, of at least 9.50 nM, of at least 10.00 nM, of at least 10.50 nM, of at least 11.00 nM, of at least 11.50 nM, of at least 12.00 nM, of at least 12.50 nM, of at least 13.00 nM, at least 13.50 nM, of at least 14.00 nM, of at least 14.50 nM, of at least 15.00 nM, of at least 15.50 nM, of at least 16.00 nM, of at least 16.50 nM, of at least 17.00 nM, of at least 17.50 nM, of at least 18.00 nM, of at least 18.50 nM, of at least 19.00 nM, of at least 19.50 nM, of at least 20.00 nM, of at least 20.50 nM, of at least 21.00 nM, of at least 21.50 nM, of at least 22.00 nM, of at least 22.50 nM, of at least 23.00 nM, of at least 23.50 nM, of at least 24.00 nM, of at least 24.50 nM, of at least 25.00 nM, of at least 25.50 nM, of at least 26.00 nM, of at least 26.50 nM, of at least 27.00 nM, of at least 27.50 nM, of at least 28.00 nM, of at least 28.50 nM, of at least 29.00 nM, of at least 29.50 nM, of at least 30.00 nM, of at least 30.05 nM, of at least 31.00 nM, of at least 31.50 nM, of at least 32.00 nM, of at least 32.50 nM, of at least 33.00 nM, of at least 33.50 nM, of at least 34.00 nM, of at least 34.50 nM, or of at least 35.00 nM. The antibody may have a $K_d$ ranging from about 0.10 nM to about 35.00 nM, from about 0.20 nM to about 35.00 nM, from about 0.30 nM to about 35.00 nM, from about 0.40 nM from about 35.00 nM, from about 0.50 nM to about 35.00 nM, from about 0.10 nM to about 34.00 nM, from about 0.20 nM to about 34.00 nM, from about 0.30 nM to about 34.00 nM, from about 0.40 nM to about 34.00 nM, from about 0.50 nM to about 34.00 nM, from about 0.10 nM to about 33.00 nM, from about 0.20 nM to about 33.00 nM, from about 0.30 nM to about 33.00 nM, from about 0.40 nM to about 33.00 nM, from about 0.50 nM to about 33.00 nM, from about 0.10 nM to about 32.00 nM, from about 0.20 nM to about 32.00 nM, from about 0.30 nM to about 32.00 nM, from about 0.40 nM to about 32.00 nM, from about 0.50 nM to about 32.00 nM, from about 0.10 nM to about 31.00 nM, from about 0.20 nM to about 31.00 nM, from about 0.30 nM to about 31.00 nM, from about 0.40 nM to about 31.00 nM, from about 0.50 nM to about 31.00 nM, from about 0.10 nM to about 30.00 nM, from about 0.20 nM to about 30.00 nM, from about 0.30 nM to about 30.00 nM, from about 0.40 nM to about 30.00 nM, or about 0.50 nM to about 30.00 nM. The fragment may be SEQ ID NO:21, SEQ ID NO:23, SEQ ID NO:50, or SEQ ID NO:51.

The antibody may significantly reduce peak sodium currents. Particularly, peak sodium currents may be reduced by the antibody inhibiting $Na_v1.7$. The antibody may inhibit $Na_v1.7$ by stabilizing the closed state of $Na_v1.7$. The maximum degree of $Na_v1.7$ inhibition may increase with higher frequency pulses, for example, from 84% inhibition to 99% inhibition. Additionally, the $IC_{50}$ of the antibody may be increased or enhanced with higher frequency pulses, for example, from about 106 nM to about 17 nM. Accordingly, the $IC_{50}$ of the antibody may be about 200 nM to about 1 nM. The $IC_{50}$ may be about 150 nM to about 5 nM, about 140 nM to about 5 nM, about 130 nM to about 5 nM, or about 120 nM to about 5 nM. The $IC_{50}$ may also be about 5 nM, about 6 nM, about 7 nM, about 8 nM, about 9 nM, about 10 nM, about 11 nM, about 12 nM, about 13 nM, about 14 nM, about 15 nM, about 16 nM, about 17 nM, about 18 nM, about 19 nM, about 20 nM, about 21 nM, about 22 nM, about 23 nM, about 24 nM, about 25 nM, about 30 nM, about 35 nM, about 40 nM, about 45 nM, about 50 nM, about 55 nM, about 60 nM, about 65 nM, about 70 nM, about 75 nM, about 80 nM, about 85 nM, about 90 nM, about 95 nM, about 96 nM, about 97 nM, about 98 nM, about 99 nM, about 100 nM, about 101 nM, about 102 nM, about 103 nM, about 104 nM, about 105 nM, about 106 nM, about 107 nM, about 108 nM, about 109 nM, about 110 nM, about 115 nM or about 120 nM. The $IC_{50}$ may be about 17 nM.

The antibody may stabilize the closed state of $Na_v1.7$ (i.e., the pore domain is closed and sodium cations are not transported across the membrane). Such a stabilization of the closed state to inhibit $Na_v1.7$ may occur by a mechanism different than a mechanism utilized by known inhibitors of voltage-gated ion channels (e.g., Hanatoxin and Pro-Tx-II). The antibody may inhibit $Na_v1.7$ by stabilizing the closed state of $Na_v1.7$ differently than how the toxin Pro-Tx-II stabilizes the closed state of $Na_v1.7$.

The antibody is specific (selective) for $Na_v1.7$ over other $Na_v$ channel subtypes. The antibody may exhibit a selectivity of about 50-fold to about 2500-fold, about 100-fold to about 2200-fold, about 200-fold to about 2000-fold, about 300-fold to about 1800-fold, or about 400-fold to about 1500-fold. The antibody may exhibit a selectivity of about 400-fold to about 1500-fold. The antibody may also exhibit a selectivity of about 50-fold, about 100-fold, about 200-fold, about 300-fold, about 325-fold, about 350-fold, about 375-fold, about 400-fold, about 425-fold, about 450-fold, about 475-fold, about 500-fold, about 525-fold, about 550-fold, about 575-fold, about 600-fold, about 625-fold, about 650-fold, about 675-fold, about 700-fold, about 725-fold, about 750-fold, about 775-fold, about 800-fold, about 825-fold, about 850-fold, about 875-fold, about 900-fold, about 975-fold, about 1000-fold, about 1025-fold, about 1050-fold, about 1075-fold, about 1100-fold, about 1125-fold, about 1150-fold, about 1175-fold, about 1200-fold, about 1225-fold, about 1250-fold, about 1275-fold, about 1300-fold, about 1375-fold, about 1400-fold, about 1425-fold, about 1450-fold, about 1475-fold, about 1500-fold, about 1525-fold, about 1575-fold, about 1600-fold, about 1700-fold, about 1800-fold, about 1900-fold, about 2000-fold, about 2100-fold, about 2200-fold, about 2300-fold, about 2400-fold, or about 2500-fold.

The antibody may suppress pain sensation in a subject suffering from pain, for example, inflammatory pain, neuropathic pain, hyperalgesia, chronic pain, pathological pain, allodynia, hyperalgesia, paroxysmal extreme pain disorder, and inherited erythromelalgia. In some embodiments, the pain may be inflammatory pain, neuropathic pain, chronic pain, pathological pain, allodynia, cancer-associated pain, atypical pain, neuroinflammation-associated pain conditions, neurogenic inflammation-associated pain, paroxysmal extreme pain disorder, inherited erythromelalgia, or a combination thereof. The inflammatory pain may be arthritis pain, dental pain, low back pain, pain associated inflammatory bowel disease, temporomandibular joint (TMJ), or a combination thereof. The neuropathic pain may be pain associated with diabetic neuropathy, chemotherapy, human immunodeficiency virus (HIV) infection, postherpetic neuralgia (PHN; also known as shingles), surgery (e.g., amputation, thoracotomy, mastectomy, hernia surgery, and so forth), spinal cord injury, stroke, or a combination thereof. The shingles may occur after infection with varicella zoster virus (VZV). The atypical pain may be fibromyalgia or sickle cell disease associated pain. Neuroinflammation-associated pain conditions may be complex regional pain syndrome (CRPS), headache, migraine, or a combination thereof. Neurogenic inflammation-associated pain may be complex regional pain syndrome (CRPS), headache, migraine, or a combination thereof.

The pain may be associated with itch, for example, but not limited to, acute itch, chronic itch, histamine-dependent itch, histamine-independent itch, or a combination thereof. The acute itch may be gastrin-releasing peptide (GRP)-induced or mediated acute itch. The acute itch may be mediated by GRP in superficial dorsal horn neurons. The chronic itch may be associated with atopic dermatitis, allergic contact dermatitis, psoriasis, renal disease, liver disease, zoster virus, eczema, or a combination thereof.

The antibody may suppress pain sensation either centrally, systemically, peripherally, and/or locally. The antibody may suppress pain sensation in the subject from about 35% to about 85%, from about 40% to about 80%, from about 42% to about 78%, from about 44% to about 76%, or from about 46% to about 74%. The antibody may also suppress pain sensation about 35%, about 40%, about 45%, about 46%, about 47%, about 48%, about 49%, about 50%, about 51%, about 52%, about 53%, about 54%, about 55%, about 60%, about 65%, about 66%, about 67%, about 68%, about 69%, about 70%, about 71%, about 72%, about 73%, about 74%, about 75%, about 80%, or about 85%. The antibody may also suppress pain sensation in the subject by about 50% or by about 70%.

The antibody may suppress allergic contact dermatitis. The antibody may suppress neurogenic inflammation. Diseases associated with neurogenic inflammation may include, but are not limited to, asthma, arthritis, eczema, psoriasis, and migraine or headache.

The antibody may attenuate or suppress clinical symptoms associated with diseases such as neurogenic inflammation, pain, itch, inflammatory pain, neuropathic pain, chronic pain, pathological pain, allergic contact dermatitis, allodynia, hyperalgesia, paroxysmal extreme pain disorder, and inherited erythromelalgia. Diseases associated with neurogenic inflammation may include, but are not limited to, asthma, arthritis, eczema, psoriasis, and migraine or headache. In some embodiments, the pain may be inflammatory pain, neuropathic pain, hyperalgesia, chronic pain, pathological pain, allodynia, cancer-associated pain, atypical pain, neuroinflammation-associated pain conditions, neurogenic inflammation-associated pain, paroxysmal extreme pain disorder, inherited erythromelalgia, or a combination thereof. The inflammatory pain may be arthritis pain, dental pain, low back pain, pain associated inflammatory bowel disease, temporomandibular joint (TMJ), or a combination thereof. The neuropathic pain may be pain associated with diabetic neuropathy, chemotherapy, human immunodeficiency virus (HIV) infection, postherpetic neuralgia (PHN; also known as shingles), surgery (e.g., amputation, thoracotomy, mastectomy, hernia surgery, and so forth), spinal cord injury, stroke, or a combination thereof. The shingles may occur after infection with varicella zoster virus (VZV). The atypi- cal pain may be fibromyalgia or sickle cell disease associated pain. Neuroinflammation-associated pain conditions may be complex regional pain syndrome (CRPS), headache, migraine, or a combination thereof. Neurogenic inflammation-associated pain may be complex regional pain syndrome (CRPS), headache, migraine, or a combination thereof. The pain may be associated itch, for example, but not limited to, acute itch, chronic itch, histamine-dependent itch, histamine-independent itch, or a combination thereof. The chronic itch may be associated with atopic dermatitis, allergic contact dermatitis, psoriasis, renal disease, liver disease, zoster virus, eczema, or a combination thereof. The acute itch may be gastrin-releasing peptide (GRP)-induced or mediated acute itch. The acute itch may be mediated by GRP in superficial dorsal horn neurons.

The antibody may increase a pain threshold in a subject suffering from pain, for example, inflammatory pain, neuropathic pain, hyperalgesia, chronic pain, pathological pain, allodynia, hyperalgesia, paroxysmal extreme pain disorder, and inherited erythromelalgia. In some embodiments, the pain may be inflammatory pain, neuropathic pain, hyperalgesia, chronic pain, pathological pain, allodynia, cancer-associated pain, atypical pain, neuroinflammation-associated pain conditions, neurogenic inflammation-associated pain, paroxysmal extreme pain disorder, inherited erythromelalgia, or a combination thereof. The inflammatory pain may be arthritis pain, dental pain, low back pain, pain associated inflammatory bowel disease, temporomandibular joint (TMJ), or a combination thereof. The neuropathic pain may be pain associated with diabetic neuropathy, chemotherapy, human immunodeficiency virus (HIV) infection, postherpetic neuralgia (PHN; also known as shingles), surgery (e.g., amputation, thoracotomy, mastectomy, hernia surgery, and so forth), spinal cord injury, stroke, or a combination thereof. The shingles may occur after infection with varicella zoster virus (VZV). The atypical pain may be fibromyalgia or sickle cell disease associated pain. Neuroinflammation-associated pain conditions may be complex regional pain syndrome (CRPS), headache, migraine, or a combination thereof. Neurogenic inflammation-associated pain may be complex regional pain syndrome (CRPS), headache, migraine, or a combination thereof. The pain may be associated with itch, for example, but not limited to, acute itch, chronic itch, histamine-dependent itch, histamine-independent itch, or a combination thereof. The acute itch may be gastrin-releasing peptide (GRP)-induced or mediated acute itch. The acute itch may be mediated by GRP in superficial dorsal horn neurons. The chronic itch may be associated with atopic dermatitis, allergic contact dermatitis, psoriasis, renal disease, liver disease, zoster virus, eczema, or a combination thereof.

The antibody may increase the pain threshold either centrally, systemically, peripherally, and/or locally in the subject. The antibody may increase the pain threshold in the subject by about 1.2-fold to about 4-fold, about 1.5-fold to about 3-fold, or about 2-fold. The antibody may increase the pain threshold in the subject by about 1.2-fold, about 1.3-fold, about 1.4-fold, about 1.5-fold, about 1.6-fold, about 1.7-fold, about 1.8-fold, about 1.9-fold, about 2.0-fold, about 2.1-fold, about 2.2-fold, about 2.3-fold, about 2.4-fold, about 2.5-fold, about 2.6-fold, about 2.7-fold, about 2.8-fold, about 2.9-fold, about 3.0-fold, about 3.1-fold, about 3.2 fold, about 3.3-fold, about 3.4-fold, about 3.5-fold, about 3.6-fold, about 3.7-fold, about 3.8-fold, about 3.9-fold, or about 4-fold. The antibody may increase the pain threshold in the subject by about 2-fold or about 3-fold.

The antibody may increase the pain threshold in the subject by about 125% to about 400%, about 150% to about 300%, or about 200%. The antibody may increase the pain threshold in the subject by about 125%, about 130%, about 135%, about 140%, about 145%, about 150%, about 155%, about 160%, about 165%, about 170%, about 175%, about 180%, about 185%, about 190%, about 195%, about 200%, about 205%, about 210%, about 215%, about 220%, about 225%, about 230%, about 235%, about 240%, about 245%, about 250%, about 255%, about 260%, about 265%, about 270%, about 275%, about 280%, about 285%, about 290%, about 295%, about 300%, about 305%, about 310%, about 315%, about 320%, about 325%, about 330%, about 335%, about 340%, about 345%, about 350%, about 355%, about 360%, about 365%, about 370%, about 375%, about 380%, about 385%, about 390%, about 395%, or about 400%. The antibody may increase the pain threshold in the subject by about 200% or about 300%.

The antibody may suppress or alleviate itch, for example, but not limited to, acute itch, chronic itch, histamine-dependent itch, histamine-independent itch, allergic contact dermatitis, or a combination thereof in the subject. The acute itch may be gastrin-releasing peptide (GRP)-induced or mediated acute itch. The acute itch may be mediated by GRP in superficial dorsal horn neurons. The chronic itch may be associated with atopic dermatitis, allergic contact dermatitis, psoriasis, renal disease, liver disease, zoster virus, eczema, or a combination thereof. The antibody may suppress itch in the subject by at least about 40%, 50%, 60%, or 70%. The antibody may be used to manage itch in a subject suffering from acute itch, chronic itch, histamine-dependent itch, histamine-independent itch, allergic contact dermatitis, or a combination thereof.

The antibody may suppress or alleviate neurogenic inflammation. Diseases associated with neurogenic inflammation may include, but are not limited to, asthma, arthritis, eczema, psoriasis, and migraine or headache.

The antibody may suppress or reduce pathological cough. The antibody may suppress or reduce chronic cough.

(2) Antibody Structure
(a) Heavy Chain and Light Chain CDRs

The antibody may immunospecifically bind to $Na_v1.7$ (SEQ ID NO:22; FIG. 1A), a fragment thereof (SEQ ID NO:21 (Table 1), SEQ ID NO:23 (FIG. 1B and Table 1), SEQ ID NO:50 (Table 1), or SEQ ID NO:51 (Table 1)), or a variant thereof and comprise a variable heavy chain (VH) and/or variable light chain (VL) shown in Table 2 and FIGS. 3A and 3B. The variable heavy chain and/or variable light chains may be encoded by the nucleic acid sequences shown in Table 3 and FIGS. 2A and 2B. The antibody may immunospecifically bind to $Na_v1.7$, a fragment thereof, or a variant thereof, and comprises one or more of the heavy chain or light chain CDR sequences also shown in Table 2 and FIGS. 3A and 3B (CDRs shown by underlining). The one or more of the heavy chain or light chain CDR sequences may be encoded by the nucleic acid sequences shown in Table 3 and FIGS. 2A and 2B (CDRs shown by underlining).

Provided herein is an isolated nucleic acid encoding an antibody that immunospecifically binds to $Na_v1.7$, a fragment thereof, or a variant thereof. The isolated nucleic acid may comprise a nucleotide sequence that hybridizes, under stringent conditions, to the nucleic acid molecule that encodes an antibody comprising the heavy chain or light chain CDR sequences shown in Table 2.

TABLE 2

| PROTEIN - 1E16 (also known herein as SVmab1) | | |
|---|---|---|
| REGION | SEQUENCE | SEQ ID NO: |
| 1E16 (VH) | MEWNWVVLFLLSLTAGVYAQGQMQQSGAEL VKPGASVKLSCKTSGFTFSSSYISWLKQKPGQS LEWIAWIYAGTGGTSYNQKFTGKAQLTVDTSS STAYMQFSSLTTEDSAIYYCARQDGNYRYWY FDVWGAGTTVTVSS | SEQ ID NO: 4 |
| 1E16 (VH) CDR-H1 | GFTFSSSYIS | SEQ ID NO: 5 |
| 1E16 (VH) CDR-H2 | WIYAGTGGTSYNQKFTG | SEQ ID NO: 6 |
| 1E16 (VH) CDR-H3 | QDGNYRYWYFDV | SEQ ID NO: 7 |
| 1E16 (VL) | MTMFSLALLLSLLLLCVSDSRAETTVTQSPASL SMAIGEKVTIRCITSTDIDDDMNWYQQKPGEP PKLLISEGNTLRPGVPSRFSSSGYGTDFVFTIEN MLSEDVADYYCLQSDNLPLTFGGGTKLEIK | SEQ ID NO: 8 |
| 1E16 (VL) CDR-L1 | ITSTDIDDDMN | SEQ ID NO: 9 |
| 1E16 (VL) CDR-L2 | EGNTLRP | SEQ ID NO: 10 |
| 1E16 (VL) CDR-L3 | LQSDNLPLT | SEQ ID NO: 11 |

TABLE 3

| DNA - 1E16 (also known herein as SVmab1) | | |
|---|---|---|
| REGION | SEQUENCE | SEQ ID NO: |
| 1E16 (VH) | ATGGAATGGAACTGGGTCGTTCTCTTCCTCC TGTCATTAACTGCAGGTGTCTATGCCCAGGG TCAGATGCAGCAGTCTGGAGCTGAGCTGGT GAAGCCTGGGGCTTCAGTGAAGCTGTCCTGC | SEQ ID NO: 12 |

TABLE 3-continued

DNA - 1E16 (also known herein as SVmab1)

| REGION | SEQUENCE | SEQ ID NO: |
|---|---|---|
| | AAGACTTCTGGCTTCACCTTCAGCAGTAGCT<br>ATATAAGTTGGTTGAAGCAAAAGCCTGGAC<br>AGAGTCTTGAGTGGATTGCATGGATTTATGC<br>TGGAACTGGTGGTACTAGCTATAATCAGAA<br>GTTCACAGGCAAGGCCCAACTGACTGTAGA<br>CACATCCTCCAGCACAGCCTACATGCAATTC<br>AGCAGCCTGACAACTGAGGACTCTGCCATCT<br>ATTACTGTGCAAGACAAGATGGTAACTACA<br>GGTACTGGTACTTCGATGTCTGGGGCGCAGG<br>GACCACGGTCACCGTCTCCTCA | |
| 1E16 (VH) CDR-H1 | GGCTTCACCTTCAGCAGTAGCTATATAAGT | SEQ ID NO: 13 |
| 1E16 (VH) CDR-H2 | TGGATTTATGCTGGAACTGGTGGTACTAGC<br>TATAATCAGAAGTTCACAGGC | SEQ ID NO: 14 |
| 1E16 (VH) CDR-H3 | CAAGATGGTAACTACAGGTACTGGTACTTC<br>GATGTC | SEQ ID NO: 15 |
| 1E16 (VL) | ATGACCATGTTCTCACTAGCTCTTCTCCTCA<br>GTCTTCTTCTCCTCTGTGTCTCTGATTCTAGG<br>GCAGAAACAACTGTGACCCAGTCTCCAGCA<br>TCCCTGTCCATGGCTATAGGAGAAAAAGTCA<br>CCATCAGATGCATAACCAGCACTGATATTGA<br>TGATGATATGAACTGGTACCAGCAGAAGCC<br>AGGGGAACCTCCTAAGCTCCTTATTTCAGAA<br>GGCAATACTCTTCGTCCTGGAGTCCCATCCC<br>GATTCTCCAGCAGTGGCTATGGTACAGATTT<br>TGTTTTTACAATTGAAAACATGCTCTCAGAA<br>GATGTTGCAGATTACTACTGTTTGCAAAGTG<br>ATAACTTGCCTCTCACGTTCGGAGGGGGAC<br>CAAGCTGGAAATAAAA | SEQ ID NO: 16 |
| 1E16 (VL) CDR-L1 | ATAACCAGCACTGATATTGATGATGATATGA<br>AC | SEQ ID NO: 17 |
| 1E16 (VL) CDR-L2 | GAAGGCAATACTCTTCGTCCT | SEQ ID NO: 18 |
| 1E16 (VL) CDR-L3 | TTGCAAAGTGATAACTTGCCTCTCACG | SEQ ID NO: 19 |

The antibody or variant or derivative thereof may contain one or more amino acid sequences that are greater than 99%, 98%, 97%, 96%, 95%, 94%, 93%, 92%, 91%, 90%, 85%, 80%, 75%, 70%, 65%, 60%, 55%, or 50% identical to one or more of SEQ ID NOs:4-11. The antibody or variant or derivative thereof may be encoded by one or more nucleic acid sequences that are greater than 99%, 98%, 97%, 96%, 95%, 94%, 93%, 92%, 91%, 90%, 85%, 80%, 75%, 70%, 65%, 60%, 55%, or 50% identical to one or more of SEQ ID NOs:12-19. Polypeptide identity and homology can be determined, for example, by the algorithm described in the report: Wilbur, W. J. and Lipman, D. J. Proc. Natl. Acad. Sci. USA 80, 726-730 (1983). The herein described antibody, variant, or derivative thereof may be encoded by a nucleic acid that hybridizes under stringent conditions with the complement of one or more of SEQ ID NOs: 12-19.

The antibody may be an IgG, IgE, IgM, IgD, IgA, and IgY molecule class (for example, IgG1, IgG2, IgG3, IgG4, IgA1 and IgA2) or subclass.

c. Antibody Preparation/Production

Antibodies may be prepared by any of a variety of techniques. In general, antibodies can be produced by cell culture techniques, including the generation of monoclonal antibodies via conventional techniques, or via transfection of antibody genes, heavy chains, and/or light chains into suitable bacterial or mammalian cell hosts, in order to allow for the production of antibodies, wherein the antibodies may be recombinant. The various forms of the term "transfection" are intended to encompass a wide variety of techniques commonly used for the introduction of exogenous DNA into a prokaryotic or eukaryotic host cell, e.g., electroporation, calcium-phosphate precipitation, DEAE-dextran transfection and the like. Although it is possible to express the antibodies of the invention in either prokaryotic or eukaryotic host cells, expression of antibodies in eukaryotic cells is preferable, and most preferable in mammalian host cells, because such eukaryotic cells (and in particular mammalian cells) are more likely than prokaryotic cells to assemble and secrete a properly folded and immunologically active antibody.

Exemplary mammalian host cells for expressing the recombinant antibodies of the invention include Chinese Hamster Ovary (CHO cells) (including dhfr-CHO cells, described in Urlaub and Chasin, Proc. Natl. Acad. Sci. USA, 77: 4216-4220 (1980)), used with a DHFR selectable marker, e.g., as described in Kaufman and Sharp, J. Mol. Biol., 159: 601-621 (1982), NS0 myeloma cells, COS cells, and SP2 cells. When recombinant expression vectors encoding antibody genes are introduced into mammalian host cells, the antibodies are produced by culturing the host cells for a period of time sufficient to allow for expression of the antibody in the host cells or, more preferably, secretion of the antibody into the culture medium in which the host cells are grown. Antibodies can be recovered from the culture medium using standard protein purification methods.

Host cells can also be used to produce functional antibody fragments, such as Fab fragments or scFv molecules. It will be understood that variations on the above procedure are within the scope of the present invention. For example, it may be desirable to transfect a host cell with DNA encoding functional fragments of either the light chain and/or the heavy chain of an antibody of this invention. Recombinant DNA technology may also be used to remove some, or all, of the DNA encoding either or both of the light and heavy chains that is not necessary for binding to the antigens of interest. The molecules expressed from such truncated DNA molecules are also encompassed by the antibodies of the invention. In addition, bifunctional antibodies may be produced in which one heavy and one light chain are an antibody of the invention (i.e., binds Nav1.7) and the other heavy and light chain are specific for an antigen other than Nav1.7 by crosslinking an antibody of the invention to a second antibody by standard chemical crosslinking methods.

In a preferred system for recombinant expression of an antibody, or antigen-binding portion thereof, of the invention, a recombinant expression vector encoding both the antibody heavy chain and the antibody light chain is introduced into dhfr-CHO cells by calcium phosphate-mediated transfection. Within the recombinant expression vector, the antibody heavy and light chain genes are each operatively linked to CMV enhancer/AdMLP promoter regulatory elements to drive high levels of transcription of the genes. The recombinant expression vector also carries a DHFR gene, which allows for selection of CHO cells that have been transfected with the vector using methotrexate selection/amplification. The selected transformant host cells are cultured to allow for expression of the antibody heavy and light chains and intact antibody is recovered from the culture medium. Standard molecular biology techniques are used to prepare the recombinant expression vector, transfect the host cells, select for transformants, culture the host cells, and recover the antibody from the culture medium. Still further, the invention provides a method of synthesizing a recombinant antibody of the invention by culturing a host cell of the invention in a suitable culture medium until a recombinant antibody of the invention is synthesized. The method can further comprise isolating the recombinant antibody from the culture medium.

Methods of preparing monoclonal antibodies involve the preparation of immortal cell lines capable of producing antibodies having the desired specificity. Such cell lines may be produced from spleen cells obtained from an immunized animal. The animal may be immunized with $Na_v1.7$ or a fragment and/or variant thereof. For example, any of SEQ ID NOS:21-23, 50, and/or 51 may be used to immunize the animal. The peptide used to immunize the animal may comprise amino acids encoding human Fc, for example the fragment crystallizable region or tail region of human antibody. The spleen cells may then be immortalized by, for example, fusion with a myeloma cell fusion partner. A variety of fusion techniques may be employed. For example, the spleen cells and myeloma cells may be combined with a nonionic detergent for a few minutes and then plated at low density on a selective medium that supports that growth of hybrid cells, but not myeloma cells. One such technique uses hypoxanthine, aminopterin, thymidine (HAT) selection. Another technique includes eletrofusion. After a sufficient time, usually about 1 to 2 weeks, colonies of hybrids are observed. Single colonies are selected and their culture supernatants tested for binding activity against the polypeptide. Hybridomas having high reactivity and specificity may be used.

Monoclonal antibodies may be isolated from the supernatants of growing hybridoma colonies. In addition, various techniques may be employed to enhance the yield, such as injection of the hybridoma cell line into the peritoneal cavity of a suitable vertebrate host, such as a mouse. Monoclonal antibodies may then be harvested from the ascites fluid or the blood. Contaminants may be removed from the antibodies by conventional techniques, such as chromatography, gel filtration, precipitation, and extraction. Affinity chromatography is an example of a method that can be used in a process to purify the antibodies.

The proteolytic enzyme papain preferentially cleaves IgG molecules to yield several fragments, two of which (the F(ab) fragments) each comprise a covalent heterodimer that includes an intact antigen-binding site. The enzyme pepsin is able to cleave IgG molecules to provide several fragments, including the F(ab')2 fragment, which comprises both antigen-binding sites.

The Fv fragment can be produced by preferential proteolytic cleavage of an IgM, and on rare occasions IgG or IgA immunoglobulin molecules. The Fv fragment may be derived using recombinant techniques. The Fv fragment includes a non-covalent VH::VL heterodimer including an antigen-binding site that retains much of the antigen recognition and binding capabilities of the native antibody molecule.

The antibody, antibody fragment, or derivative may comprise a heavy chain and a light chain complementarity determining region ("CDR") set, respectively interposed between a heavy chain and a light chain framework ("FR") set which provide support to the CDRs and define the spatial relationship of the CDRs relative to each other. The DR set may contain three hypervariable regions of a heavy or light chain V region. Proceeding from the N-terminus of a heavy or light chain, these regions are denoted as "CDR1," "CDR2," and "CDR3," respectively. An antigen-binding site, therefore, may include six CDRs, comprising the CDR set from each of a heavy and a light chain V region. A polypeptide comprising a single CDR, (e.g., a CDR1, CDR2, or CDR3) may be referred to as a "molecular recognition unit." Crystallographic analyses of antigen-antibody complexes have demonstrated that the amino acid residues of CDRs form extensive contact with bound antigen, wherein the most extensive antigen contact is with the heavy chain CDR3. Thus, the molecular recognition units may be primarily responsible for the specificity of an antigen-binding site. In general, the CDR residues are directly and most substantially involved in influencing antigen binding.

Other suitable methods of producing or isolating antibodies of the requisite specificity can be used, including, but not limited to, methods that select recombinant antibody from a peptide or protein library (e.g., but not limited to, a bacteriophage, ribosome, oligonucleotide, RNA, cDNA, yeast or the like, display library); e.g., as available from various commercial vendors such as Cambridge Antibody Technologies (Cambridgeshire, UK), MorphoSys (Martinsreid/Planegg, Del.), Biovation (Aberdeen, Scotland, UK) BioInvent (Lund, Sweden), using methods known in the art. See U.S. Pat. Nos. 4,704,692; 5,723,323; 5,763,192; 5,814,476; 5,817,483; 5,824,514; 5,976,862. Alternative methods rely upon immunization of transgenic animals (e.g., SCID mice, Nguyen et al. (1997) Microbiol. Immunol. 41:901-907; Sandhu et al. (1996) Crit. Rev. Biotechnol. 16:95-118; Eren et al. (1998) Immunol. 93:154-161) that are capable of producing a repertoire of human antibodies, as known in the art and/or as described herein. Such techniques, include, but are not limited to, ribosome display (Hanes et al. (1997) Proc. Natl. Acad. Sci. USA, 94:4937-4942; Hanes et al.

(1998) Proc. Natl. Acad. Sci. USA, 95:14130-14135); single cell antibody producing technologies (e.g., selected lymphocyte antibody method ("SLAM") (U.S. Pat. No. 5,627,052, Wen et al. (1987) J. Immunol. 17:887-892; Babcook et al. (1996) Proc. Natl. Acad. Sci. USA 93:7843-7848); gel microdroplet and flow cytometry (Powell et al. (1990) Biotechnol. 8:333-337; One Cell Systems, (Cambridge, Mass.).; Gray et al. (1995) J. Imm. Meth. 182:155-163; Kenny et al. (1995) Bio/Technol. 13:787-790); B-cell selection (Steenbakkers et al. (1994) Molec. Biol. Reports 19:125-134 (1994)).

An affinity matured antibody may be produced by any one of a number of procedures that are known in the art. For example, see Marks et al., BioTechnology, 10: 779-783 (1992) describes affinity maturation by VH and VL domain shuffling. Random mutagenesis of CDR and/or framework residues is described by Barbas et al., Proc. Nat. Acad. Sci. USA, 91: 3809-3813 (1994); Schier et al., Gene, 169: 147-155 (1995); Yelton et al., J. Immunol., 155: 1994-2004 (1995); Jackson et al., J. Immunol., 154(7): 3310-3319 (1995); Hawkins et al, J. Mol. Biol., 226: 889-896 (1992). Selective mutation at selective mutagenesis positions and at contact or hypermutation positions with an activity enhancing amino acid residue is described in U.S. Pat. No. 6,914,128 B1.

Antibody variants of the present invention can also be prepared using delivering a polynucleotide encoding an antibody of this invention to a suitable host such as to provide transgenic animals or mammals, such as goats, cows, horses, sheep, and the like, that produce such antibodies in their milk. These methods are known in the art and are described for example in U.S. Pat. Nos. 5,827,690; 5,849,992; 4,873,316; 5,849,992; 5,994,616; 5,565,362; and 5,304,489.

Antibody variants also can be prepared by delivering a polynucleotide of this invention to provide transgenic plants and cultured plant cells (e.g., but not limited to tobacco, maize, and duckweed) that produce such antibodies, specified portions or variants in the plant parts or in cells cultured therefrom. For example, Cramer et al. (1999) Curr. Top. Microbol. Immunol. 240:95-118 and references cited therein, describe the production of transgenic tobacco leaves expressing large amounts of recombinant proteins, e.g., using an inducible promoter. Transgenic maize have been used to express mammalian proteins at commercial production levels, with biological activities equivalent to those produced in other recombinant systems or purified from natural sources. See, e.g., Hood et al., Adv. Exp. Med. Biol. (1999) 464:127-147 and references cited therein. Antibody variants have also been produced in large amounts from transgenic plant seeds including antibody fragments, such as single chain antibodies (scFv's), including tobacco seeds and potato tubers. See, e.g., Conrad et al. (1998) Plant Mol. Biol. 38:101-109 and reference cited therein. Thus, antibodies of the present invention can also be produced using transgenic plants, according to known methods.

Antibody derivatives can be produced, for example, by adding exogenous sequences to modify immunogenicity or reduce, enhance or modify binding, affinity, on-rate, off-rate, avidity, specificity, half-life, or any other suitable characteristic. Generally, part or all of the non-human or human CDR sequences are maintained while the non-human sequences of the variable and constant regions are replaced with human or other amino acids.

Small antibody fragments may be diabodies having two antigen-binding sites, wherein fragments comprise a heavy chain variable domain (VH) connected to a light chain variable domain (VL) in the same polypeptide chain (VH VL). See for example, EP 404,097; WO 93/11161; and Hollinger et al., (1993) Proc. Natl. Acad. Sci. USA 90:6444-6448. By using a linker that is too short to allow pairing between the two domains on the same chain, the domains are forced to pair with the complementary domains of another chain and create two antigen-binding sites. See also, U.S. Pat. No. 6,632,926 to Chen et al. which is hereby incorporated by reference in its entirety and discloses antibody variants that have one or more amino acids inserted into a hypervariable region of the parent antibody and a binding affinity for a target antigen which is at least about two fold stronger than the binding affinity of the parent antibody for the antigen.

The antibody may be a linear antibody. The procedure for making a linear antibody is known in the art and described in Zapata et al. (1995) Protein Eng. 8(10):1057-1062. Briefly, these antibodies comprise a pair of tandem Fd segments (VH-CH1-VH-CH1) which form a pair of antigen binding regions. Linear antibodies can be bispecific or monospecific.

The antibodies may be recovered and purified from recombinant cell cultures by known methods including, but not limited to, protein A purification, ammonium sulfate or ethanol precipitation, acid extraction, anion or cation exchange chromatography, phosphocellulose chromatography, hydrophobic interaction chromatography, affinity chromatography, hydroxylapatite chromatography and lectin chromatography. High performance liquid chromatography ("HPLC") can also be used for purification.

It may be useful to detectably or therapeutically label the antibody. Methods for conjugating antibodies to these agents are known in the art. For the purpose of illustration only, antibodies can be labeled with a detectable moiety such as a radioactive atom, a chromophore, a fluorophore, or the like. Such labeled antibodies can be used for diagnostic techniques, either in vivo, or in an isolated test sample. Antibodies can also be conjugated, for example, to a pharmaceutical agent, such as chemotherapeutic drug or a toxin. They can be linked to a cytokine, to a ligand, to another antibody. Suitable agents for coupling to antibodies to achieve an anti-tumor effect include cytokines, such as interleukin 2 (IL-2) and Tumor Necrosis Factor (TNF); photosensitizers, for use in photodynamic therapy, including aluminum (III) phthalocyanine tetrasulfonate, hematoporphyrin, and phthalocyanine; radionuclides, such as iodine-131 (1314 yttrium-90 (90Y), bismuth-212 (212Bi), bismuth-213 (213Bi), technetium-99m (99mTc), rhenium-186 (186Re), and rhenium-188 (188Re); antibiotics, such as doxorubicin, adriamycin, daunorubicin, methotrexate, daunomycin, neocarzinostatin, and carboplatin; bacterial, plant, and other toxins, such as diphtheria toxin, pseudomonas exotoxin A, staphylococcal enterotoxin A, abrin-A toxin, ricin A (deglycosylated ricin A and native ricin A), TGF-alpha toxin, cytotoxin from chinese cobra (naja atra), and gelonin (a plant toxin); ribosome inactivating proteins from plants, bacteria and fungi, such as restrictocin (a ribosome inactivating protein produced by *Aspergillus restrictus*), saporin (a ribosome inactivating protein from *Saponaria officinalis*), and RNase; tyrosine kinase inhibitors; ly207702 (a difluorinated purine nucleoside); liposomes containing anti cystic agents (e.g., antisense oligonucleotides, plasmids which encode for toxins, methotrexate, etc.); and other antibodies or antibody fragments, such as F(ab).

The antibodies can be sequenced and replicated by recombinant or synthetic means. They also can be further sequenced down to the linear sequence of nucleotides that encode them. Accordingly, this invention provides these polynucleotides, alone or in combination with a carrier, vector or host cell as described above, that encode a sequence of an antibody of this invention.

Antibody production via the use of hybridoma technology, the selected lymphocyte antibody method (SLAM), transgenic animals, and recombinant antibody libraries is described in more detail below.

(1) Anti-Nav1.7 Monoclonal Antibodies Using Hybridoma Technology

Monoclonal antibodies can be prepared using a wide variety of techniques known in the art including the use of hybridoma, recombinant, and phage display technologies, or a combination thereof. For example, monoclonal antibodies can be produced using hybridoma techniques including those known in the art and taught, for example, in Harlow et al., Antibodies: A Laboratory Manual, second edition, (Cold Spring Harbor Laboratory Press, Cold Spring Harbor, 1988); Hammerling, et al., In Monoclonal Antibodies and T-Cell Hybridomas, (Elsevier, N.Y., 1981). It is also noted that the term "monoclonal antibody" as used herein is not limited to antibodies produced through hybridoma technology. The term "monoclonal antibody" refers to an antibody that is derived from a single clone, including any eukaryotic, prokaryotic, or phage clone, and not the method by which it is produced.

In an embodiment, the present invention provides methods of generating monoclonal antibodies as well as antibodies produced by the method. The method may comprise culturing a hybridoma cell secreting an antibody of the invention wherein, preferably, the hybridoma is generated by fusing splenocytes isolated from an animal, e.g., a rat or a mouse, immunized with Nav1.7 with myeloma cells and then screening the hybridomas resulting from the fusion for hybridoma clones that secrete an antibody able to bind a polypeptide of the invention. Briefly, rats can be immunized with an Nav1.7 antigen. In a preferred embodiment, the Nav1.7 antigen is administered with an adjuvant to stimulate the immune response. Such adjuvants include complete or incomplete Freund's adjuvant, RIBI (muramyl dipeptides) or ISCOM (immunostimulating complexes). Such adjuvants may protect the polypeptide from rapid dispersal by sequestering it in a local deposit, or they may contain substances that stimulate the host to secrete factors that are chemotactic for macrophages and other components of the immune system. Preferably, if a polypeptide is being administered, the immunization schedule will involve two or more administrations of the polypeptide, spread out over several weeks; however, a single administration of the polypeptide may also be used.

After immunization of an animal with a $Na_v1.7$ antigen, antibodies and/or antibody-producing cells may be obtained from the animal. An anti-$Na_v1.7$ antibody-containing serum is obtained from the animal by bleeding or sacrificing the animal. The serum may be used as it is obtained from the animal, an immunoglobulin fraction may be obtained from the serum, or the anti-$Na_v1.7$ antibodies may be purified from the serum. Serum or immunoglobulins obtained in this manner are polyclonal, thus having a heterogeneous array of properties.

Once an immune response is detected, e.g., antibodies specific for the antigen Nav1.7 are detected in the rat serum, the rat spleen is harvested and splenocytes isolated. The splenocytes are then fused by well-known techniques to any suitable myeloma cells, for example, cells from cell line SP20 available from the American Type Culture Collection (ATCC, Manassas, Va., US). Hybridomas are selected and cloned by limited dilution. The hybridoma clones are then assayed by methods known in the art for cells that secrete antibodies capable of binding Nav1.7. Ascites fluid, which generally contains high levels of antibodies, can be generated by immunizing rats with positive hybridoma clones.

In another embodiment, antibody-producing immortalized hybridomas may be prepared from the immunized animal. After immunization, the animal is sacrificed and the splenic B cells are fused to immortalized myeloma cells as is well known in the art. See, e.g., Harlow and Lane, supra. In a preferred embodiment, the myeloma cells do not secrete immunoglobulin polypeptides (a non-secretory cell line). After fusion and antibiotic selection, the hybridomas are screened using $Na_v1.7$, or a portion thereof, or a cell expressing $Na_v1.7$. In a preferred embodiment, the initial screening is performed using an enzyme-linked immunosorbent assay (ELISA) or a radioimmunoassay (RIA), preferably an ELISA. An example of ELISA screening is provided in PCT Publication No. WO 00/37504.

Anti-$Na_v1.7$ antibody-producing hybridomas are selected, cloned, and further screened for desirable characteristics, including robust hybridoma growth, high antibody production, and desirable antibody characteristics. Hybridomas may be cultured and expanded in vivo in syngeneic animals, in animals that lack an immune system, e.g., nude mice, or in cell culture in vitro. Methods of selecting, cloning and expanding hybridomas are well known to those of ordinary skill in the art.

In a preferred embodiment, hybridomas are rat hybridomas. In another embodiment, hybridomas are produced in a non-human, non-rat species such as mice, sheep, pigs, goats, cattle, or horses. In yet another preferred embodiment, the hybridomas are human hybridomas, in which a human non-secretory myeloma is fused with a human cell expressing an anti-$Na_v1.7$ antibody.

Antibody fragments that recognize specific epitopes may be generated by known techniques. For example, Fab and F(ab')2 fragments of the invention may be produced by proteolytic cleavage of immunoglobulin molecules, using enzymes such as papain (to produce two identical Fab fragments) or pepsin (to produce a $F(ab')_2$ fragment). A F(ab')2 fragment of an IgG molecule retains the two antigen-binding sites of the larger ("parent") IgG molecule, including both light chains (containing the variable light chain and constant light chain regions), the CH1 domains of the heavy chains, and a disulfide-forming hinge region of the parent IgG molecule. Accordingly, a F(ab')2 fragment is still capable of crosslinking antigen molecules like the parent IgG molecule.

(2) Anti-Nav1.7 Monoclonal Antibodies Using SLAM

In another aspect of the invention, recombinant antibodies are generated from single, isolated lymphocytes using a procedure referred to in the art as the selected lymphocyte antibody method (SLAM), as described in U.S. Pat. No. 5,627,052; PCT Publication No. WO 92/02551; and Babcook et al., Proc. Natl. Acad. Sci. USA, 93: 7843-7848 (1996). In this method, single cells secreting antibodies of interest, e.g., lymphocytes derived from any one of the immunized animals are screened using an antigen-specific hemolytic plaque assay, wherein the antigen $Na_v1.7$, a subunit of $Na_v1.7$, or a fragment thereof, is coupled to sheep red blood cells using a linker, such as biotin, and used to identify single cells that secrete antibodies with specificity for $Na_v1.7$. Following identification of antibody-secreting cells of interest, heavy- and light-chain variable region cDNAs are rescued from the cells by reverse transcriptase-PCR (RT-PCR) and these variable regions can then be expressed, in the context of appropriate immunoglobulin constant regions (e.g., human, cow, dog, horse, cat, or pig constant regions), in mammalian host cells, such as COS or CHO cells. The host cells transfected with the amplified immunoglobulin sequences, derived from in vivo selected lymphocytes, can then undergo further analysis and selection in vitro, for example, by panning the transfected cells to isolate cells expressing antibodies to $Na_v1.7$. The amplified immunoglobulin sequences further can be manipulated in vitro, such as by in vitro affinity maturation method. See, for example, PCT Publication No. WO 97/29131 and PCT Publication No. WO 00/56772.

(3) Anti-Nav1.7 Monoclonal Antibodies Using Transgenic Animals

In another embodiment of the invention, antibodies are produced by immunizing a non-human animal comprising some, or all, of the human immunoglobulin locus with a $Na_v1.7$ antigen. In an embodiment, the non-human animal is a XENOMOUSE® transgenic mouse, an engineered mouse strain that comprises large fragments of the human immunoglobulin loci and is deficient in mouse antibody production. See, e.g., Green et al., Nature Genetics, 7: 13-21 (1994) and U.S. Pat. Nos. 5,916,771; 5,939,598; 5,985,615; 5,998, 209; 6,075,181; 6,091,001; 6,114,598; and 6,130,364. See also PCT Publication Nos. WO 91/10741; WO 94/02602; WO 96/34096; WO 96/33735; WO 98/16654; WO 98/24893; WO 98/50433; WO 99/45031; WO 99/53049; WO 00/09560; and WO 00/37504. The XENOMOUSE® transgenic mouse produces an adult-like human repertoire of fully human antibodies, and generates antigen-specific human monoclonal antibodies. The XENOMOUSE® transgenic mouse contains approximately 80% of the human antibody repertoire through introduction of megabase sized, germline configuration YAC fragments of the human heavy chain loci and x light chain loci. See Mendez et al., Nature Genetics, 15: 146-156 (1997), Green and Jakobovits, J. Exp. Med., 188: 483-495 (1998), the disclosures of which are hereby incorporated by reference.

(4) Anti-Nav1.7 Monoclonal Antibodies Using Recombinant Antibody Libraries

In vitro methods also can be used to make the antibodies of the invention, wherein an antibody library is screened to identify an antibody having the desired $Na_v1.7$-binding specificity. Methods for such screening of recombinant antibody libraries are well known in the art and include methods described in, for example, U.S. Pat. No. 5,223,409 (Ladner et al.); PCT Publication No. WO 92/18619 (Kang et al.); PCT Publication No. WO 91/17271 (Dower et al.); PCT Publication No. WO 92/20791 (Winter et al.); PCT Publication No. WO 92/15679 (Markland et al.); PCT Publication No. WO 93/01288 (Breitling et al.); PCT Publication No. WO 92/01047 (McCafferty et al.); PCT Publication No. WO 92/09690 (Garrard et al.); Fuchs et al., Bio/Technology, 9: 1369-1372 (1991); Hay et al., Hum. Antibod. Hybridomas, 3: 81-85 (1992); Huse et al., Science, 246: 1275-1281 (1989); McCafferty et al., Nature, 348: 552-554 (1990); Griffiths et al., EMBO J., 12: 725-734 (1993); Hawkins et al., J. Mol. Biol., 226: 889-896 (1992); Clackson et al., Nature, 352: 624-628 (1991); Gram et al., Proc. Natl. Acad. Sci. USA, 89: 3576-3580 (1992); Garrard et al., Bio/Technology, 9: 1373-1377 (1991); Hoogenboom et al., Nucl. Acids Res., 19: 4133-4137 (1991); Barbas et al., Proc. Natl. Acad. Sci. USA, 88: 7978-7982 (1991); US Patent Application Publication No. 2003/0186374; and PCT Publication No. WO 97/29131, the contents of each of which are incorporated herein by reference.

The recombinant antibody library may be from a subject immunized with Nav1.7, or a portion of $Na_v1.7$. Alternatively, the recombinant antibody library may be from a naive subject, i.e., one who has not been immunized with $Na_v1.7$, such as a human antibody library from a human subject who has not been immunized with human $Na_v1.7$. Antibodies of the invention are selected by screening the recombinant antibody library with the peptide comprising human $Na_v1.7$ to thereby select those antibodies that recognize $Na_v1.7$. Methods for conducting such screening and selection are well known in the art, such as described in the references in the preceding paragraph. To select antibodies of the invention having particular binding affinities for Nav1.7, such as those that dissociate from $Na_v1.7$ with a particular $K_{off}$ rate constant, the art-known method of surface plasmon resonance can be used to select antibodies having the desired $K_{off}$ rate constant. To select antibodies of the invention having a particular neutralizing activity for $Na_v1.7$, such as those with a particular $IC_{50}$, standard methods known in the art for assessing the inhibition of $Na_v1.7$ activity may be used.

In one aspect, the invention pertains to an isolated antibody, or an antigen-binding portion thereof, that binds human $Na_v1.7$. Preferably, the antibody is a neutralizing antibody. In various embodiments, the antibody is a recombinant antibody or a monoclonal antibody.

For example, antibodies of the present invention can also be generated using various phage display methods known in the art. In phage display methods, functional antibody domains are displayed on the surface of phage particles which carry the polynucleotide sequences encoding them. Such phage can be utilized to display antigen-binding domains expressed from a repertoire or combinatorial antibody library (e.g., human or murine or cow, dog, horse, cat, or pig). Phage expressing an antigen binding domain that binds the antigen of interest can be selected or identified with antigen, e.g., using labeled antigen or antigen bound or captured to a solid surface or bead. Phage used in these methods are typically filamentous phage including fd and M13 binding domains expressed from phage with Fab, Fv, or disulfide stabilized Fv antibody domains recombinantly fused to either the phage gene III or gene VIII protein. Examples of phage display methods that can be used to make the antibodies of the present invention include those disclosed in Brinkmann et al., J. Immunol. Methods, 182: 41-50 (1995); Ames et al., J. Immunol. Methods, 184:177-186 (1995); Kettleborough et al., Eur. J. Immunol., 24: 952-958 (1994); Persic et al., Gene, 187: 9-18 (1997); Burton et al., Advances in Immunology, 57: 191-280 (1994); PCT Publication No. WO 92/01047; PCT Publication Nos. WO 90/02809; WO 91/10737; WO 92/01047; WO 92/18619; WO 93/11236; WO 95/15982; WO 95/20401; and U.S. Pat. Nos. 5,698,426; 5,223,409; 5,403,484; 5,580,717; 5,427,908; 5,750,753; 5,821,047; 5,571,698; 5,427,908; 5,516,637; 5,780,225; 5,658,727; 5,733,743; and 5,969,108.

As described in the above references, after phage selection, the antibody coding regions from the phage can be isolated and used to generate whole antibodies including human antibodies or any other desired antigen binding fragment, and expressed in any desired host, including mammalian cells, insect cells, plant cells, yeast, and bacteria, e.g., as described in detail below. For example, techniques to recombinantly produce Fab, Fab', and $F(ab')_2$ fragments can also be employed using methods known in the art such as those disclosed in PCT publication No. WO 92/22324; Mullinax et al., BioTechniques, 12(6): 864-869 (1992); Sawai et al., Am. J. Reprod. Immunol., 34: 26-34 (1995); and Better et al., Science, 240: 1041-1043 (1988).

Examples of techniques which can be used to produce single-chain Fvs and antibodies include those described in U.S. Pat. Nos. 4,946,778 and 5,258,498; Huston et al., Methods in Enzymology, 203: 46-88 (1991); Shu et al., Proc. Natl. Acad. Sci. USA, 90: 7995-7999 (1993); and Skerra et al., Science, 240: 1038-1041 (1988).

Alternative to screening of recombinant antibody libraries by phage display, other methodologies known in the art for screening large combinatorial libraries can be applied to the identification of antibodies of the invention. One type of alternative expression system is one in which the recombinant antibody library is expressed as RNA-protein fusions, as described in PCT Publication No. WO 98/31700 (Szostak and Roberts), and in Roberts and Szostak, Proc. Natl. Acad. Sci. USA, 94: 12297-12302 (1997). In this system, a covalent fusion is created between an mRNA and the peptide or protein that it encodes by in vitro translation of synthetic mRNAs that carry puromycin, a peptidyl acceptor antibiotic, at their 3' end. Thus, a specific mRNA can be enriched from a complex mixture of mRNAs (e.g., a combinatorial library) based on the properties of the encoded peptide or protein, e.g., antibody, or portion thereof, such as binding of the antibody, or portion thereof, to the dual specificity antigen. Nucleic acid sequences encoding antibodies, or portions thereof, recovered from screening of such libraries can be expressed by recombinant means as described above (e.g., in mammalian host cells) and, moreover, can be subjected to further affinity maturation by either additional rounds of screening of mRNA-peptide fusions in which mutations have been introduced into the originally selected sequence(s), or by other methods for affinity maturation in vitro of recombinant antibodies, as described above. A preferred example of this methodology, is PROfusion display technology.

In another approach, the antibodies of the present invention can also be generated using yeast display methods known in the art. In yeast display methods, genetic methods are used to tether antibody domains to the yeast cell wall and display them on the surface of yeast. In particular, such yeast can be utilized to display antigen-binding domains expressed from a repertoire or combinatorial antibody library (e.g., human or murine or bovine, canine, equine, feline, or porcine). Examples of yeast display methods that can be used to make the antibodies of the present invention include those disclosed in U.S. Pat. No. 6,699,658 (Wittrup et al.) incorporated herein by reference.

d. Production of Recombinant Nav1.7 Antibodies

Antibodies of the present invention may be produced by any of a number of techniques known in the art. For example, expression from host cells, wherein expression vector(s) encoding the heavy and light chains is (are) transfected into a host cell by standard techniques. The various forms of the term "transfection" are intended to encompass a wide variety of techniques commonly used for the introduction of exogenous DNA into a prokaryotic or eukaryotic host cell, e.g., electroporation, calcium-phosphate precipitation, DEAE-dextran transfection, and the like. Although it is possible to express the antibodies of the invention in either prokaryotic or eukaryotic host cells, expression of antibodies in eukaryotic cells is preferable, and most preferable in mammalian host cells, because such eukaryotic cells (and in particular mammalian cells) are more likely than prokaryotic cells to assemble and secrete a properly folded and immunologically active antibody.

Exemplary mammalian host cells for expressing the recombinant antibodies of the invention include Chinese Hamster Ovary (CHO cells) (including dhfr-CHO cells, described in Urlaub and Chasin, Proc. Natl. Acad. Sci. USA, 77: 4216-4220 (1980), used with a DHFR selectable marker, e.g., as described in Kaufman and Sharp, J. Mol. Biol., 159: 601-621 (1982), NS0 myeloma cells, COS cells, and SP2 cells. When recombinant expression vectors encoding antibody genes are introduced into mammalian host cells, the antibodies are produced by culturing the host cells for a period of time sufficient to allow for expression of the antibody in the host cells or, more preferably, secretion of the antibody into the culture medium in which the host cells are grown. Antibodies can be recovered from the culture medium using standard protein purification methods.

Host cells can also be used to produce functional antibody fragments, such as Fab fragments or scFv molecules. It will be understood that variations on the above procedure are within the scope of the present invention. For example, it may be desirable to transfect a host cell with DNA encoding functional fragments of either the light chain and/or the heavy chain of an antibody of this invention. Recombinant DNA technology may also be used to remove some, or all, of the DNA encoding either or both of the light and heavy chains that is not necessary for binding to the antigens of interest. The molecules expressed from such truncated DNA molecules are also encompassed by the antibodies of the invention. In addition, bifunctional antibodies may be produced in which one heavy and one light chain are an antibody of the invention (i.e., binds $Na_v1.7$) and the other heavy and light chain are specific for an antigen other than $Na_v1.7$ by crosslinking an antibody of the invention to a second antibody by standard chemical crosslinking methods.

In a preferred system for recombinant expression of an antibody, or antigen-binding portion thereof, of the invention, a recombinant expression vector encoding both the antibody heavy chain and the antibody light chain is introduced into dhfr-CHO cells by calcium phosphate-mediated transfection. Within the recombinant expression vector, the antibody heavy and light chain genes are each operatively linked to CMV enhancer/AdMLP promoter regulatory elements to drive high levels of transcription of the genes. The recombinant expression vector also carries a DHFR gene, which allows for selection of CHO cells that have been transfected with the vector using methotrexate selection/ amplification. The selected transformant host cells are cultured to allow for expression of the antibody heavy and light chains and intact antibody is recovered from the culture medium. Standard molecular biology techniques are used to prepare the recombinant expression vector, transfect the host cells, select for transformants, culture the host cells, and recover the antibody from the culture medium. Still further, the invention provides a method of synthesizing a recombinant antibody of the invention by culturing a host cell of the invention in a suitable culture medium until a recombinant antibody of the invention is synthesized. The method can further comprise isolating the recombinant antibody from the culture medium.

(1) Humanized Antibody

The humanized antibody may be an antibody or a variant, derivative, analog or portion thereof which immunospecifically binds to an antigen of interest and which comprises a framework (FR) region having substantially the amino acid sequence of a human antibody and a complementary determining region (CDR) having substantially the amino acid sequence of a non-human antibody. The humanized antibody may be from a non-human species antibody that binds the desired antigen having one or more complementarity determining regions (CDRs) from the non-human species and framework regions from a human immunoglobulin molecule.

As used herein, the term "substantially" in the context of a CDR refers to a CDR having an amino acid sequence at least 90%, at least 95%, at least 98% or at least 99% identical to the amino acid sequence of a non-human antibody CDR. A humanized antibody comprises substantially all of at least one, and typically two, variable domains (Fab, Fab', F(ab')2, FabC, Fv) in which all or substantially all of the CDR regions correspond to those of a non-human immunoglobulin (i.e., donor antibody) and all or substantially all of the framework regions are those of a human immunoglobulin consensus sequence. According to one aspect, a humanized antibody also comprises at least a portion of an immunoglobulin constant region (Fc), typically that of a human immunoglobulin. In some embodiments, a humanized antibody contains both the light chain as well as at least the variable domain of a heavy chain. The antibody also may include the CH1, hinge, CH2, CH3, and CH4 regions of the heavy chain. In some embodiments, a humanized antibody only contains a humanized light chain. In some embodiments, a humanized antibody only contains a humanized heavy chain. In specific embodiments, a humanized antibody only contains a humanized variable domain of a light chain and/or of a heavy chain.

The humanized antibody can be selected from any class of immunoglobulins, including IgM, IgG, IgD, IgA and IgE, and any isotype, including without limitation IgG 1, IgG2, IgG3, and IgG4. The humanized antibody may comprise sequences from more than one class or isotype, and particular constant domains may be selected to optimize desired effector functions using techniques well-known in the art.

The framework and CDR regions of a humanized antibody need not correspond precisely to the parental sequences, e.g., the donor antibody CDR or the consensus framework may be mutagenized by substitution, insertion and/or deletion of at least one amino acid residue so that the CDR or framework residue at that site does not correspond to either the donor antibody or the consensus framework. In one embodiment, such mutations, however, will not be extensive. Usually, at least 90%, at least 95%, at least 98%, or at least 99% of the humanized antibody residues will correspond to those of the parental FR and CDR sequences. As used herein, the term "consensus framework" refers to the framework region in the consensus immunoglobulin sequence. As used herein, the term "consensus immunoglobulin sequence" refers to the sequence formed from the most frequently occurring amino acids (or nucleotides) in a family of related immunoglobulin sequences (See e.g., Winnaker, From Genes to Clones (Verlagsgesellschaft, Weinheim, Germany 1987)). In a family of immunoglobulins, each position in the consensus sequence is occupied by the amino acid occurring most frequently at that position in the family. If two amino acids occur equally frequently, either can be included in the consensus sequence.

The humanized antibody may be designed to minimize unwanted immunological response toward rodent anti-human antibodies, which limits the duration and effectiveness of therapeutic applications of those moieties in human recipients. The humanized antibody may have one or more amino acid residues introduced into it from a source that is non-human. These non-human residues are often referred to as "import" residues, which are typically taken from a variable domain. Humanization may be performed by substituting hypervariable region sequences for the corresponding sequences of a human antibody. Accordingly, such "humanized" antibodies are chimeric antibodies wherein substantially less than an intact human variable domain has been substituted by the corresponding sequence from a non-human species. For example, see U.S. Pat. No. 4,816,567, the contents of which are herein incorporated by reference. The humanized antibody may be a human antibody in which some hypervariable region residues, and possibly some FR residues are substituted by residues from analogous sites in rodent antibodies. Humanization or engineering of antibodies of the present invention can be performed using any known method, such as but not limited to those described in U.S. Pat. Nos. 5,723,323; 5,976,862; 5,824,514; 5,817,483; 5,814,476; 5,763,192; 5,723,323; 5,766,886; 5,714,352; 6,204,023; 6,180,370; 5,693,762; 5,530,101; 5,585,089; 5,225,539; and 4,816,567.

The humanized antibody may retain high affinity for $Na_v1.7$ and other favorable biological properties. The humanized antibody may be prepared by a process of analysis of the parental sequences and various conceptual humanized products using three-dimensional models of the parental and humanized sequences. Three-dimensional immunoglobulin models are commonly available. Computer programs are available that illustrate and display probable three-dimensional conformational structures of selected candidate immunoglobulin sequences. Inspection of these displays permits analysis of the likely role of the residues in the functioning of the candidate immunoglobulin sequence, i.e., the analysis of residues that influence the ability of the candidate immunoglobulin to bind its antigen. In this way, FR residues can be selected and combined from the recipient and import sequences so that the desired antibody characteristics, such as increased affinity for $Na_v1.7$, is achieved. In general, the hypervariable region residues may be directly and most substantially involved in influencing antigen binding.

As an alternative to humanization, human antibodies (also referred to herein as "fully human antibodies") can be generated. For example, it is possible to isolate human antibodies from libraries via PROfusion and/or yeast related technologies. It is also possible to produce transgenic animals (e.g. mice that are capable, upon immunization, of producing a full repertoire of human antibodies in the absence of endogenous immunoglobulin production. For example, the homozygous deletion of the antibody heavy-chain joining region ($J_H$) gene in chimeric and germ-line mutant mice results in complete inhibition of endogenous antibody production. Transfer of the human germ-line immunoglobulin gene array in such germ-line mutant mice will result in the production of human antibodies upon antigen challenge. The humanized or fully human antibodies may be prepared according to the methods described in U.S. Pat. Nos. 5,770,429; 5,833,985; 5,837,243; 5,922,845; 6,017,517; 6,096,311; 6,111,166; 6,270,765; 6,303,755; 6,365,116; 6,410,690; 6,682,928; and 6,984,720, the contents each of which are herein incorporated by reference.

(2) Bovinized Antibody

The boviniezed antibody may be an antibody or a variant, derivative, analog or portion thereof which immunospecifically binds to an antigen of interest and which comprises a framework (FR) region having substantially the amino acid sequence of a bovine antibody and a complementary determining region (CDR) having substantially the amino acid sequence of a non-bovine antibody. The bovinized antibody may be from a non-bovine species antibody that binds the desired antigen having one or more complementarity determining regions (CDRs) from the non-bovine species and framework regions from a bovine immunoglobulin molecule.

As used herein, the term "substantially" in the context of a CDR refers to a CDR having an amino acid sequence at least 90%, at least 95%, at least 98% or at least 99% identical to the amino acid sequence of a non-bovine antibody CDR. A bovinized antibody comprises substantially all of at least one, and typically two, variable domains (Fab, Fab', F(ab')2, FabC, Fv) in which all or substantially all of the CDR regions correspond to those of a non-bovine immunoglobulin (i.e., donor antibody) and all or substantially all of the framework regions are those of a bovine immunoglobulin consensus sequence. According to one aspect, a bovinized antibody also comprises at least a portion of an immunoglobulin constant region (Fc), typically that of a bovine immunoglobulin. In some embodiments, a bovinized antibody contains both the light chain as well as at least the variable domain of a heavy chain. The antibody also may include the CH1, hinge, CH2, CH3, and CH4 regions of the heavy chain. In some embodiments, a bovinized antibody only contains a bovinized light chain. In some embodiments, a bovinized antibody only contains a bovinized heavy chain. In specific embodiments, a bovinized antibody only contains a bovinized variable domain of a light chain and/or of a heavy chain.

The bovinized antibody can be selected from any class of immunoglobulins and any isotype. The bovinized antibody may comprise sequences from more than one class or isotype, and particular constant domains may be selected to optimize desired effector functions using techniques well-known in the art.

The framework and CDR regions of a bovinized antibody need not correspond precisely to the parental sequences, e.g., the donor antibody CDR or the consensus framework may be mutagenized by substitution, insertion and/or deletion of at least one amino acid residue so that the CDR or framework residue at that site does not correspond to either the donor antibody or the consensus framework. In one embodiment, such mutations, however, will not be extensive. Usually, at least 90%, at least 95%, at least 98%, or at least 99% of the bovinized antibody residues will correspond to those of the parental FR and CDR sequences. As used herein, the term "consensus framework" refers to the framework region in the consensus immunoglobulin sequence. As used herein, the term "consensus immunoglobulin sequence" refers to the sequence formed from the most frequently occurring amino acids (or nucleotides) in a family of related immunoglobulin sequences (See e.g., Winnaker, From Genes to Clones (Verlagsgesellschaft, Weinheim, Germany 1987)). In a family of immunoglobulins, each position in the consensus sequence is occupied by the amino acid occurring most frequently at that position in the family. If two amino acids occur equally frequently, either can be included in the consensus sequence.

The bovinized antibody may be designed to minimize unwanted immunological response toward rodent anti-bovine antibodies, which limits the duration and effectiveness of therapeutic applications of those moieties in bovine recipients. The bovinized antibody may have one or more amino acid residues introduced into it from a source that is non-bovine. These non-bovine residues are often referred to as "import" residues, which are typically taken from a variable domain. Bovinization may be performed by substituting hypervariable region sequences for the corresponding sequences of a bovine antibody. Accordingly, such "bovinized" antibodies are chimeric antibodies wherein substantially less than an intact bovine variable domain has been substituted by the corresponding sequence from a non-bovine species. The bovinized antibody may be a bovine antibody in which some hypervariable region residues, and possibly some FR residues are substituted by residues from analogous sites in rodent antibodies.

The bovinized antibody may retain high affinity for $Na_v1.7$ and other favorable biological properties. The bovinized antibody may be prepared by a process of analysis of the parental sequences and various conceptual bovinized products using three-dimensional models of the parental and bovinized sequences. Three-dimensional immunoglobulin models are commonly available. Computer programs are available that illustrate and display probable three-dimensional conformational structures of selected candidate immunoglobulin sequences. Inspection of these displays permits analysis of the likely role of the residues in the functioning of the candidate immunoglobulin sequence, i.e., the analysis of residues that influence the ability of the candidate immunoglobulin to bind its antigen. In this way, FR residues can be selected and combined from the recipient and import sequences so that the desired antibody characteristics, such as increased affinity for $Na_v1.7$, is achieved. In general, the hypervariable region residues may be directly and most substantially involved in influencing antigen binding.

(3) Caninized Antibody

The caninized antibody may be an antibody or a variant, derivative, analog or portion thereof which immunospecifically binds to an antigen of interest and which comprises a framework (FR) region having substantially the amino acid sequence of a canine antibody and a complementary determining region (CDR) having substantially the amino acid sequence of a non-canine antibody. The caninized antibody may be from a non-canine species antibody that binds the desired antigen having one or more complementarity determining regions (CDRs) from the non-canine species and framework regions from a canine immunoglobulin molecule.

As used herein, the term "substantially" in the context of a CDR refers to a CDR having an amino acid sequence at least 90%, at least 95%, at least 98% or at least 99% identical to the amino acid sequence of a non-canine antibody CDR. A caninized antibody comprises substantially all of at least one, and typically two, variable domains (Fab, Fab', F(ab')2, FabC, Fv) in which all or substantially all of the CDR regions correspond to those of a non-canine immunoglobulin (i.e., donor antibody) and all or substantially all of the framework regions are those of a canine immunoglobulin consensus sequence. According to one aspect, a caninized antibody also comprises at least a portion of an immunoglobulin constant region (Fc), typically that of a canine immunoglobulin. In some embodiments, a caninized antibody contains both the light chain as well as at least the variable domain of a heavy chain. The antibody also may include the CH1, hinge, CH2, CH3, and CH4 regions of the heavy chain. In some embodiments, a caninized antibody only contains a caninized light chain. In some embodiments, a caninized antibody only contains a caninized heavy chain. In specific embodiments, a caninized antibody only contains a caninized variable domain of a light chain and/or of a heavy chain.

The caninized antibody can be selected from any class of immunoglobulins and any isotype. The caninized antibody may comprise sequences from more than one class or isotype, and particular constant domains may be selected to optimize desired effector functions using techniques well-known in the art.

The framework and CDR regions of a caninized antibody need not correspond precisely to the parental sequences, e.g., the donor antibody CDR or the consensus framework may be mutagenized by substitution, insertion and/or deletion of at least one amino acid residue so that the CDR or framework residue at that site does not correspond to either the donor antibody or the consensus framework. In one embodiment, such mutations, however, will not be extensive. Usually, at least 90%, at least 95%, at least 98%, or at least 99% of the caninized antibody residues will correspond to those of the parental FR and CDR sequences. As used herein, the term "consensus framework" refers to the framework region in the consensus immunoglobulin sequence. As used herein, the term "consensus immunoglobulin sequence" refers to the sequence formed from the most frequently occurring amino acids (or nucleotides) in a family of related immunoglobulin sequences (See e.g., Winnaker, From Genes to Clones (Verlagsgesellschaft, Weinheim, Germany 1987)). In a family of immunoglobulins, each position in the consensus sequence is occupied by the amino acid occurring most frequently at that position in the family. If two amino acids occur equally frequently, either can be included in the consensus sequence.

The caninized antibody may be designed to minimize unwanted immunological response toward rodent anti-canine antibodies, which limits the duration and effectiveness of therapeutic applications of those moieties in canine recipients. The caninized antibody may have one or more amino acid residues introduced into it from a source that is non-canine. These non-canine residues are often referred to as "import" residues, which are typically taken from a variable domain. Caninization may be performed by substituting hypervariable region sequences for the corresponding sequences of a canine antibody. Accordingly, such "caninized" antibodies are chimeric antibodies wherein substantially less than an intact canine variable domain has been substituted by the corresponding sequence from a non-canine species. The caninized antibody may be a canine antibody in which some hypervariable region residues, and possibly some FR residues are substituted by residues from analogous sites in rodent antibodies.

The caninized antibody may retain high affinity for $Na_v1.7$ and other favorable biological properties. The caninized antibody may be prepared by a process of analysis of the parental sequences and various conceptual caninized products using three-dimensional models of the parental and caninized sequences. Three-dimensional immunoglobulin models are commonly available. Computer programs are available that illustrate and display probable three-dimensional conformational structures of selected candidate immunoglobulin sequences. Inspection of these displays permits analysis of the likely role of the residues in the functioning of the candidate immunoglobulin sequence, i.e., the analysis of residues that influence the ability of the candidate immunoglobulin to bind its antigen. In this way, FR residues can be selected and combined from the recipient and import sequences so that the desired antibody characteristics, such as increased affinity for $Na_v1.7$, is achieved. In general, the hypervariable region residues may be directly and most substantially involved in influencing antigen binding.

(4) Equinized Antibody

The equinized antibody may be an antibody or a variant, derivative, analog or portion thereof which immunospecifically binds to an antigen of interest and which comprises a framework (FR) region having substantially the amino acid sequence of an equine antibody and a complementary determining region (CDR) having substantially the amino acid sequence of a non-equine antibody. The equinized antibody may be from a non-equine species antibody that binds the desired antigen having one or more complementarity determining regions (CDRs) from the non-equine species and framework regions from an equine immunoglobulin molecule.

As used herein, the term "substantially" in the context of a CDR refers to a CDR having an amino acid sequence at least 90%, at least 95%, at least 98% or at least 99% identical to the amino acid sequence of a non-equine antibody CDR. A equinized antibody comprises substantially all of at least one, and typically two, variable domains (Fab, Fab', F(ab')2, FabC, Fv) in which all or substantially all of the CDR regions correspond to those of a non-equine immunoglobulin (i.e., donor antibody) and all or substantially all of the framework regions are those of an equine immunoglobulin consensus sequence. According to one aspect, an equinized antibody also comprises at least a portion of an immunoglobulin constant region (Fc), typically that of an equine immunoglobulin. In some embodiments, an equinized antibody contains both the light chain as well as at least the variable domain of a heavy chain. The antibody also may include the CH1, hinge, CH2, CH3, and CH4 regions of the heavy chain. In some embodiments, an equinized antibody only contains an equinized light chain. In some embodiments, an equinized antibody only contains an equinized heavy chain. In specific embodiments, a equinized antibody only contains a equinized variable domain of a light chain and/or of a heavy chain.

The equinized antibody can be selected from any class of immunoglobulins and any isotype. The equinized antibody may comprise sequences from more than one class or isotype, and particular constant domains may be selected to optimize desired effector functions using techniques well-known in the art.

The framework and CDR regions of an equinized antibody need not correspond precisely to the parental sequences, e.g., the donor antibody CDR or the consensus framework may be mutagenized by substitution, insertion and/or deletion of at least one amino acid residue so that the CDR or framework residue at that site does not correspond to either the donor antibody or the consensus framework. In one embodiment, such mutations, however, will not be extensive. Usually, at least 90%, at least 95%, at least 98%, or at least 99% of the equinized antibody residues will correspond to those of the parental FR and CDR sequences. As used herein, the term "consensus framework" refers to the framework region in the consensus immunoglobulin sequence. As used herein, the term "consensus immunoglobulin sequence" refers to the sequence formed from the most frequently occurring amino acids (or nucleotides) in a family of related immunoglobulin sequences (See e.g., Winnaker, From Genes to Clones (Verlagsgesellschaft, Weinheim, Germany 1987)). In a family of immunoglobulins, each position in the consensus sequence is occupied by the amino acid occurring most frequently at that position in the family. If two amino acids occur equally frequently, either can be included in the consensus sequence.

The equinized antibody may be designed to minimize unwanted immunological response toward rodent anti-equine antibodies, which limits the duration and effectiveness of therapeutic applications of those moieties in equine recipients. The equinized antibody may have one or more amino acid residues introduced into it from a source that is non-equine. These non-equine residues are often referred to as "import" residues, which are typically taken from a variable domain. Humanization may be performed by substituting hypervariable region sequences for the corresponding sequences of an equine antibody. Accordingly, such "equinized" antibodies are chimeric antibodies wherein substantially less than an intact equine variable domain has been substituted by the corresponding sequence from a non-equine species. The equinized antibody may be an equine antibody in which some hypervariable region residues, and possibly some FR residues are substituted by residues from analogous sites in rodent antibodies.

The equinized antibody may retain high affinity for $Na_v1.7$ and other favorable biological properties. The equinized antibody may be prepared by a process of analysis of the parental sequences and various conceptual equinized products using three-dimensional models of the parental and equinized sequences. Three-dimensional immunoglobulin models are commonly available. Computer programs are available that illustrate and display probable three-dimensional conformational structures of selected candidate immunoglobulin sequences. Inspection of these displays permits analysis of the likely role of the residues in the functioning of the candidate immunoglobulin sequence, i.e., the analysis of residues that influence the ability of the candidate immunoglobulin to bind its antigen. In this way, FR residues can be selected and combined from the recipient and import sequences so that the desired antibody characteristics, such as increased affinity for $Na_v1.7$, is achieved. In general, the hypervariable region residues may be directly and most substantially involved in influencing antigen binding.

(5) Felinized Antibody

The felinized antibody may be an antibody or a variant, derivative, analog or portion thereof which immunospecifically binds to an antigen of interest and which comprises a framework (FR) region having substantially the amino acid sequence of a feline antibody and a complementary determining region (CDR) having substantially the amino acid sequence of a non-feline antibody. The felinized antibody may be from a non-feline species antibody that binds the desired antigen having one or more complementarity determining regions (CDRs) from the non-feline species and framework regions from a feline immunoglobulin molecule.

As used herein, the term "substantially" in the context of a CDR refers to a CDR having an amino acid sequence at least 90%, at least 95%, at least 98% or at least 99% identical to the amino acid sequence of a non-feline antibody CDR. A felinized antibody comprises substantially all of at least one, and typically two, variable domains (Fab, Fab', F(ab')2, FabC, Fv) in which all or substantially all of the CDR regions correspond to those of a non-feline immunoglobulin (i.e., donor antibody) and all or substantially all of the framework regions are those of a feline immunoglobulin consensus sequence. According to one aspect, a humanized antibody also comprises at least a portion of an immunoglobulin constant region (Fc), typically that of a feline immunoglobulin. In some embodiments, a felinized antibody contains both the light chain as well as at least the variable domain of a heavy chain. The antibody also may include the CH1, hinge, CH2, CH3, and CH4 regions of the heavy chain. In some embodiments, a felinized antibody only contains a felinized light chain. In some embodiments, a felinized antibody only contains a felinized heavy chain. In specific embodiments, a felinized antibody only contains a felinized variable domain of a light chain and/or of a heavy chain.

The felinized antibody can be selected from any class of immunoglobulins and any isotype. The felinized antibody may comprise sequences from more than one class or isotype, and particular constant domains may be selected to optimize desired effector functions using techniques well-known in the art.

The framework and CDR regions of a felinized antibody need not correspond precisely to the parental sequences, e.g., the donor antibody CDR or the consensus framework may be mutagenized by substitution, insertion and/or deletion of at least one amino acid residue so that the CDR or framework residue at that site does not correspond to either the donor antibody or the consensus framework. In one embodiment, such mutations, however, will not be extensive. Usually, at least 90%, at least 95%, at least 98%, or at least 99% of the felinized antibody residues will correspond to those of the parental FR and CDR sequences. As used herein, the term "consensus framework" refers to the framework region in the consensus immunoglobulin sequence. As used herein, the term "consensus immunoglobulin sequence" refers to the sequence formed from the most frequently occurring amino acids (or nucleotides) in a family of related immunoglobulin sequences (See e.g., Winnaker, From Genes to Clones (Verlagsgesellschaft, Weinheim, Germany 1987)). In a family of immunoglobulins, each position in the consensus sequence is occupied by the amino acid occurring most frequently at that position in the family. If two amino acids occur equally frequently, either can be included in the consensus sequence.

The felinized antibody may be designed to minimize unwanted immunological response toward rodent anti-feline antibodies, which limits the duration and effectiveness of therapeutic applications of those moieties in feline recipients. The felinized antibody may have one or more amino acid residues introduced into it from a source that is non-feline. These non-feline residues are often referred to as "import" residues, which are typically taken from a variable domain. Felinization may be performed by substituting hypervariable region sequences for the corresponding sequences of a feline antibody. Accordingly, such "felinized" antibodies are chimeric antibodies wherein substantially less than an intact feline variable domain has been substituted by the corresponding sequence from a non-feline species. The felinized antibody may be a feline antibody in which some hypervariable region residues, and possibly some FR residues are substituted by residues from analogous sites in rodent antibodies.

The felinized antibody may retain high affinity for $Na_v1.7$ and other favorable biological properties. The felinized antibody may be prepared by a process of analysis of the parental sequences and various conceptual felinized products using three-dimensional models of the parental and felinized sequences. Three-dimensional immunoglobulin models are commonly available. Computer programs are available that illustrate and display probable three-dimensional conformational structures of selected candidate immunoglobulin sequences. Inspection of these displays permits analysis of the likely role of the residues in the functioning of the candidate immunoglobulin sequence, i.e., the analysis of residues that influence the ability of the candidate immunoglobulin to bind its antigen. In this way, FR residues can be selected and combined from the recipient and import sequences so that the desired antibody characteristics, such as increased affinity for $Na_v1.7$, is achieved. In general, the hypervariable region residues may be directly and most substantially involved in influencing antigen binding.

(6) Porcinized Antibody

The porcinized antibody may be an antibody or a variant, derivative, analog or portion thereof which immunospecifically binds to an antigen of interest and which comprises a framework (FR) region having substantially the amino acid sequence of a porcine antibody and a complementary determining region (CDR) having substantially the amino acid sequence of a non-porcine antibody. The porcinized antibody may be from a non-porcine species antibody that binds the desired antigen having one or more complementarity determining regions (CDRs) from the non-porcine species and framework regions from a porcine immunoglobulin molecule.

As used herein, the term "substantially" in the context of a CDR refers to a CDR having an amino acid sequence at least 90%, at least 95%, at least 98% or at least 99% identical to the amino acid sequence of a non-porcine antibody CDR. A porcinized antibody comprises substantially all of at least one, and typically two, variable domains (Fab, Fab', F(ab')2, FabC, Fv) in which all or substantially all of the CDR regions correspond to those of a non-porcine immunoglobulin (i.e., donor antibody) and all or substantially all of the framework regions are those of a porcine immunoglobulin consensus sequence. According to one aspect, a porcinized antibody also comprises at least a portion of an immunoglobulin constant region (Fc), typically that of a porcine immunoglobulin. In some embodiments, a porcinized antibody contains both the light chain as well as at least the variable domain of a heavy chain. The antibody also may include the CH1, hinge, CH2, CH3, and CH4 regions of the heavy chain. In some embodiments, a porcinized antibody only contains a porcinized light chain. In some embodiments, a porcinized antibody only contains a porcinized heavy chain. In specific embodiments, a porcinized antibody only contains a porcinized variable domain of a light chain and/or of a heavy chain.

The porcinized antibody can be selected from any class of immunoglobulins and any isotype. The porcinized antibody may comprise sequences from more than one class or isotype, and particular constant domains may be selected to optimize desired effector functions using techniques well-known in the art.

The framework and CDR regions of a porcinized antibody need not correspond precisely to the parental sequences, e.g., the donor antibody CDR or the consensus framework may be mutagenized by substitution, insertion and/or deletion of at least one amino acid residue so that the CDR or framework residue at that site does not correspond to either the donor antibody or the consensus framework. In one embodiment, such mutations, however, will not be extensive. Usually, at least 90%, at least 95%, at least 98%, or at least 99% of the porcinized antibody residues will correspond to those of the parental FR and CDR sequences. As used herein, the term "consensus framework" refers to the framework region in the consensus immunoglobulin sequence. As used herein, the term "consensus immunoglobulin sequence" refers to the sequence formed from the most frequently occurring amino acids (or nucleotides) in a family of related immunoglobulin sequences (See e.g., Winnaker, From Genes to Clones (Verlagsgesellschaft, Weinheim, Germany 1987)). In a family of immunoglobulins, each position in the consensus sequence is occupied by the amino acid occurring most frequently at that position in the family. If two amino acids occur equally frequently, either can be included in the consensus sequence.

The porcinized antibody may be designed to minimize unwanted immunological response toward rodent anti-porcine antibodies, which limits the duration and effectiveness of therapeutic applications of those moieties in porcine recipients. The porcinized antibody may have one or more amino acid residues introduced into it from a source that is non-porcine. These non-porine residues are often referred to as "import" residues, which are typically taken from a variable domain. Porcinization may be performed by substituting hypervariable region sequences for the corresponding sequences of a porcine antibody. Accordingly, such "porcinized" antibodies are chimeric antibodies wherein substantially less than an intact porcine variable domain has been substituted by the corresponding sequence from a non-porcine species. The porcinized antibody may be a porcine antibody in which some hypervariable region residues, and possibly some FR residues are substituted by residues from analogous sites in rodent antibodies.

The porcinized antibody may retain high affinity for $Na_v1.7$ and other favorable biological properties. The porcinized antibody may be prepared by a process of analysis of the parental sequences and various conceptual porcinized products using three-dimensional models of the parental and porcinized sequences. Three-dimensional immunoglobulin models are commonly available. Computer programs are available that illustrate and display probable three-dimensional conformational structures of selected candidate immunoglobulin sequences. Inspection of these displays permits analysis of the likely role of the residues in the functioning of the candidate immunoglobulin sequence, i.e., the analysis of residues that influence the ability of the candidate immunoglobulin to bind its antigen. In this way, FR residues can be selected and combined from the recipient and import sequences so that the desired antibody characteristics, such as increased affinity for $Na_v1.7$, is achieved. In general, the hypervariable region residues may be directly and most substantially involved in influencing antigen binding.

e. Anti-$Na_v1.7$ Antibodies

Anti-$Na_v1.7$ antibodies may be generated using the techniques described above. The anti-$Na_v1.7$ antibody may be 1E16 monoclonal antibody (also known herein as SVmab1), or an antibody fragment thereof.

(1) 1E16 Antibody

As used herein, "1E16" or "1E16 mAb" or "SVmab1" refers to a monoclonal antibody produced by a hybridoma cell line. The 1E16 antibody was made using Balb/C mice strain that was immunized with SEQ ID NO:21 or 23. The spleen cells of the mice were fused with the mouse myeloma cell line SP2/0. The hybridoma cells were cloned using single cell sorting in HAT medium. The antibodies secreted by the different clones were then assayed for their ability to bind the antigen using an ELISA. The most productive and stable clones were selected. The selected hybridomas were grown in RPMI-1640 media supplemented with Newborn Calf Serum (20%) and Glutamine and frozen in the same media.

1E16 binds to an epitope on $Na_v1.7$ (SEQ ID NO:21 or 23) and recognizes full length $Na_v1.7$. 1E16 has a heavy chain amino acid sequence of SEQ ID NO:4, which is encoded by a nucleotide sequence of SEQ ID NO:12, and a light chain amino acid sequence of SEQ ID NO:8, which is encoded by SEQ ID NO:16. 1E16 includes CDR-H1 (SEQ ID NO:5), CDR-H2 (SEQ ID NO:6), CDR-H3 (SEQ ID NO:7), CDR-L1 (SEQ ID NO:9), CDR-L2 (SEQ ID NO:10), and CDR-L3 (SEQ ID NO:11), which are encoded by nucleotide sequences of SEQ ID NOS:13-15 and 17-19, respectively.

3. Pharmaceutical Compositions

The antibody may be a component in a pharmaceutical composition. The pharmaceutical composition may also contain a pharmaceutically acceptable carrier. The pharmaceutical compositions comprising antibodies of the invention are for use in, but not limited to, diagnosing, detecting, or monitoring a disorder, in preventing, treating, managing, or ameliorating of a disorder or one or more symptoms thereof, and/or in research. In a specific embodiment, a composition comprises one or more antibodies of the invention. In another embodiment, the pharmaceutical composition comprises one or more antibodies of the invention and one or more prophylactic or therapeutic agents other than antibodies of the invention for treating a disorder in which activity of a targeted Nav1.7 is detrimental. In a further embodiment, the prophylactic or therapeutic agents are known to be useful for, or have been, or are currently being used in the prevention, treatment, management, or amelioration of a disorder, or one or more symptoms thereof. In accordance with these embodiments, the composition may further comprise of a carrier, diluent, or excipient.

The antibodies of the invention can be incorporated into pharmaceutical compositions suitable for administration to a subject. Typically, the pharmaceutical composition comprises an antibody of the invention and a pharmaceutically acceptable carrier. As used herein, "pharmaceutically acceptable carrier" includes any and all solvents, dispersion media, coatings, antibacterial and antifungal agents, isotonic and absorption delaying agents, and the like that are physiologically compatible. Examples of pharmaceutically acceptable carriers include one or more of water, saline, phosphate buffered saline, dextrose, glycerol, ethanol and the like, as well as combinations thereof. In many cases, it will be preferable to include isotonic agents, for example, sugars, polyalcohols such as mannitol, sorbitol, or sodium chloride in the composition. Pharmaceutically acceptable carriers may further comprise minor amounts of auxiliary substances such as wetting or emulsifying agents, preservatives, or buffers, which enhance the shelf life or effectiveness of the antibody.

Various delivery systems are known and can be used to administer one or more antibodies of the invention or the combination of one or more antibodies of the invention and a prophylactic agent or therapeutic agent useful for preventing, managing, treating, or ameliorating a disorder or one or more symptoms thereof, e.g., encapsulation in liposomes, microparticles, microcapsules, recombinant cells capable of expressing the antibody or antibody fragment, receptor-mediated endocytosis (see, e.g., Wu and Wu, J. Biol. Chem. 262:4429-4432 (1987)), construction of a nucleic acid as part of a retroviral or other vector, etc. Methods of administering a prophylactic or therapeutic agent of the invention include, but are not limited to, parenteral administration (e.g., intradermal, intramuscular, intraperitoneal, intravenous and subcutaneous), epidurala administration, intratumoral administration, and mucosal administration (e.g., intranasal and oral routes). In addition, pulmonary administration can be employed, e.g., by use of an inhaler or nebulizer, and formulation with an aerosolizing agent. See, e.g., U.S. Pat. Nos. 6,019,968; 5,985,320; 5,985,309; 5,934,272; 5,874,064; 5,855,913; 5,290,540; and 4,880,078; and PCT Publication Nos. WO 92/19244; WO97/32572; WO97/44013; WO98/31346; and WO99/66903, each of which is incorporated herein by reference in their entireties. In one embodiment, an antibody of the invention or a composition of the invention is administered using Alkermes AIR® pulmonary drug delivery technology (Alkermes, Inc., Cambridge, Mass.). In a specific embodiment, prophylactic or therapeutic agents of the invention are administered intramuscularly, intravenously, intratumorally, orally, intranasally, pulmonary, or subcutaneously. The prophylactic or therapeutic agents may be administered by any convenient route, for example by infusion or bolus injection, by absorption through epithelial or mucocutaneous linings (e.g., oral mucosa, rectal and intestinal mucosa, etc.) and may be administered together with other biologically active agents. Administration can be systemic or local.

In a specific embodiment, it may be desirable to administer the antibodies of the invention locally to the area in need of treatment; this may be achieved by, for example, and not by way of limitation, local infusion, by injection, or by means of an implant, said implant being of a porous or non-porous material, including membranes and matrices, such as sialastic membranes, polymers, fibrous matrices (e.g., Tissuel®), or collagen matrices. In one embodiment, an effective amount of one or more antibodies of the invention is administered locally to the affected area to a subject to prevent, treat, manage, and/or ameliorate a disorder or a symptom thereof.

In another embodiment, the antibody can be delivered in a controlled release or sustained release system. In one embodiment, a pump may be used to achieve controlled or sustained release (see Langer, supra; Sefton, 1987, CRC Crit. Ref. Biomed. Eng. 14:20; Buchwald et al., 1980, Surgery 88:507; Saudek et al., 1989, N. Engl. J. Med. 321:574). In another embodiment, polymeric materials can be used to achieve controlled or sustained release of the therapies of the invention (see e.g., Medical Applications of Controlled Release, Langer and Wise (eds.), CRC Pres., Boca Raton, Fla. (1974); Controlled Drug Bioavailability, Drug Product Design and Performance, Smolen and Ball (eds.), Wiley, N.Y. (1984); Ranger and Peppas, 1983, J., Macromol. Sci. Rev. Macromol. Chem. 23:61; see also Levy et al., 1985, Science 228:190; During et al., 1989, Ann. Neurol. 25:351; Howard et al., 1989, J. Neurosurg. 7 1:105); U.S. Pat. No. 5,679,377; U.S. Pat. No. 5,916,597; U.S. Pat. No. 5,912,015; U.S. Pat. No. 5,989,463; U.S. Pat. No. 5,128,326; PCT Publication No. WO99/15154; and PCT Publication No. WO99/20253. Examples of polymers used in sustained release formulations include, but are not limited to, poly(2-hydroxy ethyl methacry-late), poly(methyl methacrylate), poly(acrylic acid), poly(ethylene-co-vinyl acetate), poly(methacrylic acid), polyglycolides (PLG), polyanhydrides, poly(N-vinyl pyrrolidone), poly(vinyl alcohol), polyacrylamide, poly(ethylene glycol), polylactides (PLA), poly(lactide-co-glycolides) (PLGA), and polyorthoesters. In a particular embodiment, the polymer used in a sustained release formulation is inert, free of leachable impurities, stable on storage, sterile, and biodegradable. In yet another embodiment, a controlled or sustained release system can be placed in proximity of the prophylactic or therapeutic target, thus requiring only a fraction of the systemic dose (see, e.g., Goodson, in Medical Applications of Controlled Release, supra, vol. 2, pp. 115-138 (1984)).

Controlled release systems are discussed in the review by Langer (1990, Science 249:1527-1533). Any technique known to one of skill in the art can be used to produce sustained release formulations comprising one or more antibodies of the invention. See, e.g., U.S. Pat. No. 4,526,938, PCT publication WO91/05548, PCT publication WO96/20698, Ning et al., 1996, "Intratumoral Radioimmunotheraphy of a Human Colon Cancer Xenograft Using a Sustained-Release Gel," Radiotherapy &Oncology 39:179-189; Song et al., 1995, "Antibody Mediated Lung Targeting of Long-Circulating Emulsions," PDA Journal of Pharmaceutical Science & Technology 50:372-397; Cleek et al., 1997, "Biodegradable Polymeric Carriers for a bFGF Antibody for Cardiovascular Application," Pro. Int'l. Symp. Control. Rel. Bioact. Mater. 24:853-854; and Lam et al., 1997, "Microencapsulation of Recombinant Humanized Monoclonal Antibody for Local Delivery," Proc. Int'l. Symp. Control Rel. Bioact. Mater. 24:759-760, each of which is incorporated herein by reference in their entireties.

In a specific embodiment, where the composition of the invention is a nucleic acid encoding an antibody, the nucleic acid can be administered in vivo to promote expression of its encoded antibody, by constructing it as part of an appropriate nucleic acid expression vector and administering it so that it becomes intracellular, e.g., by use of a retroviral vector (see U.S. Pat. No. 4,980,286), or by direct injection, or by use of microparticle bombardment (e.g., a gene gun; Biolistic, Dupont), or coating with lipids or cell-surface receptors or transfecting agents, or by administering it in linkage to a homeobox-like peptide which is known to enter the nucleus (see, e.g., Joliot et al., 1991, Proc. Natl. Acad. Sci. USA 88:1864-1868). Alternatively, a nucleic acid can be introduced intracellularly and incorporated within host cell DNA for expression by homologous recombination.

A pharmaceutical composition of the invention is formulated to be compatible with its intended route of administration. Examples of routes of administration include, but are not limited to, parenteral, e.g., intravenous, intradermal, subcutaneous, oral, intranasal (e.g., inhalation), transdermal (e.g., topical), transmucosal, and rectal administration. Inhalation may include, in some embodiments, use of a vaporizer to administer the pharmaceutical composition to the subject. In a specific embodiment, the composition is formulated in accordance with routine procedures as a pharmaceutical composition adapted for intravenous, subcutaneous, intramuscular, oral, intranasal, or topical administration to human beings. Typically, compositions for intravenous administration are solutions in sterile isotonic aqueous buffer. Where necessary, the composition may also include a solubilizing agent and a local anesthetic such as lignocaine to ease pain at the site of the injection.

If the compositions of the invention are to be administered topically, the compositions can be formulated in the form of an ointment, cream, transdermal patch, lotion, gel, shampoo, spray, aerosol, solution, emulsion, or other form well-known to one of skill in the art. See, e.g., Remington's Pharmaceutical Sciences and Introduction to Pharmaceutical Dosage Forms, 19th ed., Mack Pub. Co., Easton, Pa. (1995). For non-sprayable topical dosage forms, viscous to semi-solid or solid forms comprising a carrier or one or more excipients compatible with topical application and having a dynamic viscosity greater than water are typically employed. Suitable formulations include, without limitation, solutions, suspensions, emulsions, creams, ointments, powders, liniments, salves, and the like, which are, if desired, sterilized or mixed with auxiliary agents (e.g., preservatives, stabilizers, wetting agents, buffers, or salts) for influencing various properties, such as, for example, osmotic pressure. Other suitable topical dosage forms include sprayable aerosol preparations wherein the active ingredient, for example in combination with a solid or liquid inert carrier, is packaged in a mixture with a pressurized volatile (e.g., a gaseous propellant, such as freon) or in a squeeze bottle. Moisturizers or humectants can also be added to pharmaceutical compositions and dosage forms if desired. Examples of such additional ingredients are well-known in the art.

If the method of the invention comprises intranasal administration of a composition, the composition can be formulated in an aerosol form, spray, mist or in the form of drops. In particular, prophylactic or therapeutic agents for use according to the present invention can be conveniently delivered in the form of an aerosol spray presentation from pressurized packs or a nebuliser, with the use of a suitable propellant (e.g., dichlorodifluoromethane, trichloro-fluoromethane, dichlorotetrafluoroethane, carbon dioxide or other suitable gas). In the case of a pressurized aerosol the dosage unit may be determined by providing a valve to deliver a metered amount. Capsules and cartridges (composed of, e.g., gelatin) for use in an inhaler or insufflator may be formulated containing a powder mix of the compound and a suitable powder base such as lactose or starch.

If the method of the invention comprises oral administration, compositions can be formulated orally in the form of tablets, capsules, cachets, gelcaps, solutions, suspensions, and the like. Tablets or capsules can be prepared by conventional means with pharmaceutically acceptable excipients such as binding agents (e.g., pregelatinised maize starch, polyvinylpyrrolidone, or hydroxypropyl methylcellulose); fillers (e.g., lactose, microcrystalline cellulose, or calcium hydrogen phosphate); lubricants (e.g., magnesium stearate, talc, or silica); disintegrants (e.g., potato starch or sodium starch glycolate); or wetting agents (e.g., sodium lauryl sulphate). The tablets may be coated by methods well-known in the art. Liquid preparations for oral administration may take the form of, but not limited to, solutions, syrups or suspensions, or they may be presented as a dry product for constitution with water or other suitable vehicle before use. Such liquid preparations may be prepared by conventional means with pharmaceutically acceptable additives such as suspending agents (e.g., sorbitol syrup, cellulose derivatives, or hydrogenated edible fats); emulsifying agents (e.g., lecithin or acacia); non-aqueous vehicles (e.g., almond oil, oily esters, ethyl alcohol, or fractionated vegetable oils); and preservatives (e.g., methyl or propyl-p-hydroxybenzoates or sorbic acid). The preparations may also contain buffer salts, flavoring, coloring, and sweetening agents as appropriate. Preparations for oral administration may be suitably formulated for slow release, controlled release, or sustained release of a prophylactic or therapeutic agent(s).

The method of the invention may comprise pulmonary administration, e.g., by use of an inhaler or nebulizer, of a composition formulated with an aerosolizing agent. See, e.g., U.S. Pat. Nos. 6,019,968; 5,985,320; 5,985,309; 5,934,272; 5,874,064; 5,855,913; 5,290,540; and 4,880,078; and PCT Publication Nos. WO 92/19244; WO 97/32572; WO 97/44013; WO 98/31346; and WO 99/66903, each of which is incorporated herein by reference their entireties. In a specific embodiment, an antibody of the invention and/or composition of the invention is administered using Alkermes AIR pulmonary drug delivery technology (Alkermes, Inc., Cambridge, Mass.).

The method of the invention may comprise administration of a composition formulated for parenteral administration by injection (e.g., by bolus injection or continuous infusion). Formulations for injection may be presented in unit dosage form (e.g., in ampoules or in multi-dose containers) with an added preservative. The compositions may take such forms as suspensions, solutions or emulsions in oily or aqueous vehicles, and may contain formulatory agents such as suspending, stabilizing and/or dispersing agents. Alternatively, the active ingredient may be in powder form for constitution with a suitable vehicle (e.g., sterile pyrogen-free water) before use. The methods of the invention may additionally comprise of administration of compositions formulated as depot preparations. Such long acting formulations may be administered by implantation (e.g., subcutaneously or intramuscularly) or by intramuscular injection. Thus, for example, the compositions may be formulated with suitable polymeric or hydrophobic materials (e.g., as an emulsion in an acceptable oil) or ion exchange resins, or as sparingly soluble derivatives (e.g., as a sparingly soluble salt).

The methods of the invention encompass administration of compositions formulated as neutral or salt forms. Pharmaceutically acceptable salts include those formed with anions such as those derived from hydrochloric, phosphoric, acetic, oxalic, tartaric acids, etc., and those formed with cations such as those derived from sodium, potassium, ammonium, calcium, ferric hydroxides, isopropylamine, triethylamine, 2-ethylamino ethanol, histidine, procaine, etc.

Generally, the ingredients of compositions are supplied either separately or mixed together in unit dosage form, for example, as a dry lyophilized powder or water free concentrate in a hermetically sealed container such as an ampoule or sachette indicating the quantity of active agent. Where the mode of administration is infusion, composition can be dispensed with an infusion bottle containing sterile pharmaceutical grade water or saline. Where the mode of administration is by injection, an ampoule of sterile water for injection or saline can be provided so that the ingredients may be mixed prior to administration.

In particular, the invention also provides that one or more of the antibodies, or pharmaceutical compositions, of the invention is packaged in a hermetically sealed container such as an ampoule or sachette indicating the quantity of the antibody. In one embodiment, one or more of the antibodies, or pharmaceutical compositions of the invention is supplied as a dry sterilized lyophilized powder or water free concentrate in a hermetically sealed container and can be reconstituted (e.g., with water or saline) to the appropriate concentration for administration to a subject. In one embodiment, one or more of the antibodies or pharmaceutical compositions of the invention is supplied as a dry sterile lyophilized powder in a hermetically sealed container at a unit dosage of at least 5 mg, for example at least 10 mg, at least 15 mg, at least 25 mg, at least 35 mg, at least 45 mg, at least 50 mg, at least 75 mg, or at least 100 mg. The lyophilized antibodies or pharmaceutical compositions of the invention should be stored at between 2° C. and 8° C. in its original container and the antibodies, or pharmaceutical compositions of the invention should be administered within 1 week, for example within 5 days, within 72 hours, within 48 hours, within 24 hours, within 12 hours, within 6 hours, within 5 hours, within 3 hours, or within 1 hour after being reconstituted. In an alternative embodiment, one or more of the antibodies or pharmaceutical compositions of the invention is supplied in liquid form in a hermetically sealed container indicating the quantity and concentration of the antibody. In a further embodiment, the liquid form of the administered composition is supplied in a hermetically sealed container at least 0.25 mg/ml, for example at least 0.5 mg/ml, at least 1 mg/ml, at least 2.5 mg/ml, at least 5 mg/ml, at least 8 mg/ml, at least 10 mg/ml, at least 15 mg/ml, at least 25 mg/ml, at least 50 mg/ml, at least 75 mg/ml or at least 100 mg/ml. The liquid form should be stored at between 2° C. and 8° C. in its original container.

The antibodies of the invention can be incorporated into a pharmaceutical composition suitable for parenteral administration. In one aspect, antibodies will be prepared as an injectable solution containing 0.1-250 mg/ml antibody. The injectable solution can be composed of either a liquid or lyophilized dosage form in a flint or amber vial, ampule or pre-filled syringe. The buffer can be L-histidine (1-50 mM), optimally 5-10 mM, at pH 5.0 to 7.0 (optimally pH 6.0). Other suitable buffers include but are not limited to, sodium succinate, sodium citrate, sodium phosphate or potassium phosphate. Sodium chloride can be used to modify the tonicity of the solution at a concentration of 0-300 mM (optimally 150 mM for a liquid dosage form). Cryoprotectants can be included for a lyophilized dosage form, principally 0-10% sucrose (optimally 0.5-1.0%). Other suitable cryoprotectants include trehalose and lactose. Bulking agents can be included for a lyophilized dosage form, principally 1-10% mannitol (optimally 2-4%). Stabilizers can be used in both liquid and lyophilized dosage forms, principally 1-50 mM L-Methionine (optimally 5-10 mM). Other suitable bulking agents include glycine, arginine, can be included as 0-0.05% polysorbate-80 (optimally 0.005-0.01%). Additional surfactants include but are not limited to polysorbate 20 and BRIJ surfactants. The pharmaceutical composition comprising the antibodies of the invention prepared as an injectable solution for parenteral administration, can further comprise an agent useful as an adjuvant, such as those used to increase the absorption, or dispersion of the antibody. A particularly useful adjuvant is hyaluronidase, such as Hylenex® (recombinant human hyaluronidase). Addition of hyaluronidase in the injectable solution improves human bioavailability following parenteral administration, particularly subcutaneous administration. It also allows for greater injection site volumes (i.e. greater than 1 ml) with less pain and discomfort, and minimum incidence of injection site reactions. (See International Appln. Publication No. WO 04/078140 and U.S. Patent Appln. Publication No. US2006104968, incorporated herein by reference.)

The compositions of this invention may be in a variety of forms. These include, for example, liquid, semi-solid and solid dosage forms, such as liquid solutions (e.g., injectable and infusible solutions), dispersions or suspensions, tablets, pills, powders, liposomes and suppositories. The preferred form depends on the intended mode of administration and therapeutic application. Compositions can be in the form of injectable or infusible solutions, such as compositions similar to those used for passive immunization of humans or mammals (e.g., bovine, canine, equine, feline, and porcine) with other antibodies. In one embodiment, the antibody is administered by intravenous infusion or injection. In another embodiment, the antibody is administered by intramuscular or subcutaneous injection.

Therapeutic compositions typically must be sterile and stable under the conditions of manufacture and storage. The composition can be formulated as a solution, microemulsion, dispersion, liposome, or other ordered structure suitable to high drug concentration. Sterile injectable solutions can be prepared by incorporating the active compound (i.e., a binding protein, e.g. an antibody, of the present invention) in the required amount in an appropriate solvent with one or a combination of ingredients enumerated above, as required, followed by filtered sterilization. Generally, dispersions are prepared by incorporating the active compound into a sterile vehicle that contains a basic dispersion medium and the required other ingredients from those enumerated above. In the case of sterile, lyophilized powders for the preparation of sterile injectable solutions, methods of preparation comprise vacuum drying and spray-drying that yields a powder of the active ingredient plus any additional desired ingredient from a previously sterile-filtered solution thereof. The proper fluidity of a solution can be maintained, for example, by the use of a coating such as lecithin, by the maintenance of the required particle size in the case of dispersion and by the use of surfactants. Prolonged absorption of injectable compositions can be brought about by including, in the composition, an agent that delays absorption, for example, monostearate salts and gelatin.

The antibodies of the present invention can be administered by a variety of methods known in the art. For many therapeutic applications, the route/mode of administration may be subcutaneous injection, intravenous injection, inhalation, or infusion. As will be appreciated by the skilled artisan, the route and/or mode of administration will vary depending upon the desired results. In certain embodiments, the active compound may be prepared with a carrier that will protect the compound against rapid release, such as a controlled release formulation, including implants, transdermal patches, and microencapsulated delivery systems. Biodegradable, biocompatible polymers can be used, such as ethylene vinyl acetate, polyanhydrides, polyglycolic acid, collagen, polyorthoesters, and polylactic acid. Many methods for the preparation of such formulations are patented or generally known to those skilled in the art. See, e.g., Sustained and Controlled Release Drug Delivery Systems, J. R. Robinson, ed., Marcel Dekker, Inc., New York, 1978.

In certain embodiments, an antibody of the invention may be orally administered, for example, with an inert diluent or an assimilable edible carrier. The antibody (and other ingredients, if desired) may also be enclosed in a hard or soft shell gelatin capsule, compressed into tablets, or incorporated directly into the subject's diet. For oral therapeutic administration, the antibody may be incorporated with excipients and used in the form of ingestible tablets, buccal tablets, troches, capsules, elixirs, suspensions, syrups, wafers, and the like. To administer an antibody of the invention by other than parenteral administration, it may be necessary to coat the antibody with, or co-administer the antibody with, a material to prevent its inactivation.

In certain embodiments, an antibody of the invention is linked to a half-life extending vehicle known in the art. Such vehicles include, but are not limited to, the Fc domain, polyethylene glycol, and dextran. Such vehicles are described, e.g., in U.S. application Ser. No. 09/428,082 and published PCT Application No. WO 99/25044, which are hereby incorporated by reference for any purpose.

In a specific embodiment, nucleic acid sequences comprising nucleotide sequences encoding an antibody of the invention are administered to treat, prevent, manage, or ameliorate a disorder or one or more symptoms thereof by way of gene therapy. Gene therapy refers to therapy performed by the administration to a subject of an expressed or expressible nucleic acid. In this embodiment of the invention, the nucleic acids produce their encoded antibody of the invention that mediates a prophylactic or therapeutic effect.

Any of the methods for gene therapy available in the art can be used according to the present invention. For general reviews of the methods of gene therapy, see Goldspiel et al., 1993, Clinical Pharmacy 12:488-505; Wu and Wu, 1991, Biotherapy 3:87-95; Tolstoshev, 1993, Ann. Rev. Pharmacol. Toxicol. 32:573-596; Mulligan, Science 260:926-932 (1993); and Morgan and Anderson, 1993, Ann. Rev. Biochem. 62:191-217; May, 1993, TIBTECH 11(5):155-215. Methods commonly known in the art of recombinant DNA technology which can be used are described in Ausubel et al. (eds.), Current Protocols in Molecular Biology, John Wiley & Sons, NY (1993); and Kriegler, Gene Transfer and Expression, A Laboratory Manual, Stockton Press, NY (1990). Detailed description of various methods of gene therapy are disclosed in US20050042664 A1 which is incorporated herein by reference.

Antibodies of the invention can be used alone or in combination to treat diseases or conditions associated with pain, or any other disease or condition associated with $Na_v1.7$. It should further be understood that the combinations are those combinations useful for their intended purpose.

The pharmaceutical compositions may include a "therapeutically effective amount" or a "prophylactically effective amount" of an antibody. A "therapeutically effective amount" refers to an amount effective, at dosages and for periods of time necessary, to achieve the desired therapeutic result. A therapeutically effective amount of the antibody may be determined by a person skilled in the art and may vary according to factors such as the disease state, age, sex, and weight of the individual, and the ability of the antibody to elicit a desired response in the individual. A therapeutically effective amount is also one in which toxic or detrimental effects, if any, of the antibody are outweighed by the therapeutically beneficial effects. A "prophylactically effective amount" refers to an amount effective, at dosages and for periods of time necessary, to achieve the desired prophylactic result. Typically, since a prophylactic dose is used in subjects prior to or at an earlier stage of disease, the prophylactically effective amount will be less than the therapeutically effective amount.

Dosage regimens may be adjusted to provide the optimum desired response (e.g., a therapeutic or prophylactic response). For example, a single bolus may be administered, several divided doses may be administered over time or the dose may be proportionally reduced or increased as indicated by the exigencies of the therapeutic situation. It is especially advantageous to formulate parenteral compositions in dosage unit form for ease of administration and uniformity of dosage. Dosage unit form as used herein refers to physically discrete units suited as unitary dosages for the mammalian subjects to be treated; each unit containing a predetermined quantity of active compound calculated to produce the desired therapeutic effect in association with the required pharmaceutical carrier. The specification for the dosage unit forms are dictated by and directly dependent on (a) the unique characteristics of the active compound and the particular therapeutic or prophylactic effect to be achieved, and (b) the limitations inherent in the art of compounding such an active compound for the treatment of sensitivity in individuals.

An exemplary, non-limiting range for a therapeutically or prophylactically effective amount of the antibody is a dose of between 0.1 and 200 mg/kg, for example between 0.1 and 10 mg/kg. The therapeutically or prophylactically effective amount of the antibody may be between 1 and 200 mg/kg, 10 and 200 mg/kg, 20 and 200 mg/kg, 50 and 200 mg/kg, 75 and 200 mg/kg, 100 and 200 mg/kg, 150 and 200 mg/kg, 50 and 100 mg/kg, 5 and 10 mg/kg, or 1 and 10 mg/kg. It is to be noted that dosage values may vary with the type and severity of the condition to be alleviated. Further, the antibody dose may be determined by a person skilled in the art and may vary according to factors such as the disease state, age, sex, and weight of the individual, and the ability of the antibody to elicit a desired response in the individual. The dose is also one in which toxic or detrimental effects, if any, of the antibody are outweighed by the therapeutically beneficial effects. It is to be further understood that for any particular subject, specific dosage regimens should be adjusted over time according to the individual need and the professional judgment of the person administering or supervising the administration of the compositions, and that dosage ranges set forth herein are exemplary only and are not intended to limit the scope or practice of the claimed composition.

4. $Na_v1.7$ Detection

The present invention also is directed to method of detecting and measuring $Na_v1.7$ in a sample from a subject using the $Na_v1.7$ antibodies described above to bind to different $Na_v1.7$ epitopes. The method includes (a) obtaining a biological sample from a subject, (b) contacting the biological sample with a capture antibody, which binds to an epitope on $Na_v1.7$ or $Na_v1.7$ fragment to form a capture antibody-$Na_v1.7$ antigen complex, (c) contacting the capture antibody-$Na_v1.7$ antigen complex with a detection antibody which includes a detectable label and binds to an epitope on $Na_v1.7$ or $Na_v1.7$ fragment that is not bound by the capture antibody, to form a capture antibody-$Na_v1.7$ antigen-detection antibody, and (d) determining the presence, amount or concentration of $Na_v1.7$ or $Na_v1.7$ fragment in the biological sample based on the signal generated by the detectable label in the capture antibody-$Na_v1.7$ antigen-detection antibody complex.

Levels of at least 0.05 ng/mL, 0.06 ng/mL, 0.07 ng/mL, 0.08 ng/mL, 0.09 ng/mL, 0.10 ng/mL, 0.11 ng/mL, 0.12 ng/mL, 0.13 ng/mL, 0.14 ng/mL, 0.15 ng/mL, 0.16 ng/mL, 0.17 ng/mL, 0.18 ng/mL, 0.19 ng/mL, 0.20 ng/mL, 0.25 ng/mL, 0.30 ng/mL, 0.35 ng/mL, 0.40 ng/mL, 0.45 ng/mL, 0.50 ng/mL, 0.55 ng/mL, 1 ng/mL, 5 ng/mL, 10 ng/mL, 15 ng/mL, 20 ng/mL, 21 ng/mL, 22 ng/mL, 23 ng/mL, 24 ng/mL, 25 ng/mL, 26 ng/mL, 27 ng/mL, 28 ng/mL, 29 ng/mL, or 30 ng/mL of Nav1.7 in a biological sample may be detected. Ranges of Nav1.7 detection have at least 5%, 10%, 25%, 50%, 75%, 100%, 110%, 120%, 130%, 140%, 150%, 160%, 170%, 180%, 190%, 200%, 210%, 220%, 230%, 240%, 250%, 260%, 270%, 280%, 290%, 300%, 400%, or 500% improved range size compared to other available $Na_v1.7$ immunoassays. Ranges of about 0 ng/mL to about 30 ng/mL, about 0.05 ng/mL to about 30 ng/mL, about 0.06 ng/mL to about 30 ng/mL, about 0.07 ng/mL to about 30 ng/mL, about 0.08 ng/mL to about 30 ng/mL, about 0.09 ng/mL to about 30 ng/mL, about 0.095 ng/mL to about 30 ng/mL, about 0.10 ng/mL to about 30 ng/mL, about 0.105 ng/mL to about 30 ng/mL, about 0.11 ng/mL to about 30 ng/mL, about 0.12 ng/mL to about 30 ng/mL, about 0.13 ng/mL to about 30 ng/mL, about 0.14 ng/mL to about 30 ng/mL, about 0.15 ng/mL to about 30 ng/mL, about 0.20 ng/mL to about 30 ng/mL, about 1.00 ng/mL to about 30, about 0 ng/mL to about 27.5 ng/mL, 0.05 ng/mL to about 27.5 ng/mL, 0.06 ng/mL to about 27.5 ng/mL, 0.07 ng/mL to about 27.5 ng/mL, 0.08 ng/mL to about 27.5 ng/mL, 0.09 ng/mL to about 27.5 ng/mL, 0.095 ng/mL to about 27.5 ng/mL, 0.10 ng/mL to about 27.5 ng/mL, 0.105 ng/mL to about 27.5 ng/mL, 0.11 ng/mL to about 27.5 ng/mL, 0.12 ng/mL to about 27.5 ng/mL, 0.13 ng/mL to about 27.5 ng/mL, 0.14 ng/mL to about 27.5 ng/mL, 0.15 ng/mL to about 27.5 ng/mL, 0.20 ng/mL to about 27.5 ng/mL, 1.00 ng/mL to about 27.5 ng/mL, about 0 ng/mL to about 26 ng/mL, about 0.05 ng/mL to about 26 ng/mL, 0.06 ng/mL to about 26 ng/mL, 0.07 ng/mL to about 26 ng/mL, 0.08 ng/mL to about 26 ng/mL, 0.09 ng/mL to about 26 ng/mL, 0.095 ng/mL to about 26 ng/mL, 0.10 ng/mL to about 26 ng/mL, 0.105 ng/mL to about 26 ng/mL, 0.11 ng/mL to about 26 ng/mL, 0.12 ng/mL to about 26 ng/mL, 0.13 ng/mL to about 26 ng/mL, 0.14 ng/mL to about 26 ng/mL, 0.15 ng/mL to about 26 ng/mL, 0.20 ng/mL to about 26 ng/mL, 1.00 ng/mL to about 26 ng/mL, about 0 ng/mL to about 25 ng/mL, 0.05 ng/mL to about 25 ng/mL, 0.06 ng/mL to about 25 ng/mL, 0.07 ng/mL to about 25 ng/mL, 0.08 ng/mL to about 25 ng/mL, 0.09 ng/mL to about 25 ng/mL, 0.095 ng/mL to about 25 ng/mL, 0.10 ng/mL to about 25 ng/mL, 0.105 ng/mL to about 25 ng/mL, 0.11 ng/mL to about 25 ng/mL, 0.12 ng/mL to about 25 ng/mL, 0.13 ng/mL to about 25 ng/mL, 0.14 ng/mL to about 25 ng/mL, 0.15 ng/mL to about 25 ng/mL, 0.20 ng/mL to about 25 ng/mL, 1.00 ng/mL to about 25 ng/mL, about 0 ng/mL to about 24 ng/mL, 0.05 ng/mL to about 24 ng/mL, 0.06 ng/mL to about 24 ng/mL, 0.07 ng/mL to about 24 ng/mL, 0.08 ng/mL to about 24 ng/mL, 0.09 ng/mL to about 24 ng/mL, 0.095 ng/mL to about 24 ng/mL, 0.10 ng/mL to about 24 ng/mL, 0.105 ng/mL to about 24 ng/mL, 0.11 ng/mL to about 24 ng/mL, 0.12 ng/mL to about 24 ng/mL, 0.13 ng/mL to about 24 ng/mL, 0.14 ng/mL to about 24 ng/mL, 0.15 ng/mL to about 24 ng/mL, 0.20 ng/mL to about 24 ng/mL, 1.00 ng/mL to about 24 ng/mL, about 0 ng/mL to about 22.5 ng/mL, 0.05 ng/mL to about 22.5 ng/mL, 0.06 ng/mL to about 22.5 ng/mL, 0.07 ng/mL to about 22.5 ng/mL, 0.08 ng/mL to about 22.5 ng/mL, 0.09 ng/mL to about 22.5 ng/mL, 0.0950 ng/mL to about 22.5 ng/mL, 0.10 ng/mL to about 22.5 ng/mL, 0.105 ng/mL to about 22.5 ng/mL, 0.11 ng/mL to about 22.5 ng/mL, 0.12 ng/mL to about 22.5 ng/mL, 0.13 ng/mL to about 22.5 ng/mL, 0.14 ng/mL to about 22.5 ng/mL, 0.15 ng/mL to about 22.5 ng/mL, 0.20 ng/mL to about 22.5 ng/mL, 1.00 ng/mL to about 22.5 ng/Ml, about 0 ng/mL to about 20 ng/mL, 0.05 ng/mL to about 20 ng/mL, 0.06 ng/mL to about 20 ng/mL, 0.07 ng/mL to about 20 ng/mL, 0.08 ng/mL to about 20 ng/mL, 0.09 ng/mL to about 20 ng/mL, 0.095 ng/mL to about 20 ng/mL, 0.10 ng/mL to about 20 ng/mL, 0.105 ng/mL to about 20 ng/mL, 0.11 ng/mL to about 20 ng/mL, 0.12 ng/mL to about 20 ng/mL, 0.13 ng/mL to about 20 ng/mL, 0.14 ng/mL to about 20 ng/mL, 0.15 ng/mL to about 20 ng/mL, 0.20 ng/mL to about 20 ng/mL, or 1.00 ng/mL to about 20 ng/mL of Nav1.7 may be detected.

a. Immunoassay

Nav1.7, and/or peptides or fragments thereof, i.e., $Na_v1.7$ fragments, may be analyzed using the antibodies described above in an immunoassay. The presence or amount of $Na_v1.7$ or $Na_v1.7$ fragment can be determined using antibodies and detecting specific binding to $Na_v1.7$ or $Na_v1.7$ fragment. For example, the antibody, or antibody fragment thereof, may specifically bind to $Na_v1.7$ or $Na_v1.7$ fragment. If desired, one or more of the antibodies can be used in combination with one or more commercially available monoclonal/polyclonal antibodies. Such antibodies are available from companies such as R&D Systems, Inc. (Minneapolis, Minn.) and Enzo Life Sciences International, Inc. (Plymouth Meeting, Pa.).

The presence or amount of $Na_v1.7$ or $Na_v1.7$ fragment present in a body sample may be readily determined using an immunoassay, such as sandwich immunoassay (e.g., monoclonal-polyclonal sandwich immunoassays, including radioisotope detection (radioimmunoassay (RIA)) and enzyme detection (enzyme immunoassay (EIA) or enzyme-linked immunosorbent assay (ELISA) (e.g., Quantikine ELISA assays, R&D Systems, Minneapolis, Minn.)). A chemiluminescent microparticle immunoassay is an example of a preferred immunoassay. Other methods include, for example, mass spectrometry and immunohistochemistry (e.g. with sections from tissue biopsies) using Nav1.7 antibodies (monoclonal, polyclonal, chimeric, humanized, human etc) or antibody fragments thereof against Nav1.7. Other methods of detection include those described in, for example, U.S. Pat. Nos. 6,143,576; 6,113,855; 6,019,944; 5,985,579; 5,947,124; 5,939,272; 5,922,615; 5,885,527; 5,851,776; 5,824,799; 5,679,526; 5,525,524; and 5,480,792, each of which is hereby incorporated by reference in its entirety. Specific immunological binding of the antibody to the $Na_v1.7$ can be detected via direct labels, such as fluorescent or luminescent tags, metals and radionuclides attached to the antibody or via indirect labels, such as alkaline phosphatase or horseradish peroxidase.

The use of immobilized antibodies or antibody fragments thereof may be incorporated into the immunoassay. The antibodies may be immobilized onto a variety of supports, such as magnetic or chromatographic matrix particles, the surface of an assay plate (such as microtiter wells), pieces of a solid substrate material, and the like. An assay strip can be prepared by coating the antibody or plurality of antibodies in an array on a solid support. This strip can then be dipped into the test biological sample and processed quickly through washes and detection steps to generate a measurable signal, such as a colored spot.

A heterogeneous format may be used. For example, after the test sample is obtained from a subject, a first mixture is prepared. The mixture contains the test sample being assessed for $Na_v1.7$ or $Na_v1.7$ fragment and a first specific binding partner, wherein the first specific binding partner and any $Na_v1.7$ contained in the test sample form a first specific binding partner-$Na_v1.7$ antigen complex. The first specific binding partner may be an anti-$Na_v1.7$ antibody that binds to an epitope having an amino acid sequence comprising at least three contiguous (3) amino acids of SEQ ID NO:21, 22, 23, 50, and/or 51. The order in which the test sample and the first specific binding partner are added to form the mixture is not critical. The first specific binding partner may be immobilized on a solid phase. The solid phase used in the immunoassay (for the first specific binding partner and, optionally, the second specific binding partner) can be any solid phase known in the art, such as, but not limited to, a magnetic particle, a bead, a test tube, a microtiter plate, a cuvette, a membrane, a scaffolding molecule, a film, a filter paper, a disc, and a chip.

After the mixture containing the first specific binding partner-$Na_v1.7$ antigen complex is formed, any unbound $Na_v1.7$ is removed from the complex using any technique known in the art. For example, the unbound $Na_v1.7$ can be removed by washing. Desirably, however, the first specific binding partner is present in excess of any $Na_v1.7$ present in the test sample, such that all $Na_v1.7$ that is present in the test sample is bound by the first specific binding partner.

After any unbound $Na_v1.7$ is removed, a second specific binding partner is added to the mixture to form a first specific binding partner-$Na_v1.7$ antigen-second specific binding partner complex. The second specific binding partner may be an anti-$Na_v1.7$ antibody that binds to an epitope having an amino acid sequence comprising at least three contiguous (3) amino acids of SEQ ID NO:21, 22, 23, 50, and/or 51. Moreover, the second specific binding partner is labeled with or contains a detectable label as described above.

The use of immobilized antibodies or antibody fragments thereof may be incorporated into the immunoassay. The antibodies may be immobilized onto a variety of supports, such as magnetic or chromatographic matrix particles, the surface of an assay plate (such as microtiter wells), pieces of a solid substrate material, and the like. An assay strip can be prepared by coating the antibody or plurality of antibodies in an array on a solid support. This strip can then be dipped into the test biological sample and processed quickly through washes and detection steps to generate a measurable signal, such as a colored spot.

(1) Sandwich ELISA

The Sandwich ELISA measures the amount of antigen between two layers of antibodies (i.e., at least one capture antibody) and a detection antibody (i.e. at least one detection antibody). The capture antibody and the detection antibody bind to different epitopes on the antigen, e.g., $Na_v1.7$. Desirably, binding of the capture antibody to an epitope does not interfere with binding of the detection antibody to an epitope. Either monoclonal or polyclonal antibodies may be used as the capture and detection antibodies in the sandwich ELISA.

Generally, at least two antibodies are employed to separate and quantify $Na_v1.7$ or $Na_v1.7$ fragment in a test sample. More specifically, the at least two antibodies bind to certain epitopes of $Na_v1.7$ or a $Na_v1.7$ fragment forming an immune complex which is referred to as a "sandwich". One or more antibodies can be used to capture the $Na_v1.7$ or $Na_v1.7$ fragment in the test sample (these antibodies are frequently referred to as a "capture" antibody or "capture" antibodies) and one or more antibodies is used to bind a detectable (namely, quantifiable) label to the sandwich (these antibodies are frequently referred to as the "detection" antibody or "detection" antibodies). In a sandwich assay, the binding of an antibody to its epitope desirably is not diminished by the binding of any other antibody in the assay to its respective epitope. Antibodies are selected so that the one or more first antibodies brought into contact with a test sample suspected of containing $Na_v1.7$ or $Na_v1.7$ fragment do not bind to all or part of an epitope recognized by the second or subsequent antibodies, thereby interfering with the ability of the one or more second detection antibodies to bind to the $Na_v1.7$ or $Na_v1.7$ fragment.

The antibodies may be used as a first antibody in said immunoassay. The antibody immunospecifically binds to epitopes on $Na_v1.7$. In addition to the antibodies of the present invention, said immunoassay may comprise a second antibody that immunospecifically binds to epitopes that are not recognized or bound by the first antibody.

A test sample suspected of containing $Na_v1.7$ or $Na_v1.7$ fragment can be contacted with at least one first capture antibody (or antibodies) and at least one second detection antibodies either simultaneously or sequentially. In the sandwich assay format, a test sample suspected of containing $Na_v1.7$ or $Na_v1.7$ fragment is first brought into contact with the at least one first capture antibody that specifically binds to a particular epitope under conditions which allow the formation of a first antibody-$Na_v1.7$ antigen complex. If more than one capture antibody is used, a first multiple capture antibody-$Na_v1.7$ antigen complex is formed. In a sandwich assay, the antibodies, preferably, the at least one capture antibody, are used in molar excess amounts of the maximum amount of $Na_v1.7$ or $Na_v1.7$ fragment expected in the test sample. For example, from about 5 μg/ml to about 1 mg/ml of antibody per ml of microparticle coating buffer may be used.

(a) Anti-$Na_v1.7$ Capture Antibody

Optionally, prior to contacting the test sample with the at least one first capture antibody, the at least one first capture antibody can be bound to a solid support which facilitates the separation the first antibody-$Na_v1.7$ antigen complex from the test sample. Any solid support known in the art can be used, including but not limited to, solid supports made out of polymeric materials in the forms of wells, tubes, or beads. The antibody (or antibodies) can be bound to the solid support by adsorption, by covalent bonding using a chemical coupling agent or by other means known in the art, provided that such binding does not interfere with the ability of the antibody to bind $Na_v1.7$ or $Na_v1.7$ fragment. Moreover, if necessary, the solid support can be derivatized to allow reactivity with various functional groups on the antibody. Such derivatization requires the use of certain coupling agents such as, but not limited to, maleic anhydride, N-hydroxysuccinimide and 1-ethyl-3-(3-dimethylaminopropyl) carbodiimide.

After the test sample suspected of containing $Na_v1.7$ or $Na_v1.7$ fragment is brought into contact with the at least one first capture antibody, the test sample is incubated in order to allow for the formation of a first capture antibody (or multiple antibody)-$Na_v1.7$ antigen complex. The incubation can be carried out at a pH of from about 4.5 to about 10.0, at a temperature of from about 2° C. to about 45° C., and for a period from at least about one (1) minute to about eighteen (18) hours, from about 2-6 minutes, or from about 3-4 minutes.

(b) Detection Antibody

After formation of the first/multiple capture antibody-$Na_v1.7$ antigen complex, the complex is then contacted with at least one second detection antibody (under conditions that allow for the formation of a first/multiple antibody-$Na_v1.7$ antigen-second antibody complex). If the first antibody-$Na_v1.7$ antigen complex is contacted with more than one detection antibody, then a first/multiple capture antibody-$Na_v1.7$ antigen-multiple antibody detection complex is formed. As with first antibody, when the at least second (and subsequent) antibody is brought into contact with the first antibody-$Na_v1.7$ antigen complex, a period of incubation under conditions similar to those described above is required for the formation of the first/multiple antibody-$Na_v1.7$ antigen-second/multiple antibody complex. Preferably, at least one second antibody contains a detectable label. The detectable label can be bound to the at least one second antibody prior to, simultaneously with or after the formation of the first/multiple antibody-$Na_v1.7$ antigen-second/multiple antibody complex. Any detectable label known in the art can be used.

Chemiluminescent assays can be performed in accordance with the methods described in Adamczyk et al., Anal. Chim. Acta 579(1): 61-67 (2006). While any suitable assay format can be used, a microplate chemiluminometer (Mithras LB-940, Berthold Technologies U.S.A., LLC, Oak Ridge, Tenn.) enables the assay of multiple samples of small volumes rapidly. The chemiluminometer can be equipped with multiple reagent injectors using 96-well black polystyrene microplates (Costar #3792). Each sample can be added into a separate well, followed by the simultaneous/sequential addition of other reagents as determined by the type of assay employed. Desirably, the formation of pseudobases in neutral or basic solutions employing an acridinium aryl ester is avoided, such as by acidification. The chemiluminescent response is then recorded well-by-well. In this regard, the time for recording the chemiluminescent response will depend, in part, on the delay between the addition of the reagents and the particular acridinium employed.

The order in which the test sample and the specific binding partner(s) are added to form the mixture for chemiluminescent assay is not critical. If the first specific binding partner is detectably labeled with an acridinium compound, detectably labeled first specific binding partner-$Na_v1.7$ antigen complexes form. Alternatively, if a second specific binding partner is used and the second specific binding partner is detectably labeled with an acridinium compound, detectably labeled first specific binding partner-$Na_v1.7$ antigen-second specific binding partner complexes form. Any unbound specific binding partner, whether labeled or unlabeled, can be removed from the mixture using any technique known in the art, such as washing.

Hydrogen peroxide can be generated in situ in the mixture or provided or supplied to the mixture before, simultaneously with, or after the addition of an above-described acridinium compound. Hydrogen peroxide can be generated in situ in a number of ways such as would be apparent to one skilled in the art.

Alternatively, a source of hydrogen peroxide can be simply added to the mixture. For example, the source of the hydrogen peroxide can be one or more buffers or other solutions that are known to contain hydrogen peroxide. In this regard, a solution of hydrogen peroxide can simply be added.

Upon the simultaneous or subsequent addition of at least one basic solution to the sample, a detectable signal, namely, a chemiluminescent signal, indicative of the presence of $Na_v1.7$ or $Na_v1.7$ fragment is generated. The basic solution contains at least one base and has a pH greater than or equal to 10, preferably, greater than or equal to 12. Examples of basic solutions include, but are not limited to, sodium hydroxide, potassium hydroxide, calcium hydroxide, ammonium hydroxide, magnesium hydroxide, sodium carbonate, sodium bicarbonate, calcium hydroxide, calcium carbonate, and calcium bicarbonate. The amount of basic solution added to the sample depends on the concentration of the basic solution. Based on the concentration of the basic solution used, one skilled in the art can easily determine the amount of basic solution to add to the sample.

The chemiluminescent signal that is generated can be detected using routine techniques known to those skilled in the art. Based on the intensity of the signal generated, the amount of $Na_v1.7$ or $Na_v1.7$ fragment in the sample can be quantified. Specifically, the amount of $Na_v1.7$ in the sample is proportional to the intensity of the signal generated. The amount of $Na_v1.7$ present can be quantified by comparing the amount of light generated to a standard curve for $Na_v1.7$ or by comparison to a reference standard. The standard curve can be generated using serial dilutions or solutions of known concentrations of $Na_v1.7$ by mass spectroscopy, gravimetric methods, and other techniques known in the art.

(2) Methods of Using Anti-$Na_v1.7$ Antibodies

The present invention is directed to a method for determining the presence, amount, or concentration of $Na_v1.7$ or $Na_v1.7$ fragment in a test sample using the disclosed anti-$Na_v1.7$ antibodies, or antibody fragments thereof. The method includes the steps of (a) contacting the test sample with a capture antibody, which binds to an epitope on $Na_v1.7$ or $Na_v1.7$ fragment, so as to form a capture antibody-$Na_v1.7$ antigen complex; (b) contacting the capture antibody-$Na_v1.7$ antigen complex with at least one detection antibody, which comprises a detectable label and binds to an epitope on $Na_v1.7$ or $Na_v1.7$ fragment that is not bound by the capture antibody, to form a capture antibody-$Na_v1.7$ antigen-detection antibody complex; and (c) determining the presence, amount or concentration of $Na_v1.7$ or $Na_v1.7$ fragment in the test sample based on the signal generated by the detectable label in the capture antibody-$Na_v1.7$ antigen-detection antibody complex whereupon the presence, amount, or concentration of $Na_v1.7$ or $Na_v1.7$ fragment in the test sample is determined.

The capture antibody and detection antibody may be an anti-Nav1.7 antibody described above. For example, the capture antibody may include the 1E16 antibody or a domain or region of: a variable heavy domain comprising the amino acid sequence of SEQ ID NO:4; a variable light domain comprising the amino acid sequence of SEQ ID NO:8; a variable heavy domain comprising the amino acid sequence of SEQ ID NO:4 and a variable light domain comprising the amino acid sequence of SEQ ID NO:8; a variable heavy chain comprising a complementarity determining region (CDR)1 comprising the amino acid sequence of SEQ ID NO:5 a CDR2 comprising the amino acid sequence of SEQ ID NO:6, and a CDR3 comprising the amino acid sequence of SEQ ID NO:7; a variable light chain comprising a CDR1 comprising the amino acid sequence of SEQ ID NO:9, a CDR2 comprising the amino acid sequence of SEQ ID NO:10; and a CDR3 comprising the amino acid sequence of SEQ ID NO:11; or a variable heavy chain comprising a CDR1 comprising the amino acid sequence of SEQ ID NO:5, a CDR2 comprising the amino acid sequence of SEQ ID NO:6, and a CDR3 comprising the amino acid sequence of SEQ ID NO:7 and a variable light chain comprising a CDR1 comprising the amino acid sequence of SEQ ID NO:9, a CDR2 comprising the amino acid sequence of SEQ ID NO:10, and a CDR3 comprising the amino acid sequence of SEQ ID NO:11.

b. Controls

It may be desirable to include a control sample. The control sample may be analyzed concurrently with the sample from the subject as described above. The results obtained from the subject sample can be compared to the results obtained from the control sample. Standard curves may be provided, with which assay results for the biological sample may be compared. Such standard curves present levels of marker as a function of assay units, i.e. fluorescent signal intensity, if a fluorescent label is used. Using samples taken from multiple donors, standard curves can be provided for control levels of the $Na_v1.7$ in normal healthy tissue, as well as for "at-risk" levels of the $Na_v1.7$ in tissue taken from donors, who may have one or more of the characteristics set forth above.

Thus, in view of the above, a method for determining the presence, amount, or concentration of $Na_v1.7$ or $Na_v1.7$ fragment in a test sample is provided. The method comprises assaying the test sample for $Na_v1.7$ by an immunoassay, for example, employing at least one capture antibody that binds to an epitope on $Na_v1.7$ or a fragment of $Na_v1.7$ and at least one detection antibody that binds to an epitope on $Na_v1.7$ which is different from the epitope for the capture antibody and optionally includes a detectable label, and comprising comparing a signal generated by the detectable label as a direct or indirect indication of the presence, amount or concentration of $Na_v1.7$ in the test sample to a signal generated as a direct or indirect indication of the presence, amount or concentration of $Na_v1.7$ in a calibrator. The calibrator is optionally, and is preferably, part of a series of calibrators in which each of the calibrators differs from the other calibrators in the series by the concentration of $Na_v1.7$.

5. Method of Treatment

The present invention is also directed to a method of treating pain and/or itch in a subject in need thereof. The method comprises administering the $Na_v1.7$ antibody described above or antibody fragment thereof to the subject. The pain and/or itch may be localized, peripheral, or systemic in the subject, and thus, the antibody may be administered centrally, locally, peripherally, and/or systemically. Systemic administration of the antibody may not result in an adapted response (i.e., a decreased sensitivity to the effects of the antibody) in the subject over time and/or after repeated administrations (e.g., 1, 2, 3, 4, 5, 6, 7, 8, 9, 10, or more administrations) of the antibody to the subject. In some embodiments, the antibody may be administered via inhalation (e.g., with a vaporizer).

In some embodiments, the pain may be inflammatory pain, neuropathic pain, hyperalgesia, chronic pain, pathological pain, allodynia, hyperalgesia, paroxysmal extreme pain disorder, inherited erythromelalgia, cancer-associated pain, atypical pain, neuroinflammation-associated pain conditions, neurogenic inflammation-associated pain, or a combination thereof. The inflammatory pain may be arthritis pain, dental pain, low back pain, pain associated inflammatory bowel disease, temporomandibular joint (TMJ), or a combination thereof. The neuropathic pain may be pain associated with diabetic neuropathy, chemotherapy, human immunodeficiency virus (HIV) infection, postherpetic neuralgia (PHN; also known as shingles), surgery (e.g., amputation, thoracotomy, mastectomy, hernia surgery, and so forth), spinal cord injury, stroke, or a combination thereof. The shingles may occur after infection with varicella zoster virus (VZV). The atypical pain may be fibromyalgia or sickle cell disease associated pain. Neuroinflammation-associated pain conditions may be complex regional pain syndrome (CRPS), headache, migraine, or a combination thereof. Neurogenic inflammation-associated pain conditions may be complex regional pain syndrome (CRPS), headache, migraine, or a combination thereof.

The pain may be associated with itch, for example, but not limited, acute itch, chronic itch, histamine-dependent itch, histamine-independent itch, or a combination thereof. The acute itch may be gastrin-releasing peptide (GRP)-induced or mediated acute itch. The acute itch may be mediated by GRP in superficial dorsal horn neurons. The chronic itch may be associated with atopic dermatitis, allergic contact dermatitis, psoriasis, renal disease, liver disease, zoster virus, eczema, or a combination thereof. The pain may be caused by a gain-of-function mutation and/or over-expression of $Na_v1.7$.

The itch may be acute itch, chronic itch, histamine-dependent itch, histamine-independent itch, or a combination thereof. The acute itch may be gastrin-releasing peptide (GRP)-induced or mediated acute itch. The acute itch may be mediated by GRP in superficial dorsal horn neurons. The chronic itch may be associated with atopic dermatitis, allergic contact dermatitis, psoriasis, renal disease, liver disease, zoster virus, eczema, or a combination thereof.

The method may also comprise suppressing pain in the subject. In some embodiments, the pain may be inflammatory pain, neuropathic pain, hyperalgesia, chronic pain, pathological pain, allodynia, hyperalgesia, paroxysmal extreme pain disorder, inherited erythromelalgia, cancer-associated pain, atypical pain, neuroinflammation-associated pain conditions, neurogenic inflammation-associated pain, or a combination thereof. The inflammatory pain may be arthritis pain, dental pain, low back pain, pain associated inflammatory bowel disease, temporomandibular joint (TMJ), or a combination thereof. The neuropathic pain may be pain associated with diabetic neuropathy, chemotherapy, human immunodeficiency virus (HIV) infection, postherpetic neuralgia (PHN; also known as shingles), surgery (e.g., amputation, thoracotomy, mastectomy, hernia surgery, and so forth), spinal cord injury, stroke, or a combination thereof. The shingles may occur after infection with varicella zoster virus (VZV). The atypical pain may be fibromyalgia or sickle cell disease associated pain. Neuroinflammation-associated pain conditions may be complex regional pain syndrome (CRPS), headache, migraine, or a combination thereof. Neurogenic inflammation-associated pain conditions may be complex regional pain syndrome (CRPS), headache, migraine, or a combination thereof. The pain may be associated with itch, for example, but not limited, acute itch, chronic itch, histamine-dependent itch, histamine-independent itch, or a combination thereof. The acute itch may be gastrin-releasing peptide (GRP)-induced or mediated acute itch. The acute itch may be mediated by GRP in superficial dorsal horn neurons. The chronic itch may be associated with atopic dermatitis, allergic contact dermatitis, psoriasis, renal disease, liver disease, zoster virus, eczema, or a combination thereof. The pain may be caused by a gain-of-function mutation and/or over-expression of $Na_v1.7$.

The pain may be suppressed from about 35% to about 85%, from about 40% to about 80%, from about 42% to about 78%, from about 44% to about 76%, or from about 46% to about 74%. The antibody may also suppress pain sensation about 35%, about 40%, about 45%, about 46%, about 47%, about 48%, about 49%, about 50%, about 51%, about 52%, about 53%, about 54%, about 55%, about 60%, about 65%, about 66%, about 67%, about 68%, about 69%, about 70%, about 71%, about 72%, about 73%, about 74%, about 75%, about 80%, or about 85%. The pain may also be suppressed by about 50% or by about 70%.

The method may further comprise increasing a threshold of pain in the subject. In some embodiments, the pain may be inflammatory pain, neuropathic pain, hyperalgesia, chronic pain, pathological pain, allodynia, hyperalgesia, paroxysmal extreme pain disorder, inherited erythromelalgia, cancer-associated pain, atypical pain, neuroinflammation-associated pain conditions, neurogenic inflammation-associated pain, or a combination thereof. The inflammatory pain may be arthritis pain, dental pain, low back pain, pain associated inflammatory bowel disease, temporomandibular joint (TMJ), or a combination thereof. The neuropathic pain may be pain associated with diabetic neuropathy, chemotherapy, human immunodeficiency virus (HIV) infection, postherpetic neuralgia (PHN; also known as shingles), surgery (e.g., amputation, thoracotomy, mastectomy, hernia surgery, and so forth), spinal cord injury, stroke, or a combination thereof. The shingles may occur after infection with varicella zoster virus (VZV). The atypical pain may be fibromyalgia or sickle cell disease associated pain. Neuroinflammation-associated pain conditions may be complex regional pain syndrome (CRPS), headache, migraine, or a combination thereof. Neurogenic inflammation-associated pain conditions may be complex regional pain syndrome (CRPS), headache, migraine, or a combination thereof. The pain may be associated with itch, for example, but not limited, acute itch, chronic itch, histamine-dependent itch, histamine-independent itch, or a combination thereof. The acute itch may be gastrin-releasing peptide (GRP)-induced or mediated acute itch. The acute itch may be mediated by GRP in superficial dorsal horn neurons. The chronic itch may be associated with atopic dermatitis, allergic contact dermatitis, psoriasis, renal disease, liver disease, zoster virus, eczema, or a combination thereof. The pain may be caused by a gain-of-function mutation and/or over-expression of $Na_v1.7$.

The pain threshold may be increased by about 1.2-fold to about 4-fold, about 1.5-fold to about 3-fold, or about 2-fold. The pain threshold may be increased by about 1.2-fold, about 1.3-fold, about 1.4-fold, about 1.5-fold, about 1.6-fold, about 1.7-fold, about 1.8-fold, about 1.9-fold, about 2.0-fold, about 2.1-fold, about 2.2-fold, about 2.3-fold, about 2.4-fold, about 2.5-fold, about 2.6-fold, about 2.7-fold, about 2.8-fold, about 2.9-fold, about 3.0-fold, about 3.1-fold, about 3.2 fold, about 3.3-fold, about 3.4-fold, about 3.5-fold, about 3.6-fold, about 3.7-fold, about 3.8-fold, about 3.9-fold, or about 4-fold. The pain threshold may be increased by about 2-fold or by about 3-fold.

The pain threshold may also be increased by about 125% to about 400%, about 150% to about 300%, or about 200%. The pain threshold may be increased by about 125%, about 130%, about 135%, about 140%, about 145%, about 150%, about 155%, about 160%, about 165%, about 170%, about 175%, about 180%, about 185%, about 190%, about 195%, about 200%, about 205%, about 210%, about 215%, about 220%, about 225%, about 230%, about 235%, about 240%, about 245%, about 250%, about 255%, about 260%, about 265%, about 270%, about 275%, about 280%, about 285%, about 290%, about 295%, about 300%, about 305%, about 310%, about 315%, about 320%, about 325%, about 330%, about 335%, about 340%, about 345%, about 350%, about 355%, about 360%, about 365%, about 370%, about 375%, about 380%, about 385%, about 390%, about 395%, or about 400%. The pain threshold may be increased by about 200% or by about 300%.

The method may also comprise suppressing or alleviating itch in the subject. The itch may be, but is not limited to, acute itch, chronic itch, histamine-dependent itch, histamine-independent itch, allergic contact dermatitis, or a combination thereof. The acute itch may be gastrin-releasing peptide (GRP)-induced or mediated acute itch. The acute itch may be mediated by GRP in superficial dorsal horn neurons. The chronic itch may be associated with atopic dermatitis, allergic contact dermatitis, psoriasis, renal disease, liver disease, zoster virus, eczema, or a combination thereof. The itch may be suppressed by at least about 40%, 50%, 60%, or 70%. The method may further comprise managing itch in the subject.

The present invention is also directed to a method of treating allergic contact dermatitis in a subject in need thereof. The method comprises administering the antibody described herein or antibody fragment to the subject.

The present invention is further directed to a method of treating neurogenic inflammation in a subject in need thereof. The method comprises administering the $Na_v1.7$ antibody described above or antibody fragment to the subject. The neurogenic inflammation may be localized, peripheral, or systemic in the subject, and thus, the antibody may be administered centrally, locally, peripherally, and/or systemically. In some embodiments, the neurogenic inflammation may be associated with a disease such as, but not limited to, asthma, arthritis, eczema, psoriasis, and migraine or headache.

The method may also comprise suppressing or alleviating neurogenic inflammation in the subject. In some embodiments, the neurogenic inflammation may be associated with asthma, arthritis, eczema, psoriasis, and migraine or headache.

The present invention is also directed to a method of treating cough in the subject in need thereof. The method may comprise administering the antibody described herein or antibody fragment thereof to the subject. The method may reduce or suppress cough in the subject. The cough may be pathological cough. The cough may be chronic cough. Accordingly, the method may reduce or suppress pathological cough in the subject.

6. Kit For Detecting $Na_v1.7$

Provided herein is a kit, which may be used for assaying a test sample for $Na_v1.7$ or $Na_v1.7$ fragment. The kit comprises at least one component for assaying the test sample for $Na_v1.7$ or $Na_v1.7$ fragment and instructions for assaying the test sample for $Na_v1.7$ or $Na_v1.7$ fragment. For example, the kit can comprise instructions for assaying the test sample for $Na_v1.7$ or $Na_v1.7$ fragment by immunoassay, e.g., chemiluminescent microparticle immunoassay. Instructions included in kits can be affixed to packaging material or can be included as a package insert. While the instructions are typically written or printed materials they are not limited to such. Any medium capable of storing such instructions and communicating them to an end user is contemplated by this disclosure. Such media include, but are not limited to, electronic storage media (e.g., magnetic discs, tapes, cartridges, chips), optical media (e.g., CD ROM), and the like. As used herein, the term "instructions" can include the address of an internet site that provides the instructions.

The at least one component may include at least one composition comprising one or more isolated antibodies or antibody fragments thereof that specifically bind to $Na_v1.7$ or Nav1.7 fragment. The antibody may be a $Na_v1.7$ capture antibody and/or a $Na_v1.7$ detection antibody. The antibody may include the 1E16 antibody, or antibody fragments thereof. The antibody is optionally detectably labeled.

Alternatively or additionally, the kit can comprise a calibrator or control, e.g., purified, and optionally lyophilized, $Na_v1.7$ or $Na_v1.7$ fragment, and/or at least one container (e.g., tube, microtiter plates or strips, which can be already coated with an anti-$Na_v1.7$ monoclonal antibody) for conducting the assay, and/or a buffer, such as an assay buffer or a wash buffer, either one of which can be provided as a concentrated solution, a substrate solution for the detectable label (e.g., an enzymatic label), or a stop solution. Preferably, the kit comprises all components, i.e., reagents, standards, buffers, diluents, etc., which are necessary to perform the assay. The instructions also can include instructions for generating a standard curve.

The kit may further comprise reference standards for quantifying $Na_v1.7$. The reference standards may be employed to establish standard curves for interpolation and/or extrapolation of $Na_v1.7$ concentrations. The reference standards may include a high $Na_v1.7$ concentration level, for example, about 100 ng/mL, about 125 ng/mL, about 150 ng/mL, about 175 ng/mL, about 200 ng/mL, about 225 ng/mL, about 250 ng/mL, about 275 ng/mL, or about 300 ng/mL; a medium $Na_v1.7$ concentration level, for example, about 25 ng/mL, about 40 ng/mL, about 45 ng/mL, about 50 ng/mL, about 55 ng/mL, about 60 ng/mL, about 75 ng/mL or about 100 ng/mL; and/or a low Nav1.7 concentration level, for example, about 1 ng/mL, about 5 ng/mL, about 10 ng/mL, about 12.5 ng/mL, about 15 ng/mL, about 20 ng/mL, or about 25 ng/mL.

Any antibodies, which are provided in the kit, such as recombinant antibodies specific for Nav1.7, can incorporate a detectable label, such as a fluorophore, radioactive moiety, enzyme, biotin/avidin label, chromophore, chemiluminescent label, or the like, or the kit can include reagents for labeling the antibodies or reagents for detecting the antibodies (e.g., detection antibodies) and/or for labeling the analytes or reagents for detecting the analyte. The antibodies, calibrators, and/or controls can be provided in separate containers or pre-dispensed into an appropriate assay format, for example, into microtiter plates.

Optionally, the kit includes quality control components (for example, sensitivity panels, calibrators, and positive controls). Preparation of quality control reagents is well-known in the art and is described on insert sheets for a variety of immunodiagnostic products. Sensitivity panel members optionally are used to establish assay performance characteristics, and further optionally are useful indicators of the integrity of the immunoassay kit reagents, and the standardization of assays.

The kit can also optionally include other reagents required to conduct a diagnostic assay or facilitate quality control evaluations, such as buffers, salts, enzymes, enzyme co-factors, substrates, detection reagents, and the like. Other components, such as buffers and solutions for the isolation and/or treatment of a test sample (e.g., pretreatment reagents), also can be included in the kit. The kit can additionally include one or more other controls. One or more of the components of the kit can be lyophilized, in which case the kit can further comprise reagents suitable for the reconstitution of the lyophilized components.

The various components of the kit optionally are provided in suitable containers as necessary, e.g., a microtiter plate. The kit can further include containers for holding or storing a sample (e.g., a container or cartridge for a urine, plasma, or serum sample). Where appropriate, the kit optionally also can contain reaction vessels, mixing vessels, and other components that facilitate the preparation of reagents or the test sample. The kit can also include one or more instrument for assisting with obtaining a test sample, such as a syringe, pipette, forceps, measured spoon, or the like.

If the detectable label is at least one acridinium compound, the kit can comprise at least one acridinium-9-carboxamide, at least one acridinium-9-carboxylate aryl ester, or any combination thereof. If the detectable label is at least one acridinium compound, the kit also can comprise a source of hydrogen peroxide, such as a buffer, solution, and/or at least one basic solution. If desired, the kit can contain a solid phase, such as a magnetic particle, bead, test tube, microtiter plate, cuvette, membrane, scaffolding molecule, film, filter paper, disc, or chip.

If desired, the kit can further comprise one or more components, alone or in further combination with instructions, for assaying the test sample for another analyte, which can be a biomarker, such as a biomarker of liver disease or disorder.

a. Adaptation of Kit

The kit (or components thereof), as well as the method for determining the concentration of $Na_v1.7$ in a test sample by an immunoassay as described herein, can be adapted for use in a variety of automated and semi-automated systems (including those wherein the solid phase comprises a microparticle). Some of the differences between an automated or semi-automated system as compared to a non-automated system (e.g., ELISA) include the substrate to which the first specific binding partner (e.g., analyte antibody or capture antibody) is attached (which can affect sandwich formation and analyte reactivity), and the length and timing of the capture, detection, and/or any optional wash steps. Whereas a non-automated format such as an ELISA may require a relatively longer incubation time with sample and capture reagent (e.g., about 2 hours), an automated or semi-automated format may have a relatively shorter incubation time (e.g., approximately 18 minutes). Similarly, whereas a non-automated format such as an ELISA may incubate a detection antibody such as the conjugate reagent for a relatively longer incubation time (e.g., about 2 hours), an automated or semi-automated format may have a relatively shorter incubation time (e.g., approximately 4 minutes).

The present invention has multiple aspects, illustrated by the following non-limiting examples.

7. Control Antibody For $Na_v1.7$ Inhibition

The present invention also relates to a control antibody for $Na_v1.7$ inhibition. The control antibody may bind $Na_v1.7$, but does not inhibit $Na_v1.7$. The control antibody may not stabilize the closed state of $Na_v1.7$, and thus, not inhibit $Na_v1.7$. The control antibody may not effect gating of $Na_v1.7$. Accordingly, the control antibody may be used in methods to study the function or biology of Na$_v$1.7 and employed by a user of these methods as a negative control.

The control antibody may bind to an epitope of Na$_v$1.7. This epitope may be a loop between S1 and S2 of DII of Na$_v$1.7. This epitope may have the amino acid sequence HHPMTEEFKN (SEQ ID NO:20). This control antibody may be 1I5, which is also known herein as CTmab.

8. Examples

It will be readily apparent to those skilled in the art that other suitable modifications and adaptations of the methods of the present disclosure described herein are readily applicable and appreciable, and may be made using suitable equivalents without departing from the scope of the present disclosure or the aspects and embodiments disclosed herein. Having now described the present disclosure in detail, the same will be more clearly understood by reference to the following examples, which are merely intended only to illustrate some aspects and embodiments of the disclosure, and should not be viewed as limiting to the scope of the disclosure. The disclosure of all journal references, U.S. patents, and publications referred to herein are hereby incorporated by reference in their entireties.

Example 1

Materials and Methods for Examples 2-12

Antibody Generation and Purification. Mouse monoclonal antibodies were generated by Abmart using the peptides with the following sequences: HHPMTEEFKN (1I5 (also known herein as CTmab); SEQ ID NO:20) and VELFLADVEG (1E16 (also known herein as SVmab1); SEQ ID NO:21). Both antibodies are IgG1. After receipt of the hybridomas, multiple rounds of limiting dilution cloning were performed to select a stable monoclonal cell population. Enzyme-linked immunosorbent assay (ELISA) assays using recombinant Na$_v$1.7 DII VSD were used for screening. Hybridoma cells of 1E16 and 1I5 were incubated in a hollow fiber bioreactor (Fibercell Systems Inc, US) and then the supernatant was collected every two days. Each harvested supernatant was screened by ELISA assays and purified on a protein G agarose column according to the manufacturer's protocol (Invitrogen, US).

Whole-Cell Patch-Clamp Recordings in HEK293 Cells. HEK293 cells were transfected with plasmids containing Na$_v$ channel cDNAs mixed with the plasmid containing GFP using lipofectamine 2000 (Invitrogen) at 1 µg of DNA per well of a 6-well plate. Particularly, the Na$_v$ channel cDNAs were hNa$_v$1.7, rNa$_v$1.8, hNa$_v$1.3, hNa$_v$1.4, hNa$_v$1.1, rNa$_v$1.2, mNa$_v$1.5, and mNa$_v$1.6 cDNAs.

Approximately 24 hr after transfection, whole-cell recordings were performed on a single isolated green cell identified under a fluorescence microscope at room temperature. Glass pipettes (Sutter instrument Co.) were prepared (2-3 MS2) using a vertical puller (Sutter instrument Co.). Data were acquired with an Axopatch 200B amplifier controlled by Clampex via a Digidata 1440A data acquisition system (Axon Instruments). Currents were sampled at a rate of 10 kHz and filtered at 3 kHz. The pipette solution contained (in mM): 10 NaCl, 110 CsCl, 20 TEA, 2.5 MgCl$_2$, 5 EGTA, 3 ATP, 5 HEPES, pH 7.0 (adjusted with CsOH), and the osmolarity was adjusted to 300 mOsmol/L with glucose. The extracellular bath solution contained (in mM): 100 NaCl, 5 CsCl, 30 TEA, 1.8 CaCl$_2$, 1 MgCl$_2$, 0.1 CdCl$_2$, 5 HEPES, 25 Glucose, 5 4-aminopyridine, pH 7.4 (adjusted with CsOH), and the osmolarity was adjusted to 300 mOs-mol/L with glucose.

To record current-voltage relationship, after establishing whole cell configuration, cells were held at −120 mV and currents traces were elicited by 30 ms voltage steps between −80 and +60 mV with 10 mV increments. I-V curves were generated by plotting normalized peak currents (I/Imax) as a function of depolarization potential.

The voltage-dependence of Na$_v$ channel activation was calculated by measuring the peak current at test potentials ranging from −90 mV to +10 mV evoked in 5 mV increments from a holding potential of −120 mV. The conductance ($G_{Na}$) was calculated according to the equation, $G_{Na}=I_{Na}/(V_g-V_r)$, where $I_{Na}$ was the peak amplitude of the Na$^+$ current, $V_g$ was the test potential, and $V_r$ was the reversal potential for Na$^+$. The conductance-voltage curves were drawn according to the equation $G_{Na}/_{max}G_{Na}=1/\{1+\exp[(V_{g0.5}-V_g)/kg]\}$, where $_{max}G_{Na}$ was the maximum value for $G_{Na}$, $V_{g0.5}$ was the potential at which $G_{Na}$ was $0.5_{max}G_{Na}$, and kg is the slope factor (potential required for an e-fold change). The voltage-dependence of Na$_v$ channel inactivation was determined using 500 ms conditioning pre-pulses ranging from −110 mV to −30 mV from a holding potential of −120 mV in 5 mV increments, followed by a test pulse to −10 mV for 30 ms. The peak $I_{Na}$ was normalized to its respective maximum value ($_{max}I_{Na}$) and plotted as a function of the pre-pulse potential. The steady-state inactivation curves were drawn according to the equation $I_{Na}/_{max}I_{Na}=1/\{1+\exp[(V_h-V_{h0.5})/kh]\}$, where $V_h$ was pre-pulse potential, $V_{h0.5}$ was the potential at which $I_{Na}$ was $0.5_{max}I_{Na}$, and kh was the slope factor. Data analysis and curve fitting were performed with OrignPro (OriginLab Corp).

Animal and Pain Models. Adult CD1 mice (male, 25-35 g) were used for all the behavioral studies. Young mice (4-6 weeks) were used for electrophysiological studies in spinal cord slices. To produce inflammatory pain, diluted formalin (5%, 20 µl) was injected into the plantar surface of a hindpaw. Neuropathic pain was produced by chronic constriction injury (CCI) of the sciatic nerve. Mice were anesthetized with isoflurane, and three ligatures with 7-0 prolene were placed around the nerve proximal to the trifurcation (1 mm between ligatures). The ligatures were loosely tied until a short flick of the ipsilateral hind limb was observed. For spinal intrathecal injection, spinal cord puncture was made with a 30 G needle between the L5 and L6 level to deliver reagents (10 µl) to the cerebral spinal fluid.

Behavioral Testing of Pain.

Animals were habituated to the environment for at least 2 days before the testing. All the behaviors were tested blindly. Formalin-evoked spontaneous inflammatory pain was assessed by measuring the time (seconds) mice spent licking or flinching the affected paw every 5 min for 45 min. For testing mechanical sensitivity after nerve injury, mice were confined in boxes placed on an elevated metal mesh floor and stimulated their hindpaws with a series of von Frey hairs with logarithmically increasing stiffness (0.02-2.56 g, Stoelting), presented perpendicularly to the central plantar surface. The 50% paw withdrawal threshold was determined by Dixon's up-down method. Thermal sensitivity was tested using Hargreaves radiant heat apparatus (IITC Life Science) and expressed as paw-withdrawal latency (PWL). The radiant heat intensity was adjusted so that basal PWL was between 9 and 12 s, with a cutoff of 20 s to prevent tissue damage.

For testing motor function, a rota-rod system was used. Mice were tested for three trails separated by 10 minute intervals and during the tests, the speed of rotation was accelerated from 2 to 20 revolutions per minute (r.p.m.) in 3 minutes and the falling latency was recorded.

Spinal Cord Slice Preparation and Patch Clamp Recordings. A portion of the lumbar spinal cord (L4-L5) was removed from mice (4-7 weeks old) under urethane anesthesia (1.5-2.0 g/kg, i.p.) and kept in pre-oxygenated ice-cold Krebs solution. Transverse slices (400-600 μm) were cut on a vibrating microslicer. The slices were perfused with Kreb's solution (8-10 ml/min) that was saturated with 95% $O_2$ and 5% $CO_2$ at 36±° C. for at least 1-3 h prior to experiment. The Kreb's solution contained (in mM): NaCl 117, KCl 3.6, $CaCl_2$ 2.5, $MgCl_2$ 1.2, $NaH_2PO_4$ 1.2, $NaHCO_3$ 25, and glucose 11.

The whole cell patch-clamp recordings were made from lamina IIo neurons in voltage clamp mode. Patch pipettes were fabricated from thin-walled, borosilicate, glass-capillary tubing (1.5 mm o.d., World Precision Instruments). After establishing the whole-cell configuration, neurons were held at the potential of −70 mV to record sEPSCs. The resistance of a typical patch pipette is 5-10 MΩ. The internal solution contains (in mM): potassium gluconate 135, KCl 5, $CaCl_2$ 0.5, $MgCl_2$ 2, EGTA 5, HEPES 5, and ATP-Mg 5. Membrane currents were amplified with an Axopatch 200B amplifier (Axon Instruments) in voltage-clamp mode. Signals were filtered at 2 kHz and digitized at 5 kHz. Data were stored with a personal computer using pCLAMP 10 software and analyzed with Mini Analysis (Synaptosoft Inc.).

Data Analysis. To obtain the concentration-response curves describing the effect of 1E16 on $Na_v$ channel currents, the peak amplitudes at different concentrations of 1E16 were plotted. The Origin software (Origin, Northampton, Mass., USA) was then used to fit the plot to the Hill equation, $y/y_{max}=[A]^{n_H}/([A]^{n_H}+[IC_{50}]^{n_H})$, where y was the peak current at a given concentration of 1E16, $y_{max}$ was the maximal peak current, $IC_{50}$ was the concentration of 1E16 that produces a half-maximum effect, [A] was the concentration of 1E16, and $n_H$ was the Hill coefficient. $IC_{50}$ values were obtained using the Origin software. All values are presented as means±S.E.M. The differences between the means of the control and treatment values were determined using an unpaired t-test. A value of p<0.05 was considered to be statistically significant. All data were expressed as means±S.E.M. For electrophysiology in the spinal cord, slices that showed greater than 5% change from the baseline level during drug perfusion were regarded as responding ones. The baseline recordings were collected for 2 min and the recordings in the first 2 min of drug treatment were analyzed using the unpaired two-tailed student's t-test. Behavioral data were analyzed using student's t-test (two groups) or One-Way ANOVA followed by post-hoc Bonferroni test. The criterion for statistical significance was P<0.05.

Voltage Sensor Domain (VSD) Expression, Purification, and ELISA Assays. The part of the $Na_v1.7$ gene corresponding to human $Na_v1.7$ DII VSD was cloned into the pFastbac1 vector, and recombinant baculovirus was obtained following the manufacturer's protocol (Bac-to-Bac expression system, Invitrogen). For protein expression, sf9 cells were infected with recombinant baculovirus and harvested by centrifugation after 72 hr infection. Cells were broken by homogenization and then incubated with stirring in resuspension buffer (150 mM NaCl, 50 mM Tris, pH 8.0) supplemented with 1 g dodecylmaltoside (DDM, Affymetrix) per 10 g cell weight. Detergent-insoluble material was removed by centrifugation (30,000 g×20 min), and the supernatant was incubated with $Co^{2+}$ resin (TALON Metal Affinity Resins, Clontech). The resin was washed with the resuspension buffer containing 1 mM DDM and then the voltage sensor domain was eluted with elution buffer (300 mM NaCl, 20 mM Tris, 1 mM DDM, pH 8.0) supplemented with 400 mM imidazol. VSD protein (1 μg) was added to each well of MaxiSorp 96 well plate (MAXISORP flat-bottom 96 well plate, Nunc) and then incubated at 4° C. overnight. Each well were washed 3 times with PBS with 0.5 mM DDM and then blocked with blocking buffer (0.5% BSA and 0.5 mM DDM in PBS) at room temperature with shaking Both 1I5 and 1E16 (2 μg each) were incubated for 1 hr at RT. Secondary Abs (1 ng peroxidase conjugated anti-mouse) were incubated for 1 hr at RT, and the plates were developed with TMB (3,3',5,5'-tetramethylbenzidine) peroxidase substrate system (SUREBLUE RESERVE TMB Microwell Peroxidase Substrate, KPL), stopped with 1N sulfuric acid, and then the resulting absorbance were measured at 405 nm.

Peptide Blocking Experiments. The peptide-blocking experiments were performed using whole-cell patch-clamp recording in HEK293 cells transiently transfected with $Na_v1.7$ cDNA. Once the whole-cell configuration was established, current-voltage relationships were recorded first in the absence of both 1E16 and the peptide, then after addition of both 1E16 (100 nM) and the peptide (1 μM). After washout, only 1E16 (100 nM) was added and then current-voltage relationship were recorded. To record current-voltage relationship, cells were held at −120 mV and currents traces were elicited by 30 ms voltage steps between −80 and +60 mV with 10 mV increments. I-V curves were generated by plotting normalized peak currents (I/Imax) as a function of depolarization potential.

DRG Electrophysical Recording. Mice (6-8 weeks) were anesthetized with urethane (50 mg/kg, i.p.) and the L4-L5 dorsal root ganglions (DRGs) were removed from the vertebral column and placed in cold oxygenated ACSF. The ACSF contained (in mM): NaCl 125, KCl 2.5, $NaH_2PO_4$ 1.2, $MgCl_2$ 1.0, $CaCl_2$ 2.0, $NaHCO_3$ 25, and D-glucose 10. The connective tissue was gently removed under a microscope and ganglia were digested with a mixture of 1.0 mg/ml proteinase (Sigma) and 1.6 mg/ml collagenase (Sigma) for 30 min at 37 degrees Celsius while agitated by gentle bubbling with 95% $O_2$ and 5% $CO_2$. The glass recording pipettes were filled with a $Cs^+$-based solution (which contained (in mM): $Cs_2SO_4$ 110, $MgCl_2$ 3, $CaCl_2$ 1, EGTA 3, HEPES 40 and NaCl 5), while $K^+$ and $Ca^{2+}$ channel blockers were added to the bath (the solution contained in mM: NaCl 100, KCl 3, $NaH_2PO_4$ 1.2, $MgCl_2$ 1.0, $CaCl_2$ 1.0, TEA-Cl 40, $BaCl_2$ 1, CsCl 1, 4-AP 2, $CdCl_2$ 0.1, HEPES 10, and D-glucose 100). Under a holding potential of −60 mV, persistent sodium current ($I_{NaP}$) was recorded in small-sized DRG neurons by applying a 3 second (s) depolarization ramp current from −80 mV to 0 mV.

Itch Models and Behavioral Testing of Itch. Compound 48/80 and chloroquine were purchased from Sigma-Aldrich. Mice were habituated to the testing environment daily for at least two days before analysis. Mice were shaved at the back of the neck the day before injection. Mice were left in small plastic chambers (14×18×12 cm) on an elevated metal mesh floor and allowed 30 min for habituation before examination. To elicit acute itch, 50 μl of pruritic agent compound 48/80 (100 μg) or chloroquine (200 μg) was injected intradermally in the nape of the neck, or GRP (1 nmol) intrathecally, and the number of scratches were counted every 5 min for 30 min after the injection. A scratch was counted when a mouse lifted its hindpaw to scratch the shaved region and returned the paw to the floor or to the mouth for licking.

To induce chronic itch, the neck skin was painted with acetone and diethyether (1:1) followed by water (AEW) twice a day for 4 days, and spontaneous itch was examined by counting the number of scratches for 60 min on day 5. To determine chronic itch-induced synaptic plasticity in the lumbar superficial spinal cord, the hindpaw was also painted with AEW.

The allergic contact dermatitis (ACD) model of chronic itch was generated by applying hapten 1-fluoro-2,4-dinitrobenzen (DNFB) on the back skin. DNFB was dissolved in a mixture of acetone:olive oil (4:1) for sensitization and challenge. Mice were sensitized with 0.5% DNFB solution (50 µl) by topical application to an about 2 cm² area of shaved abdominal skin. Five days later, mice were challenged with 0.2% DNFB solution (30 µl) by painting the shaved neck area, then every other day for one week. Spontaneous scratching behaviors were videoed for 1 hour, at 24 hours after each challenge.

The behavioral tests were performed blindly.

Spinal Cord Drug Delivery. For spinal intrathecal injection, spinal cord puncture was made with a 30 G needle between the L5 and L6 level to deliver reagents (10 µl) to the cerebral spinal fluid.

Whole-cell Patch Clamp Recordings in Dissociated DRG Neurons and Whole Mount DRG.

The dissociated DRGs were removed aseptically from mice (4-6 weeks) and incubated with collagenase (1.25 mg/ml, Roche)/dispase-II (2.4 units/ml, Roche) at 37° C. for 90 min, then digested with 0.25% trypsin for 8 min at 37° C., followed by 0.25% trypsin inhibitor. Cells were mechanically dissociated with a flame polished Pasteur pipette in the presence of 0.05% DNAse I (Sigma). DRG cells were plated on glass cover slips and grown in a neurobasal defined medium (with 2% B27 supplement, Invitrogen) with 5 µM AraC and 5% carbon dioxide at 36.5° C. DRG neurons were grown for 24 hours before use.

The L4-L5 whole mount DRGs were carefully removed from the vertebral column and placed in cold oxygenated ACSF. The connective tissue was gently removed under a microscope and the ganglia were digested with a mixture of 1.0 mg/ml protease and 1.6 mg/ml collagenase (Sigma) for 30 min at 37° C. The ganglion was transferred into a holding chamber containing normal $Mg^{2+}$-free ACSF with CNQX (2 µM) bubbled with 95% $O_2$ and 5% $CO_2$ at room temperature.

Whole-cell voltage and current clamp recordings were performed at room temperature (28° C.) to measure transient and persistent sodium currents and action potentials, respectively, with Axopatch-200B amplifier (Axon Instruments) and Digidata 1440A data acquisition system (Axon Instruments). The patch pipettes were pulled from borosilicate capillaries (Chase Scientific Glass Inc.). When filled with the pipette solution, the resistance of the pipettes was 4-5 MΩ. The recording chamber (300 µl) was continuously superfused (3-4 ml/min). Series resistance was compensated for (>80%), and leak subtraction was performed. Data were low-pass-filtered at 2 KHz, sampled at 10 KHz. The pClamp10 (Axon Instruments) software was used during experiments and analysis.

For sodium current recording, pipette solution contained (in mM): CsCl 100, sodium L-glutamic acid 5, TEACl 30, $CaCl_2$ 0.1, $MgCl_2$ 2, EGTA 11, HEPES 10, adjusted to pH 7.4 with CsOH. The external solution was composed of (in mM): NaCl 90, choline chloride 30, TEACl 20, $CaCl_2$ 0.1, $MgCl_2$ 5, $CoCl_2$ 5, HEPES 10, glucose 10 adjusted to pH 7.4 with NaOH. In voltage-clamp experiments, the transient sodium current ($I_{Na}$) was evoked by a test pulse to +0 mV from the holding potential, −70 mV. The persistent sodium current ($I_{Na}P$) was recorded by applying a 3 s depolarization ramp current from −80 to −10 mV at a holding potential of −60 mV (Xie et al., 2011). The plot was fitted using the Origin software (Origin, Northampton, Mass., USA). The pipette solution for current-clamp experiments was composed of (in mM): K-gluconate 145, $MgCl_2$ 2, $CaCl_2$ 1, EGTA 10, HEPES 5, $K_2ATP$ 5, adjusted to pH 7.4 with KOH. The external solution contained (in mM): NaCl 140, KCl 5, $MgCl_2$ 1, $CaCl_2$ 2, HEPES 10, glucose 10, adjusted to pH 7.4 with NaOH. In current-clamp experiments, action potentials were recorded under current clamp (−60 mV), with 1 second depolarizing current pulses with 200 pA amplitude.

Example 2

Monoclonal Antibody (mAb) Generation

Figure 4:
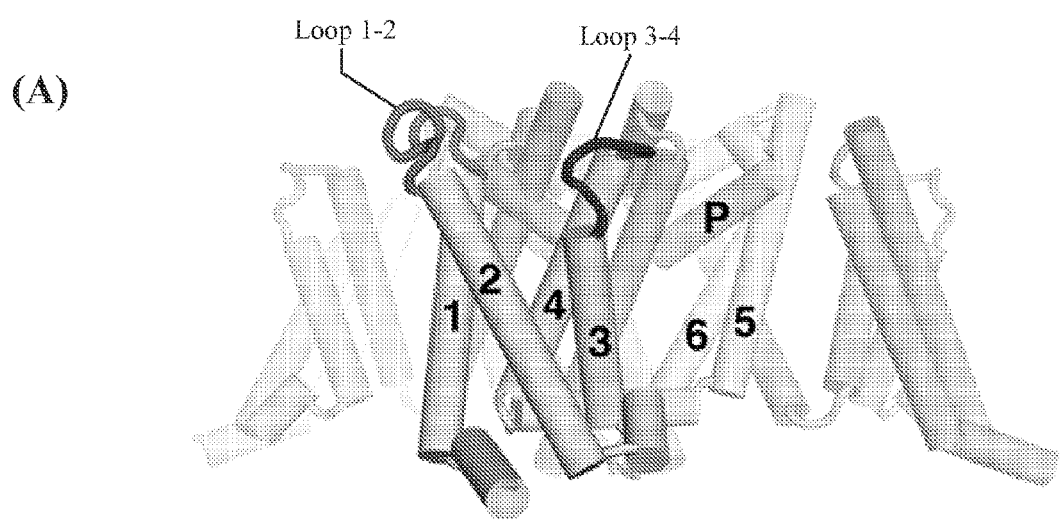
FIG. 4 shows (A) the crystal structure of a bacterial $Na_v$ channel, in which the respective loops between transmembrane helices S1 and S2 (i.e., loop 1-2) and S3 and S4 (i.e., loop 3-4) from domain II (DII) are indicated by lead lines; (B) an alignment of the respective amino acid sequences of loop 3-4 from DII of from human $Na_v$ subtypes, in which the bracket denotes the amino acid sequence chosen for generating the 1E16 monoclonal antibody (mAb); and (C) an alignment of the respective amino acid sequences of loop 1-2 from human $Na_v$ subtypes, in which the bracket denotes the amino acid sequence chosen for generating the 1I5 mAb.
Figure 5:
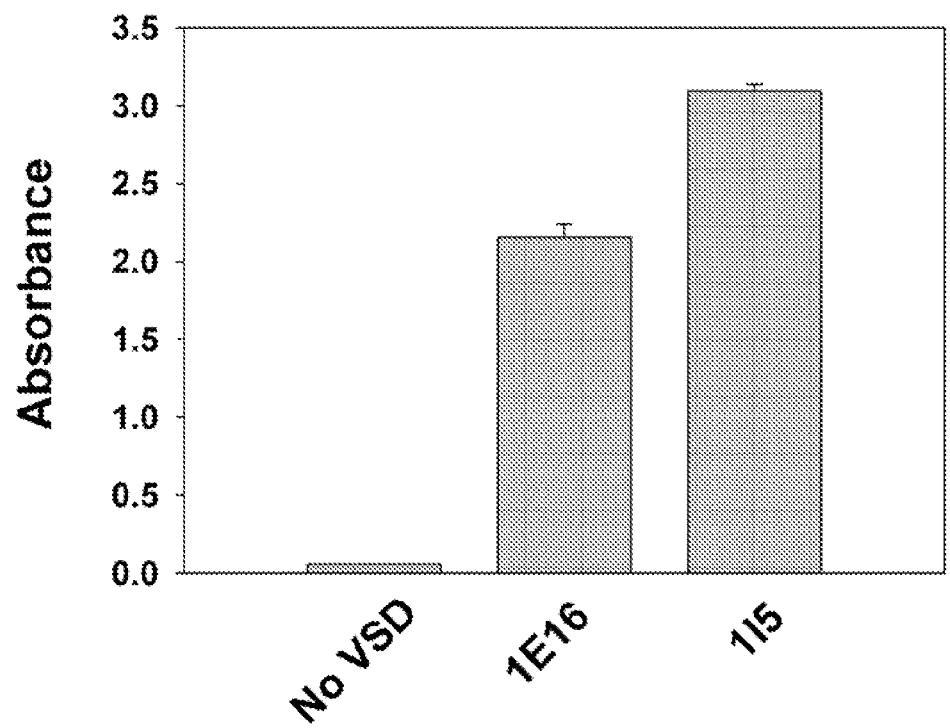
FIG. 5 shows ELISA responses of 1E16 mAb and 1I5 mAb using intact $Na_v1.7$ DII VSD. Data are shown as means±S.E.M (n=3).

Instead of using the intact channel as an antigen for raising antibodies, a peptide was chosen that corresponds to the tip (loop) of the DII voltage sensor paddle (i.e., the S3-S4 loop) of $Na_v1.7$ on the basis of the crystal structure of the bacterial $Na_v$ channel $Na_vAb$ (FIG. 4B). A peptide was also chosen that corresponds to the DII S1-S2 loop of $Na_v1.7$ as a negative control since the S1-S2 loop does not move upon membrane potential change, and thus a mAb that binds to the S1-S2 loop would not significantly affect the gating of the $Na_v1.7$ channel (FIG. 4C). One mAb was raised for each region: 1E16 monoclonal antibody (i.e., a sodium channel voltage sensor monoclonal antibody (thus, also known herein as SVmab1)) recognizes the S3-S4 loop of $Na_v1.7$ and the control 1I5 monoclonal antibody (also known herein as CTmab) recognizes the S1-S2 loop of $Na_v1.7$. Both antibodies belonged to the same subtype and showed positive ELISA responses against the recombinant DII voltage sensor domain, confirming that these mAbs recognized their respective target loops in the intact voltage sensor domain (FIG. 5).

Example 3

Figure 6:
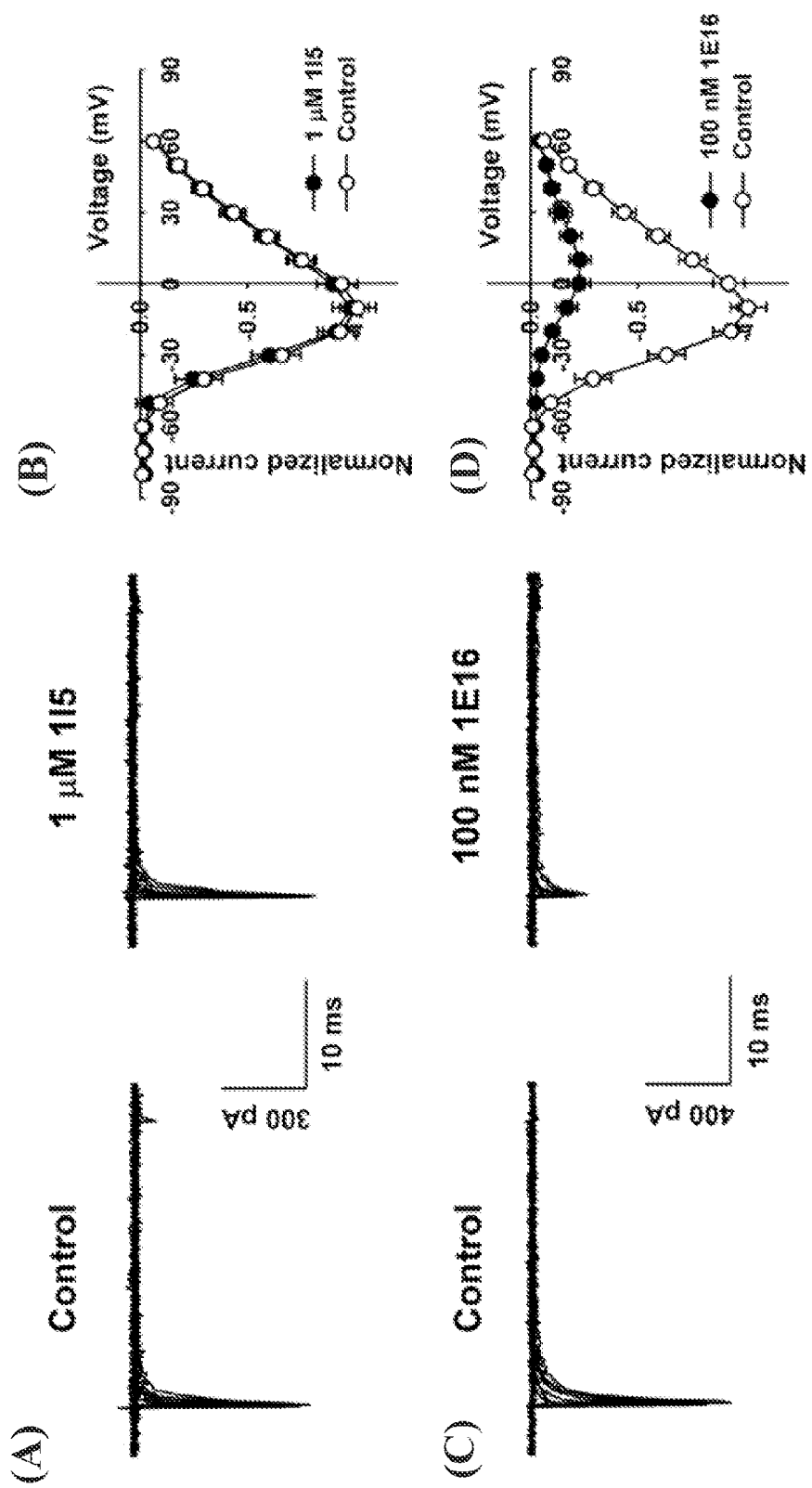
FIG. 6 shows the voltage-sensor-targeting 1E16 inhibits human $Na_v1.7$ in HEK293 cells. Representative current traces from HEK293 cells expressing $hNa_v1.7$ in the absence or presence of 1 µM 1I5 (A) and 100 nM 1E16 (C). Current-voltage relationships in the absence (○) or presence (●) of 1 µM 1I5 (B) and 100 nM 1E16 (D) were generated using 30 ms voltage steps between −80 and +60 mV with 10 mV increments from a holding potential of −120 mV. (E) Voltage dependence of steady-state activation in the absence (○) or presence (●) of 100 nM 1E16. Steady-state activation curves were generated using a 30-ms test pulse in 5 mV increments from −90 to +10 mV from a holding potential of −120 mV. Values from individual cells were normalized to the maximum conductance value ($G_o$) in the absence of 1E16. Normalized curves were fit using the Boltzmann equation. The solid squares (■) show the same 1E16-modified activation curve as shown with the solid circles (●) but scaled to the curve in the absence of 1E16 (○). The half-activation voltage ($V_{mid}$) in the presence of 1E16 (●) was −24.0±0.2 mV compared with −43.9±0.2 mV in the absence of 1E16 (○). (F) Steady-state inactivation curves in the absence (○) or presence (●) of 100 nM 1E16 were obtained using 5 mV increments from −110 mV to −30 mV for 500 ms followed by a test pulse to −10 mV for 30 ms. The solid squares (■) show the same 1E16-modified steady-state inactivation curve as shown with the solid circles (●) but scaled to the curve in the absence of 1E16 (○). The half-inactivation voltage was unaffected by 1E16 (−79.3±0.3 mV in the absence of 1E16 (○) and −78.6±0.2 mV in the presence of 1E16(●)). Data are means±S.E.M. (n=10-12/group).

1E16 mAb Stabilizes the Closed State of $Na_v1.7$ in a Use (State)-Dependent Manner To test the effects of 1E16 and 1I5 mAbs on $Na_v1.7$, electrophysiological recordings (i.e., patch-clamp recordings) were performed on HEK293 cells transiently expressing $Na_v1.7$, using the whole-cell voltage clamp configuration. Current traces were elicited by 30 ms voltage steps between −80 and +60 mV with 10 mV increments from a holding potential of −120 mV. When 1 µM of 1I5 mAb was added to the extracellular side, no significant changes were observed on peak sodium currents (FIGS. 6A and 6B). However, 100 nM of 1E16 mAb produced a significant reduction of the peak sodium currents (FIGS. 6C and 6D). Comparison of conductance-voltage relationships for the control 1I5 mAb- and 1E16 mAb-modified currents showed a depolarized shift (about 20 mV) upon addition of 100 nM of 1E16 mAb (FIG. 6E). In contrast, comparison of the steady-state inactivation curves showed no changes in half-inactivation voltage upon addition of 1E16 mAb (FIG. 6F).

Figure 7:
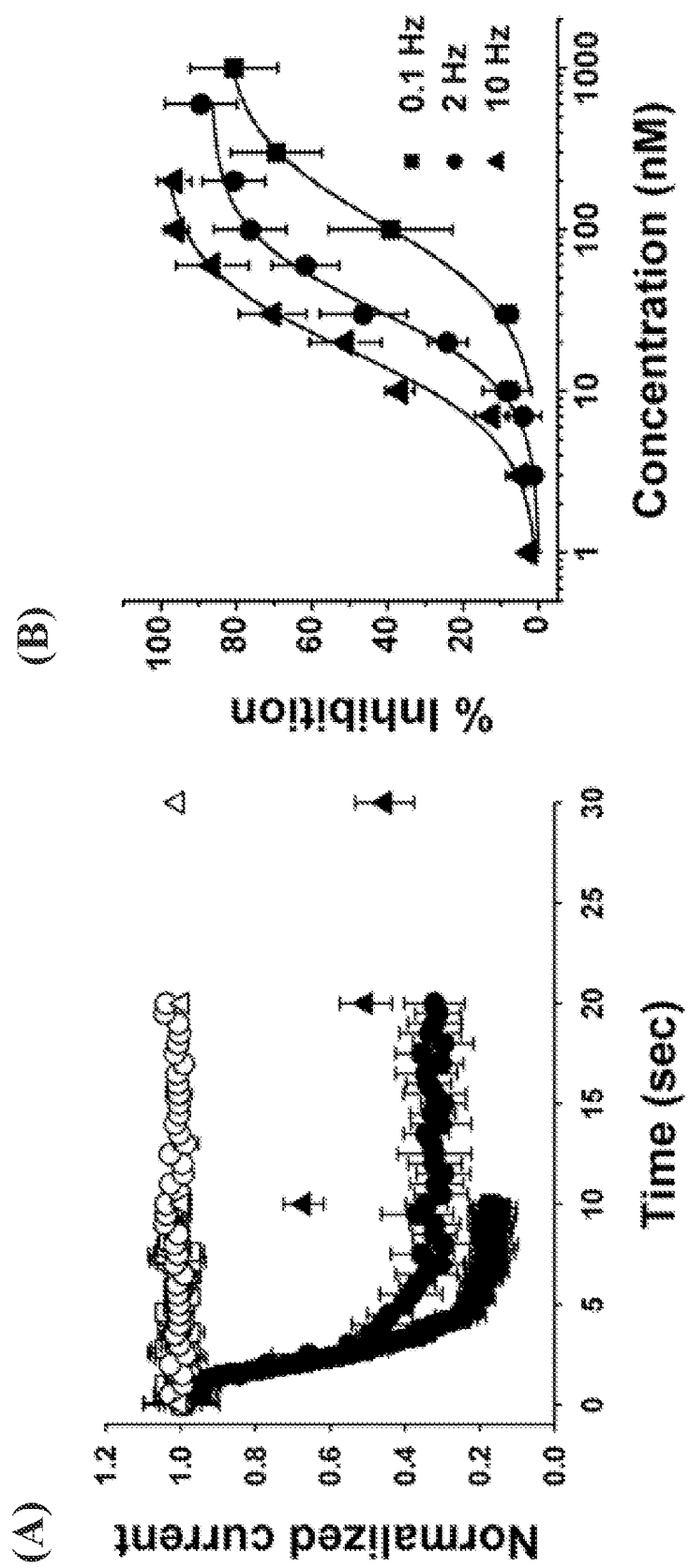
FIG. 7 shows 1E16 inhibits $Na_v1.7$ in a subtype-specific and state-dependent manner in HEK293 cells. (A) State (use)-dependent inhibition of human $Na_v1.7$ by 1E16. Plot of normalized current amplitudes during 30-ms depolarizing pulses to −10 mV applied from a holding potential of −120 mV at 0.1 (▲), 2 (●), and 10 (■) Hz in the presence of 100 nM 1E16. (B) Concentration-response curves of 1E16 inhibition of human $Na_v1.7$ currents at different frequencies (0.1, 2, and 10 Hz). $IC_{50}$ and maximum inhibition values are 106.7±18.0 nM and 83.7±5.6% for 0.1 Hz, 30.7±1.9 nM and 86.0±2.3% for 2 Hz, and 16.7±1.6 nM and 98.6±4.1 for 10 Hz. (C) Current-voltage relationships of the seven different $Na_v$ channel subtypes in the absence (Control, ○) and presence (●) of 10 μM 1E16. Voltage steps were applied from −80 to +60 mV taken in 10-mV increments for 30 ms at a holding potential of −120 mV. (D) Concentration-response curves of $Na_v$ channel subtypes by 1E16 ($IC_{50}$=30.7±1.9 nM for $Na_v1.7$, 6.3±2.2 μM for $Na_v1.6$, and >5 μM for $Na_v1.1$, 1.2, 1.3, 1.4, 1.5, and 1.8). Sodium currents were elicited by stepping to −10 mV from a holding potential of −120 mV for a duration of 30 ms at a frequency of 2 Hz. Data are given as means±S.E.M. (n=6-10/group).

Current drugs targeting $Na_v$ channels exhibit modest selectivity for state (use)-dependent inhibition. Accordingly, to test whether the effect of 1E16 mAb on $Na_v1.7$ was state-dependent, currents were elicited during 30 ms depolarizing pulses to −10 mV from a holding potential of −120 mV at three different frequencies (0.1, 2, and 10 Hz) with and without 100 nM 1E16 mAb (FIGS. 7A and 16). When higher frequency pulses were applied, the rates of channel inhibition increased. Surprisingly, the maximum degrees of channel inhibition by 1E16 mAb also increased with higher frequencies (FIGS. 7A and 16). Concentration-response relationships at the above frequencies showed that both potency ($IC_{50}$ from 106 nM to 16.7 nM) and efficacy (the degree of the maximum inhibition from 84% to 99%) are enhanced upon an increase in frequency from 0.1 to 10 Hz (FIG. 7B).

The reduction of current amplitudes and the depolarized shift in current-voltage relationships of $Na_v1.7$ by 1E16 mAb indicated that 1E16 mAb inhibited $Na_v1.7$ at least partly by stabilizing the closed state of $Na_v1.7$. This stabilization of the closed state is similar to the effects of the peptide toxin Hanatoxin on $K_v$ 2.1 or ProTx-II on $Na_v$ channels. However, unlike Hanatoxin or ProTx-II, 1E16 mAb exhibited state-dependent inhibition of $Na_v1.7$, and thus inhibition of $Na_v1.7$ by 1E16 mAb occurred through a different mechanism.

Example 4

1E16 mAb is Specific for $Na_v1.7$

To test whether the effect of 1E16 mAb on $Na_v1.7$ is subtype-specific, electrophysiological recordings were performed on different $Na_v$ subtypes ($Na_v1.1$-$Na_v1.8$), which were expressed transiently in HEK293 cells. Addition of 10 μM of 1E16 mAb to the extracellular side showed no appreciable inhibition on most $Na_v$ subtypes (except for partial effects on $Na_v1.6$) when current-voltage curves were plotted (FIG. 7C). The partial inhibitory effects of 1E16 mAb on $Na_v1.6$ at high concentrations of 1E16 mAb were expected given the sequence similarity between the S3 and S4 loops of $Na_v1.6$ and $Na_v1.7$ (FIGS. 4B and 8). Although $Na_v1.9$ was not tested, it is unlikely that 1E16 mAb would have had a significant effect on $Na_v1.9$ given the significant differences in the amino acid sequences of the S3-S4 loop between $Na_v1.7$ and $Na_v1.9$ (FIG. 4B). When the dose-response curve was plotted, 1E16 mAb was observed to be highly specific for $Na_v1.7$ in terms of potency and efficacy (FIG. 7D). 1E16 mAb affected NaV1.6 with about 200-fold less potency and about 2-fold less efficacy (about 44% maximum inhibition). 1E16 mAb had no significant effect on the rest of the $Na_v$ subtypes, as the maximum inhibitory effects were about 10-20% even at 30 μM of 1E16 mAb and several hundred fold less potencies were observed. If potency and efficacy are considered together, 1E16 mAb was 400- to 1500-fold more selective to $Na_v1.7$ than the rest of $Na_v$ subtypes (Table 4).

TABLE 4

|  | Maximum inhibition (%) | $IC_{50}$ (μM)* | Selectivity for $Na_v1.7$ |
|---|---|---|---|
| Nav1.1 | 20.7 ± 9.2 | 6.3 ± 4.4 | 861.5 |
| Nav1.2 | 18.7 ± 9.9 | 9.0 ± 9.8 | 1362.3 |
| Nav1.3 | 16.2 ± 7.6 | 8.7 ± 4.8 | 1520.1 |
| Nav1.4 | 21.5 ± 9.4 | 7.9 ± 6.6 | 1040.1 |
| Nav1.5 | 19.1 ± 7.5 | 5.6 ± 7.7 | 829.9 |
| Nav1.6 | 44.2 ± 5.9 | 6.3 ± 2.2 | 403.5 |
| Nav1.7 | 86.9 ± 2.9 | 0.0307 ± 0.0019 | 1 |
| Nav1.8 | 22.1 ± 7.8 | 5.2 ± 6.9 | 666.1 |

Selectivity = ($Max_{Nav1.7}/Max_{Nav1.x}$) × ($IC_{50Nav1.x}/IC_{50Nav1.7}$)
*$IC_{50}$ values were measured at 2 Hz and shown as means ± SEM, n = 6-10 per each subtype.

Example 5

Figure 9:
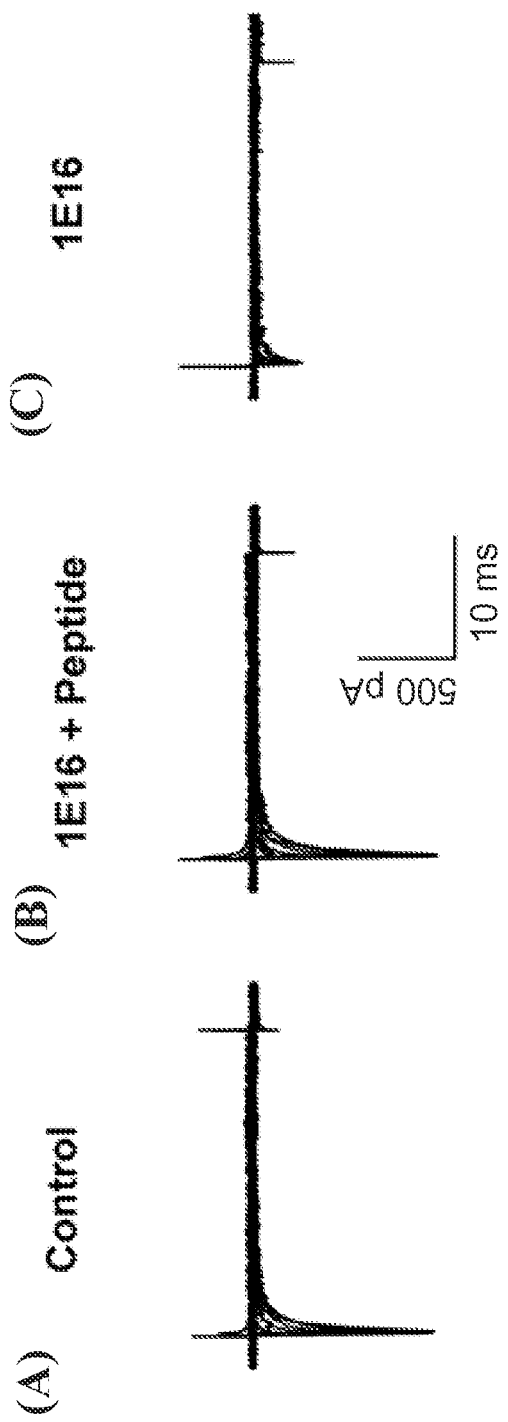
FIG. 9 shows the effects of the 1E16 mAb on $Na_v1.7$ resulted from specific interactions between the tip (loop) of the voltage-sensor paddle and 1E16. Representative traces and current-voltage relationship from HEK293 cells expressing human $Na_v1.7$ channels (A), in the presence of 1E16 (100 nM) and the peptide (1 μM) (B), and after washout in the presence of 1E16 (100 nM) only (C).

1E16 mAb Interacts with the Loop of the Voltage-Sensor Paddle of $Na_v1.7$ to Inhibit $Na_v1.7$ To test whether the observed effects of 1E16 mAb arose from specific interactions with the tip (loop) of the voltage-sensor paddle of $Na_v1.7$, electrophysiological recordings of Nav1.7 were performed in the presence of both 1E16 mAb and the peptide (i.e., SEQ ID NO:21) that was used as an antigen to raise 1E16 mAb (FIG. 9). The presence of 1 μM peptide essentially blocked the inhibitory effects of 100 nM 1E16 mAb on $Na_v1.7$, confirming that the inhibitory effects observed were due to the interactions between the tip (loop) of the voltage-sensor paddle of $Na_v1.7$ and 1E16.

Example 6

1E16 mAb Reduces Inflammatory Pain

The 1st and 2nd phase pain in the formalin model (i.e., a mouse inflammatory pain model) are suppressed after deletion of $Na_v1.7$ in DRG neurons. The formalin model was examined to determine if 1E16 mAb, by inhibiting $Na_v1.7$, could reduce or block pain sensation (i.e., provide pain relief) in the formalin model. Specifically, 1E16 mAb was administered by a spinal intrathecal (i.t.) route via lumbar puncture to target both the spinal cord and dorsal root ganglion (DRG) primary sensory neurons to determine if 1E16 mAb could attenuate formalin-induced inflammatory pain. The peptide (SEQ ID NO:21) used to raise the 1E16 mAb has an amino acid sequence which is identical between human and mouse, and thus, similar inhibitory effects were expected by the 1E16 mAb with mouse $Na_v1.7$ ($mNa_v1.7$) and human $Na_v1.7$ ($hNa_v1.7$).

Figure 10:
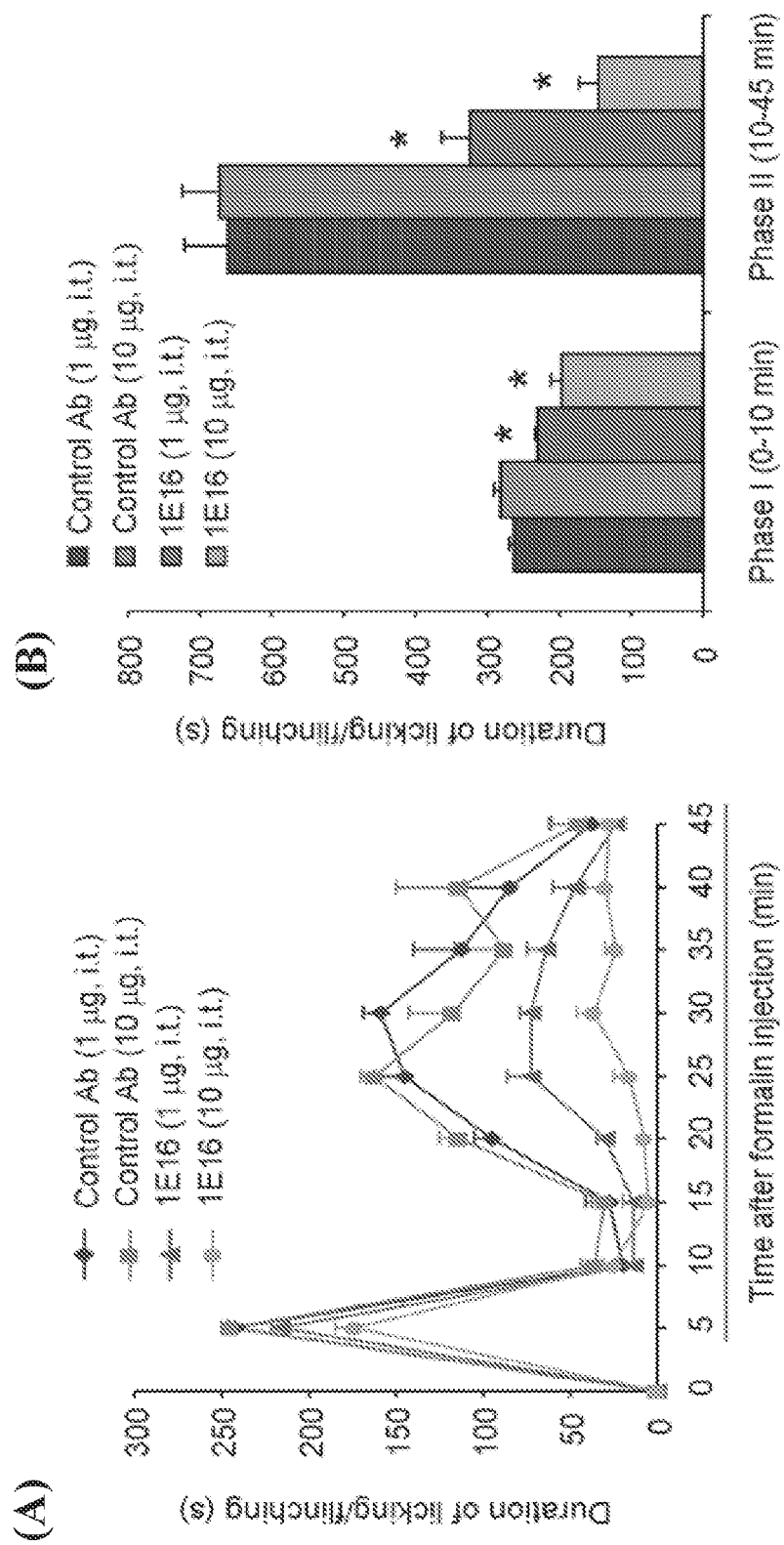
FIG. 10 shows that 1E16 reduced inflammatory and neuropathic pain and suppressed spinal cord synaptic transmission in mice. (A, B) Intrathecal injection of 1E16 reduces the formalin-induced inflammatory pain. (A) Time course of licking and flinching behavior following intraplantar injection of 5% formalin. (B) Phase-I (1-10 min) and Phase-II (10-45 min) responses following formalin injection.

Intraplatar injection of diluted formalin (5%) was administered by intraplatar injection, which elicited two-phase inflammatory pain for 45 min (representative data are shown in FIGS. 10A and 22A). Intratheally administered 1E16 mAb (1 and 10 μg, i.e., 0.006 and 0.06 nmol) produced substantial inhibition of the second phase pain and moderate inhibition of the first phase pain (representative data are shown in FIGS. 10A, 10B, 22A and 22B). Specifically, spinal injection of 1E16 mAb (1 and 10 μg) produced a dose-dependent inhibition in the 2nd phase of pain (FIGS. 10A, 10B). A moderate inhibition in the 1st phase of pain by the 1 E16 mAb (10 μg) was also observed. The control antibody (1I5) showed no effect on inflammatory pain in this model in both the first and second phases (representative data are shown in FIGS. 10A, 10B, 22A, and 22B). Accordingly, the 1E16 mAb, which was specific for $Na_v1.7$, inhibited inflammatory pain.

Systemic injection of 1E16 mAb (SVmab1) via intravenous (i.v.) route (10 and 50 mg/kg, i.e., 0.06 and 0.3 μmol/kg) also dose-dependently inhibited formalin-induced pain in both phases of pain (FIGS. 22D and E). As expected, intraplantar injection 1E16 mAb (50 μg, i. pl.) also effectively reduced the first and second phases of pain (FIG. 24).

The analgesic doses of 1E16 mAb (0.06 nmol, i.t. and 0.3 μmol/kg, i.v.) are lower than that of morphine (0.1-1 nmol, i.t., and 0.3-3 μmol/kg, i.v.), a widely used analgestic.

Additionally, formalin-induced paw edema was suppressed by systemic 1E16 mAb (SVmab1, FIG. 22F), indicating that $Na_v1.7$ also contributed to neurogenic inflammation.

Example 7

1E16 mAb Reduces Neuropathic Pain

Neuropathic pain may be more resistant to analgesics, and thus, the efficacy of the 1E16 mAb was examined in a neuropathic pain mouse model. Such a neuropathic pain model is induced by chronic constriction injury (CCI) of the sciatic nerve.

Mechanical allodynia, a cardinal feature of neuropathic pain, is revealed by a decrease in paw withdrawal threshold (representative data are shown in FIGS. 10C and 22G) as evident 3 days after CCI surgery. This allodynia was transiently reversed for several hours by intrathecal injection of 1E16 mAb (50 μg, i.e., about 0.3 nmol) (representative data are shown in FIGS. 10C and 22G). Furthermore, systemic injection of 1E16 mAb via i.v. route (10 mg/kg), administered 7 days after nerve injury, was also effective in reducing mechanical allodynia (FIG. 10D). Additionally, systemic injection of 1E16 mAb (SVmab1) via i.v. route (10 and 50 mg/kg) was also effective in reversing established mechanical allodynia and the analgesic effect lasted 24 hours after the injection (FIG. 22H). Multiple injections of 1E16 mAb showed no signs of antinociceptive tolerance (FIG. 22H). Thus, targeting $Na_v1.7$ with the 1E16 mAb alleviated both inflammatory (as described above) and neuropathic pain via central mechanisms (intrathecal/spinal route) and peripheral mechanisms (systemic route).

The effects of the antibody on synaptic transmission in neuropathic pain was also investigated. sEPSC in lamina IIo neurons was increased in neuropathic pain after CCI (representative data are shown in FIGS. 14A, 14B, 23K, and 23L). Strikingly, 1E16 mAb (SVmab1) was more effective in suppressing sEPSC in neuropathic pain (about 50%) and there is no difference between the TTX (1 μM) and 1E16 mAb (300 nM) treated group (representative data are shown in FIGS. 14A, 14B, 23K, and 23L). Thus, $Na_v1.7$ played a major role in spinal cord nociceptive synaptic transmission and contributed predominantly to synaptic transmission mediated by the TTX-sensitive sodium channels in neuropathic pain.

Since DRGs are located in the peripheral nervous system and $Na_v1.7$ is expressed by small nociceptive DRG neurons, the effects of the 1E16 mAb were also tested on $Na_v1.7$-mediated persistent sodium currents in small-sized DRG neurons. Whole mount DRG recordings revealed that persistent sodium currents ($I_{Na}P$) in DRG neurons were partially (about 42% and about 37%, FIGS. 11B and 17, respectively, which show representative data) inhibited by 1E16 mAb (300 nM, FIGS. 11A and 11B and FIG. 17). Nerve injury by CCI increased $I_{Na}P$ currents, and the 1E16 mAb (300 nM) produced a greater inhibition of the current (about 51% and about 50%) in this neuropathic pain condition (FIGS. 11B and 17, respectively, which show representative data). This higher inhibition of the current by the 1E16 mAb in the neuropathic pain condition was consistent with the state-dependent inhibition of $Na_v1.7$ by the 1E16 mAb observed in HEK293 cell as described above.

Example 8

1E16 mAb Reduced sEPSC Frequency in a Dose-dependent Manner and Suppressed Nociceptive Synaptic Transmission in Spinal Cord Dorsal Horn To determine the synaptic mechanisms by which spinal administration of the 1E16 mAb (SVmab1) elicited pain relief, patch clamp recordings were conducted in spinal cord slices to measure spontaneous excitatory postsynaptic currents (sEPSCs) in lamina IIo neurons, which are critical for pain transmission. Lamina IIo interneurons formed a pain circuit with C-fibers as input and lamina I projection neurons as output. Perfusion of spinal cord slices with 1E16 mAb (7, 70, and 300 nM) reduced sEPSC frequency in a dose-dependent manner (representative data are shown in FIGS. 10E, 10F, 23I, and 23J) and did not affect the amplitude of sEPSCs. At the dose of 300 nM, 1E16 mAb suppressed the frequency of sEPSCs by 48%. 1E16 mAb also delayed the conduction of action potentials in lamina IIO neurons induced by dorsal root stimulation at C-fiber intensity (FIG. 20). In contrast, the control mAb 1I5 (300 nM) had no effect on sEPSCs frequency (representative data are shown in FIGS. 10E, 10F, 23I, and 23J).

For comparison, Tetradotoxin (TTX) (1 μM) reduced sEPSC frequency by 60% (FIG. 10F). This was significantly higher than that of 300 nM 1E16 mAb (FIG. 23J). TTX is a small-molecule toxin that inhibits subclasses of sodium channels, including $Na_v1.7$. These channels are known as TTX-sensitive channels. This data showed that among TTX-sensitive channels that contribute to sEPSC, Nav1.7 plays a major role because the 1E16 antibody reduced sEPSC substantially. Accordingly, these data also indicated that $Na_v1.7$ plays a role in spinal cord nociceptive synaptic transmission as mediated by the TTX-sensitive sodium channels. Together, 1E16 mAB attenuated acute and chronic pain by suppressing both $Na_v1.7$-mediated sodium currents in DRG neurons (as described in Examples 6 and 7 above) and synaptic transmission in spinal cord neurons.

Example 9

Intrathecal Injection of the 1E16 mAb does not Affect Motor Coordination and Balance in Mice As discussed above, the 1E16 mAb inhibited $Na_v1.7$ by stabilizing the closed state of $Na_v1.7$. Such inhibition of $Na_v1.7$ by the 1E16 mAb reduced persistent sodium currents and suppressed the frequency of sEPSCs. Additionally, the 1E16 mAb, through its inhibition of $Na_v1.7$, alleviated inflammatory pain and neuropathic pain by both central mechanisms (intrathecal/spinal route) and peripheral mechanisms (systemic route). To determine if administration of the 1E16 mAb resulted in effects other than those described above (i.e., side effects), motor coordination and balance were examined in mice before and after injection of the control mAb 1I5 and 1E16 mAb.

In particular, the falling latency (i.e., the time on a rota-rod) of mice was measured before (i.e., BL (baseline)) in FIGS. 12 and 22C) and after intrathecal injection of 1I5 (50 μg) and 1E16 (50 μg). The falling latency was measured 2.5 hours (h) after injection of the respective antibodies, and the number of mice examined in each group was 5. As shown in the representative data of FIGS. 12 and 22C, the 1E16 mAb (at a high dose via i.t. route) had no effect on motor function (P>0.05), and thus, the effects of the 1E16 mAb were specific to $Na_v1.7$ and alleviating pain. These data demonstrated that the 1E16 mAb may alleviate pain while not affecting other functions such as motor coordination and balance.

Example 10

Apparent $K_D$ of 1E16 Antibody Binding to Human $Na_v1.7$

The affinity of the 1E16 antibody for human $Na_v1.7$ (h$Na_v1.7$) was examined by obtaining the dissociation constant ($K_D$) from electrophysiological recordings. In particular, h$Na_v1.7$ was expressed in HEK293 cells and the electrophysiological recordings were obtained using a whole-cell voltage clamp configuration. In the presence of various concentrations of the 1E16 antibody, currents were elicited during 30 millisecond (ms) depolarizing pulses to −10 mV from a holding potential of −120 mV at a frequency of 10 Hz.

The $K_D$ value was obtained using the one-site binding equation: $Y=B_{max} \cdot X/(K_D+X)$. Y was the fraction bound or the specific binding. $B_{max}$ was the maximum number of binding sites. $K_D$ was the apparent dissociation constant. X was the concentration of the 1E16 antibody. Additionally, $Y=1-I/I_O$. I was the peak sodium current after the addition of the 1E16 antibody. $I_O$ was the sodium current before addition of the 1E16 antibody.

FIG. 13 shows the concentration of the 1E16 antibody vs. the fraction bound. The data are shown as means±S.E.M. (n=10). The fitted value for $B_{max}$ was 1.2±0.1 and the fitted value for $K_D$ was 22.9±5.7 nM.

Example 11

Acute and Chronic Itch and Chronic Itch-related Synaptic Transmission are Reduced by 1E16 mAb To study the role of $Na_v1.7$ in itch sensation, the effects of 1E16 mAb on acute itch were examined by observing the scratching behaviors in mice following intradermal injection of histamine-dependent prutitic agent (compound 48/80) and histamine-independent pruritic agent (chloroquine, CQ) into the nape of the neck. Intrathecal injection of 1E16 mAb (50 µg) not only suppressed compound 48/80-induced scratching (representative data are shown in FIGS. 15A, 18A, and 21), but also inhibited CQ-induced scratching significantly (representative data are shown in FIGS. 15B, 18B, and 21), indicating that $Na_v1.7$ was required for eliciting both histamine-dependent and independent itch.

To understand the inhibition mechanism of acute itch sensation by 1E16 mAb, whether 1E16 mAb attenuated intrathecally introduced gastrin-releasing peptide (GRP)-induced acute itch. GRP mediates itch by binding and activating the GRP receptor (GRPR) in superficial dorsal horn neurons. Intrathecal injection of 1E16 mAb (50 µg) effectively suppressed GRP (1 nmol, i.t.) mediated acute itch (i.e., scratching), thereby indicating that $Na_v1.7$ was expressed in itch-responsive neurons, played a role in acute itch sensation, and was involved in spinal GRPR-mediated itch transmission (representative data are shown in FIGS. 15C and 18C).

To determine the role of $Na_v1.7$ in chronic itch, mouse back skin was painted with acetone and diethyether following by water (AEW) for 5 days to induce dry skin lesion. Five days after AEW treatment, mice showed spontaneous scratching, and this AEW-evoked spontaneous itch was also suppressed by the 1E16 mAb via either intrathecal route (50 µg, representative data are shown in FIGS. 15D and 18D) or i.v. route (10 mg/kg, representative data are shown in FIGS. 15E and 18E).

Whether 1E16 mAb also modulated itch-related synaptic transmission in lamina IIo neurons of spinal cord slices was examined. AEW treatment increased sEPSC in lamina II neurons (representative data are shown in FIGS. 15F, 15G, 18I, and 18J), indicating that chronic itch potentiated excitatory synaptic transmission. 1E16 mAb also effectively suppressed sEPSC by about 25% in chronic itch (FIGS. 15F and 15G).

An allergic contact dermatitis (ACD) model of chronic itch was generated by hapten 2,4-dinitrofluorobenzene (DNFB). Treatment of the back skin with DNFB induced progressive scratching (FIG. 18F), which was reduced by both i.t. 1E16 mAb (50 µg) and i.v. 1E16 mAb (50 mg/kg) (FIGS. 18G and 18H).

Example 12

1E16 mAb Regulated Sodium Currents and Action Potentials in Native DRG Neurons

Since $Na_v1.7$ was heavily expressed by small-sized nociceptive DRG neurons, it was examined whether 1E16 mAb would also modulate $Na_v1.7$ in native neurons by recording transient sodium currents ($I_{Na}$s) in dissociated small-sized DRG neurons. Current-voltage relationship showed that 1E16 mAb (7, 70, and 300 nM) dose-dependently inhibited peak $I_{Na}$s, but 1I5 mAb (300 nM) had no effect (FIG. 23A). Further analysis revealed that 1E16 mAb at 300 nM suppressed $I_{Na}$s by 70% (FIGS. 23B and 23C). By contrast, $I_{Na}$s in large-sized DRG neurons was only inhibited by TTX (1 µM) but not 1E16 mAb (300 nM), indicating a specific effect of 1E16 mAb on small-sized neurons (FIG. 23D). 1E16 mAb also suppressed action potentials in dissociated small-sized DRG neurons following current injection (FIGS. 23E, 23F, and 19A).

The effects of 1E16 mAb (SVmab1) were also tested on $Na_v1.7$-mediated persistent sodium currents ($I_{Na}P$) in small-sized DRG neurons. 1E16 mAb, but not 1I5 (300 nM), largely inhibited $I_{Na}P$ (62%, FIG. 19B). $I_{Na}P$ was also recorded in an ex vivo condition using whole mount DRG. In this preparation, $I_{Na}P$ in small-sized neurons were partially (about 37%) inhibited by 1E16 mAb (300 nM, FIGS. 23G and 23H). The discrepancy in $I_{Na}P$ inhibition in dissociated DRG neurons (about 62%) and whole mount DRG neurons (about 37%) reflected limited antibody access in whole mount recordings. Nerve injury by CCI increased $I_{Na}P$, and 1E16 mAb (300 nM) produced a greater inhibition of the current (about 50%) in this neuropathic pain condition, consistent with its state-dependent inhibition properties shown in HEK293 cells (FIGS. 23G and 23H). 1E16 mAb (300 nM) also inhibited action potentials and $I_{Na}$s in whole mount DRG neurons (FIGS. 19C and 19D).

In summary, the above Examples demonstrated a role for $Na_v1.7$ in modulating spinal cord synaptic transmission in the context of pain and itch. sEPSC frequency (i.e., excitatory synaptic transmission) in IIo neurons was greatly potentiated in both chronic pain and itch conditions. Under normal conditions, $Na_v1.7$ contributed to TTX-sensitive sodium channel-mediated excitatory synaptic transmission. In neuropathic pain, $Na_v1.7$ played a role in excitatory synaptic transmission since sEPSC suppression by TTX was completely precluded by 1E16 mAb. Thus, apart from the demonstrated peripheral mechanism of $Na_v1.7$ in pain initiation (FIGS. 23A-23H), the results presented herein also demonstrated a central mechanism of $Na_v1.7$ in modulating excitatory synaptic transmission in the spinal cord pain circuitry (FIG. 25).

The above Examples also demonstrated that intrathecal 1E16 mAb not only inhibited pain and itch, but also suppressed the excitatory synaptic transmission in lamina IIo intraneurons in the superficial dorsal horn in the normal and chronic pain and itch conditions. The above Examples further demonstrated that part of the glutamate transmission, underlying the expression of sEPSCs recorded in lamina IIo, was required for the transmission of pain and itch (FIG. 25). Accordingly, 1E16 mAb may block GRP-induced itch via suppression of glutamatergic neurotransmission.

The above Examples also demonstrated that 1E16 mAb altered Na$_v$1.7 channel function in intact lamina IIo and DRG neurons and provided therapeutic effects without impairing motor function. These therapeutic effects included suppression of inflammatory and neuropathic pain. The therapeutic effects also included suppression of acute and chronic itch.

Example 13

Crystal Structure of the Fab Fragment of 1E16 mAb

The structure of the Fab fragment of 1E16 mAb (also known herein as SVmab1) was determined using x-ray crystallography. The structure is shown in FIGS. 26A and 26B. Specifically, FIG. 26A shows a stick representation of the epitope-binding region of 1E16 mAb. FIG. 26B shows an overall representation of the Fab fragment as a ribbon diagram.

The structure was refined to 1.8 Å. $R_{work}/Rf_{ree}$=19.9/24.0. The space group was $P2_1$ with unit cell parameters as follows: a=43.1, b=71.9, c=67.8 Å, alpha=90°, beta=97.8°, gamma=90°.

It is understood that the foregoing detailed description and accompanying examples are merely illustrative and are not to be taken as limitations upon the scope of the invention, which is defined solely by the appended claims and their equivalents.

Various changes and modifications to the disclosed embodiments will be apparent to those skilled in the art. Such changes and modifications, including without limitation those relating to the chemical structures, substituents, derivatives, intermediates, syntheses, compositions, formulations, or methods of use of the invention, may be made without departing from the spirit and scope thereof.

What is claimed is:

1. An isolated antibody or antibody fragment which comprises a variable heavy domain comprising the amino acid sequence of SEQ ID NO:4 and a variable light domain comprising the amino acid sequence of SEQ ID NO:8.

2. A method of treating pain, itch, or neurogenic inflammation in a subject in need thereof, the method comprising administering the antibody or antibody fragment of claim 1 to the subject.

3. The method of claim 2, wherein the pain is inflammatory pain, neuropathic pain, hyperalgesia, allodynia, paroxysmal extreme pain disorder, inherited erythromelalgia, cancer-associated pain, atypical pain, neurogenic inflammation-associated pain, chronic pain, pathological pain, or a combination thereof.

4. The method of claim 3, wherein: the inflammatory pain is arthritis pain, dental pain, low back pain, pain associated with inflammatory bowel disease, pain associated with temporomandibular joint (TMJ), or a combination thereof,
   (a) the neuropathic pain is associated with diabetic neuropathy, chemotherapy, human immunodeficiency virus (HIV) infection, postherpetic neuralgia (PHN), surgery, spinal cord injury, stroke, or a combination thereof,
   (b) the neurogenic inflammation-associated pain is complex regional pain syndrome (CRPS), headache, migraine, or a combination thereof.

5. The method of claim 4, wherein the surgery is an amputation, thoracotomy, hernia surgery, or mastectomy.

6. The method of claim 2, wherein the pain is associated with itch.

7. The method of claim 2, wherein the itch is acute itch, chronic itch, histamine-dependent itch, histamine-independent itch, or a combination thereof.

8. The method of claim 2, wherein the chronic itch is associated with atopic dermatitis, allergic contact dermatitis, psoriasis, renal disease, liver disease, zoster virus, eczema, or a combination thereof.

9. The method of claim 2, wherein the itch is associated with allergic contact dermatitis.

10. The method of claim 2, wherein the neurogenic inflammation is associated with asthma, arthritis, eczema, headache, migraine, psoriasis, or a combination thereof.

11. The method of claim 2, wherein the subject is human, bovine, canine, equine, feline, or porcine.

12. An isolated antibody or antibody fragment which comprises a variable heavy chain comprising the CDR1 comprising the amino acid sequence of SEQ ID NQ:5, the CDR2 comprising the amino acid sequence of SEQ ID NO:6, and the CDR3 comprising the amino acid sequence of SEQ ID NO:7, and a variable light chain comprising the CDR1 comprising the amino acid sequence of SEQ ID NO:9, the CDR2 comprising the amino acid sequence of SEQ ID NO:10, and the CDR3 comprising the amino acid sequence of SEQ ID NO:11.

13. A method of treating pain, itch, or neurogenic inflammation in a subject in need thereof, the method comprising administering the antibody or antibody fragment of claim 12 to the subject.

14. The method of claim 13, wherein the pain is inflammatory pain, neuropathic pain, hyperalgesia, allodynia, paroxysmal extreme pain disorder, inherited erythromelalgia, cancer-associated pain, atypical pain, neurogenic inflammation-associated pain, chronic pain, pathological pain, or a combination thereof.

15. The method of claim 14, wherein the inflammatory pain is arthritis pain, dental pain, low back pain, pain associated with inflammatory bowel disease, pain associated with temporomandibular joint (TMJ), or a combination thereof,
- (a) the neuropathic pain is associated with diabetic neuropathy, chemotherapy, human immunodeficiency virus (HIV) infection, postherpetic neuralgia (PHN), surgery, spinal cord injury, stroke, or a combination thereof,
- (b) the neurogenic inflammation-associated pain is complex regional pain syndrome (CRPS), headache, migraine, or a combination thereof.

16. The method of claim 15, wherein the surgery is an amputation, thoracotomy, hernia surgery, or mastectomy.

17. The method of claim 13, wherein the pain is associated with itch.

18. The method of claim 13, wherein the itch is acute itch, chronic itch, histamine-dependent itch, histamine-independent itch, or a combination thereof.

19. The method of claim 13, wherein the chronic itch is associated with atopic dermatitis, allergic contact dermatitis, psoriasis, renal disease, liver disease, zoster virus, eczema, or a combination thereof.

20. The method of claim 13, wherein the itch is associated with allergic contact dermatitis.

21. The method of claim 13, wherein the neurogenic inflammation is associated with asthma, arthritis, eczema, headache, migraine, psoriasis, or a combination thereof.

22. The method of claim 13, wherein the subject is human, bovine, canine, equine, feline, or porcine.

* * * * *